(12) United States Patent  
Ware et al.

(10) Patent No.: US 8,349,320 B2  
(45) Date of Patent: Jan. 8, 2013

(54) COMPOSITIONS AND METHODS FOR MODULATING RESPONSES MEDIATED OR ASSOCIATED WITH BTLA ACTIVITY

(75) Inventors: Carl F. Ware, Solana Beach, CA (US); Carl De Trez, Brussels (BE); Michael Croft, San Diego, CA (US); Timothy C. Cheung, Sydney (AU); Ian R. Humphreys, St. Brides Major (GB); Karen G. Potter, San Diego, CA (US); Christopher A. Benedict, Encinitas, CA (US); Mitchell Kronenberg, Del Mar, CA (US); Marcos W. Steinberg, San Diego, CA (US)

(73) Assignee: La Jolla Institute for Allergy and Immunology, La Jolla, CA (US)

( * ) Notice: Subject to any disclaimer, the term of this patent is extended or adjusted under 35 U.S.C. 154(b) by 265 days.

(21) Appl. No.: 12/482,426

(22) Filed: Jun. 10, 2009

(65) Prior Publication Data

US 2010/0104559 A1 Apr. 29, 2010

Related U.S. Application Data

(63) Continuation-in-part of application No. 11/721,308, filed as application No. PCT/US2005/044296 on Dec. 9, 2005, now abandoned.

(60) Provisional application No. 61/060,421, filed on Jun. 10, 2008, provisional application No. 61/078,997, filed on Jul. 8, 2008, provisional application No. 60/635,034, filed on Dec. 9, 2004, provisional application No. 60/700,636, filed on Jul. 19, 2005.

(51) Int. Cl.  
*A61K 39/395* (2006.01)

(52) U.S. Cl. .................................. 424/130.1

(58) Field of Classification Search ........................ None  
See application file for complete search history.

(56) References Cited

U.S. PATENT DOCUMENTS

| 7,479,544 | B2 * | 1/2009 | Clark et al. ................. 530/387.1 |
| 2003/0215442 | A1 | 11/2003 | Fraser et al. |
| 2004/0175380 | A1 * | 9/2004 | Allison et al. ............. 424/144.1 |
| 2004/0248257 | A1 | 12/2004 | Kaye et al. |
| 2005/0152893 | A1 | 7/2005 | Kaye |
| 2007/0292435 | A1 | 12/2007 | Ware |
| 2009/0081229 | A1 | 3/2009 | Clark et al. |
| 2009/0175855 | A1 | 7/2009 | Clark et al. |

FOREIGN PATENT DOCUMENTS

| EP | 1 336 619 A2 | 8/2003 |
| WO | 2004/096976 A2 | 11/2004 |
| WO | 2006/044333 A2 | 4/2006 |
| WO | 2006/054961 A2 | 5/2006 |
| WO | 2006/063067 A2 | 6/2006 |
| WO | 2007/001459 A2 | 1/2007 |
| WO | 2007/010692 A1 | 1/2007 |
| WO | 2008/076560 A3 | 6/2008 |

OTHER PUBLICATIONS

Cai G., et al., CD160 Inhibits Activation of Human CD4+ T Cells Through Interaction with Herpesvirus Entry Mediator, Nature Immunology, 2008, 9(2):176-185.

Cheung, T.C., et al., Evolutionarily Divergent Herpesviruses Modulate T Cell Activation by Targeting the Herpesvirus Entry Mediator Cosignaling Pathway, PNAS, 2005, 102(37):13218-13223.

Cheung, T.C., et al., Unconventional Ligand Activation of Herpesvirus Entry Mediator Signals Cell Survival, PNAS, 2009, 106(15):6244-6249.

Compaan. D.M., et al., Attenuating Lymphocyte Activity: the Crystal Structure of the BTLA-HVEM Complex, J. Biol. Chem., 2005, 280(47):39553-39561.

Nelson, C.A., et al., Structural Determinants of Herpesvirus Entry Mediator Recognition by Murine B and T Lymphocyte Attenuator, J. of Immunology, 2008, 180:940-947.

Ware, C.F., Targeting Lymphocyte Activation Through the Lymphotoxin and LIGHT Pathways, Immunol Rev., 2008, 223:186-201.

Arav-Boger, R., et al., Polymorphisms of the Cytomegalovirus (CMV)-Encoded Tumor Necrosis Factor-α and β-Chemokine Receptors in Congenital CMV Disease, Database Swissprot [Online], 2004, XP002395809 accession No. Q8BDC7.

Ni, J., et al., Tumour Necrosis Factor Receptor (TNFR) Domain of 4-1BB Protein, Database EMBL, 2001, XP002395812 accession No. AAY94714.

Sedy, J.R., et al., B and T Lymphocyte Attenuator Regulates T Cell Activation Through Interaction with Herpesvirus Entry Mediator, Nature Immunology, 2005, 6(1):90-98.

Nicola, A.V., et al., Monoclonal Antibodies to Distinct Sites on Herpes Simplex Virus (HSV) Glycoprotein D Block HSV Binding to HVEM, Journal of Virology, 1998, 72(5):3595-3601.

(Continued)

*Primary Examiner* — Ilia Ouspenski  
(74) *Attorney, Agent, or Firm* — Pillsbury Winthrop Shaw Pittman LLP

(57) ABSTRACT

Herpesvirus entry mediator (HVEM) is a member of the tumor necrosis factor receptor superfamily (TNFRSF) and acts as a molecular switch that modulates T cell activation by propagating positive signals from the TNF related ligand, LIGHT (p30, TNFSF14), or inhibitory signals through the immunoglobulin superfamily member, B and T lymphocyte attenuator (BTLA). A novel binding site for BTLA is disclosed, located in cysteine-rich domain-1 of HVEM. BTLA binding site on HVEM overlaps with the binding site for the Herpes Simplex virus-1 envelope glycoprotein D (gD), but is distinct from where LIGHT binds, yet gD inhibits the binding of both ligands. A BTLA activating protein present in human cytomegalovirus is identified as UL144. UL144 binds BTLA, but not LIGHT, and inhibits T cell proliferation.

17 Claims, 53 Drawing Sheets

OTHER PUBLICATIONS

Sarrias, M.R., et al., The Three HveA Receptor Ligands, gD, LT-α and LIGHT Bind to Distinct Sites on HveA, Molecular Immunology, 2000, 37:665-673.

Ashkenazi, A.J., Extracellular Region of Human CD27 (hCD27)) Protein, Database EMBL, 2003, XP002395810 accession No. ADA49704.

Ashkenazi, A.J., Extracellular Region of Human OX40 (hOX40) Protein, Database EMBL, 2003, XP002395811 accession No. ADA49706.

Benedict, C.A., et al., Cutting Edge: A Novel Viral TNF Receptor Superfamily Member in Virulent Strains of Human Cytomegalovirus, Journal of Immunology, 1999, 162(12):6987-6970.

Hurchla, M.A., et al., Unexpected Role of B and T Lymphocyte Attenuator in Sustaining Cell Survival During Chronic Allostimulation, J. Immunol. 2007, 178:6073-6082.

Watanabe, N., et al., BTLA is a Lymphocyte Inhibitory Receptor With Similarities to CTLA-4 and PD-1, Nature Immunology, 2003, 4(7):670-679.

* cited by examiner

Figure 10

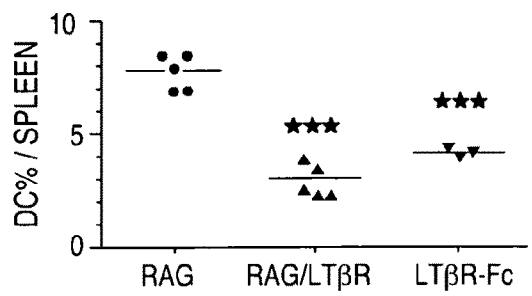 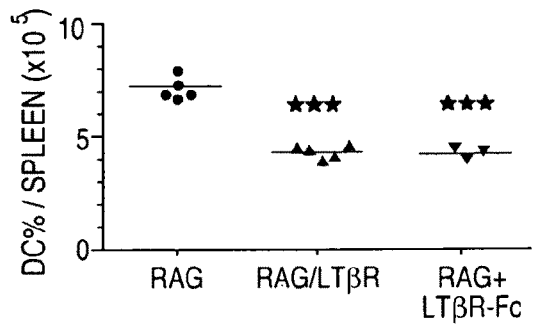
Figure 14A         Figure 14B
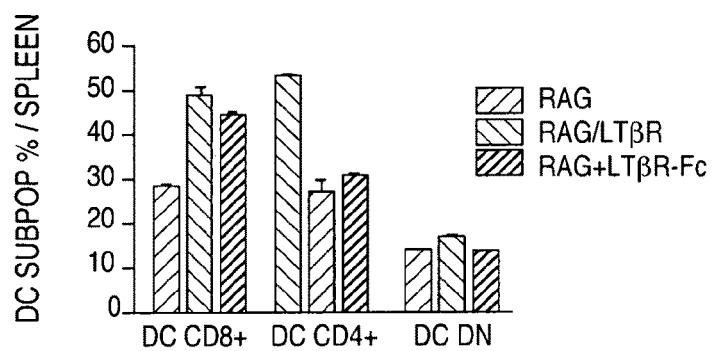
Figure 14C
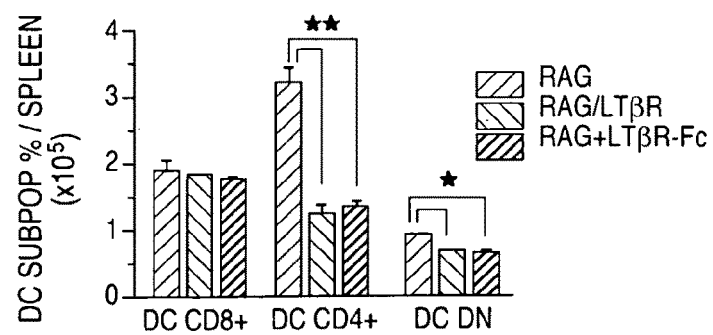
Figure 14D

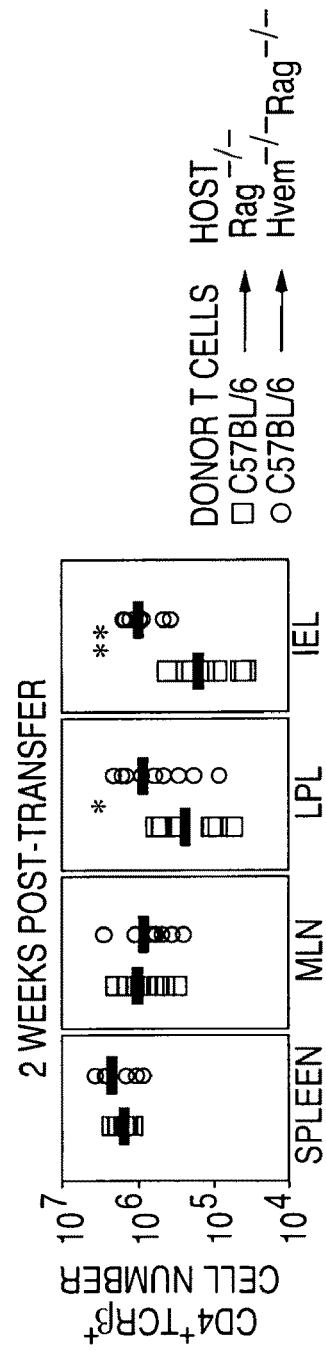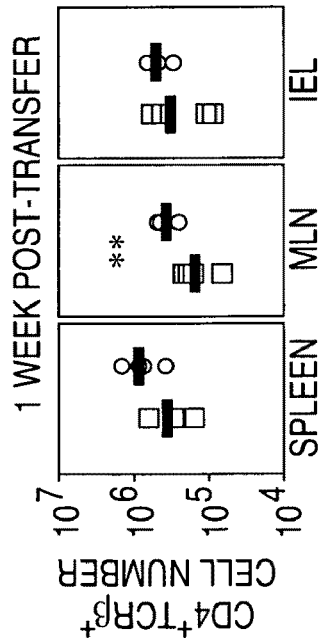
Figure 19A
Figure 19B

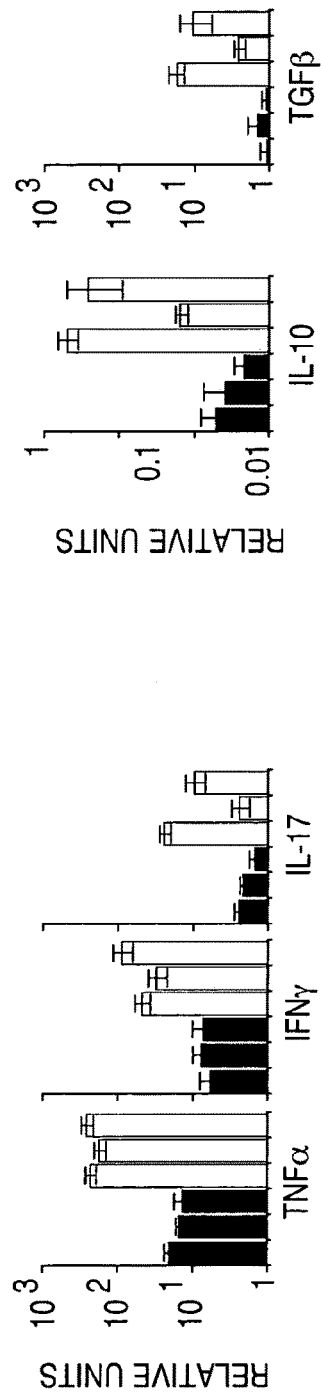
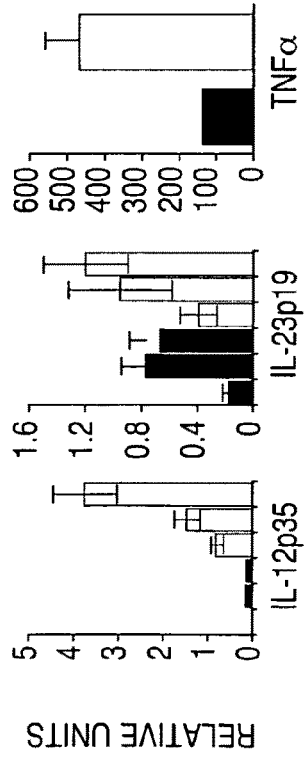
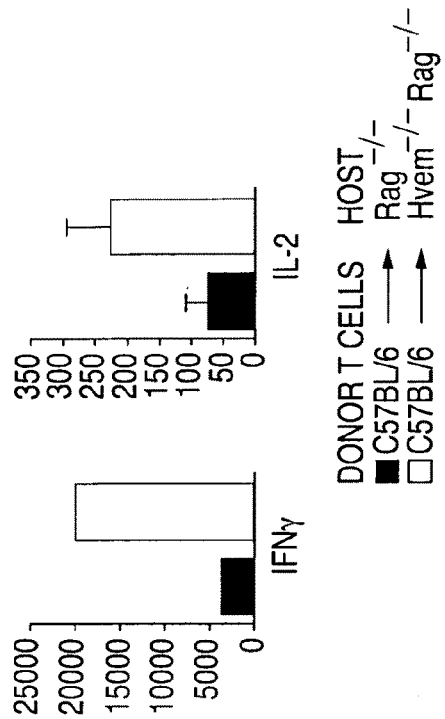
Figure 19C
Figure 19D
Figure 19E
Figure 19F

Figure 21A
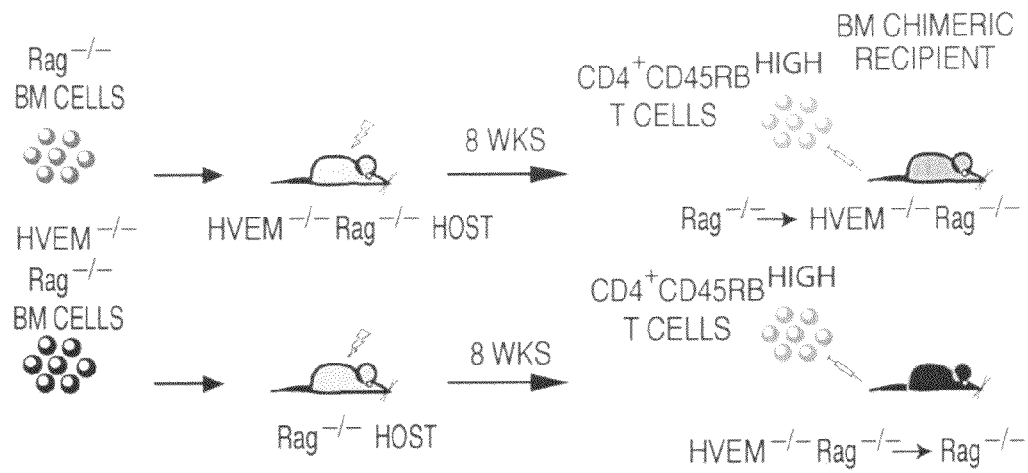
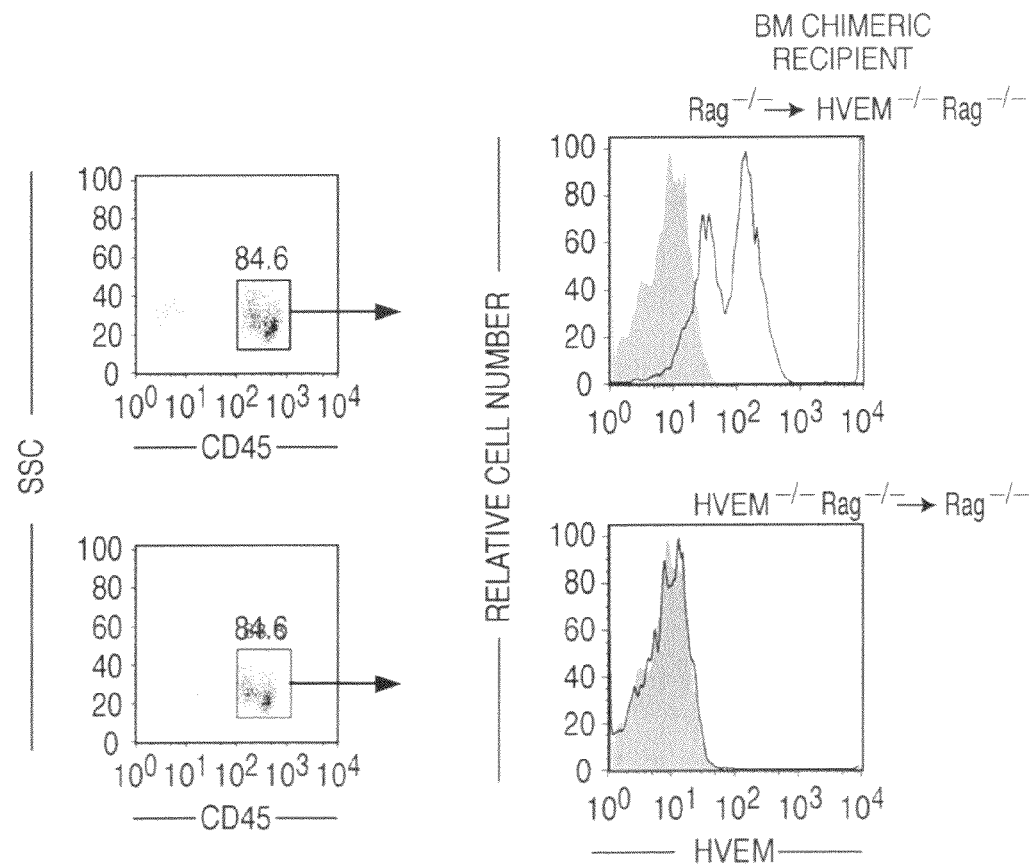
Figure 21B

Figure 25C
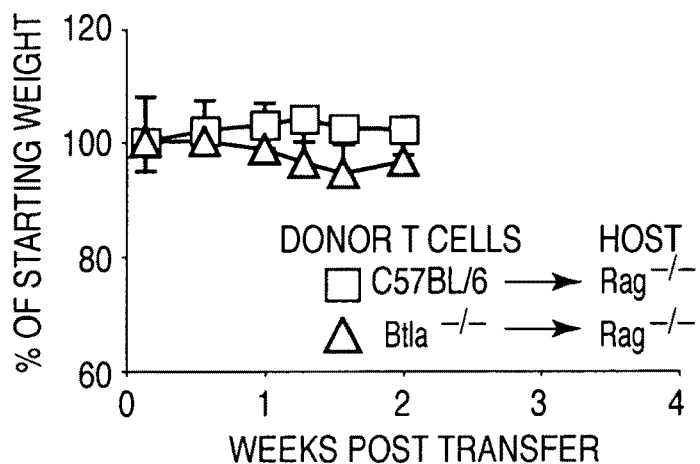
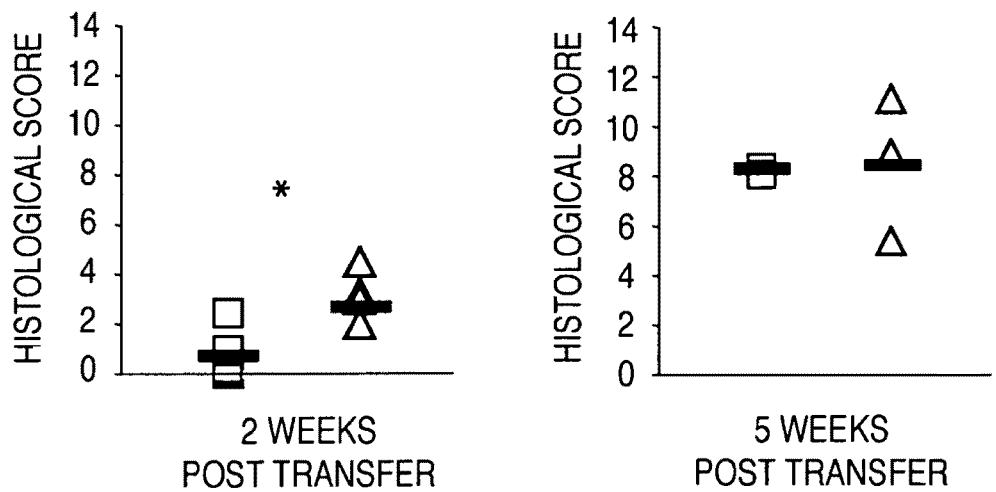
Figure 25D

Reduced arthritis scores in mice treated
with the αBTLA mAb

Reduced joint inflammation in DBA mice treated with the αBTLA mAb

Delayed onset and lower incidence of CIA in mice treated with the αBTLA mAb

T-BLUE STRAINING OF ANKLES FROM ARTHRITIC MICE

1. An 2, High Score, Ankle, 25x.  2. An 2, High Score, Ankle, 100x.

PBS

3. An 10, Low Score, Ankle, 25x.  4. An 10, Low Score, Ankle, 100x.

αBTLA 1, 2. Ankle from animal with the highest score has marked inflammation and severe cartilage damage with marked pannus and bone resorption. Arrows identify affected joints.

3, 4. Ankle from animal with the lowest score is normal.

PROLIFERATIVE RESPONSE OF ANTIGEN-SPECIFIC T CELLS
FOLLOWING IN VITRO STIMULATION WITH TYPE II COLLAGEN

FEMALES CFA

MALES IFA

ANTI-BTLA mAb TREATMENT ATTENUATES PROLIFERATION
OF PATHOGENIC T-CELLS a BTLA treatment specifically deplete BTLA⁺
follicular B cells (B220⁺CD23ʰⁱCD21ⁱⁿᵗ)

SEQUENCE LISTING

```
<160> NUMBER OF SEQ ID NOS: 34

<210> SEQ ID NO 1
<211> LENGTH: 25
<212> TYPE: PRT
<213> ORGANISM: Homo sapiens

<400> SEQUENCE: 1

Cys Pro Lys Cys Ser Pro Gly Tyr Arg Val Lys Glu Ala Cys Gly Glu
1               5                   10                  15

Leu Thr Gly Thr Val Cys Glu Pro Cys
            20                  25

<210> SEQ ID NO 2
<211> LENGTH: 25
<212> TYPE: PRT
<213> ORGANISM: Homo sapiens

<400> SEQUENCE: 2

Cys Pro Met Cys Asn Pro Gly Tyr His Val Lys Gln Val Cys Ser Glu
1               5                   10                  15

His Thr Gly Thr Val Cys Ala Pro Cys
            20                  25

<210> SEQ ID NO 3
<211> LENGTH: 132
<212> TYPE: PRT
<213> ORGANISM: Homo sapiens

<400> SEQUENCE: 3

Met Lys Pro Leu Ile Met Leu Ile Cys Phe Ala Val Ile Leu Leu Gln
1               5                   10                  15

Leu Gly Val Thr Lys Val Cys Gln His Asn Glu Val Gln Leu Gly Asn
            20                  25                  30
```

```
Glu Cys Cys Pro Pro Cys Gly Ser Gly Gln Arg Val Thr Lys Val Cys
        35                  40                  45

Thr Asp Tyr Thr Ser Val Thr Cys Thr Pro Cys Pro Asn Gly Thr Tyr
 50                  55                  60

Val Ser Gly Leu Tyr Asn Cys Thr Asp Cys Thr Gln Cys Asn Val Thr
 65                  70                  75                  80

Gln Val Met Ile Arg Asn Cys Thr Ser Thr Asn Asn Thr Val Cys Ala
                 85                  90                  95

Ser Lys Asn Tyr Thr Ser Phe Ser Ile Ser Gly Val Gln His Lys
                100                 105                 110

Gln Arg Gln Asn His Thr Ala His Val Thr Val Lys Gly Lys Ser
             115                 120                 125

Gly Arg His Thr
         130

<210> SEQ ID NO 4
<211> LENGTH: 133
<212> TYPE: PRT
<213> ORGANISM: Homo sapiens

<400> SEQUENCE: 4

Met Lys Pro Leu Ile Met Leu Ile Cys Phe Ala Val Ile Leu Leu Gln
 1               5                  10                  15

Leu Gly Val Thr Lys Val Cys Gln His Asn Glu Val Gln Leu Gly Asn
                 20                  25                  30

Glu Cys Cys Pro Pro Cys Gly Ser Gly Gln Arg Val Thr Lys Val Cys
        35                  40                  45

Thr Asp Tyr Thr Ser Val Thr Cys Thr Pro Cys Pro Asn Gly Thr Tyr
 50                  55                  60

Val Ser Gly Leu Tyr Asn Cys Thr Asp Cys Thr Gln Cys Asn Val Thr
 65                  70                  75                  80

Gln Val Met Ile Arg Asn Cys Thr Ser Thr Asn Asn Thr Val Cys Ala
                 85                  90                  95

Pro Lys Asn His Thr Tyr Phe Ser Thr Pro Gly Val Gln His His Lys
                100                 105                 110

Gln Arg Gln Gln Asn His Thr Ala His Ile Thr Val Lys Gln Gly Lys
             115                 120                 125

Ser Gly Arg His Thr
         130

<210> SEQ ID NO 5
<211> LENGTH: 132
<212> TYPE: PRT
<213> ORGANISM: Homo sapiens

<400> SEQUENCE: 5

Met Lys Pro Leu Val Met Leu Ile Leu Leu Ser Met Leu Leu Ala Cys
 1               5                  10                  15

Ile Gly Lys Thr Glu Ile Cys Lys Pro Glu Glu Val Gln Leu Gly Asn
                 20                  25                  30

Gln Cys Cys Pro Pro Cys Lys Gln Gly Tyr Arg Val Thr Gly Gln Cys
        35                  40                  45

Thr Gln Tyr Thr Ser Thr Thr Cys Thr Leu Cys Pro Asn Gly Thr Tyr
 50                  55                  60

Val Ser Gly Leu Tyr Asn Cys Thr Asn Cys Thr Glu Cys Asn Asp Thr
 65                  70                  75                  80
```

Glu Val Thr Ile Arg Asn Cys Thr Ser Thr Asn Asn Thr Val Cys Ala
                85                  90                  95

Ser Lys Asn Tyr Thr Ser Leu Ser Val Pro Gly Val Gln His His Lys
            100                 105                 110

Gln Arg Gln Asn His Thr Ala His Val Thr Val Lys Gln Gly Lys Ser
        115                 120                 125

Gly Arg His Thr
    130

<210> SEQ ID NO 6
<211> LENGTH: 133
<212> TYPE: PRT
<213> ORGANISM: Homo sapiens

<400> SEQUENCE: 6

Met Lys Pro Leu Val Met Leu Ile Cys Phe Ala Val Ile Leu Leu Gln
1               5                   10                  15

Leu Gly Val Thr Lys Val Cys Gln His Asn Glu Val Gln Leu Gly Asn
            20                  25                  30

Glu Cys Cys Pro Pro Cys Gly Ser Gly Gln Arg Val Thr Lys Val Cys
        35                  40                  45

Thr Asp Tyr Thr Ser Val Thr Cys Thr Pro Cys Pro Asn Gly Thr Tyr
    50                  55                  60

Val Ser Gly Leu Tyr Asn Cys Thr Asp Cys Thr Gln Cys Asn Val Thr
65                  70                  75                  80

Gln Val Met Ile Arg Asn Cys Thr Ser Thr Asn Asn Thr Val Cys Ala
                85                  90                  95

Pro Lys Asn His Thr Tyr Phe Ser Thr Pro Gly Val Gln His His Lys
            100                 105                 110

Gln Arg Gln Gln Asn His Thr Ala His Ile Thr Val Lys Gln Arg Lys
        115                 120                 125

Ser Gly Arg His Thr
    130

<210> SEQ ID NO 7
<211> LENGTH: 132
<212> TYPE: PRT
<213> ORGANISM: Homo sapiens

<400> SEQUENCE: 7

Met Lys Pro Leu Val Met Leu Ile Leu Leu Ser Met Leu Leu Asp Cys
1               5                   10                  15

Asn Gly Lys Thr Glu Ile Cys Lys Pro Glu Glu Val Gln Leu Gly Asn
            20                  25                  30

Gln Cys Cys Pro Pro Cys Lys Gln Gly Tyr Arg Val Thr Gly Gln Cys
        35                  40                  45

Thr Gln Tyr Thr Ser Thr Thr Cys Thr Leu Cys Pro Asn Gly Thr Tyr
    50                  55                  60

Val Ser Gly Leu Tyr Asn Cys Thr Asn Cys Thr Glu Cys Asn Asp Thr
65                  70                  75                  80

Glu Val Thr Ile Arg Asn Cys Thr Ser Thr Asn Asn Thr Val Cys Ala
                85                  90                  95

Ser Lys Asn Tyr Thr Ser Phe Ser Val Pro Gly Val Gln His His Lys
            100                 105                 110

-continued

Gln Arg Gln Asn His Thr Ala His Val Thr Val Lys Gln Gly Lys Ser
         115                 120                 125

Gly Arg His Thr
    130

<210> SEQ ID NO 8
<211> LENGTH: 133
<212> TYPE: PRT
<213> ORGANISM: Homo sapiens

<400> SEQUENCE: 8

Met Lys Pro Leu Val Met Leu Ile Cys Phe Gly Val Phe Leu Leu Gln
1               5                   10                  15

Leu Gly Gly Ser Lys Met Cys Lys Pro Asp Glu Val Lys Leu Gly Asn
            20                  25                  30

Gln Cys Cys Pro Pro Cys Gly Ser Gly Gln Lys Val Thr Lys Val Cys
        35                  40                  45

Thr Glu Ile Ser Gly Ile Thr Cys Thr Leu Cys Pro Asn Gly Thr Tyr
    50                  55                  60

Leu Thr Gly Leu Tyr Asn Cys Thr Asn Cys Thr Gln Cys Asn Asp Thr
65                  70                  75                  80

Gln Ile Thr Val Arg Asn Cys Thr Ser Thr Asn Asn Thr Ile Cys Ala
                85                  90                  95

Ser Lys Asn His Thr Ser Phe Ser Ser Pro Gly Val Gln His His Lys
            100                 105                 110

Gln Arg Gln Asn His Thr Ala His Val Thr Val Lys Gln Arg Lys
        115                 120                 125

Ser Gly Arg His Thr
    130

<210> SEQ ID NO 9
<211> LENGTH: 128
<212> TYPE: PRT
<213> ORGANISM: Homo sapiens

<400> SEQUENCE: 9

Met Leu Leu Leu Ser Val Ile Trp Ala Ala Val Leu Ala Ser Arg Ser
1               5                   10                  15

Ala Ala Pro Ala Cys Lys Gln Asp Glu Tyr Ala Val Gly Ser Glu Cys
            20                  25                  30

Cys Pro Lys Cys Gly Lys Gly Tyr Arg Val Lys Thr Asn Cys Ser Glu
        35                  40                  45

Thr Thr Gly Thr Val Cys Glu Pro Cys Pro Ala Gly Ser Tyr Asn Asp
    50                  55                  60

Lys Arg Glu Thr Ile Cys Thr Gln Cys Asp Thr Cys Asn Ser Ser Ser
65                  70                  75                  80

Ile Ala Val Asn Arg Cys Asn Thr Thr His Asn Val Arg Cys Arg Leu
                85                  90                  95

Ala Asn Ser Ser Thr Ala Ser Ala His Val Asp Ser Gly Gln His Gln
            100                 105                 110

Gln Ala Gly Asn His Ser Val Leu Pro Glu Asp Asp Ala Ala Arg Asp
        115                 120                 125

<210> SEQ ID NO 10
<211> LENGTH: 26
<212> TYPE: PRT
<213> ORGANISM: Homo sapiens -continued

```
<400> SEQUENCE: 10

Cys Gln Met Cys Glu Pro Gly Thr Phe Leu Val Lys Asp Cys Asp Gln
1               5                   10                  15

His Arg Lys Ala Ala Gln Cys Asp Pro Cys
            20                  25

<210> SEQ ID NO 11
<211> LENGTH: 24
<212> TYPE: PRT
<213> ORGANISM: Homo sapiens

<400> SEQUENCE: 11

Cys His Glu Cys Arg Pro Gly Asn Gly Met Val Ser Arg Cys Ser Arg
1               5                   10                  15

Ser Gln Asn Thr Val Cys Arg Pro
            20

<210> SEQ ID NO 12
<211> LENGTH: 21
<212> TYPE: PRT
<213> ORGANISM: Homo sapiens

<400> SEQUENCE: 12

Cys Ser Asn Cys Pro Ala Gly Thr Phe Cys Asp Asn Asn Arg Asn Gln
1               5                   10                  15

Ile Cys Ser Pro Cys
            20

<210> SEQ ID NO 13
<211> LENGTH: 38
<212> TYPE: DNA
<213> ORGANISM: Artificial Sequence
<220> FEATURE:
<223> OTHER INFORMATION: Description of Artificial Sequence: Forward
      primer

<400> SEQUENCE: 13
cctggcaagc ttgccaccat gaagacattg cctgccat                              38

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence: Reverse
      primer

<400> SEQUENCE: 14
cgctcggtcg acgcttgcca cttcgtcctt gga                                   33

<210> SEQ ID NO 15
<211> LENGTH: 35
<212> TYPE: DNA
<213> ORGANISM: Artificial Sequence
<220> FEATURE:
<223> OTHER INFORMATION: Description of Artificial Sequence: Forward
      primer

<400> SEQUENCE: 15
acgtggatcc tcgtattaca aaccgcggag aggat                                 35

<210> SEQ ID NO 16
<211> LENGTH: 30
<212> TYPE: DNA
<213> ORGANISM: Artificial Sequence
```

```
<220> FEATURE:
<223> OTHER INFORMATION: Description of Artificial Sequence: Reverse
      primer

<400> SEQUENCE: 16
acgtctcgag actcagacac ggttccgtaa                                          30

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Reverse
      primer

<400> SEQUENCE: 17
catcttctca aaattcgagt gacaa                                               25

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Forward
      primer

<400> SEQUENCE: 18
tgggagtaga caaggtacaa ccc                                                 23

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Reverse
      primer

<400> SEQUENCE: 19
tcaagtggca tagatgtgga agaa                                                24

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Forward
      primer

<400> SEQUENCE: 20
tggctctgca ggattttcat g                                                   21

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Reverse
      primer

<400> SEQUENCE: 21
acaggagaag ggacgccat                                                      19

<210> SEQ ID NO 22
<211> LENGTH: 21
<212> TYPE: DNA
<213> ORGANISM: Artificial Sequence
```

```
<220> FEATURE:
<223> OTHER INFORMATION: Description of Artificial Sequence: Forward
      primer

<400> SEQUENCE: 22
gaagccctac agacgagctc a                                              21

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Reverse
      primer

<400> SEQUENCE: 23
ggtcaacctc aaagtcttta actc                                           24

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Forward
      primer

<400> SEQUENCE: 24
ttaaaaatgc aagtaagttt gctg                                           24

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Reverse
      primer

<400> SEQUENCE: 25
tgaagacggc cagagaaaaa c                                              21

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Forward
      primer

<400> SEQUENCE: 26
aaggaaccct tagagtgctt act                                            23

<210> SEQ ID NO 27
<211> LENGTH: 27
<212> TYPE: DNA
<213> ORGANISM: Artificial Sequence
<220> FEATURE:
<223> OTHER INFORMATION: Description of Artificial Sequence: Reverse
      primer

<400> SEQUENCE: 27
agcgggacat atgaatctac taagaga                                        27

<210> SEQ ID NO 28
<211> LENGTH: 25
<212> TYPE: DNA
<213> ORGANISM: Artificial Sequence
```

```
<220> FEATURE:
<223> OTHER INFORMATION: Description of Artificial Sequence: Forward
      primer

<400> SEQUENCE: 28
gtcctagtag ggaggtgtga agttg                                          25

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Reverse
      primer

<400> SEQUENCE: 29
ggttgccaag ccttatcgga                                                20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Forward
      primer

<400> SEQUENCE: 30
acctgctcca ctgccttgct                                                20

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Reverse
      primer

<400> SEQUENCE: 31
tgacgtcact ggagttgtac gg                                             22

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Forward
      primer

<400> SEQUENCE: 32
ggttcatgtc atggatggtg c                                              21

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Reverse
      primer

<400> SEQUENCE: 33
gaaactggcg gaaaccca                                                  18

<210> SEQ ID NO 34
<211> LENGTH: 20
<212> TYPE: DNA
<213> ORGANISM: Artificial Sequence
```

```
<220> FEATURE:
<223> OTHER INFORMATION: Description of Artificial Sequence: Forward
      primer

<400> SEQUENCE: 34
ggatctggcc cttgaacctt                                              20
```

COMPOSITIONS AND METHODS FOR MODULATING RESPONSES MEDIATED OR ASSOCIATED WITH BTLA ACTIVITY

RELATED APPLICATIONS

This application is a continuation-in part of application Ser. No. 11/721,308, filed Jun. 22, 2009, now abandoned which is a national phase of PCT/US2005/044296, filed Dec. 9, 2005, and also claims the benefit of priority of application Ser. No. 61/060,421, filed Jun. 10, 2008, application Ser. No. 61/078,997, filed Jul. 8, 2008, application Ser. No. 60/635,034, filed Dec. 9, 2004, and application Ser. No. 60/700,636, filed Jul. 19, 2005, all of which applications are expressly incorporated herein by reference in their entirety.

GOVERNMENT SPONSORSHIP

This invention was made with government funding under grants AI033068, CA069381, AI048073, AI067890, and AI061516 awarded by the National Institutes of Health. The government has certain rights in the invention.

TECHNICAL FIELD

The invention relates to polypeptides that include a binding site for immunoregulatory molecule B-T lymphocyte attenuator (BTLA). Furthermore, the invention relates to ligands, such as antibodies, that bind to a binding site for immunoregulatory molecule B-T lymphocyte attenuator (BTLA), and methods of use.

Introduction

Efficient activation and differentiation of T cells depends upon recognition of antigen and cooperating signals (cosignaling) that provoke either positive or inhibitory effects. Inhibitory pathways help control immune tolerance to self tissues, although in the absence of inhibitory signals or with sustained positive cosignaling tolerance can be overridden leading to autoimmune responses. Two major groups of cosignaling receptors are recognized, those with an the Ig-like fold, such as CTLA-4 (Egen, J. G., et al., (2002) *Nat Immunol* 3, 611-8), CD28 (Sharpe, A. H. et al., (2002) *Nat Rev Immunol* 2 116-26.), PD1 (Greenwald, R. J., et al., (2002) *Curr Opin Immunol* 14, 391-6) and BTLA (B and T lymphocyte attenuator) (Watanabe et al., *Nat Immunol* 4:670 (2003), Han et al., *J Immunol* 172:5931 (2004)), and those belonging to the tumor necrosis factor receptor superfamily (TNFRSF), including OX40, 41BB, CD27, CD30 and HVEM (herpesvirus entry mediator, TNFRSF 14) among others (Locksley et al., Cell 104:487 (2001), Croft, *Nat Rev Immunol* 3:609 (2003), Schneider et al., *Immunol Rev* 202:49 (2004), Bertram et al., *Semin Immunol* 16:185 (2004)).

Generally, positive cosignaling receptors in the Ig family act by sustaining antigen receptor-associated kinase activity, whereas inhibitory counterparts contain an immunoreceptor tyrosine-based inhibitory motif (ITIM) that recruits phosphatases (e.g., SHP1, SHIP) attenuating antigen receptor signaling (Egen et al. *Nat Immunol* 3:611 (2002), Sharpe et al., *Nat Rev Immunol* 2:116 (2002), Keir et al., *Immunol Rev* 204:128 (2005)). By contrast, the cosignaling TNF receptors activate serine kinases promoting expression of survival and proinflammatory genes through the transcription factors nuclear factor-κB (NFκB) and activator protein-1 (AP-1), whereas some other TNFR induce apoptosis, negatively regulating T cells by cellular elimination (Locksley et al., Cell 104:487 (2001)).

SUMMARY

The invention is based, at least in part, on the identification of multiple sequences that bind immunoregulatory molecule B-T lymphocyte attenuator (BTLA). For example, a binding site for immunoregulatory molecule B-T lymphocyte attenuator (BTLA) is located in CRD1 of HVEM, a site distinct from the site occupied by LIGHT but overlapping the gD binding site. In addition, a binding site for immunoregulatory molecule B-T lymphocyte attenuator (BTLA) is located on UL144, present in a human cytomegalovirus (CMV) (β herpesvirus) that is evolutionarily divergent from HSV-1 (α-herpesvirus). UL144 binds to BTLA but not LIGHT, and inhibits T cell proliferation and may selectively mimic the inhibitory co-signaling function of HVEM.

The findings reveal a novel inhibitory cosignaling pathway for T cells, which involves the engagement of BTLA by HVEM, UL144 and other proteins having a BTLA binding site. This engagement connects the Ig and TNFR cosignaling families. HVEM binding activates tyrosine phosphorylation of the ITIM in BTLA and induces the association with the protein tyrosine phosphatases Src homology domain (SHP)-1 and SHP-2 required for inhibitory signaling (Gavrieli et al., *Biochem Biophys Res Commun* 312:1236 (2003)). However, HVEM can also act as a positive cosignaling receptor (reviewed in (Schneider et al., *Immunol Rev* 202:49 (2004)) by binding TNF-related ligands LIGHT (TNFSF14) and lymphotoxin-α (LTα, TNFSF2) (Mauri et al., *Immunity* 8:21 (1998)). A fourth ligand of HVEM is envelope glycoprotein D (gD) of Herpes Simplex virus (HSV-1; α-herpesvirus) from which its name was derived (Montgomery et al. Cell 87:427 (1996), Spear, *Cell Microbiol* 6:401 (2004)). Thus, HVEM may serve as a molecular switch mediating either positive or inhibitory signaling for the proliferation survival, differentiation or death of T cells, antigen presenting cells (dendritic cells) and B cells, depending on which of the four ligands are bound to HVEM. Accordingly, sequences based upon or derived from HVEM, UL144 and others which retain or lack binding to one or more of BTLA, LIGHT, lymphotoxin-α (LTα) and envelope glycoprotein D (gD) can be used to selectively or non-selectively modulate one or more of the various interacting signaling pathways and consequent immunological responses and processes in vitro, ex vivo and in vivo.

In accordance with the invention, provided are isolated and purified polypeptides including an amino acid sequence consisting of a binding site for immunoregulatory molecule B-T lymphocyte attenuator (BTLA), as well as compositions including an amino acid sequence consisting of a binding site for immunoregulatory molecule B-T lymphocyte attenuator (BTLA). In various embodiments, a binding site for immunoregulatory molecule B-T lymphocyte attenuator (BTLA) includes a portion of HVEM polypeptide, a portion of human cytomegalovirus (HCMV) UL144 protein, a portion of CD27, a portion of 41BB, or a portion of OX40. In additional embodiments, a binding site for immunoregulatory molecule B-T lymphocyte attenuator (BTLA) includes an amino acid sequence with at least about 75%, 80%, 90%, 95% or more homology to said binding site for immunoregulatory molecule B-T lymphocyte attenuator (BTLA). Polypeptide sequences can be based upon homology with, or derived or obtained from, for example, binding sites for immunoregulatory molecule B-T lymphocyte attenuator (BTLA), e.g., mammalian (human, murine), viral, etc.

In further embodiments, a polypeptide of the invention has a sequence that is less than the length of a full length native sequence, e.g., less than a full length mammalian HVEM (e.g., human or murine), UL144, CD27, 41BB or OX40 sequence. In particular aspects, length of a polypeptide is from about 5 to 15, 20 to 25, 25, to 50, 50 to 100, 100 to 150, 150 to 200, or 200 to 280 amino acids in length, provided that said portion is less than full-length HVEM, UL144, CD27, 41BB or OX40 polypeptide sequence.

Exemplary sequences include, for example, a CRD 1 sequence of human HVEM, murine HVEM, or UL144, as set forth in FIG. 7, a subsequence thereof or an amino acid substitution thereof. More particularly, a sequence of a portion of human HVEM polypeptide comprises or consists of CPKCSPGYRVKEACGELTGTVCEPC (SEQ. ID. NO:1), a subsequence thereof or an amino acid substitution thereof; and a sequence of a portion of murine HVEM polypeptide, comprises or consists of CPMCNPGYHVKQVCSEHT-GTVCAPC (SEQ. ID. NO:2), a subsequence thereof or an amino acid substitution thereof. Exemplary sequences also include one or more of: a VK dipeptide; at least one K residue; an RVK tripeptide; or an RVKE tetrapeptide. Exemplary sequences further include one or more of: an HVK tripeptide; or an HVKQ tetrapeptide. Exemplary sequences additionally include polypeptides based upon, derived or obtained from HVEM, such as a polypeptide sequence that does not bind BTLA, or that binds BTLA with reduced affinity as compared to wild type human HVEM; a polypeptide sequence that does not bind BTLA, or that binds BTLA with reduced affinity as compared to wild type human HVEM, but binds to glycoprotein D of herpes simplex virus (gD), LIGHT or LTα; a polypeptide sequence, having a mutation or deletion of arginine at position 62, lysine at position 64, or glutamate at position 65, with reference to residue positions indicated in FIG. 6; a polypeptide sequence having an alanine residue at one or more of positions 62, 64 or 65, with reference to residue positions indicated in FIG. 6; and a polypeptide sequence that binds BTLA, or that binds BTLA with reduced affinity as compared to wild type human HVEM, but does not bind to glycoprotein D of herpes simplex virus (gD), LIGHT or LTα.

Exemplary HCMV UL144 sequences include:
MKPLIMLICFAVILLQLGVTKVCQHNEVQLGNECCP-
PCGSGQRVTKVCTDYTSVTCTPCPNGTYVSGLYN-
CTDCTQCNVTQVMIRNCTSTNNTVCASKNYTSFS-
ISGGVQHKQRQNHTAHVTVKQGKSGRHT (HCMV
toledo) (SEQ. ID. NO:3), a subsequence of or an amino
acid substitution thereof;
MKPLIMLICFAVILLQLGVTKVCQHNEVQLGNECCP-
PCGSGQRVTKVCTDYTSVTCTPCPNGTYVSGLYN-
CTDCTQCNVTQVMIRNCTSTNNTVCAPKNHTYFS-
TPGVQHHKQRQQNHTAHITVKQGKSGRHT (HCM
V fiala) (SEQ. ID. NO:4), a subsequence of or an amino
acid substitution thereof;
MKPLVMLILLSMLLACIGKIBICKPEEVQLGNQCCP-
PCKQGYRVTGQCTQYTSTTCTLCPNGTYVSGLYN-
CTNCTECNDTEVTIRNCTSTNNTVCASKNYTSLSV-
PGVQHHKQRQNHTAHVTVKQGKSGRHT (AAF09
105) (SEQ. ID. NO:5), a subsequence of or an amino acid
substitution thereof;
MKPLVMLICFAVILLQLGVTKVCQHNEVQLGNECCP-
PCGSGQRVTKVCTDYTSVTCTPCPNGTYVSGLYN-
CTDCTQCNVTQVMIRNCTSTNNTVCAPKNHTYFS-
TPGVQHHKQRQQNHTAHITVKQRKSGRHT (AAF09
116) (SEQ. ID. NO:6), a subsequence of or an amino acid
substitution thereof;
MKPLVMLILLSMLLDCNGKTEICKPEEVQLGNQCCP-
PCKQGYRVTGQCTQYTSTTCTLCPNGTYVSGLYN-
CTNCTECNDTEVTIRNCTSTNNTVCASKNYTSFSV-
PGVQHHKQRQNHTAHVTVKQGKSGRHT (AF1791
98_1) (SEQ. ID. NO:7), a subsequence of or an amino acid
substitution thereof;
MKPLVMLICFGVFLLQLGGSKMCKPDEVKLGNQCC-
PPCGSGQKVTKVCTEISGITCTLCPNGTYLTGLYN-
CTNCTQCNDTQITVRNCTSTNNTICASKNHTSFSS-
PGVQHHKQRQQNHTAHVTVKQRKSGRHT (AF179
199_1) (SEQ. ID. NO:8), a subsequence of or an amino
acid substitution thereof; and
MLLLSVIWAAVLASRSAAPACKQDEYAVGSECCPKC-
GKGYRVKTNCSETTGTVCEPCPAGSYNDKRETICT-
QCDTCNSSSIAVNRCNTTHNVRCRLANSSTASAHV-
DSGQHQQAGNHSVLPEDDAARD (RhCMV515566
18) (SEQ. ID. NO:9), a subsequence of or an amino acid
substitution thereof.

In various aspects, a portion or subsequence of HCMV UL144 protein comprises or consists of a UL144-CRD1 or -CRD2 sequence, 1A, 1B, 1C, 2 or 3, as set forth in FIG. 7.

Exemplary CD27 sequences include: CQMCEPGT-FLVKDCDQHRKAAQCDPC (SEQ. ID. NO:10), a subsequence thereof or an amino acid substitution thereof.

Exemplary OX40 sequences include: CHECRPGNGM-VSRCSRSQNTVCRP (SEQ. ID. NO:11), a subsequence thereof or an amino acid substitution thereof.

Exemplary 41BB sequences include: CSNCPAGTFCDN-NRNQICSPC (SEQ. ID. NO:12), a subsequence thereof or an amino acid substitution thereof.

Polypeptide sequences of the invention further include portions/subsequences having at least 5, 10, 15, 20, 25, or more amino acid residues. Polypeptide sequences of the invention additionally include substitutions of native BTLA binding sites that may retain or may not retain at least partial binding to BTLA (e.g., reduces or destroys binding to BTLA). Exemplary polypeptides include one or more amino acid substitutions of, an F for a Y residue (Y47F or Y61F), an A for an S residue (S58A), an A for an E residue (E65A or E76A) or an A for an R residue (R113A), with reference to residue positions indicated in FIG. 6.

Polypeptide sequences of the invention further include substitutions of native BTLA binding sites that may retain or may not retain at least partial binding to BTLA (e.g., reduces or destroys binding to BTLA), but that retain binding to other ligands (e.g., LIGHT (p30), LTα, or glycoprotein D (gD) of herpes simplex virus). Polypeptide sequences of the invention additionally include substitutions of native BTLA binding sites that may retain or may not retain at least partial binding to BTLA (e.g., reduces or destroys binding to BTLA), but that exhibit reduced or no detectable binding to other ligands (e.g., lack a binding site for LIGHT (p30), LTα, or glycoprotein D (gD) of herpes simplex virus). Exemplary polypeptide sequences include, for example, an amino acid substitution in HVEM that reduces or destroys binding of the substituted HVEM to B-T lymphocyte attenuator (BTLA), but does not destroy binding of the substituted HVEM to LIGHT (p30 polypeptide). Exemplary substituted polypeptide sequences include one or more amino acid substitutions of, an F for a Y residue (Y61F), an A for a K residue (K64A), or an A for an E residue (E65A), with reference to residue positions indicated in FIG. 6.

In accordance with the invention, nucleic acids encoding the polypeptide sequences of the invention are provided, e.g., binding sites for BTLA. Nucleic acids may be included in vectors, which can be used for manipulation and to produce transformed host cells.

In accordance with the invention, isolated and purified antibodies that specifically bind to a binding site for immunoregulatory molecule B-T lymphocyte attenuator (BTLA), are provided. In various embodiments, an antibody specifically binds to HVEM (e.g., mammalian, such as human or murine) binding site for immunoregulatory molecule B-T lymphocyte attenuator (BTLA), or a subsequence thereof or an amino acid substitution thereof; human cytomegalovirus (HCMV) UL144 protein binding site for immunoregulatory molecule B-T lymphocyte attenuator (BTLA), or a subsequence thereof or an amino acid substitution thereof; CD27 binding site for immunoregulatory molecule B-T lymphocyte attenuator (BTLA), or a subsequence thereof or an amino acid substitution thereof; 41BB binding site for immunoregulatory molecule B-T lymphocyte attenuator (BTLA), or a subsequence thereof or an amino acid substitution thereof; or OX40 binding site for immunoregulatory molecule B-T lymphocyte attenuator (BTLA), or a subsequence thereof or an amino acid substitution thereof. In particular aspects, an antibody specifically binds to a sequence comprising or consisting of human HVEM sequence CPKCSPGYRVKEACG-ELTGTVCEPC (SEQ. ID. NO:1), a subsequence thereof or an amino acid substitution thereof. In further embodiments, an antibody specifically binds to a binding site for immunoregulatory molecule B-T lymphocyte attenuator (BTLA) is an agonist or antagonist of HVEM, BTLA, UL144, CD27, 41BB or OX40 binding or activity. In various aspects, antibody inhibits, reduces, or stimulates or increases binding of BTLA to HVEM binding site for immunoregulatory molecule B-T lymphocyte attenuator (BTLA); antibody inhibits, reduces, or stimulates or increases binding of BTLA to human cytomegalovirus (HCMV) UL144 protein; or antibody modulates a response mediated or associated with immunoregulatory molecule B-T lymphocyte attenuator (BTLA) activity or expression (e.g., lymphocyte or hematopoetic cell proliferation or inflammation; or proliferation, survival, differentiation, death, or activity of T cells, antigen presenting cells or B cells).

Antibodies include monoclonal and polyclonal human, humanized, primatized and chimeric forms, as well as antibody subsequences or fragments (e.g., single-chain Fv, Fab', (Fab')$_2$, Fd, disulfide-linked Fv, light chain variable (VL) or heavy chain variable (VH) sequence) that specifically bind to a binding site for immunoregulatory molecule B-T lymphocyte attenuator (BTLA).

In accordance with the invention, provided are methods of selectively modulating a response mediated or associated with immunoregulatory molecule B-T lymphocyte attenuator (BTLA) activity or expression, and a response mediated or associated with LIGHT (p30) activity or expression, in solution, in vitro, ex vivo and in vivo. In one embodiment, BTLA is contacted with a ligand that modulates a response mediated or associated with immunoregulatory molecule B-T lymphocyte attenuator (BTLA) activity or expression. In another embodiment, a response is mediated or associated with immunoregulatory molecule B-T lymphocyte attenuator (BTLA) activity or expression, without destroying binding between HVEM and LIGHT or HVEM and LTα, by contacting HVEM with a ligand that binds to HVEM binding site for immunoregulatory molecule B-T lymphocyte attenuator (BTLA) to modulate binding of BTLA to the HVEM binding site, thereby modulating a response mediated or associated with immunoregulatory molecule B-T lymphocyte attenuator (BTLA) activity or expression. In a further embodiment, a response is mediated or associated with LIGHT (p30) activity or expression, by contacting LIGHT (p30) with a ligand that binds to and modulates a response mediated or associated with LIGHT (p30), but exhibits no detectable binding or reduced binding to immunoregulatory molecule B-T lymphocyte attenuator (BTLA) to the extent that binding modulates a response mediated or associated with immunoregulatory molecule B-T lymphocyte attenuator (BTLA) expression or activity, thereby selectively modulating a response mediated or associated with LIGHT (p30) activity or expression.

Ligands include, for example, small molecules and polypeptides, such as the various polypeptides (e.g., a binding site for BTLA) and antibodies of the invention (an antibody that binds to a binding site for BTLA). Ligands therefore include agonist or antagonists of BTLA binding to HVEM, HVEM binding to BTLA, BTLA or HVEM activity; increasing or reducing a response mediated or associated with immunoregulatory molecule B-T lymphocyte attenuator (BTLA) binding to HVEM, or a response mediated or associated with immunoregulatory molecule B-T lymphocyte attenuator (BTLA) activity or expression, such as lymphocyte or hematopoetic cell proliferation or inflammation, proliferation; survival, differentiation, death, or activity of T cells, antigen presenting cells or B cells, etc. Exemplary activities include secretion of a cytokine (e.g., TNF, lymphotoxin (LT)-alpha, LT-beta, LIGHT (p30), or a ligand for CD27, OX40, 41BB), chemokine (e.g., CCL21, 19, or CXCL13), interleukin (e.g., IL10, IL2, IL7, or IL15), or interferon (e.g., type 1, or Interferon-gamma); cytotoxic or helper activity of activated T cells; and B cell production of antibody.

Methods of the invention include in solution, in vitro, ex vivo and in vivo methods. Thus, methods include administering a ligand to a subject, such as a mammal (e.g., a human). Subjects include those in need of treatment, having or at risk of having, a disorder treatable by increasing or reducing a response mediated or associated with immunoregulatory molecule B-T lymphocyte attenuator (BTLA) binding to HVEM, immunoregulatory molecule B-T lymphocyte attenuator (BTLA) activity or expression, LIGHT (p30) binding to HVEM, or by modulating a response mediated or associated with LIGHT (p30) activity or expression. Exemplary disorders include, an undesirable or aberrant immune response, immune disorder, or immune disease; undesirable or aberrant acute or chronic inflammatory response or inflammation, graft vs. host disease; undesirable or aberrant proliferation, survival, differentiation, death, or activity of a T cell, antigen presenting cell or B cell; a pathogenic or non-pathogenic infection; and hyperproliferative disorders. Non-limiting examples of immune disorders and immune diseases include autoimmune disorders and autoimmune diseases, such as type I or type II diabetes, systemic lupus erythematosus (SLE), juvenile rheumatoid arthritis, rheumatoid arthritis, multiple sclerosis, inflammatory bowel disease, ulcerative colitis, or Crohn's disease. Non-limiting examples of pathogen infections include infection with a bacteria, virus (e.g., lentivirus, HIV, hepatitis A, B, or C, or herpesvirus), fungus, prion or parasite. Non-limiting examples of hyperproliferative disorders include a benign hyperplasia, or a non-metastatic or metastatic tumor.

In accordance with the invention, also provided are methods of identifying (screening) an agent that binds to a herpesvirus entry mediator (HVEM) or a human cytomegalovirus (HCMV) UL144 binding site for immunoregulatory molecule B-T lymphocyte attenuator (BTLA), as well as methods for identifying an agent (screening) that inhibits or prevents lymphocyte or hematopoetic cell proliferation or inflammation. In one embodiment, a method includes contacting a binding site for immunoregulatory molecule B-T lymphocyte attenuator (BTLA), said binding site comprising a portion of full length HVEM polypeptide or human cytomegalovirus (HCMV) UL144 protein, with a test agent; and measuring binding of the test agent to the binding site for immunoregulatory molecule B-T lymphocyte attenuator (BTLA). Binding of the test agent to the binding site identifies the test agent as an agent that binds to a herpesvirus entry mediator (HVEM) or human cytomegalovirus (HCMV) UL144 binding site for immunoregulatory molecule B-T lymphocyte attenuator (BTLA). In one embodiment, a method includes contacting a binding site for immunoregulatory molecule B-T lymphocyte attenuator (BTLA), said binding site comprising a portion of full length HVEM polypeptide or human cytomegalovirus (HCMV) UL144 protein, with a test agent; measuring binding of the test agent to the binding site for immunoregulatory molecule B-T lymphocyte attenuator (BTLA); wherein binding of the test agent to the binding site identifies the test agent as an agent that binds to a herpesvirus entry mediator (HVEM) binding site for immunoregulatory molecule B-T lymphocyte attenuator (BTLA); and determining whether the test agent inhibits or prevents lymphocyte or hematopoetic cell proliferation or inflammation. Inhibiting or preventing lymphocyte or hematopoetic cell proliferation or inflammation, identifies the test agent as an agent that inhibits or prevents lymphocyte or hematopoetic cell proliferation or inflammation. Test agents include, for example, small molecules, polypeptides (e.g., antibodies), and organic molecules.

In accordance with the invention, further provided are methods for screening a sample for the presence of an HVEM polypeptide sequence that binds to BTLA, as well as methods for screening for the presence of an HVEM polypeptide sequence that does not bind to BTLA. In various embodiments, a method includes analyzing the sample for the presence of an HVEM polypeptide sequence that binds or does not bind to BTLA. Screening methods are applicable to detecting an HVEM sequence with an arginine at position 62, a lysine at position 64, or glutamate at position 65, with reference to residue positions indicated in FIG. 6. Screening methods also are applicable to detecting an HVEM sequence with a mutation (e.g., alanine) or deletion of lysine at position 64, with reference to residue positions indicated in FIG. 6. Exemplary analysis include nucleic acid sequencing and hybridization, or measuring (detecting) binding between HVEM sequence and BTLA. Additional method steps include, analyzing for HVEM binding to one or more of glycoprotein D of herpes simplex virus (gD), LIGHT or LTα.

In accordance with the invention, additionally provided are methods for inhibiting, reducing or preventing proliferation, survival, differentiation, death, or activity of T cells, antigen presenting cells or B cells. In one embodiment, a method includes contacting BTLA (e.g., in vitro or in vivo) with an amount of a ligand (e.g., a polypeptide or peptidomimetic) that binds to BTLA effective to inhibit, reduce or prevent proliferation, survival, differentiation, death, or activity of T cells, antigen presenting cells or B cells, wherein said ligand does not bind to p30. In another embodiment, a method includes contacting BTLA (e.g., in vitro or in vivo) with an amount of a ligand (e.g., a polypeptide or peptidomimetic) that binds to BTLA effective to inhibit, reduce or prevent proliferation, survival, differentiation, death, or activity of T cells, antigen presenting cells or B cells, wherein said ligand binds to glycoprotein D of herpes simplex virus (gD). In an additional embodiment, a method includes contacting BTLA (e.g., in vitro or in vivo) with an amount of a ligand (e.g., a polypeptide or peptidomimetic) that binds to BTLA effective to inhibit, reduce or prevent proliferation, survival, differentiation, death, or activity of T cells, antigen presenting cells or B cells, wherein said ligand does not bind to glycoprotein D of herpes simplex virus (gD). Exemplary ligands include an HVEM polypeptide or a portion thereof; a human cytomegalovirus (HCMV) UL144 protein or a portion thereof; a CD27 or a portion thereof, 41BB or a portion thereof; an OX40 or a portion thereof; or an amino acid sequence with at least about 75%, 80%, 90%, 95% or more homology to a human cytomegalovirus (HCMV) UL144 protein or portion thereof; CD27 or portion thereof; 41BB or portion thereof; or OX40 or portion thereof.

Methods performed in vivo include, contacting a subject in need of inhibiting, reducing or preventing proliferation, survival, differentiation, death, or activity of T cells, antigen presenting cells or B cells. Exemplary subjects include a subject having or at risk of having undesirable inflammation; a subject having or at risk of having an undesirable or aberrant immune response, immune disorder or immune disease; a subject having or at risk of having graft vs. host disease. Additional exemplary subjects include a subject having or at risk of having type I or type II diabetes, systemic lupus erythematosus (SLE), juvenile rheumatoid arthritis, rheumatoid arthritis, multiple sclerosis, inflammatory bowel disease, ulcerative colitis, or Crohn's disease.

In accordance with the invention, still further provided are methods of inhibiting, reducing or preventing acute or chronic inflammation. In one embodiment, a method includes administering to a subject an amount of a ligand (e.g., a polypeptide or peptidomimetic) that binds to BTLA effective to inhibit, reduce or prevent acute or chronic inflammation in the subject, wherein said ligand does not bind to p30. In another embodiment, a method includes administering to a subject an amount of a ligand (e.g., a polypeptide or peptidomimetic) that binds to BTLA effective to inhibit, reduce or prevent acute or chronic inflammation in the subject, wherein said ligand binds to glycoprotein D of herpes simplex virus (gD). In an additional embodiment, a method includes administering to a subject an amount of a ligand (e.g., a polypeptide or peptidomimetic) that binds to BTLA effective to inhibit, reduce or prevent acute or chronic inflammation in the subject, wherein said ligand does not bind to glycoprotein D of herpes simplex virus (gD). Exemplary ligands include an HVEM polypeptide or a portion thereof; a human cytomegalovirus (HCMV) UL144 protein or a portion thereof; a CD27 or a portion thereof, 41BB or a portion thereof; an OX40 or a portion thereof; or an amino acid sequence with at least about 75%, 80%, 90%, 95% or more homology to a human cytomegalovirus (HCMV) UL144 protein or portion thereof; CD27 or portion thereof; 41 BB or portion thereof; or OX40 or portion thereof.

In accordance with the invention, moreover provided are methods of treating an undesirable or aberrant immune response, immune disorder or immune disease. In one embodiment, a method includes administering to a subject an amount of a ligand (e.g., a polypeptide or peptidomimetic) that binds to BTLA effective to treat the undesirable immune response, autoimmune disorder or immune disease in the subject, wherein said ligand does not bind to p30. In another embodiment, a method includes administering to a subject an amount of a ligand (e.g., a polypeptide or peptidomimetic) that binds to BTLA effective to treat the undesirable immune response, autoimmune disorder or immune disease in the subject, wherein said ligand binds to glycoprotein D of herpes simplex virus (gD). In an additional embodiment, a method includes administering to a subject an amount of a ligand (e.g., a polypeptide or peptidomimetic) that binds to BTLA effective to treat the undesirable immune response, autoimmune disorder or immune disease in the subject, wherein said ligand does not bind to glycoprotein D of herpes simplex virus (gD).

In accordance with the invention, still further provided are methods of increasing, inducing or stimulating proliferation, survival, differentiation, death, or activity of T cells, antigen presenting cells or B cells, in vitro and in vivo. In one embodiment, a method includes contacting a binding site for BTLA, said binding site comprising HVEM polypeptide or a portion thereof, with an amount of a ligand (e.g., a polypeptide or peptidomimetic) that binds to the binding site for BTLA effective to increase, induce or stimulate proliferation, survival, differentiation, death, or activity of T cells, antigen presenting cells or B cells. In various aspects, a portion of HVEM polypeptide includes or consists of a CRD 1 sequence of human HVEM, as set forth in FIG. 7, or a subsequence thereof (e.g., includes or consists of a sequence set forth in CPKCSPGYRVKEACGELTGTVCEPC (SEQ. ID. NO:1)). Exemplary ligands include polypeptides and antibodies (e.g., that bind to a binding site for BTLA, such as a sequence set forth as CPKCSPGYRVKEACGELTGTVCEPC (SEQ. ID. NO:1), or a subsequence thereof) and subsequences thereof.

Methods performed in vivo include, administering a subject in need of increasing, inducing or stimulating proliferation, survival, differentiation, death, or activity of T cells, antigen presenting cells or B cells. Exemplary subjects include a subject having or at risk of having a pathogen infection, such as, a bacterial (e.g., *Mycobacterium tuberculosis*), viral (e.g., lentivirus, HIV, hepatitis A, B, or C, vaccinia, influenza, or a human herpesvirus), fungal (e.g., *pneumocystis carrini*), prion or parasitic infection. Exemplary subjects also include a subject having or at risk of having a hyperproliferative disorder. Non-limiting hyperproliferative disorders include a benign hyperplasia, or a non-metastatic or metastatic tumors (e.g., a solid or liquid tumor, myeloma, lymphoma, leukemia, carcinoma, sarcoma, melanoma, neural, reticuloendothelial and haematopoietic neoplasia).

DESCRIPTION OF DRAWINGS

FIG. 10: Sequence conservation between HVEM and various other TNFR family members.

FIGS. 14A-D: Impaired spleen CD4+ and DN DC subsets in LTβR-deficient and LTβR-Fc-treated RAG mice. The frequencies (A) and numbers (B) of DCs in control (filled circle), LTβR-deficient (filled triangle) and LTβR-Fc-treated RAG mice (filled reverse triangle). The frequencies (C) and number (D) of CD4+, CD8αα and DN DC subsets within gate DCs were calculated in WT, LTβR-deficient and LTβR-Fc-treated RAG mice. Each dot represents the value obtained from an individual animal (A, B). Bars show the mean±SD from at least two mice per group and the data re representative of two independent studies (C, D). A study was performed on A, B and D between the indicated groups and one, two and three asterisks mean $p<0.05$, $p<0.01$ and $p<0.001$, respectively.

FIG. 19A-E: Increased T cells and cytokines in Hvem$^{-/-}$Rag$^{-/-}$ recipients. The number of CD4+ TCRβ+ cells in the spleen, MLN and large intestine of recipient mice was assessed at the indicated times. (A) One week post-transfer, Rag$^{-/-}$ (squares) and Hvem$^{-/-}$Rag$^{-/-}$ (circles) mice, four in each group, were analyzed by flow cytometry for T cells in the spleen, large intestine epithelium (IEL), and MLN. (B) Shows same as in (A) but including lamina propria lymphocytes (LPL) and analyzed two weeks after transfer. Each symbol represents an individual mouse with a total of 7-10 mice per group. *, $p<0.05$; **, $p<0.005$. (C-E) Real time PCR performed on tissue samples isolated from the large intestine of individual Rag$^{-/-}$ (filled bars) or Hvem$^{-/-}$Rag$^{-/-}$ (open bars) recipients two weeks after transfer. Error bars represent s.d. of triplicate measurements. (F) LPL isolated from transferred Hvem$^{-/-}$Rag$^{-/-}$ (open bars) and Rag$^{-/-}$ (filled bars) recipients at two weeks were stimulated ex-vivo with PMA and ionomycin. After 48 h, cytokines in the supernatant were measured by ELISA.

FIG. 21A-D HVEM expression by radio-resistant Rag$^{-/-}$ cells prevents colitis acceleration. (A) Experimental design. Lethally irradiated Hvem$^{-/-}$ Rag$^{-/-}$ mice were transplanted with Rag$^{-/-}$ BM cells to generate Rag$^{-/-}$ ⇒ Hvem$^{-/-}$Rag$^{-/-}$ chimeric mice. Reciprocal Hvem$^{-/-}$Rag$^{-/-}$ ⇒ Rag$^{-/-}$ chimeras also were generated. Ten weeks after transplant, chimeric mice were used as recipients of CD4+CD45RB$^{high}$ T cells. (B) Analysis of reconstitution. HVEM expression in peripheral blood cells of the chimeric animals was assessed eight weeks after bone marrow cell transplant by flow cytometry analysis for HVEM expression by CD45+ cells. Open histograms represent HVEM staining and filled histograms the isotype control. Representative data are shown from one of many similar analyses of blood cells and cells from immune organs. (C) Transfer of 5×10$^5$ CD4+CD45RB$^{high}$ T cells into Hvem$^{-/-}$Rag$^{-/-}$ ⇒ Rag$^{-/-}$ (squares) and Rag$^{-/-}$ ⇒ Hvem$^{-/-}$Rag$^{-/-}$ (gray circles) chimeric recipients. Weight loss curves correspond to the average of 6-8 chimeric mice per group. (D) Histological scores determined two weeks after transfer. Each symbol represents a single mouse of a total of 7 Hvem$^{-/-}$Rag$^{-/-}$ ⇒ Rag$^{-/-}$ (squares) and 8 Rag$^{-/-}$ ⇒ Hvem$^{-/-}$ Rag$^{-/-}$ (circles) chimeric mice. **, p<0.005. Data shown are representative from one of two independent experiments.

FIG. 25A-D: Minimal effect of T cell BTLA deficiency on colitis pathogenesis. (A) BTLA expression on freshly isolated naïve CD4+ T cells and by CD4+ T cells stimulated in vitro with an anti-CD3ε mAb in the presence of irradiated T cell-depleted splenocytes. (B) BTLA expression on transferred CD4+ T cells isolated from Hvem$^{-/-}$Rag$^{-/-}$ recipients two weeks post transfer. Histograms represent BTLA expression by gated CD4+CD45TCRβ+ cells from the indicated sites. (C) Transfer of Btla$^{-/-}$ CD4CD45RB$^{high}$ T cells into Rag$^{-/-}$ recipients. Weight loss curves of Rag$^{-/-}$ recipients transferred with either WT T cells (squares) or Btla$^{-/-}$ T cells (triangles). Data shown represent the average of 6-8 mice in each group. (D) Histological scores were evaluated 2 weeks (left panel), or 5 weeks (right panel) after the transfer of T cells. Each symbol represents an individual mouse (n=5-8). Data are representative of 4 independent experiments. *, p<0.05.

CD45.1+ (upper dot-plots) and CD45.1− (lower dot-plots) T cells isolated from Rag−/− mice and re-stimulated ex vivo with PMA and ionomycin. Data shown correspond to a single mouse in a total of four mice per group and are representative of two independent experiments.

FIG. 27: Agonistic effect of the anti-BTLA mAb. $10^5$ negatively selected WT, Hvem−/−, or Btla−/− CD4+CD25− T cells were cultured with $5\times10^5$ irradiated Thy 1.2-depleted WT or Hvem−/− splenocytes as APCs in the presence of 1 μg/ml anti-CD3e mAb. 10 μg/ml of an anti-BTLA mAb (filled histogram and symbols) or an IgG1 isotype control (open histogram and symbols; BD Biosciences) was added at the beginning of the culture. Culture supernatants were collected every 24 h, and IL-2 production was measured by ELISA. At 96 h after culture, the expression of CD25 on CD4+ Thy1.2+ T cells was monitored by flow cytometry. *, P<0.05; **, P<0.005.

FIG. 28A-D: Signaling through BTLA prevents colitis acceleration in Hvem−/−Rag−/− recipients. (A) Weight loss curves of Hvem−/−Rag−/− mice recipients of WT T cells, treated with either 100 μg of anti-BTLA mAb (clone 6F7) or IgG1 isotype control twice a week beginning at the time of T cell transfer. Data shown represent the average of 4 mice in each group and are representative of two independent experiments. (B) Histological scoring performed three weeks after T cell transfer revealed milder intestinal inflammation in samples obtained from Hvem−/−Rag−/− animals treated with the anti-BTLA mAb. Each circle represents a single mouse in a total of eight mice per group. *, p<0.05. (C) Same as (A) except that Hvem−/−Rag−/− animals were transferred with Btla−/− CD4+CD45RB$^{high}$ T cells. (D) Histological analysis three weeks after transfer revealed equivalent intestinal inflammation in all transferred Hvem−/−Rag−/− animals regardless the treatment with the anti-BTLA mAb. Each circle represents a single mouse in a total of five mice per group.

FIG. 29A-D: Accelerated colitis in Btla−/−Rag−/− recipients. (A) Weight loss curves of Rag−/− (squares) and Btla−/−Rag−/− (triangles) recipients transferred with $5\times10^5$ WT T cells. Data correspond to the average of 4-6 mice per group. (B) Combined proximal and distal colon histological scores were evaluated 2 weeks following T cell transfer. Each symbol represents an individual mouse from a total of 6-7 animals per group. (C) Weight loss curves of Hvem−/−Rag−/− (circles) and Btla−/−Rag−/− (open triangles) recipients transferred with $5\times10^5$ WT T cells, and Btla−/−Rag−/− mice transferred with $5\times10^5$ Btla−/− T cells (filled triangles). Data correspond to the average of 4-6 mice per group and are representative of two independent experiments. (D) Histological scores performed on samples obtained from two independent experiments, 2 weeks after T cell transfer. Each symbol represents an individual mouse from a total of 5-11 animals per group. *, p<0.05.

Figure 30:
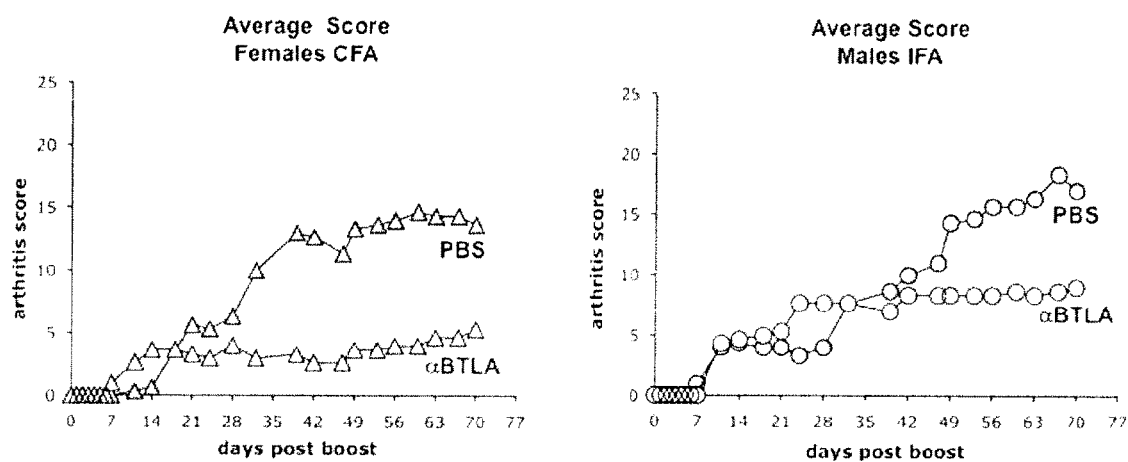

FIG. 30: DBA/1 mice treated weekly with 200 ug of the anti-BTLA antibody presented lower inflammatory scores than animals treated with PBS.

Figure 31:
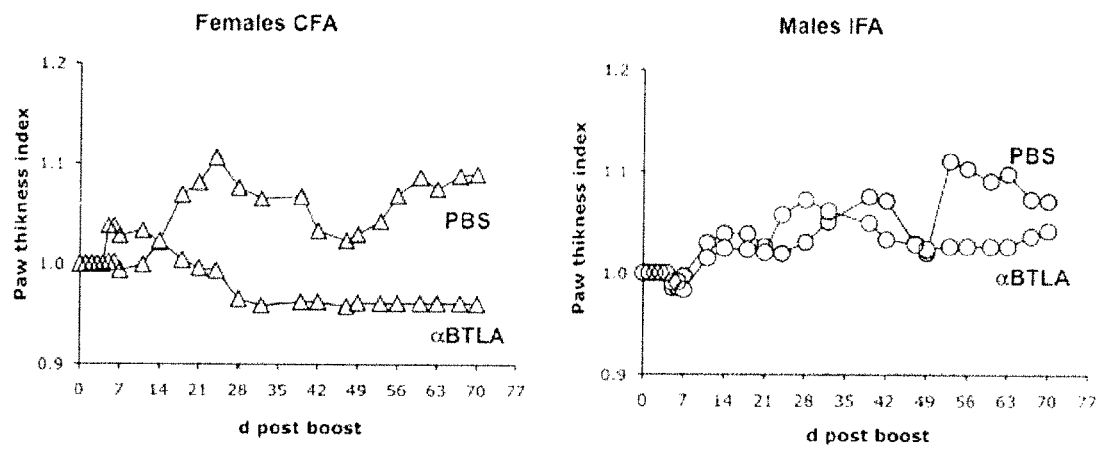

FIG. 31: Animals treated with the anti-BTLA antibody presented reduced joint inflammation compared to animals treated with PBS, as assessed by measuring the thickness of the paws.

Figure 32:
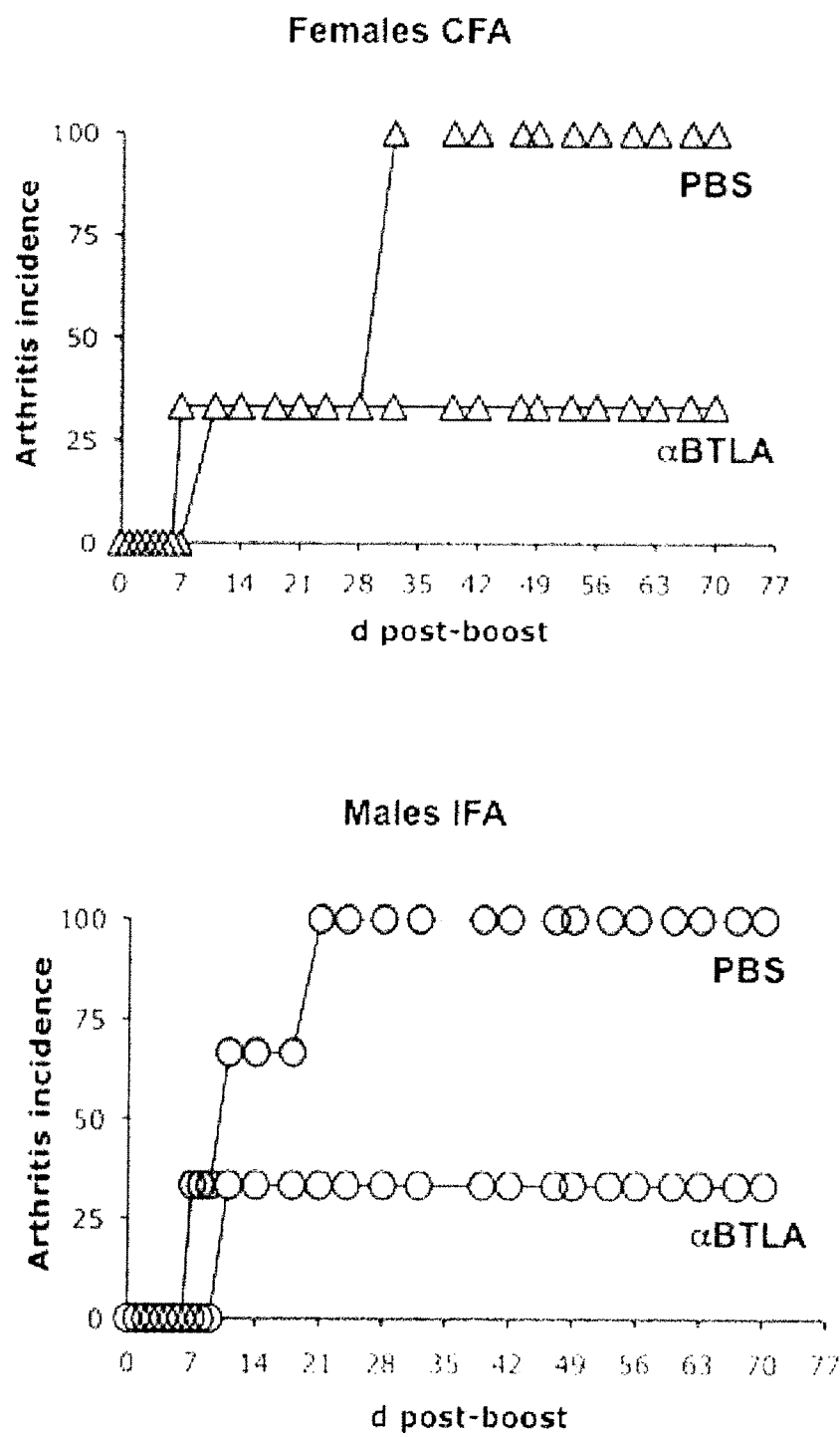

FIG. 32: Agonistic engagement of BTLA leads to a significantly lower disease incidence, compare with DBA mice treated with PBS FIG. 33: Differences in joint inflammation between PBS and anti-BTLA antibody treated animals confirmed by histological analysis of affected joints. More severe inflammation in PBS treated mice compared to animals treated with the anti-BTLA antibody.

Figure 34:
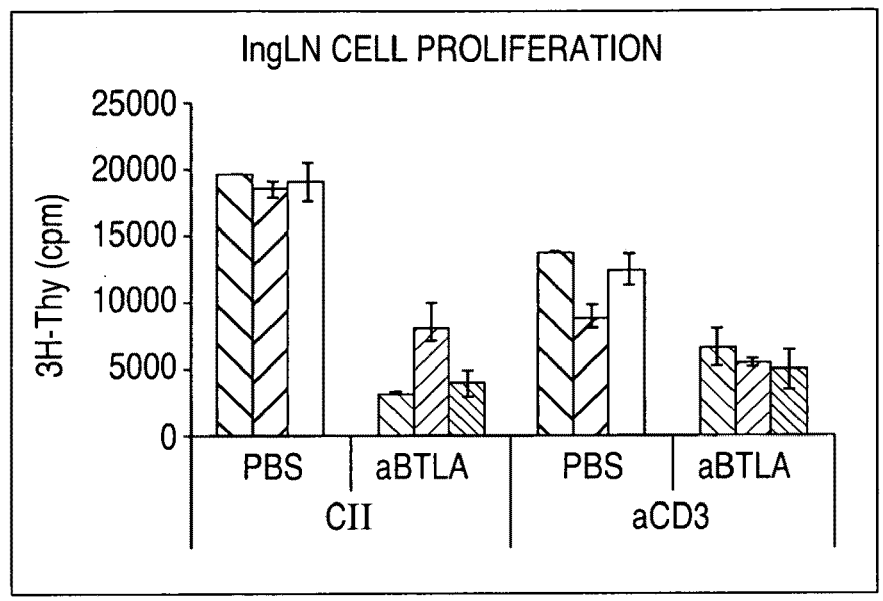
Figure 34:
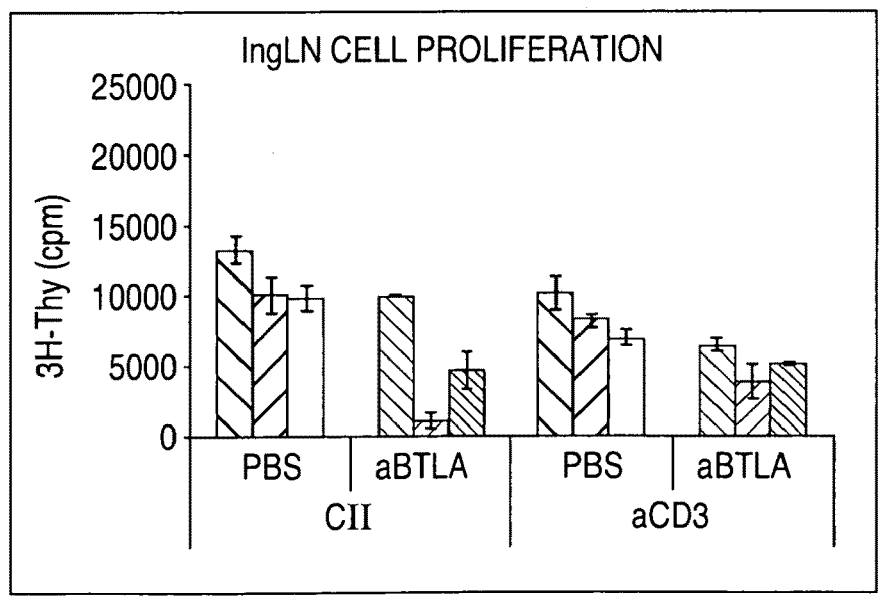

FIG. 34: T cell proliferative responses assessed by $H^3$-Thymidine incorporation following restimulation of lymph node (LN) cells with collagen or an anti-CD3ε antibody were significantly reduced in cells isolated from anti-BTLA antibody treated mice.

Figure 35:
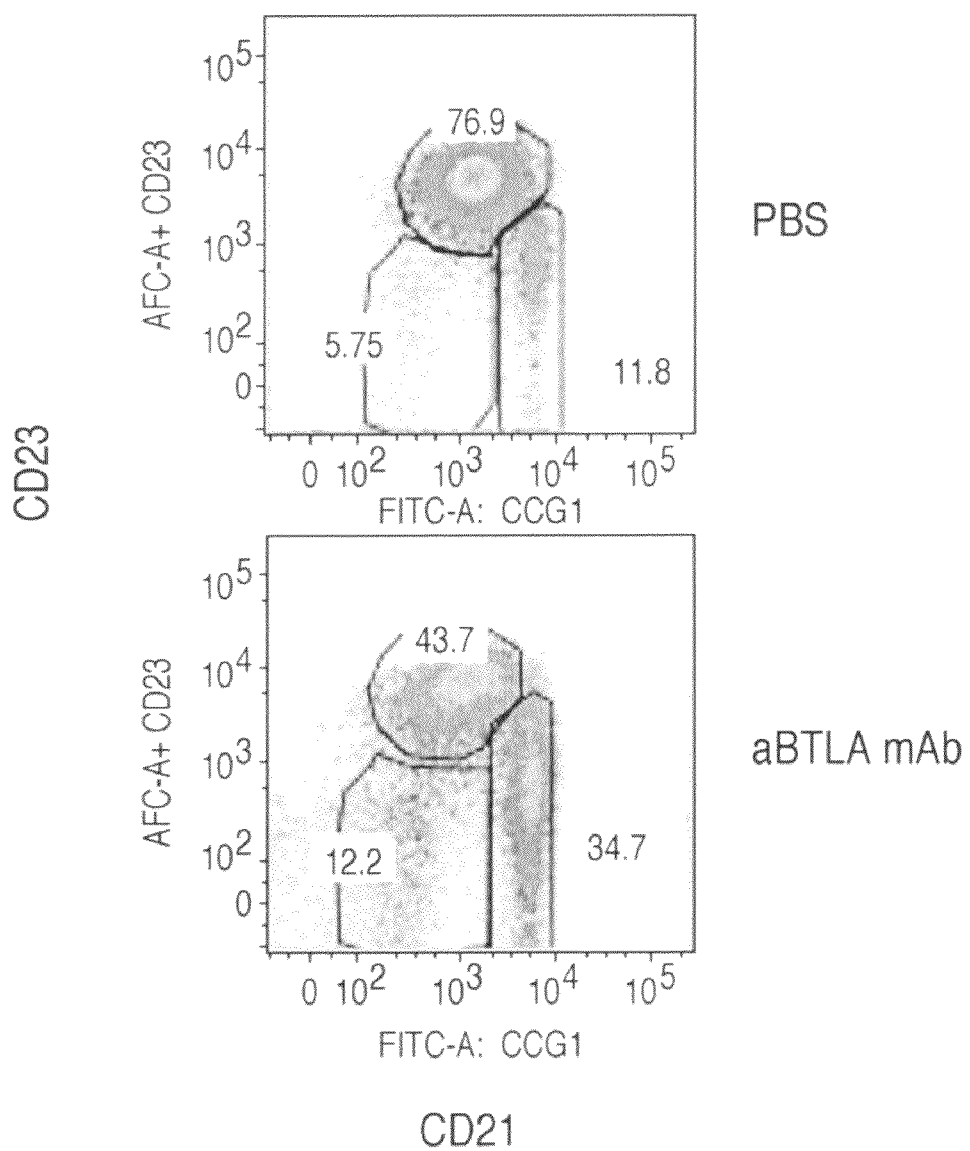

FIG. 35: A subset of follicular B cells expressing high levels of surface BTLA and surface markers B220, CD23hi and CD21int, was preferentially targeted for reduction by anti-BTLA antibody treatment.

DETAILED DESCRIPTION

In accordance with the invention, there are provided isolated and purified polypeptides, and compositions including the polypeptides, wherein the polypeptides have an amino acid sequence including or consisting of a binding site for immunoregulatory molecule B-T lymphocyte attenuator (BTLA). In one embodiment, a polypeptide having a sequence consisting of a binding site for immunoregulatory molecule B-T lymphocyte attenuator (BTLA) includes a portion of HVEM polypeptide (e.g., mammalian or human HVEM). In another embodiment, a polypeptide having a sequence consisting of a binding site for immunoregulatory molecule B-T lymphocyte attenuator (BTLA) includes a portion of human cytomegalovirus (HCMV) UL144 protein. In an additional embodiment, a polypeptide having a sequence consisting of a binding site for immunoregulatory molecule B-T lymphocyte attenuator (BTLA) includes a portion of CD27 (e.g., mammalian or human CD27, TNFR). In a further embodiment, a polypeptide having a sequence consisting of a binding site for immunoregulatory molecule B-T lymphocyte attenuator (BTLA) includes a portion of 41BB (e.g., mammalian or human 41BB, TNFR). In still another embodiment, a polypeptide having a sequence consisting of a binding site for immunoregulatory molecule B-T lymphocyte attenuator (BTLA) includes a portion of OX40 (e.g., mammalian or human OX40, TNFR). In still further embodiments, a polypeptide having a sequence consisting of a binding site for immunoregulatory molecule B-T lymphocyte attenuator (BTLA) includes an amino acid sequence with at least about 75%, 80%, 90%, 95% or more homology (identity) to a binding site for immunoregulatory molecule B-T lymphocyte attenuator (BTLA).

A "polypeptide" refers to two-or more amino acids linked by an amide bond. A polypeptide can also be referred to herein, inter alia, as a protein, peptide, or an amino acid sequence. Polypeptides include any length of two-or more amino acids bound by an amide bond that has been conjugated to a distinct moiety. Polypeptides can form intra or intermolecular disulfide bonds. Polypeptides can also form higher order multimers or oligomers with the same or different polypeptide, or other molecules.

Polypeptides of the invention including binding sites for BTLA can be of any length. Exemplary lengths of polypeptides and binding sites for BTLA are from about 5 to 15, 20 to 25, 25, to 50, 50 to 100, 100 to 150, 150 to 200, or 200 to 300, or more amino acids in length. In particular aspects, the polypeptide has a length less than full-length native (naturally occurring) sequence having a binding site for BTLA, e.g., less than full-length or a portion of full length HVEM, UL144, CD27, 41BB or OX40 polypeptide.

Binding sites for BTLA are exemplified herein. In particular, for example, a binding site for BTLA in HVEM polypeptide comprises or consists of all or a portion of CRD1 sequence of human or murine HVEM, as set forth in FIG. 7. More particularly, a binding site for BTLA includes or consists of a portion of human HVEM, CPKCSPGYRVKEACGELTGTVCEPC (SEQ. ID. NO:1), or includes or consists of a portion of murine HVEM, CPMCNPGYHVKQVCSEHTGTVCAPC (SEQ. ID. NO:2), subsequences thereof and amino acid substitutions thereof.

Studies set forth herein reveal a number of amino acid residues that participate in BTLA binding, and amino acid residues that may be substituted without destroying BTLA binding. Invention polypeptides therefore further include sequences that retain BTLA binding activity, as well as sequences with decreased affinity for BTLA including sequences that exhibit little or no detectable binding to BTLA.

For example, in a human HVEM binding site for BTLA, CPKCSPGYRVKEACGELTGTVCEPC (SEQ. ID. NO:1), a K residue and a VK dipeptide appear to contribute to BTLA binding. In contrast, amino acid substitution(s) of an F for a Y residue (Y47F or Y61F), an A for an S residue (S58A), an A for an E residue (E65A or E76A), or an A for an R residue (R113A) does not destroy BTLA binding. Exemplary invention subsequences and substituted sequences (variants) therefore include a human HVEM and BTLA binding sites thereof having amino acid residues such as a K residue, a VK dipeptide, an RVK tripeptide, an RVKE tetrapeptide, and so forth, as well as amino acid substitution(s) of an F for a Y residue (Y47F or Y61F), an A for an S residue (S58A), an A for an E residue (E65A or E76A), or an A for an R residue (R113A), with reference to residue positions indicated in FIG. 6, alone or in any combination.

In another example, in a murine binding site for BTLA, CPMCNPGYHVKQVCSEHTGTVCAPC (SEQ. ID. NO:2), a K residue and a VK dipeptide appear to contribute to BTLA binding. Exemplary invention subsequences and substituted sequences (variants) therefore include murine HVEM and BTLA binding sites thereof having amino acid residues such as a K residue, a VK dipeptide, an HVK tripeptide, an HVKQ tetrapeptide, and so forth.

In accordance with the invention, there are provided modified or variant HVEM polypeptide sequences (e.g., mammalian) in which binding of modified or variant HVEM to one or more of BTLA, glycoprotein D of herpes simplex virus (gD), LIGHT or LTα has been altered, as compared to binding of native naturally occurring HVEM. In one embodiment, an HVEM polypeptide sequence does not substantially or detectably bind BTLA, or binds BTLA with reduced affinity, as compared to binding of wild type human HVEM. In another embodiment, an HVEM polypeptide sequence binds BTLA, or binds BTLA with reduced affinity as compared to binding of wild type human HVEM, but does not substantially or detectably bind to glycoprotein D of herpes simplex virus (gD), LIGHT or LTα. In an additional embodiment, an HVEM polypeptide sequence does not substantially or detectably bind BTLA, or binds to BTLA with reduced affinity, as compared to binding of wild type human HVEM, but binds to glycoprotein D of herpes simplex virus (gD), LIGHT or LTα. In particular aspects, an HVEM polypeptide sequence has a mutation or deletion of arginine at position 62, lysine at position 64, or glutamate at position 65, with reference to residue positions indicated in FIG. 6. In additional particular aspects, an HVEM polypeptide sequence has an alanine residue at positions 62, 64 or 6, with reference to residue positions indicated in FIG. 6.

The term "isolated," when used as a modifier of an invention composition (e.g., polypeptides, antibodies, modified/variant forms, subsequences, nucleic acids encoding same, etc.), means that the compositions are made by the hand of man or are separated, substantially completely or at least in part, from their naturally occurring in vivo environment. Generally, isolated compositions are substantially free of one or more materials with which they normally associate with in nature, for example, one or more protein, nucleic acid, lipid, carbohydrate, cell membrane. The term "isolated" does not exclude alternative physical forms of the composition, such as multimers/oligomers, modifications (e.g., phosphorylation, glycosylation, lipidation) or derivatized forms, or forms expressed in host cells produced by the hand of man. The term "isolated" also does not exclude forms (e.g., pharmaceutical formulations and combination compositions) in which there are combinations therein, any one of which is produced by the hand of man.

An "isolated" composition (e.g., a polypeptide, antibody, nucleic acid, etc.) can also be "purified" when free of some, a substantial number of, most or all of the materials with which it typically associates with in nature. Thus, an isolated peptide (e.g., binding site for BTLA) that also is substantially pure does not include polypeptides or polynucleotides present among millions of other sequences, such as proteins of a protein library or nucleic acids in a genomic or cDNA library, for example. A "substantially pure" composition can be combined with one or more other molecules. Thus, "substantially pure" does not exclude compositions such as pharmaceutical formulations and combination compositions.

Invention polypeptides further include subsequences and substituted sequences (variants) and modified forms of HVEM sequence that have reduced or exhibit no detectable binding to BTLA but retain detectable (at least partial) binding to one or more of LIGHT (p30 polypeptide), LTα, and glycoprotein D (gD) of herpes simplex virus, as well as subsequences and substituted sequences (variants) and modified forms of HVEM sequence that maintain detectable binding to BTLA but exhibit reduced, little or no binding to one or more of LIGHT (p30 polypeptide), LTα, and glycoprotein D (gD) of herpes simplex virus. In various embodiments, amino acid substitutions in a HVEM that reduce or destroy binding to BTLA, but do not destroy binding to LIGHT (p30 polypeptide), is an F for a Y residue (Y61F), an A for a K residue (K64A), or an A for an E residue (E65A), with reference to residue positions indicated in FIG. 6.

Non-limiting specific examples of polypeptides having a sequence in which a binding site for immunoregulatory molecule B-T lymphocyte attenuator (BTLA) is present include, for HCMV UL144:

MKPLIMLICFAVILLQLGVTKVCQHNEVQLGNECCPPCGSGQRVTKVCTD

YTSVTCTPCPNGTYVSGLYNCTDCTQCNVTQVMIRNCTSTNNTVCASKNY

TSFSISGGVQHKQRQNHTAHVTVKQGKSGRHT (HCMV Toledo);

MKPLIMLICFAVILLQLGVTKVCQHNEVQLGNECCPPCGSGQRVTKVCTD

YTSVTCTPCPNGTYVSGLYNCTDCTQCNVTQVMIRNCTSTNNTVCAPKNH

TYFSTPGVQHHKQRQQNHTAHITVKQGKSGRHT (HCMV fiala);

MKPLVMLILLSMLLACIGKTEICKPEEVQLGNQCCPPCKQGYRVTGQCTQ

YTSTTCTLCPNGTYVSGLYNCTNCTECNDTEVTIRNCTSTNNTVCASKNY

TSLSVPGVQHHKQRQNHTAHVTVKQGKSGRHT (AAF09105);

```
MKPLVMLICFAVILLQLGVTKVCQHNEVQLGNECCPPCGSGQRVTKVCTD

YTSVTCTPCPNGTYVSGLYNCTDCTQCNVTQVMIRNCTSTNNTVCAPKNH

TYFSTPGVQHHKQRQQNHTAHITVKQRKSGRHT (AAF09116);

MKPLVMLILLSMLLDCNGKTEICKPEEVQLGNQCCPPCKQGYRVTGQCTQ

YTSTTCTLCPNGTYVSGLYNCTNCTECNDTEVTIRNCTSTNNTVCASKNY

TSFSVPGVQHHKQRQNHTAHVTVKQGKSGRHT (AF179198_1);

MKPLVMLICFGVFLLQLGGSKMCKPDEVKLGNQCCPPCGSGQKVTKVCTE

ISGITCTLCPNGTYLTGLYNCTNCTQCNDTQITVRNCTSTNNTICASKNH

TSFSSPGVQHHKQRQQNHTAHVTVKQRKSGRHT (AF179199_1);
and

MLLLSVIWAAVLASRSAAPACKQDEYAVGSECCPKCGKGYRVKTNCSETT

GTVCEPCPAGSYNDKRETICTQCDTCNSSSIAVNRCNTTHNVRCRLANSS

TASAHVDSGQHQQAGNHSVLPEDDAARD (RhCMV51556618).
```

Figure 7:
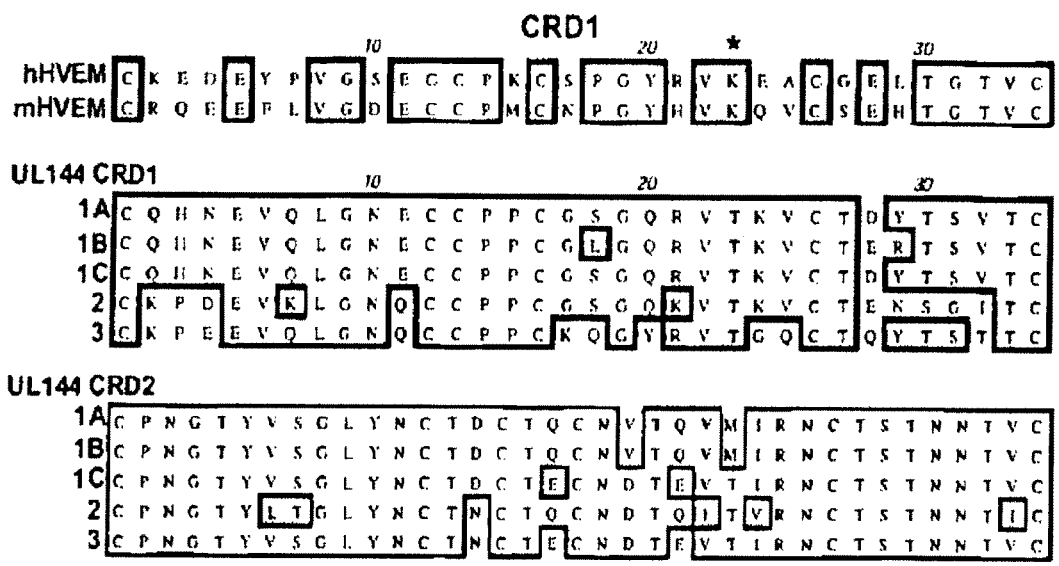
FIG. 7: Sequence alignment of HVEM and UL144 CRD1. Human and mouse HVEM CRD1 alignment and representative sequences from the five subtypes of UL144 aligned with human HVEM (ClustalW, PAM350 series, Macvector 7). Asterisk denotes lysine 64 in hHVEM critical for binding to BTLA.

Portions of HCMV UL144 protein sequences that have an amino acid sequence consisting of a binding site for BTLA include UL144-CRD1 UL144-CRD2 sequences (e.g., 1A, 1B, 1C, 2 or 3), as set forth in FIG. 7.

Additional non-limiting specific examples of polypeptides having a sequence in which a binding site for immunoregulatory molecule B-T lymphocyte attenuator (BTLA) is present include, for CD27: CQMCEPGTFLVKDCDQHR-KAAQCDPC (SEQ. ID NO:10); for OX40: CHECRPGNG-MVSRCSRSQNTVCRP (SEQ. ID NO:11); and for 41BB: CSNCPAGTFCDNNRNQICSPC (SEQ. ID NO:12).

Subsequences and amino acid substitutions of the various sequences set forth herein having a binding site for BTLA are included. In particular embodiments, a subsequence has at least 5, 10, 15, 20, 25, 30, 35, 40, 45, 50 or more amino acid residues.

The invention includes peptides and mimetics, and modified (variant) forms, provided that the modified form retains, at least partial activity or function of unmodified or reference peptide or mimetic. For example, a modified binding site for BTLA or mimetic can retain at least a part of BTLA binding activity; a modified or variant HVEM can retain at least partial binding for BTLA, LIGHT (p30 polypeptide), LTα or glycoprotein D (gD).

Modified (variant) peptides can have one or more amino acid residues substituted with another residue, added to the sequence or removed from the sequence. Specific examples include one or more amino acid substitutions, additions or deletions (e.g., 1-3, 3-5, 5-10, 10-20, or more). In a non-limiting example, a substitution is a conservative amino acid substitution. A modified (variant) peptide can have a sequence with 50%, 60%, 70%, 75%, 80%, 85%, 90%, 95%, 96%, 97%, 98%, or more identity to a reference sequence (e.g., a binding site for BTLA). The crystal structure of HVEM-BTLA can be employed to predict the effect of modifications to a binding site for BTLA (Compaan, et al., *J. Biol. Chem.* 280:39553 (2005)).

The term "identity" and "homology" and grammatical variations thereof mean that two or more referenced entities are the same. Thus, where two sequences are identical, they have the same sequence. "Areas, regions or domains of identity" mean that a portion of two or more referenced entities are the same. Thus, where two sequences are identical or homologous over one or more sequence regions, they share identity in these regions.

Due to variation in the amount of sequence conservation between structurally and functionally related proteins, the amount of sequence identity required to retain a function or activity depends upon the protein, the region and the function or activity of that region. Although there can be as little as 30% sequence identity for proteins to retain a given activity or function, typically there is more, e.g., 50%, 60%, 75%, 85%, 90%, 95%, 96%, 97%, 98%, identity to a reference sequence having the activity or function. For nucleic acid sequences, 50% sequence identity or more typically constitutes substantial homology, but again can vary depending on the comparison region and its function, if any.

The extent of identity between two sequences can be ascertained using a computer program and mathematical algorithm known in the art. Such algorithms that calculate percent sequence identity (homology) generally account for sequence gaps and mismatches over the comparison region. For example, a BLAST (e.g., BLAST 2.0) search algorithm (see, e.g., Altschul et al., *J. Mol. Biol.* 215:403 (1990), publicly available through NCBI) has exemplary search parameters as follows: Mismatch −2; gap open 5; gap extension 2. For polypeptide sequence comparisons, a BLASTP algorithm is typically used in combination with a scoring matrix, such as PAM100, PAM 250, BLOSUM 62 or BLOSUM 50. FASTA (e.g., FASTA2 and FASTA3) and SSEARCH sequence comparison programs are also used to quantitate the extent of identity (Pearson et al., *Proc. Natl. Acad. Sci. USA* 85:2444 (1988); Pearson, *Methods Mol Biol.* 132:185 (2000); and Smith et al., *J. Mol. Biol.* 147:195 (1981)). Programs for quantitating protein structural similarity using Delaunay-based topological mapping have also been developed (Bostick et al., *Biochem Biophys Res Commun.* 304:320 (2003)).

As used herein, the terms "mimetic" and "mimic" refer to a synthetic chemical compound which has substantially the same structural and/or functional characteristics as the reference molecule. The mimetic can be entirely composed of synthetic, non-natural amino acid analogues, or can be a chimeric molecule including one or more natural peptide amino acids and one or more non-natural amino acid analogs. The mimetic can also incorporate any number of natural amino acid conservative substitutions as long as such substitutions do not destroy activity. As with polypeptide variants, routine assays can be used to determine whether a mimetic has activity, e.g., BTLA binding activity.

Peptide mimetic compositions can contain any combination of non-natural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., induce or stabilize a secondary structure, e.g., a beta turn, gamma turn, beta sheet, alpha helix conformation, and the like. For example, a polypeptide can be characterized as a mimetic when one or more of the residues are joined by chemical means other than an amide bond. Individual peptidomimetic residues can be joined by amide bonds, non-natural and non-amide chemical bonds other chemical bonds or coupling means including, for example, glutaraldehyde, N-hydroxysuccinimide esters, bifunctional maleimides, N,N'-dicyclohexylcarbodiimide (DCC) or N,N'-diisopropylcarbodiimide (DIC). Linking groups alternative to the amide bond include, for example, ketomethylene (e.g., —C(=O)—CH$_2$— for —C(=O)—NH—), aminomethylene (CH$_2$—NH), ethylene, olefin (CH=CH), ether (CH$_2$—O), thioether (CH$_2$—S), tetrazole (CN$_4$—), thiazole, retroamide, thioamide, or ester (see, e.g., Spatola (1983) in *Chemistry and Biochemistry of Amino Acids, Peptides and*

*Proteins*, Vol. 7, pp 267-357, "Peptide and Backbone Modifications," Marcel Decker, N.Y.).

A "conservative substitution" is a replacement of one amino acid by a biologically, chemically or structurally similar residue. Biologically similar means that the substitution is compatible with a biological activity, e.g., BTLA binding activity. Structurally similar means that the amino acids have side chains with similar length, such as alanine, glycine and serine, or having similar size. Chemical similarity means that the residues have the same charge or are both hydrophilic or hydrophobic. Particular examples include the substitution of one hydrophobic residue, such as isoleucine, valine, leucine or methionine for another, or the substitution of one polar residue for another, such as the substitution of arginine for lysine, glutamic for aspartic acids, or glutamine for asparagine, serine for threonine, etc.

Peptides and peptidomimetics can be produced and isolated using methods known in the art. Peptides can be synthesized, whole or in part, using chemical methods known in the art (see, e.g., Caruthers (1980). *Nucleic Acids Res. Symp. Ser.* 215; Horn (1980); and Banga, A. K., *Therapeutic Peptides and Proteins, Formulation, Processing and Delivery Systems* (1995) Technomic Publishing Co., Lancaster, Pa.). Peptide synthesis can be performed using various solid-phase techniques (see, e.g., Roberge *Science* 269:202 (1995); Merrifield, *Methods Enzymol.* 289:3 (1997)) and automated synthesis may be achieved, e.g., using the ABI 431A Peptide Synthesizer (Perkin Elmer) in accordance with the manufacturer's instructions.

Individual synthetic residues and polypeptides incorporating mimetics can be synthesized using a variety of procedures and methodologies known in the art (see, e.g., *Organic Syntheses* Collective Volumes, Gilman, et al. (Eds) John Wiley & Sons, Inc., NY). Peptides and peptide mimetics can also be synthesized using combinatorial methodologies. Techniques for generating peptide and peptidomimetic libraries are well known, and include, for example, multipin, tea bag, and split-couple-mix techniques (see, for example, al-Obeidi, *Mol. Biotechnol.* 9:205 (1998); Hruby, *Curr. Opin. Chem. Biol.* 1:114 (1997); Ostergaard (1997). Mol. Divers. 3:17; and Ostresh, *Methods Enzymol.* 267:220 (1996). Modified peptides can be further produced by chemical modification methods (see, for example, Belousov, *Nucleic Acids Res.* 25:3440 (1997); Frenkel, *Free Radic. Biol. Med.* 19:373 (1995); and Blommers, *Biochemistry* 33:7886 (1994).

Amino acid substitutions may be with the same amino acid, except that a naturally occurring L-amino acid is substituted with a D-form amino acid. Modifications therefore include one or more D-amino acids substituted for L-amino acids, or mixtures of D-amino acids substituted for L-amino acids. Modifications further include structural and functional analogues, for example, peptidomimetics having synthetic or non-natural amino acids or amino acid analogues and derivatized forms.

Modifications include cyclic structures such as an end-to-end amide bond between the amino and carboxy-terminus of the molecule or intra- or inter-molecular disulfide bond. Polypeptides may be modified in vitro or in vivo, e.g., post-translationally modified to include, for example, sugar residues, phosphate groups, ubiquitin, fatty acids, lipids, etc.

Polypeptides of the invention also include chimeras or fusions with one or more additional domains covalently linked thereto to impart a distinct or complementary function or activity. A polypeptide can have one or more non-natural or derivatized amino acid residues linked to the amide linked amino acids. Peptides include chimeric proteins in which two or more amino acid sequences are linked together that do not naturally exist in nature.

Exemplary fusions include domains facilitating isolation, which include, for example, metal chelating peptides such as polyhistidine tracts and histidine-tryptophan modules that allow purification on immobilized metals; protein A domains that allow purification on immobilized immunoglobulin; and the domain utilized in the FLAGS extension/affinity purification system (Immunex Corp, Seattle Wash.). Optional inclusion of a cleavable sequence such as Factor Xa or enterokinase (Invitrogen, San Diego Calif.) between a purification domain and the peptide can be used to facilitate peptide purification. For example, an expression vector can include a peptide-encoding nucleic acid sequence linked to six histidine residues followed by a thioredoxin and an enterokinase cleavage site (see e.g., Williams, *Biochemistry* 34:1787 (1995); and Dobeli, *Protein Expr. Purif.* 12:404 (1998)). The histidine residues facilitate detection and purification of the fusion protein while the enterokinase cleavage site provides a means for purifying the peptide from the remainder of the fusion protein. Technology pertaining to vectors encoding fusion proteins and application of fusion proteins is known in the art (see e.g., Kroll, *DNA Cell. Biol.* 12:441 (1993)).

The invention further provides nucleic acids encoding peptides of the invention. In a particular embodiment, a nucleic acid encodes a binding site for immunoregulatory molecule B-T lymphocyte attenuator (BTLA). In various aspects, a nucleic acid encodes an HVEM binding site for BTLA, a UL144 binding site for BTLA, a CD27 binding site for BTLA, a 41BB binding site for BTLA, and an OX40 binding site for BTLA. In particular aspects, a nucleic acid encodes a binding site for BTLA which comprises, consists of or is within: a human HVEM sequence set forth as CPKCSPGYRVKEACGELTGTVCEPC (SEQ. ID NO:1); an HCMV UL144 sequence (e.g., set forth as MKPLIMLICFAVILLQLGVTKVCQHNEVQLGNECCPPCGSGQRVTKVCTDYTSVTCTPCPNGTYVSGLYNCTDCTQCNVTQVMIRNCTSTNNTVCASKNYTSFSISGGVQHKQRQNHTAHVTVKQGKSGRHT, (HCMV toledo) (SEQ. ID NO:3); a CD27 sequence set forth as CQMCEPGTFLVKDCDQHRKAAQCDPC (SEQ. ID NO:10); a OX40 sequence set forth as CHECRPGNGMVSRCSRSQNTVCRP (SEQ. ID NO:11); and a 41BB sequence set forth as CSNCPAGTFCDNNRNQICSPC (SEQ. ID NO:12).

Figure 6:
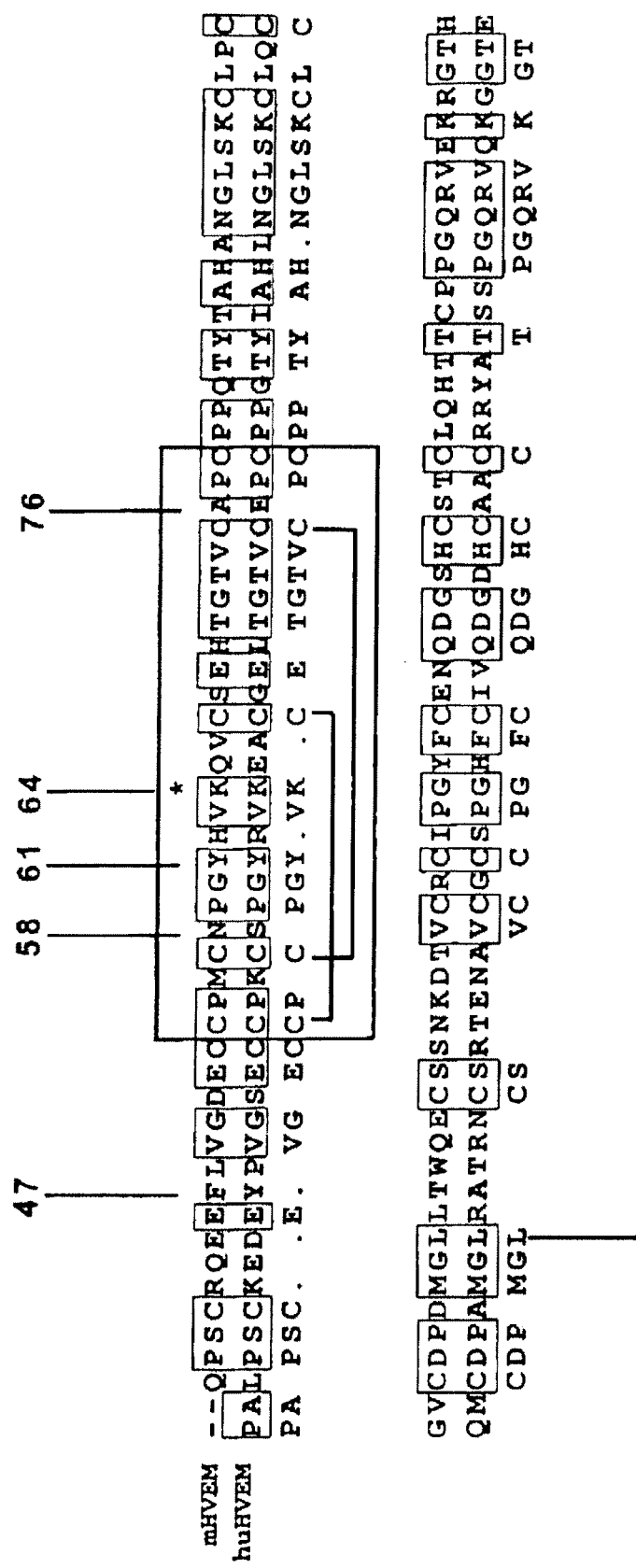
FIG. 6: Sequence conservation between human and mouse HVEM. Alignments were performed on sequence of the mature ecto domain. Paired cysteines forming disulfide bonds are shown by connecting lines.

Nucleic acids encoding invention subsequences and substituted sequences (variants), including HVEM and BTLA binding sites thereof having amino acid residues such as a K residue, a VK dipeptide. an HVK or RVK tripeptide, and RVKE or HVKQ tetrapeptide, and so forth, as well as amino acid substitution(s) of in human HVEM of an F for a Y residue (Y47F or Y61F), an A for an S residue (S58A), an A for an E residue (E65A or E76A), or an A for an R residue (R113A), with reference to residue positions indicated in FIG. 6, alone, or in any combination, are provided.

Nucleic acids encoding modified or variant HVEM polypeptide sequences (e.g., mammalian) in which binding to one or more of BTLA, glycoprotein D of herpes simplex virus (gD), LIGHT or LTα has been altered, as compared to native naturally occurring HVEM, are further provided. Nucleic acids encode HVEM polypeptide sequences that do not substantially or detectably bind BTLA, or bind BTLA with reduced affinity, as compared to wild type human HVEM; HVEM polypeptide sequences that bind BTLA, or bind BTLA with reduced affinity as compared to wild type human HVEM, but do not substantially or detectably bind to glycoprotein D of herpes simplex virus (gD), LIGHT or LTα;

HVEM polypeptide sequences that do not substantially or detectably bind BTLA, or bind BTLA with reduced affinity, as compared to wild type human HVEM, but bind to glycoprotein D of herpes simplex virus (gD), LIGHT or LTα. Nucleic acids also provided encode HVEM polypeptide sequence having one or more of: a mutation or deletion of arginine at position 62, lysine at position 64, or glutamate at position 65, or one or more alanine residues at positions 62, 64 or 65, with reference to residue positions indicated in FIG. 6.

Nucleic acids further provided encode subsequences and substituted sequences (variants) and modified forms of HVEM sequence that have reduced or exhibit no detectable binding to BTLA but retain detectable binding to one or more of LIGHT (p30 polypeptide), LTα, and glycoprotein D (gD) of herpes simplex virus, as well as subsequences and substituted sequences (variants) and modified forms of HVEM sequence that maintain detectable binding to BTLA but exhibit reduced, little or no binding to one or more of LIGHT (p30 polypeptide), LTα, and glycoprotein D (gD) of herpes simplex virus.

Nucleic acid, which can also be referred to herein as a gene, polynucleotide, nucleotide sequence, primer, oligonucleotide or probe refers to natural or modified purine- and pyrimidine-containing polymers of any length, either polyribonucleotides or polydeoxyribonucleotides or mixed polyribo-polydeoxyribo nucleotides and α-anomeric forms thereof. The two or more purine- and pyrimidine-containing polymers are typically linked by a phosphoester bond or analog thereof. The terms can be used interchangeably to refer to all forms of nucleic acid, including deoxyribonucleic acid (DNA) and ribonucleic acid (RNA). The nucleic acids can be single strand, double, or triplex, linear or circular. Nucleic acids include genomic DNA, cDNA, and antisense. RNA nucleic acid can be spliced or unspliced mRNA, rRNA, tRNA or antisense. Nucleic acids of the invention include naturally occurring, synthetic, as well as nucleotide analogues and derivatives.

Nucleic acid can be of any length. For example, nucleic acids encoding a subsequence of any of full-length HVEM, UL144, CD27, 41BB, and OX40 protein having one or more BTLA binding activities are provided. In a particular embodiment, a nucleic acid encodes a subsequence of any of full-length HVEM, UL144, CD27, 41BB, and OX40, said subsequence capable of modulating (increasing or decreasing) BTLA activity or function (e.g., HVEM binding, T cell, antigen presenting cell or B cell proliferation, survival, differentiation, death, or activity).

As a result of the degeneracy of the genetic code, nucleic acids of the invention include sequences that are degenerate with respect to sequences encoding peptides of the invention. Thus, degenerate nucleic acids encoding binding sites for immunoregulatory molecule B-T lymphocyte attenuator (BTLA), subsequences thereof and modified forms, as set forth herein, are provided.

Nucleic acid can be produced using any of a variety of known standard cloning and chemical synthesis methods, and can be altered intentionally by site-directed mutagenesis or other recombinant techniques known to those skilled in the art. Purity of polynucleotides can be determined through sequencing, gel electrophoresis, UV spectrometry.

Nucleic acids of the invention may be inserted into a nucleic acid construct in which expression of the nucleic acid is influenced or regulated by an "expression control element," referred to herein as an "expression cassette." The term "expression control element" refers to one or more nucleic acid sequence elements that regulate or influence expression of a nucleic acid sequence to which it is operatively linked. An expression control element can include, as appropriate, promoters, enhancers, transcription terminators, gene silencers, a start codon (e.g., ATG) in front of a protein-encoding gene, etc.

An expression control element operatively linked to a nucleic acid sequence controls transcription and, as appropriate, translation of the nucleic acid sequence. The term "operatively linked" refers to a juxtaposition wherein the referenced components are in a relationship permitting them to function in their intended manner. Typically expression control elements are juxtaposed at the 5' or the 3' ends of the genes but can also be intronic.

Expression control elements include elements that activate transcription constitutively, that are inducible (i.e., require an external signal for activation), or derepressible (i.e., require a signal to turn transcription off; when the signal is no longer present, transcription is activated or "derepressed"). Also included in the expression cassettes of the invention are control elements sufficient to render gene expression controllable for specific cell-types or tissues (i.e., tissue-specific control elements). Typically, such elements are located upstream or downstream (i.e., 5' and 3') of the coding sequence. Promoters are generally positioned 5' of the coding sequence. Promoters, produced by recombinant DNA or synthetic techniques, can be used to provide for transcription of the polynucleotides of the invention. A "promoter" is meant a minimal sequence element sufficient to direct transcription.

The nucleic acids of the invention may be inserted into a plasmid for propagation into a host cell and for subsequent genetic manipulation if desired. A plasmid is a nucleic acid that can be stably propagated in a host cell; plasmids may optionally contain expression control elements in order to drive expression of the nucleic acid encoding a binding site for BTLA in the host cell. A vector is used herein synonymously with a plasmid and may also include an expression control element for expression in a host cell. Plasmids and vectors generally contain at least an origin of replication for propagation in a cell and a promoter. Plasmids and vectors are therefore useful for genetic manipulation of peptide and antibody encoding nucleic acids, producing peptides and antibodies or antisense, and expressing the peptides and antibodies in host cells or organisms, for example.

Bacterial system promoters include T7 and inducible promoters such as pL of bacteriophage λ, plac, ptrp, ptac (ptrp-lac hybrid promoter) and tetracycline responsive promoters. Insect cell system promoters include constitutive or inducible promoters (e.g., ecdysone). Mammalian cell constitutive promoters include SV40, RSV, bovine papilloma virus (BPV) and other virus promoters, or inducible promoters derived from the genome of mammalian cells (e.g., metallothionein IIA promoter; heat shock promoter) or from mammalian viruses (e.g., the adenovirus late promoter; the inducible mouse mammary tumor virus long terminal repeat). Alternatively, a retroviral genome can be genetically modified for introducing and directing expression of a peptide or antibody in appropriate host cells.

Expression systems further include vectors designed for in vivo use. Particular non-limiting examples include adenoviral vectors (U.S. Pat. Nos. 5,700,470 and 5,731,172), adeno-associated vectors (U.S. Pat. No. 5,604,090), herpes simplex virus vectors (U.S. Pat. No. 5,501,979), retroviral vectors (U.S. Pat. Nos. 5,624,820, 5,693,508 and 5,674,703), BPV vectors (U.S. Pat. No. 5,719,054) and CMV vectors (U.S. Pat. No. 5,561,063).

Yeast vectors include constitutive and inducible promoters (see, e.g., Ausubel et al., In: *Current Protocols in Molecular*

Biology, Vol. 2, Ch. 13, ed., Greene Publish. Assoc. & Wiley Interscience, 1988; Grant et al. *Methods in Enzymology,* 153: 516 (1987), eds. Wu & Grossman; Bitter *Methods in Enzymology,* 152:673 (1987), eds. Berger & Kimmel, Acad. Press, N.Y.; and, Strathern et al., *The Molecular Biology of the Yeast Saccharomyces* (1982) eds. Cold Spring Harbor Press, Vols. I and II). A constitutive yeast promoter such as ADH or LEU2 or an inducible promoter such as GAL may be used (R. Rothstein In: *DNA Cloning, A Practical Approach*, Vol. 11, Ch. 3, ed. D. M. Glover, IRL Press, Wash., D.C., 1986). Vectors that facilitate integration of foreign nucleic acid sequences into a yeast chromosome, via homologous recombination for example, are known in the art. Yeast artificial chromosomes (YAC) are typically used when the inserted polynucleotides are too large for more conventional vectors (e.g., greater than about 12 Kb).

Host cells including nucleic acids encoding peptides and antibodies of the invention are also provided. In one embodiment, the host cell is a prokaryotic cell. In another embodiment, the host cell is a eukaryotic cell. In various aspects, the eukaryotic cell is a yeast or mammalian (e.g., human, primate, etc.) cell.

As used herein, a "host cell" is a cell into which a nucleic acid is introduced that can be propagated, transcribed, or encoded peptide or antibody expressed. The term also includes any progeny or subclones of the host cell. Progeny cells and subclones need not be identical to the parental cell since there may be mutations that occur during replication and proliferation. Nevertheless, such cells are considered to be host cells of the invention.

Host cells include but are not limited to microorganisms such as bacteria and yeast; and plant, insect and mammalian cells. For example, bacteria transformed with recombinant bacteriophage nucleic acid, plasmid nucleic acid or cosmid nucleic acid expression vectors; yeast transformed with recombinant yeast expression vectors; plant cell systems infected with recombinant virus expression vectors (e.g., cauliflower mosaic virus, CaMV; tobacco mosaic virus, TMV) or transformed with recombinant plasmid expression vectors (e.g., Ti plasmid); insect cell systems infected with recombinant virus expression vectors (e.g., baculovirus); and animal cell systems infected with recombinant virus expression vectors (e.g., retroviruses, adenovirus, vaccinia virus), or transformed animal cell systems engineered for stable expression, are provided.

Expression vectors also can contain a selectable marker conferring resistance to a selective pressure or identifiable marker (e.g., beta-galactosidase), thereby allowing cells having the vector to be selected for, grown and expanded. Alternatively, a selectable marker can be on a second vector that is cotransfected into a host cell with a first vector containing an invention polynucleotide.

Selection systems include but are not limited to herpes simplex virus thymidine kinase gene (Wigler et al., *Cell* 11:223 (1977)), hypoxanthine-guanine phosphoribosyltransferase gene (Szybalska et al., *Proc. Natl. Acad. Sci. USA* 48:2026 (1962)), and adenine phosphoribosyltransferase (Lowy et al., *Cell* 22:817 (1980)) genes which can be employed in tk-, hgprt- or aprt-cells, respectively. Additionally, antimetabolite resistance can be used as the basis of selection for dhfr, which confers resistance to methotrexate (O'Hare et al., *Proc. Natl. Acad. Sci. USA* 78:1527 (1981)); the gpt gene, which confers resistance to mycophenolic acid (Mulligan et al., *Proc. Natl. Acad. Sci. USA* 78:2072 (1981)); neomycin gene, which confers resistance to aminoglycoside G-418 (Colberre-Garapin et al., *J. Mol. Biol.* 150:1 (1981)); puromycin; and hygromycin gene, which confers resistance to hygromycin (Santerre et al., *Gene* 30:147 (1984)). Additional selectable genes include trpB, which allows cells to utilize indole in place of tryptophan; hisD, which allows cells to utilize histinol in place of histidine (Hartman et al., *Proc. Natl. Acad. Sci. USA* 85:8047 (1988)); and ODC (ornithine decarboxylase), which confers resistance to the ornithine decarboxylase inhibitor, 2-(difluoromethyl)-DL-ornithine, DFMO (McConlogue (1987) In: *Current Communications in Molecular Biology,* Cold Spring Harbor Laboratory).

In accordance with the invention, provided are polyclonal and monoclonal antibodies that specifically bind to a binding site for immunoregulatory molecule B-T lymphocyte attenuator (BTLA). In various embodiments, an antibody binds to an HVEM binding site for BTLA, a UL144 binding site for BTLA, a CD27 binding site for BTLA, a 41BB binding site for BTLA, or an OX40 binding site for BTLA. In particular aspects, a binding site for BTLA to which antibody binds includes, consists of or is within: a human HVEM sequence set forth as CPKCSPGYRVKEACGELTGTVCEPC (SEQ. ID NO:1); an HCMV UL144 sequence (e.g., set forth as MKPLIMLICFAVILLQLGVTKVCQH-NEVQLGNECCPPCGSGQRVTKVCTDYTSVTCT PCP-NGTYVSGLYNCTDCTQCNVTQVMIRNCT-STNNTVCASKNYTSFSISGGVQHKQ RQNHTAHVTVKQGKSGRHT, (HCMV toledo) (SEQ. ID NO:3); a CD27 sequence set forth as CQMCEPGTFLVKD-CDQHRKAAQCDPC (SEQ. ID NO:10); an OX40 sequence set forth as CHECRPGNGMVSRCSRSQNTVCRP (SEQ. ID NO:11); and a 41BB sequence set forth as CSNCPAGT-FCDNNRNQICSPC (SEQ. ID NO:12). In further aspects, antibodies bind to a subsequence or an amino acid substitution of a binding site for BTLA. In additional aspects, antibodies can modulate (stimulate or increase, or inhibit, reduce or decrease) BTLA binding or activity (agonist or antagonist of T cell, antigen presenting cell or B cell proliferation, survival, differentiation, death, or activity), for example, HVEM-BTLA binding or activity, UL144-BTLA binding or activity, CD27-BTLA binding or activity, 41BB-BTLA binding or activity, or OX40-BTLA binding or activity. In further aspects, antibodies can modulate (stimulate or increase, or inhibit, reduce or decrease) a response mediated by or associated with BTLA activity or expression, for example, lymphocyte or hematopoetic cell proliferation or inflammation; and proliferation, survival, differentiation, death, or activity of T cells, antigen presenting cells (e.g., dendritic cells) or B cells.

Antibodies of the invention are useful in detecting a binding site for immunoregulatory molecule B-T lymphocyte attenuator (BTLA). Antibodies of the invention are also useful in the methods of the invention. For example, administering an invention antibody (e.g., human, humanized or chimeric) to a subject in need thereof that specifically binds a polypeptide having an amino acid sequence that includes a binding site for BTLA (e.g., a polypeptide such as an HVEM, UL144, CD27, 41BB or OX40 amino acid sequence, or an antibody), or a ligand (e.g., an amino acid sequence or an antibody) that binds to a binding site for BTLA, in an effective amount, can be used treat a number of disorders, diseases and conditions, such as those set forth herein.

"Antibody" refers to any monoclonal or polyclonal immunoglobulin molecule, such as IgM, IgG, IgA, IgE, IgD, and any subclass thereof. Exemplary subclasses for IgG are $IgG_1$, $IgG_2$, $IgG_3$ and $IgG_4$.

Antibodies include mammalian, human, humanized or primatized forms of heavy or light chain, $V_H$ and $V_L$, respectively, immunoglobulin (Ig) molecules. Antibodies also includes functional (binding) subsequences or fragments of immunoglobulins, such as Fab, Fab', (Fab')$_2$, Fv, Fd, scFv and sdFv, disulfide-linked Fv, light chain variable (VL) or heavy chain variable (VH) sequence, unless otherwise expressly stated.

As used herein, the term "monoclonal," when used in reference to an antibody, refers to an antibody that is based upon, obtained from or derived from a single clone, including any eukaryotic, prokaryotic, or phage clone. A "monoclonal" antibody is therefore defined herein structurally, and not the method by which it is produced.

The term "HVEM antibody," "BTLA antibody," "UL144 antibody," "CD27 antibody," "41BB antibody," "OX40 antibody" means an antibody that specifically binds to HVEM, BTLA, UL144, CD27, 41BB and OX40, respectively. Specific binding is that which is selective for an epitope present in the referenced molecule, e.g., HVEM, BTLA, UL144, CD27, 41BB and OX40. Specific binding can be distinguished from non-specific binding using assays known in the art (e.g., immunoprecipitation, ELISA, Western blotting).

Antibodies may exhibit binding to different proteins when all or a part of an antigenic epitope to which the antibodies specifically bind is present on different proteins, for example. Thus, depending on the eptiope and sequence homology, an HVEM antibody may specifically bind UL144. Accordingly, antibodies may bind to different proteins when the epitope or an epitope of sufficient identity is present on different proteins.

Epitopes typically are short amino acid sequences, e.g. about five to 15 amino acids in length. Systematic techniques for identifying epitopes are also known in the art and are described, for example, in U.S. Pat. No. 4,708,871. Briefly, a set of overlapping oligopeptides derived from an HVEM, UL144, CD27, 41BB or OX40 sequence (e.g., a polypeptide having an amino acid sequence that includes a binding site for BTLA) may be synthesized and bound to a solid phase array of pins, with a unique oligopeptide on each pin. The array of pins may comprise a 96-well microtiter plate, permitting one to assay all 96 oligopeptides simultaneously, e.g., for binding to an anti-HVEM, UL144, CD27, 41BB or OX40 monoclonal antibody. Alternatively, phage display peptide library kits (New England BioLabs) are commercially available for epitope mapping. Using these methods, binding affinity for every possible subset of consecutive amino acids may be determined in order to identify the epitope that a particular antibody binds. Epitopes may also be identified by inference when epitope length peptide sequences are used to immunize animals from which antibodies that bind to the peptide sequence are obtained. Continuous epitopes can also be predicted using computer programs, such as BEPITOPE, known in the art (Odorico et al., *J. Mol. Recognit.* 16:20 (2003)).

The term "human" when used in reference to an antibody, means that the amino acid sequence of the antibody is fully human, i.e., human heavy and human light chain variable and human constant regions. Thus, all of the antibody amino acids are human or exist in a human antibody. An antibody that is non-human may be made fully human by substituting the non-human amino acid residues with amino acid residues that exist in a human antibody. Amino acid residues present in human antibodies, CDR region maps and human antibody consensus residues are known in the art (see, e.g., Kabat, *Sequences of Proteins of Immunological Interest*, 4$^{th}$ Ed. US Department of Health and Human Services. Public Health Service (1987); Chothia and Lesk (1987). A consensus sequence of human V$_H$ subgroup III, based on a survey of 22 known human V$_u$ III sequences, and a consensus sequence of human V$_L$ kappa-chain subgroup I, based on a survey of 30 known human kappa I sequences is described in Padlan *Mol.*

*Immunol.* 31:169 (1994); and Padlan *Mol. Immunol.* 28:489 (1991). Human antibodies therefore include antibodies in which one or more amino acid residues have been substituted with one or more amino acids present in any other human antibody.

The term "humanized" when used in reference to an antibody, means that the amino acid sequence of the antibody has non-human amino acid residues (e.g., mouse, rat, goat, rabbit, etc.) of one or more complementarity determining regions (CDRs) that specifically bind to the desired antigen in an acceptor human immunoglobulin molecule, and one or more human amino acid residues in the Fv framework region (FR), which are amino acid residues that flank the CDRs. Human FR residues of the immunoglobulin can be replaced with corresponding non-human residues. Residues in the human framework regions can therefore be substituted with a corresponding residue from the non-human CDR donor antibody to alter, generally to improve, antigen affinity or specificity, for example. A humanized antibody may include residues, which are found neither in the human antibody nor in the donor CDR or framework sequences. For example, a FR substitution at a particular position that is not found in a human antibody or the donor non-human antibody may be predicted to improve binding affinity or specificity human antibody at that position. Antibody framework and CDR substitutions based upon molecular modeling are well known in the art, e.g., by modeling of the interactions of the CDR and framework residues to identify framework residues important for antigen binding and sequence comparison to identify unusual framework residues at particular positions (see, e.g., U.S. Pat. No. 5,585,089; and Riechmann et al., *Nature* 332: 323 (1988)).

Antibodies referred to as "primatized" are within the meaning of "humanized" as used herein, except that the acceptor human immunoglobulin molecule and framework region amino acid residues may be any primate amino acid residue (e.g., ape, gibbon, gorilla, chimpanzees orangutan, macaque), in addition to any human residue.

As used herein, the term "chimeric" and grammatical variations thereof, when used in reference to an antibody, means that the amino acid sequence of the antibody contains one or more portions that are derived from, obtained or isolated from, or based upon two or more different species. That is, for example, a portion of the antibody may be human (e.g., a constant region) and another portion of the antibody may be non-human (e.g., a murine heavy or murine light chain variable region). Thus, an example of a chimeric antibody is an antibody in which different portions of the antibody are of different species origins. Unlike a humanized or primatized antibody, a chimeric antibody can have the different species sequences in any region of the antibody.

Human antibodies can be produced by immunizing human transchromosomic KM mice™ (WO 02/43478) or HAC mice (WO 02/092812). KM mice™ and HAC mice express human immunoglobulin genes. Using conventional hybridoma technology, splenocytes from immunized mice that were high responders to the antigen can be isolated and fused with myeloma cells. A monoclonal antibody can be obtained that binds to the antigen. An overview of the technology for producing human antibodies is described in Lonberg and Huszar (*Int. Rev. Immunol.* 13:65 (1995)). Transgenic animals with one or more human immunoglobulin genes (kappa or lambda) that do not express endogenous immunoglobulins are described, for example in, U.S. Pat. No. 5,939,598. Additional methods for producing human polyclonal antibodies and human monoclonal antibodies are described (see, e.g., Kuroiwa et al., *Nat. Biotechnol.* 20:889 (2002); WO 98/24893; WO 92/01047; WO 96/34096; WO 96/33735; U.S. Pat. Nos. 5,413,923; 5,625,126; 5,633,425; 5,569,825; 5,661,016; 5,545,806; 5,814,318; 5,885,793; 5,916,771; and 5,939,598).

Antibodies can be humanized using a variety of techniques known in the art including, for example, CDR-grafting (EP 239,400; WO91/09967; U.S. Pat. Nos. 5,225,539; 5,530,101; and 5,585,089), veneering or resurfacing (EP 592,106; EP 519,596; Padlan, *Mol. Immunol.* 28:489 (1991); Studnicka et al., *Protein Engineering* 7:805 (1994); Roguska et al., *Proc. Nat'l. Acad. Sci. USA* 91:969 (1994)), and chain shuffling (U.S. Pat. No. 5,565,332). Human consensus sequences (Padlan, *Mol. Immunol.* 31:169 (1994); and Padlan, *Mol. Immunol.* 28:489 (1991)) have been used to humanize antibodies (Carter et al., *Proc. Natl. Acad. Sci. USA* 89:4285 (1992); and Presta et al., *J. Immunol.* 151:2623 (1993)).

Methods for producing chimeric antibodies are known in the art (e.g., Morrison, *Science* 229:1202 (1985); Oi et al., *BioTechniques* 4:214 (1986); Gillies et al., *J. Immunol. Methods* 125:191 (1989); and U.S. Pat. Nos. 5,807,715; 4,816,567; and 4,816,397). Chimeric antibodies in which a variable domain from an antibody of one species is substituted for the variable domain of another species are described, for example, in Munro, *Nature* 312:597 (1984); Neuberger et al., *Nature* 312:604 (1984); Sharon et al., *Nature* 309:364 (1984); Morrison et al., *Proc. Nat'l. Acad. Sci. USA* 81:6851 (1984); Boulianne et al., *Nature* 312:643 (1984); Capon et al., *Nature* 337:525 (1989); and Traunecker et al., *Nature* 339:68 (1989).

Protein suitable for generating antibodies can be produced by any of a variety of standard protein purification or recombinant expression techniques known in the art. For example, a binding site for BTLA (e.g., an HVEM sequence) can be produced by standard peptide synthesis techniques, such as solid-phase synthesis. A portion of the protein may contain an amino acid sequence such as a T7 tag or polyhistidine sequence to facilitate purification of expressed or synthesized protein. The protein may be expressed in a cell and purified. The protein may be expressed as a part of a larger protein (e.g., a fusion or chimera) by recombinant methods.

Forms of binding site for BTLA suitable for generating an immune response include full length or subsequences of HVEM, UL144, CD27, 41BB and OX40. Additional forms include binding site for BTLA containing preparations or extracts, partially purified binding site for BTLA as well as cells or viruses that express binding site for BTLA or preparations of such expressing cells or viruses.

Monoclonal antibodies can be readily generated using techniques including hybridoma, recombinant, and phage display technologies, or a combination thereof (see U.S. Pat. Nos. 4,902,614, 4,543,439, and 4,411,993; see, also *Monoclonal Antibodies, Hybridomas: A New Dimension in Biological Analyses*, Plenum Press, Kennett, McKearn, and Bechtol (eds.), 1980, and Harlow et al., *Antibodies: A Laboratory Manual*, Cold Spring Harbor Laboratory Press, 2nd ed. 1988). Suitable techniques that additionally may be employed in the method including antigen affinity purification, non-denaturing gel purification, HPLC or RP-HPLC, purification on protein A column, or any combination of these techniques. The antibody isotype can be determined using an ELISA assay, for example, a human Ig can be identified using mouse Ig-absorbed anti-human Ig.

Animals which may be immunized include mice, rabbits, rats, sheep, cows or steer, goats, or guinea pigs; such animals include those genetically modified to include human IgG gene loci. Such animals can therefore be used to produce antibodies in accordance with the invention. Additionally, to increase the immune response, antigen can be coupled to another protein such as ovalbumin or keyhole limpet hemocyanin (KLH), thyroglobulin and tetanus toxoid, or mixed with an adjuvant such as Freund's complete or incomplete adjuvant. Initial and any optional subsequent immunization may be through intraperitoneal, intramuscular, intraocular, or subcutaneous routes. Subsequent immunizations may be at the same or at different concentrations of antigen preparation, and may be at regular or irregular intervals.

Compositions of the invention, including invention polypeptides and antibodies, such as polypeptides having an amino acid sequence including a binding site for BTLA, and ligands (e.g., polypeptides and peptidomimetics, antibodies, small molecules, etc.) that bind to a binding site for BTLA, can be used to modulate a response, activity or function, selectively or non-selectively, mediated by or associated with BTLA or HVEM, or any molecule (e.g., protein) that binds to BTLA or HVEM (e.g., LIGHT (p30), LTα, glycoprotein D of herpes simplex virus (gD), and so forth), and one or more of the various associated signal transduction pathway(s) and consequent immunological responses and processes. Thus, invention compositions can be used to selectively or non-selectively modulate a response, activity or function mediated by or associated with BTLA or HVEM, or any molecule (e.g., protein) that binds to BTLA or HVEM (e.g., LIGHT (p30), LTα, and so forth), and associated signaling pathway(s), in solid phase, in solution, in vitro, ex vivo and in vivo.

Compositions of the invention, including invention polypeptides and antibodies, such as polypeptides having an amino acid sequence including a binding site for BTLA, and ligands (e.g., polypeptides and peptidomimetics, antibodies, small molecules, etc.) that bind to a binding site for BTLA, but do not bind to or modulate one or more of LIGHT (p30), LTα, glycoprotein D of herpes simplex virus (gD), and so forth, can be used to selectively modulate a response, activity or function mediated by or associated with BTLA or HVEM, without significantly affecting one or more signaling pathway(s) associated with LIGHT (p30), LTα and glycoprotein D of herpes simplex virus (gD). Thus, invention compositions can be used to modulate a response, activity or function mediated by or associated with BTLA or HVEM, without significantly modulating a signaling pathway(s) associated with LIGHT (p30), LTα and glycoprotein D of herpes simplex virus (gD), in solid phase, in solution, in vitro, ex vivo and in vivo.

In accordance with the invention, there are provided methods of selectively modulating a response mediated or associated with immunoregulatory molecule B-T lymphocyte attenuator (BTLA) activity or expression, without destroying binding between HVEM and LIGHT or HVEM and LTα. In one embodiment, a method includes contacting HVEM with a ligand (e.g., polypeptide, peptidomimetic, antibody, small molecule, etc.) that binds to HVEM binding site for immunoregulatory molecule B-T lymphocyte attenuator (BTLA) to modulate binding of BTLA to the HVEM binding site, thereby modulating a response mediated or associated with immunoregulatory molecule B-T lymphocyte attenuator (BTLA) activity or expression. In one aspect, a ligand includes an antibody or a BTLA sequence that binds to HVEM binding site for immunoregulatory molecule B-T lymphocyte attenuator (BTLA). In a particular aspect, an antibody is an agonist or antagonist (e.g., stimulates or inhibits) of BTLA binding to HVEM or HVEM activity. In additional aspects, a ligand increases or reduces a response mediated or associated with immunoregulatory molecule B-T lymphocyte attenuator (BTLA) binding to HVEM (e.g., lymphocyte or hematopoetic cell proliferation or inflammation). In further aspects, a ligand increases or reduces proliferation, survival, differentiation, death, or activity of T cells, antigen presenting cells (e.g., dendritic cells) or B cells.

In accordance with the invention, there are also provided methods of selectively modulating a response mediated or associated with LIGHT (p30) activity or expression. In one embodiment, a method includes contacting LIGHT (p30) with a ligand (e.g., polypeptide, peptidomimetic, antibody, small molecule, etc.) that binds to and modulates a response mediated or associated with LIGHT (p30), but exhibits no detectable binding or reduced binding to immunoregulatory molecule B-T lymphocyte attenuator (BTLA) to the extent that binding modulates a response mediated or associated with immunoregulatory molecule B-T lymphocyte attenuator (BTLA) activity, thereby selectively modulating a response mediated or associated with LIGHT (p30) activity or expression. In various aspects, a ligand includes a polypeptide or peptidomimetic having an amino acid sequence consisting of an HVEM sequence with a substitution that reduces or destroys bind to BTLA, but does not destroy binding to LIGHT (p30). In a particular aspect, an HVEM amino acid sequence has an amino acid substitution of an F for a Y residue (Y61F), an A for a K residue (K64A), or an A for an E residue (E65A), with reference to residue positions indicated in FIG. 6.

In accordance with the invention, there are further provided methods of selectively modulating (e.g., increasing or reducing) a response mediated or associated with immunoregulatory molecule B-T lymphocyte attenuator (BTLA) activity or expression. In one embodiment, a method includes contacting BTLA with a ligand (e.g., polypeptide, peptidomimetic, antibody, small molecule, etc.) that modulates a response mediated or associated with immunoregulatory molecule B-T lymphocyte attenuator (BTLA) activity or expression. In various aspects, a ligand includes an antibody or a BTLA sequence that binds to HVEM (e.g., an agonist or antagonist of BTLA binding to HVEM or BTLA activity). In various aspects, a ligand includes an antibody or an HVEM, UL144, CD27, 41BB or OX40 sequence that binds to BTLA.

Exemplary responses mediated or associated with immunoregulatory molecule B-T lymphocyte attenuator (BTLA) activity or expression include lymphocyte or hematopoetic cell proliferation or inflammation. More particularly, responses that can be modulated in accordance with the invention include proliferation, survival, differentiation, death, or activity of T cells, antigen presenting cells (e.g., dendritic cells) and B cells. Non-limiting representative activities include secretion of a cytokine (e.g., TNF, lymphotoxin (LT)-alpha, LT-beta, LIGHT (p30), a ligand for CD27, OX40, 41BB), chemokine (e.g., CCL21, 19, or CXCL13), interleukin (e.g., IL10, IL2, IL7, or IL15) or interferon (e.g., type 1, or Interferon-gamma). Additional non-limiting representative activities include cytotoxic and helper activity of activated T cells, and B cell production of antibody.

The term "contacting" means direct or indirect binding or interaction between two or more entities (e.g., between a BTLA binding site, e.g., HVEM, UL144, etc., and BTLA, a cell). Contacting as used herein includes in solution, in solid phase, in vitro, ex vivo, in a cell and in vivo. Contacting in vivo can be referred to as administering, or administration.

As set forth herein, a response or function of BTLA is to provide an inhibitory signal to T cells, antigen presenting cells (e.g., dendritic cells) or B cells. Thus, in accordance with the invention, there are provided methods of inhibiting, reducing or preventing proliferation, survival, differentiation, death, or activity of T cells, antigen presenting cells or B cells.

In one embodiment, a method includes contacting BTLA with an amount of a ligand (e.g., an agonist or antagonist of BTLA binding to HVEM or BTLA activity) that binds to BTLA effective to inhibit, reduce or prevent proliferation, survival, differentiation, death, or activity of T cells, antigen presenting cells or B cells. In particular aspects, a ligand comprises a polypeptide or peptidomimetic. In additional aspects, a ligand binds to one or more of LIGHT (p30) and glycoprotein D of herpes simplex virus (gD). In further additional aspects, a ligand does not bind to one or more of LIGHT (p30) and glycoprotein D of herpes simplex virus (gD).

Ligands useful in accordance with the invention methods include polypeptides and peptidomimetics, such as sequences having a binding site for BTLA, and antibodies that bind to a binding site for BTLA. Exemplary ligands include an HVEM polypeptide or a portion thereof, a human cytomegalovirus (HCMV) UL144 protein or a portion thereof, CD27 or a portion thereof, 41BB or a portion thereof, OX40 or a portion thereof, as well as amino acid sequences with at least about 75%, 80%, 90%, 95% or more homology to the HVEM polypeptide or portion thereof, human cytomegalovirus (HCMV) UL144 protein or portion thereof, CD27 or portion thereof, 41BB or portion thereof, or OX40 or portion thereof.

Compositions and methods of the invention are applicable to treating numerous disorders. Disorders treatable in accordance with the invention include disorders in which increasing or reducing a response mediated or associated with immunoregulatory molecule B-T lymphocyte attenuator (BTLA) binding to HVEM, immunoregulatory molecule B-T lymphocyte attenuator (BTLA) activity or expression, LIGHT (p30) binding to HVEM, or modulating a response mediated or associated with LIGHT (p30) activity or expression, can provide a subject with a benefit. Disorders include undesirable or aberrant immune responses, immune disorders and immune diseases.

In accordance with the invention, additionally provided are methods for treating undesirable and aberrant immune responses, immune disorders and immune diseases. In various embodiments, methods include treating chronic and acute forms of undesirable or aberrant inflammatory responses and inflammation; treating chronic and acute forms of undesirable or aberrant proliferation, survival, differentiation, death, or activity of a T cell, antigen presenting cell (e.g., dendritic cell) or B cell. Methods include administering a ligand (e.g., a binding site for BTLA, and sequences having a binding site for BTLA that are selective or non-selective for binding or not binding one or more of LIGHT (p30 polypeptide), LTα, and glycoprotein D (gD) of herpes simplex virus, and antibody that binds to a binding site for BTLA).

As used herein, an "undesirable immune response" or "aberrant immune response" refers to any immune response, activity or function that is greater or less than desired or physiologically normal. An undesirable immune response, function or activity can be a normal response, function or activity. Thus, normal immune responses so long as they are undesirable, even if not considered aberrant, are included within the meaning of these terms. An undesirable immune response, function or activity can also be an abnormal response, function or activity. An abnormal (aberrant) immune response, function or activity deviates from normal. Undesirable and aberrant immune responses can be humoral, cell-mediated or a combination thereof, either chronic or acute.

One non-limiting example of an undesirable or aberrant immune response is where the immune response is hyperresponsive, such as in the case of an autoimmune disorder or disease. Another example of an undesirable or aberrant immune response is where an immune response leads to acute or chronic inflammatory response or inflammation in any tissue or organ, such as an allergy (e.g., allergic asthma). Yet another example of an undesirable or aberrant immune response is where an immune response leads to destruction of cells, tissue or organ, such as a transplant, as in graft vs. host disease. Still another example of an undesirable or aberrant immune response is where the immune response is hyporesponsive, such as where response to an antigen is less than desired, e.g., tolerance has occurred. For example, tolerance to a pathogen can result in increased susceptibility to or a more severe infection, and tolerance to a tumor-associated antigen (TAA) is thought to contribute to the ability of tumors to evade immune surveillance thereby surviving and proliferating in afflicted subjects.

The terms "immune disorder" and "immune disease" mean, an immune function or activity, that is greater than (e.g., autoimmunity) or less than (e.g., immunodeficiency) desired, and which is characterized by different physiological symptoms or abnormalities, depending upon the disorder or disease. Particular non-limiting examples of immune disorders and diseases to which the invention applies include autoimmune disorders and immunodeficiencies. Autoimmune disorders are generally characterized as an undesirable or aberrant increased or inappropriate response, activity or function of the immune system. Immunodeficiencies are generally characterized by decreased or insufficient humoral or cell-mediated immune responsiveness or memory, or undesirable tolerance. Disorders and diseases that can be treated in accordance with the invention include, but are not limited to, disorders and disease that cause cell or tissue/organ damage in the subject.

In accordance with the invention, additionally provided are methods for treating autoimmune disorders in a subject having or at risk of having an autoimmune disorder. In one embodiment, a method includes administering to a subject a composition of the invention, such as a polypeptide having an amino acid sequence that includes a binding site for BTLA (e.g., a polypeptide such as an HVEM, UL144, CD27, 41BB or OX40 amino acid sequence, or an antibody), or a ligand (e.g., an amino acid sequence or an antibody) that binds to a binding site for BTLA, sufficient to treat the autoimmune disorder.

Exemplary autoimmune disorders treatable in accordance with the invention include rheumatoid arthritis, juvenile rheumatoid arthritis, osteoarthritis, psoriatic arthritis, diabetes mellitus, multiple sclerosis (MS), encephalomyelitis, myasthenia gravis, systemic lupus erythematosus (SLE), autoimmune thyroiditis, atopic dermatitis, eczematous dermatitis, psoriasis, Sjören's Syndrome, Crohn's disease, inflammatory bowel disease (IBD), aphthous ulcer, iritis, conjunctivitis, keratoconjunctivitis, ulcerative colitis, asthma, allergic asthma, cutaneous lupus erythematosus, scleroderma, vaginitis, proctitis, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, interstitial lung fibrosis, Hashimoto's thyroiditis, autoimmune polyglandular syndrome, insulin-dependent diabetes mellitus (IDDM, type I diabetes), insulin-resistant diabetes mellitus (type II diabetes), immune-mediated infertility, autoimmune Addison's disease, pemphigus vulgaris, pemphigus foliaceus, dermatitis herpetiformis, autoimmune alopecia, Vitiligo, autoimmune hemolytic anemia, autoimmune thrombocytopenic purpura, pernicious anemia, Guillain-Barre syndrome, Stiff-man syndrome, acute rheumatic fever, sympathetic ophthalmia, Goodpasture's syndrome, systemic necrotizing vasculitis, antiphospholipid syndrome and allergies (e.g., allergic asthma).

In accordance with the invention, additionally provided are methods for treating immunodeficiency, chronic or acute, in a subject having or at risk of having chronic or acute immunodeficiency. In one embodiment, a method includes administering to a subject a composition of the invention, such as a polypeptide having an amino acid sequence that includes a binding site for BTLA (e.g., a polypeptide such as an HVEM, UL144, CD27, 41BB or OX40 amino acid sequence, or an antibody), or a ligand (e.g., an amino acid sequence or an antibody) that binds to a binding site for BTLA, sufficient to treat chronic or acute immunodeficiency.

Exemplary immunodeficiency treatable in accordance with the invention include severe combined immunodeficiency (SCID) such as recombinase activating gene (RAG ½) deficiency, adenosine deaminase (ADA) deficiency, interleukin receptor γ chain ($\gamma_c$) deficiency, Janus-associated kinase 3 (JAK3) deficiency and reticular dysgenesis; primary T cell immunodeficiency such as DiGeorge syndrome, Nude syndrome, T cell receptor deficiency, MHC class II deficiency, TAP-2 deficiency (MHC class I deficiency), ZAP70 tyrosine kinase deficiency and purine nucleotide phosphorylase (PNP) deficiency; predominantly antibody deficiencies such as X-linked agammaglobulinemia (Bruton's tyrosine kinase deficiency); autosomal recessive agammaglobulinemia such as Mu heavy chain deficiency; surrogate light chain (γ5/14.1) deficiency; Hyper-IgM syndrome either X-linked (CD40 ligand deficiency) and others; Ig heavy chain gene deletion; IgA deficiency; deficiency of IgG subclasses (with or without IgA deficiency); common variable immunodeficiency (CVID); antibody deficiency with normal immunoglobulins; transient hypogammaglobulinemia of infancy; interferon γ receptor (IFNGR1, IFNGR2) deficiency; interleukin 12 and interleukin 12 receptor deficiency; immunodeficiency with thymoma; Wiskott-Aldrich syndrome (WAS protein deficiency); ataxia telangiectasia (ATM deficiency); X-linked lymphoproliferative syndrome (SH2D1A/SAP deficiency); and hyper IgE syndrome). Exemplary immunodeficiencies also include disorders associated with or secondary to another disease (e.g., chromosomal instability or defective repair such as Bloom syndrome, Xeroderma pigmentosum, Fanconi anemia, ICF syndrome, Nijmegen breakage syndrome and Seckel syndrome; chromosomal defects such as Down syndrome (Trisomy 21), Turner syndrome and Deletions or rings of chromosome 18 (18p- and 18q-); skeletal abnormalities such as short-limbed skeletal dysplasia (short-limbed dwarfism) and cartilage-hair hypoplasia (metaphyseal chondroplasia); immunodeficiency associated with generalized growth retardation such as Schimke immuno-osseous dysplasia, Dubowitz syndrome, Kyphomelic dysplasia with SCID, Mulibrey's nannism, Growth retardation, facial anomalies and immunodeficiency and Progeria (Hutchinson-Gilford syndrome); immunodeficiency with dermatologic defects such as ectrodactyly-ectodermal dysplasia-clefting syndrome, immunodeficiency with absent thumbs, anosmia and ichthyosis, partial albinism, Dyskeratosis congenita, Netherton syndrome, Anhidrotic ectodermal dysplasia, Papillon-Lefevre syndrome and congenital ichthyosis; hereditary metabolic defects such as acrodermatitis enteropathica, transcobalamin 2 deficiency, type 1 hereditary orotic aciduria, intractable diarrhea, abnormal facies, trichorrhexis and immunodeficiency, methylmalonic acidemia, biotin dependent carboxylase deficiency, mannosidosis, glycogen storage disease, type 1b, Chediak-Higashi syndrome; hypercatabolism of immunoglobulin such as familial hypercatabolism, intestinal lymphangiectasia; chronic muco-cutaneous candidiasis; hereditary or congenital hyposplenia or asplenia; and Ivermark syndrome.

In accordance with the invention, additionally provided are methods for treating (e.g., reducing or inhibiting) an inflammatory response or inflammation, chronic or acute, in a subject having or at risk of having an inflammatory response or inflammation. In one embodiment, a method includes administering to a subject a composition of the invention, such as a polypeptide having an amino acid sequence that includes a binding site for BTLA (e.g., a polypeptide such as an HVEM, UL144, CD27, 41BB or OX40 amino acid sequence, or an antibody), or a ligand (e.g., an amino acid sequence or an antibody) that binds to a binding site for BTLA, sufficient to treat (e.g., reduce or inhibit) a chronic or acute inflammatory response or inflammation.

Exemplary inflammatory responses and inflammation treatable in accordance with the invention include inflammatory responses and inflammation caused by or associated with proliferation, survival, differentiation, death, or activity of T cells, antigen presenting cells (e.g., dendritic cells) or B cells. In one aspect, an inflammatory response or inflammation is, at least in part, mediated by a T cell. Methods (e.g., treatment) can result in a reduction in occurrence, frequency, severity, progression, or duration of a symptom of an inflammatory response or inflammation. Exemplary symptoms include one or more of swelling, pain, rash, headache, fever, nausea, skeletal joint stiffness, or tissue or cell damage.

Undesirable or aberrant inflammation or an inflammatory response, mediated by cellular or humoral immunity, may cause, directly or indirectly, cell, tissue or organ damage, either to multiple cells, tissues or organs, or specifically to a single cell type, tissue type or organ. Exemplary tissues and organs that can exhibit damage include epidermal or mucosal tissue, gut, bowel, pancreas, thymus, liver, kidney, spleen, skin, or a skeletal joint (e.g., knee, ankle, hip, shoulder, wrist, finger, toe, or elbow). Treatment in accordance with the invention can result in reducing, inhibiting or preventing progression or worsening of tissue damage. Such treatments can in turn lead to regeneration of a damaged organ or tissue, e.g., skin, mucosum, liver.

Undesirable or aberrant inflammation or an inflammatory response, mediated by cellular or humoral immunity, may cause, directly or indirectly, damage to a cell, tissue or organ transplant. Treatment in accordance with the invention can result in reducing, inhibiting or preventing damage to a transplanted cell, tissue or organ (e.g., graft vs. host disease).

In accordance with the invention, additionally provided are methods for inhibiting, reducing or preventing an inflammatory response or inflammation, chronic or acute, in a subject having a cell, tissue or organ transplant or a candidate for a cell, tissue or organ transplant. In one embodiment, a method includes administering to a subject a composition of the invention, such as a polypeptide having an amino acid sequence that includes a binding site for BTLA (e.g., a polypeptide such as an HVEM, UL144, CD27, 41BB or OX40 amino acid sequence, or an antibody), or a ligand (e.g., an amino acid sequence or an antibody) that binds to a binding site for BTLA, sufficient to inhibit, reduce or prevent a chronic or acute inflammatory response or inflammation directed against a transplanted cell, tissue or organ. Methods can be performed prior to, concurrently with, immediately following or after transplant of a cell, tissue or organ in a subject.

As used herein, the terms "transplant," "transplantation" and grammatical variations thereof mean grafting, implanting, or transplanting a cell, tissue or organ from one part of the body to another part, or from one individual or animal to another individual or animal. The transplanted cell, tissue or organ may therefore be an allograft or xenograft. Exemplary transplant cells include neural cells. Exemplary transplant tissues include skin, blood vessel, eye and bone marrow. Exemplary transplant organs include heart, lung, liver and kidney. The term also includes genetically modified cells, tissue and organs, e.g., by ex vivo gene therapy in which the transformed cells, tissue and organs are obtained or derived from a subject (e.g., human or animal) who then receives the transplant from a different subject (e.g., human or animal).

Methods of the invention that include treatment of an inflammatory response or inflammation include reducing, inhibiting or preventing occurrence, progression, severity, frequency or duration of a symptom or characteristic of an inflammatory response or inflammation. At the whole body, regional or local level, an inflammatory response or inflammation is generally characterized by swelling, pain, headache, fever, nausea, skeletal joint stiffness or lack of mobility, rash, redness or other discoloration. At the cellular level, an inflammatory response or inflammation is characterized by one or more of cell infiltration of the region, production of antibodies (e.g., autoantibodies), production of cytokines, lymphokines, chemokines, interferons and interleukins, cell growth and maturation factors (e.g., differentiation factors), cell proliferation, cell differentiation, cell accumulation or migration and cell, tissue or organ damage. Thus, treatment will reduce, inhibit or prevent occurrence, progression, severity, frequency or duration of any one or more of such symptoms or characteristics of an inflammatory response or inflammation.

In accordance with the invention, additionally provided are methods for treating a pathogen (exposure to or infection with). In one embodiment, a method includes administering to a subject a composition of the invention, such as a polypeptide having an amino acid sequence that includes a binding site for BTLA (e.g., a polypeptide such as an HVEM, UL144, CD27, 41BB or OX40 amino acid sequence, or an antibody), or a ligand (e.g., an amino acid sequence or an antibody) that binds to a binding site for BTLA, sufficient to treat a pathogen infection. Exemplary pathogens include bacteria, virus, fungus, prion or parasite. Exemplary bacteria include *bacillus* (e.g., *Mycobacterium tuberculosis*). Exemplary virus include a lentivirus, HIV, hepatitis (e.g., A, B, or C), vaccinia, influenza and herpesvirus (e.g. human). Exemplary fungus include *pneumocystis carrini*.

Compositions and methods of the invention can be used to stimulate an immune response. For example, proliferation, survival, differentiation, or activity of a T cell, antigen presenting cell (e.g., dendritic cell) or B cell can be stimulated, increased or induced using compositions of the invention. Thus, compositions of the invention are also applicable to treating hyperproliferative disorders.

In accordance with the invention, provided are methods of treating a hyperproliferative disorder. The term "hyperproliferative disorder" refers to any undesirable or aberrant cell survival (e.g., failure to undergo programmed cell death or apoptosis), growth or proliferation. Such disorders include benign hyperplasias, non-metastatic tumors and metastatic tumors. Such disorders can affect any cell, tissue, organ in a subject. Such disorders can be present in a subject, locally, regionally or systemically.

Compositions and methods of the invention are applicable to metastatic or non-metastatic tumor, cancer, malignancy or neoplasia of any cell, organ or tissue origin. As used herein, the terms "tumor," "cancer," "malignancy," and "neoplasia" are used interchangeably and refer to a cell or population of cells whose growth, proliferation or survival is greater than growth, proliferation or survival of a normal counterpart cell, e.g. a cell proliferative or differentiative disorder. Such disorders can affect virtually any cell or tissue type, e.g., carcinoma, sarcoma, melanoma, neural, and reticuloendothelial or haematopoietic neoplastic disorders (e.g., myeloma, lymphoma or leukemia). A tumor can arise from a multitude of tissues and organs, including but not limited to breast, lung, thyroid, head and neck, brain, lymphoid, gastrointestinal (mouth, esophagus, stomach, small intestine, colon, rectum), genito-urinary tract (uterus, ovary, cervix, bladder, testicle, penis, prostate), kidney, pancreas, liver, bone, muscle, skin, which may or may not metastasize to other secondary sites.

The tumor may be in any stage, e.g., early or advanced, such as a stage I, II, III, IV or V tumor. The tumor may have been subject to a prior treatment or be stabilized (non-progressing) or in remission.

Cells comprising a tumor may be aggregated in a cell mass or be dispersed. A "solid tumor" refers to neoplasia or metastasis that typically aggregates together and forms a mass. Specific non-limiting examples include visceral tumors such as melanomas, breast, pancreatic, uterine and ovarian cancers, testicular cancer, including seminomas, gastric or colon cancer, hepatomas, adrenal, renal and bladder carcinomas, lung, head and neck cancers and brain tumors/cancers.

Carcinomas, which refer to malignancies of epithelial or endocrine tissue, include respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from the uterine cervix, lung, prostate, breast, head and neck, colon, pancreas, testes, adrenal, kidney, esophagus, stomach, liver and ovary. The term also includes carcinosarcomas, e.g., which include malignant tumors composed of carcinomatous and sarcomatous tissues. Adenocarcinoma includes a carcinoma of a glandular tissue, or in which the tumor forms a gland like structure.

Melanoma, which refers to malignant tumors of melanocytes and other cells derived from pigment cell origin that may arise in the skin, the eye (including retina), or other regions of the body, include the cells derived from the neural crest that also gives rise to the melanocyte lineage. A premalignant form of melanoma, known as dysplastic nevus or dysplastic nevus syndrome, is associated with melanoma development.

Sarcomas refer to malignant tumors of mesenchymal cell origin. Exemplary sarcomas include for example, lymphosarcoma, liposarcoma, osteosarcoma, chondrosarcoma, leiomyosarcoma, rhabdomyosarcoma and fibrosarcoma.

Neural neoplasias include glioma, glioblastoma, meningioma, neuroblastoma, retinoblastoma, astrocytoma, oligodendrocytoma A "liquid tumor," which refers to neoplasia that is diffuse in nature, as they do not typically form a solid mass. Particular examples include neoplasia of the reticuloendothelial or haematopoetic system, such as lymphomas, myelomas and leukemias. Non-limiting examples of leukemias include acute and chronic lymphoblastic, myeolblastic and multiple myeloma. Typically, such diseases arise from poorly differentiated acute leukemias, e.g., erythroblastic leukemia and acute megakaryoblastic leukemia. Specific myeloid disorders include, but are not limited to, acute promyeloid leukemia (APML), acute myelogenous leukemia (AML) and chronic myelogenous leukemia (CML). Lymphoid malignancies include, but are not limited to, acute lymphoblastic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Specific malignant lymphomas include, non-Hodgkin lymphoma and variants, peripheral T cell lymphomas, adult T cell leukemia/lymphoma (Am), cutaneous T-cell lymphoma (CTCL), large granular lymphocytic leukemia (LGF), Hodgkin's disease and Reed-Sternberg disease.

Compositions and methods of the invention include antiproliferative, anti-tumor, anti-cancer, anti-neoplastic treatments, protocols and therapies, which include any other composition, treatment, protocol or therapeutic regimen that inhibits, decreases, retards, slows, reduces or prevents a hyperproliferative disorder, such as tumor, cancer or neoplastic growth, progression, metastasis, proliferation or survival, in vitro or in vivo. Particular non-limiting examples of an anti-proliferative (e.g., tumor) therapy include chemotherapy, immunotherapy, radiotherapy (ionizing or chemical), local thermal (hyperthermia) therapy and surgical resection. Any composition, treatment, protocol, therapy or regimen having an anti-cell proliferative activity or effect can be used in combination with a composition or method of the invention.

Anti-proliferative or anti-tumor compositions, therapies, protocols or treatments can operate by biological mechanisms that prevent, disrupt, interrupt, inhibit or delay cell cycle progression or cell proliferation; stimulate or enhance apoptosis or cell death, inhibit nucleic acid or protein synthesis or metabolism, inhibit cell division, or decrease, reduce or inhibit cell survival, or production or utilization of a necessary cell survival factor, growth factor or signaling pathway (extracellular or intracellular). Non-limiting examples of chemical agent classes having anti-cell proliferative and anti-tumor activities include alkylating agents, anti-metabolites, plant extracts, plant alkaloids, nitrosoureas, hormones, nucleoside and nucleotide analogues. Specific examples of drugs having anti-cell proliferative and anti-tumor activities include cyclophosphamide, azathioprine, cyclosporin A, prednisolone, melphalan, chlorambucil, mechlorethamine, busulphan, methotrexate, 6-mercaptopurine, thioguanine, 5-fluorouracil, cytosine arabinoside, AZT, 5-azacytidine (5-AZC) and 5-azacytidine related compounds such as decitabine (5-aza-2'deoxycytidine), cytarabine, 1-beta-D-arabinofuranosyl-5-azacytosine and dihydro-5-azacytidine, bleomycin, actinomycin D, mithramycin, mitomycin C, carmustine, lomustine, semustine, streptozotocin, hydroxyurea, cisplatin, mitotane, procarbazine, dacarbazine, taxol, vinblastine, vincristine, doxorubicin and dibromomannitol.

Additional agents that are applicable in the invention compositions and methods are known in the art and can be employed. For example, monoclonal antibodies that bind tumor cells or oncogene products, such as Rituxan® and Herceptin (Trastuzumab) (anti-Her-2 neu antibody), Bevacizumab (Avastin), Zevalin, Bexxar, Oncolym, 17-1A (Edrecolomab), 3F8 (anti-neuroblastoma antibody), MDX-CTLA4, Campath®, Mylotarg, IMC-C225 (Cetuximab), aurinstatin conjugates of cBR96 and cAC10 (Doronina et al. (2003). Nat Biotechnol 21:778) can be used in combination with, inter alia, a polypeptide having an amino acid sequence that includes a binding site for BTLA (e.g., a polypeptide such as an HVEM, UL144, CD27, 41BB or OX40 amino acid sequence, or an antibody), or a ligand (e.g., an amino acid sequence or an antibody) that binds to a binding site for BTLA, in accordance with the invention.

In accordance with the invention, methods of treating a tumor, methods of treating a subject having or at risk of having a tumor, and methods of increasing effectiveness or improving an anti-tumor therapy are provided. In respective embodiments, a method includes administering to a subject with or at risk of a tumor an amount of a polypeptide having an amino acid sequence that includes a binding site for BTLA (e.g., a polypeptide such as an HVEM, UL144, CD27, 41BB or OX40 amino acid sequence, or an antibody), or a ligand (e.g., an amino acid sequence or an antibody) that binds to a binding site for BTLA, sufficient to treat the tumor; administering to the subject an amount of a polypeptide having an amino acid sequence that includes a binding site for BTLA (e.g., a polypeptide such as an HVEM, UL144, CD27, 41BB or OX40 amino acid sequence, or an antibody), or a ligand (e.g., an amino acid sequence or an antibody) that binds to a binding site for BTLA, sufficient to treat the subject; and administering to a subject that is undergoing or has undergone tumor therapy, an amount of a polypeptide having an amino acid sequence that includes a binding site for BTLA (e.g., a polypeptide such as an HVEM, UL144, CD27, 41BB or OX40 amino acid sequence, or an antibody), or a ligand (e.g., an amino acid sequence or an antibody) that binds to a binding site for BTLA, sufficient to increase effectiveness of the anti-tumor therapy.

Methods of the invention may be practiced prior to (i.e. prophylaxis), concurrently with or after evidence of the disorder, disease or condition begins (e.g., one or more symptoms). For example, a method may be performed before infection with a pathogen, or before cell, tissue or organ transplantation. Administering a composition prior to, concurrently with or immediately following development of a symptom may decrease the occurrence, frequency, severity, progression, or duration of one or more symptoms of the disorder, disease or condition in the subject. In addition, administering a composition prior to, concurrently with or immediately following development of one or more symptoms may decrease or prevent damage to cells, tissues and organs that occurs, for example, during an undesirable or aberrant immune response, disorder or disease (e.g., autoimmunity or immunodeficiency).

Compositions and the methods of the invention, such as treatment methods, can provide a detectable or measurable therapeutic benefit or improvement to a subject. A therapeutic benefit or improvement is any measurable or detectable, objective or subjective, transient, temporary, or longer-term benefit to the subject or improvement in the condition, disorder or disease, an adverse symptom, consequence or underlying cause, of any degree, in a tissue, organ, cell or cell population of the subject. Therapeutic benefits and improvements include, but are not limited to, reducing or decreasing occurrence, frequency, severity, progression, or duration of one or more symptoms or complications associated with a disorder, disease or condition, or an underlying cause or consequential effect of the disorder, disease or condition. Compositions and methods of the invention therefore include providing a therapeutic benefit or improvement to a subject.

In the methods of the invention in which a therapeutic benefit or improvement is a desired outcome, a composition of the invention such as a polypeptide having an amino acid sequence that includes a binding site for BTLA (e.g., a polypeptide such as an HVEM, UL144, CD27, 41BB or OX40 amino acid sequence, or an antibody), or a ligand (e.g., an amino acid sequence or an antibody) that binds to a binding site for BTLA, can be administered in a sufficient or effective amount to a subject in need thereof. An "amount sufficient" or "amount effective" refers to an amount that provides, in single or multiple doses, alone or in combination, with one or more other compositions (therapeutic agents such as a drug), treatments, protocols, or therapeutic regimens agents, a detectable response of any duration of time (long or short term), a desired outcome in or a benefit to a subject of any measurable or detectable degree or for any duration of time (e.g., for minutes, hours, days, months, years, or cured). The doses or "sufficient amount" or "effective amount" for treatment (e.g., to provide a therapeutic benefit or improvement) typically are effective to ameliorate a disorder, disease or condition, or one, multiple or all adverse symptoms, consequences or complications of the disorder, disease or condition, to a measurable extent, although reducing or inhibiting a progression or worsening of the disorder, disease or condition or a symptom, is a satisfactory outcome.

The term "ameliorate" means a detectable improvement in a subject's condition. A detectable improvement includes a subjective or objective reduction in the occurrence, frequency, severity, progression, or duration of a symptom caused by or associated with a disorder, disease or condition, an improvement in an underlying cause or a consequence of the disorder, disease or condition, or a reversal of the disorder, disease or condition.

Treatment can therefore result in inhibiting, reducing or preventing a disorder, disease or condition, or an associated symptom or consequence, or underlying cause; inhibiting, reducing or preventing a progression or worsening of a disorder, disease, condition, symptom or consequence, or underlying cause; or further deterioration or occurrence of one or more additional symptoms of the disorder, disease condition, or symptom. Thus, a successful treatment outcome leads to a "therapeutic effect," or "benefit" or inhibiting, reducing or preventing the occurrence, frequency, severity, progression, or duration of one or more symptoms or underlying causes or consequences of a condition, disorder, disease or symptom in the subject. Treatment methods affecting one or more underlying causes of the condition, disorder, disease or symptom are therefore considered to be beneficial. Stabilizing a disorder or condition is also a successful treatment outcome.

A therapeutic benefit or improvement therefore need not be complete ablation of any one, most or all symptoms, complications, consequences or underlying causes associated with the condition, disorder or disease. Thus, a satisfactory endpoint is achieved when there is an incremental improvement in a subject's condition, or a partial reduction in the occurrence, frequency, severity, progression, or duration, or inhibition or reversal, of one or more associated adverse symptoms or complications or consequences or underlying causes, worsening or progression (e.g., stabilizing one or more symptoms or complications of the condition, disorder or disease), of one or more of the physiological, biochemical or cellular manifestations or characteristics of the disorder or disease, over a short or long duration of time (hours, days, weeks, months, etc.).

An amount sufficient or an amount effective can but need not be provided in a single administration and, can but need not be, administered alone or in combination with another composition (e.g., agent), treatment, protocol or therapeutic regimen. For example, the amount may be proportionally increased as indicated by the need of the subject, status of the disorder, disease or condition treated or the side effects of treatment. In addition, an amount sufficient or an amount effective need not be sufficient or effective if given in single or multiple doses without a second composition (e.g., agent), treatment, protocol or therapeutic regimen, since additional doses, amounts or duration above and beyond such doses, or additional compositions (e.g., agents), treatments, protocols or therapeutic regimens may be included in order to be considered effective or sufficient in a given subject. Amounts considered sufficient also include amounts that result in a reduction of the use of another treatment, therapeutic regimen or protocol.

An amount sufficient or an amount effective need not be effective in each and every subject treated, prophylactically or therapeutically, nor a majority of treated subjects in a given group or population. An amount sufficient or an amount effective means sufficiency or effectiveness in a particular subject, not a group or the general population. As is typical for such methods, some subjects will exhibit a greater or less response to a treatment method.

In the case of an immune disorder or disease, treatment methods include reducing or increasing numbers or an activity of lymphocytes (e.g., T cells, antigen presenting cells or B cells) towards physiologically normal baseline levels is considered a successful treatment outcome. Similarly, a reduction or increase of circulating antibodies (e.g., auto-antibodies) considered physiologically normal or beneficial is considered a successful treatment outcome.

Additional examples of a therapeutic benefit for an undesirable or aberrant immune response, immune disorder or immune disease is an improvement in a histopathological change caused by or associated with the immune response, disorder or disease. For example, preventing further or reducing skeletal joint infiltration or tissue destruction, or pancreas, thymus, kidney, liver, spleen, epidermal (skin) or mucosal tissue tissue, gut or bowel infiltration or tissue destruction.

A therapeutic benefit can also include reducing susceptibility of a subject to an acute or chronic undesirable or aberrant immune response, immune disorder or immune disease (e.g., autoimmunity, inflammation, immunodeficiency, etc.) or hastening or accelerating recovery from undesirable or aberrant immune response, immune disorder or immune disease (e.g., autoimmunity, inflammation, immunodeficiency, etc.)

Particular examples of therapeutic benefit or improvement for a hyperproliferative disorder include a reduction in cell volume (e.g., tumor size or cell mass), inhibiting an increase in cell volume, a slowing or inhibition of hyperproliferative disorder worsening or progression, stimulating cell lysis or apoptosis, reducing or inhibiting tumor metastasis, reduced mortality, prolonging lifespan. Adverse symptoms and complications associated with a hyperproliferative disorder (e.g., tumor, neoplasia, and cancer) that can be reduced or decreased include, for example, pain, nausea, lack of appetite, weakness and lethargy. Thus, inhibiting or delaying an increase in tumor cell mass or metastasis (stabilization of a disease) can increase lifespan (reduce mortality) even if only for a few days, weeks or months, even though complete ablation of the tumor has not resulted. A reduction in the occurrence, frequency, severity, progression, or duration of the underlying disorder or disease, or a symptom of the disorder or disease, such as an improvement in subjective feeling (e.g., increased energy, appetite, reduced nausea, improved mobility or psychological well being, etc.), are all examples of therapeutic benefit or improvement.

For example, a sufficient amount of a polypeptide having an amino acid sequence that includes a binding site for BTLA (e.g., a polypeptide such as an HVEM, UL144, CD27, 41BB or OX40 amino acid sequence, or an antibody), or a ligand (e.g., an amino acid sequence or an antibody) that binds to a binding site for BTLA, is considered as having a therapeutic effect if administration results in less chemotherapeutic drug, radiation or immunotherapy being required for treatment of a hyperproliferative disorder (e.g., a tumor).

Particular non-limiting examples of therapeutic benefit or improvement for a pathogen include reducing or decreasing occurrence, frequency, severity, progression, or duration of one or more symptoms or complications of pathogen infection. Additional particular non-limiting examples of therapeutic benefit or improvement for a pathogen include reducing, inhibiting, decreasing or preventing increases in pathogen titer, pathogen replication, pathogen proliferation, or a pathogen protein or nucleic acid sequence. Further particular non-limiting examples of therapeutic benefit or improvement for a pathogen include stabilizing the condition (i.e., preventing or inhibiting a worsening or progression of a symptom or complication associated with pathogen infection, or progression of the infection). Symptoms or complications associated with pathogen infection whose occurrence, frequency, severity, progression, or duration can be reduced, decreased or prevented are known in the art. A therapeutic benefit can also include reducing susceptibility of a subject to a pathogen infection or hastening or accelerating recovery from pathogen infection. In this regard, a method inhibits pathogen infection of the subject. In various aspects, the antibody is administered prior to (prophylaxis), substantially contemporaneously with or following pathogen exposure or infection of the subject (therapeutic).

As is typical for treatment or therapeutic methods, some subjects will exhibit greater or less response to a given treatment, therapeutic regiment or protocol. Thus, appropriate amounts will depend upon the condition treated (e.g., the type or stage of the tumor), the therapeutic effect desired, as well as the individual subject (e.g., the bioavailability within the subject, gender, age, etc.).

The term "subject" refers to animals, typically mammalian animals, such as humans, non human primates (apes, gibbons, chimpanzees, orangutans, macaques), domestic animals (dogs and cats), farm animals (horses, cows, goats, sheep, pigs) and experimental animal (mouse, rat, rabbit, guinea pig). Subjects include animal disease models, for example, animal models of immune disorders or diseases, such as CIA, EAE or BXSB animal models, as well as tumor models, for studying in vivo a composition of the invention, for example, a polypeptide having an amino acid sequence that includes a binding site for BTLA (e.g., a polypeptide such as an HVEM, UL144, CD27, 41BB or OX40 amino acid sequence, or an antibody), or a ligand (e.g., an amino acid sequence or an antibody) that binds to a binding site for BTLA.

Subjects appropriate for treatment include those having or at risk of having an undesirable or aberrant immune response, immune disorder or immune disease, those undergoing treatment for an undesirable or aberrant immune response, immune disorder or immune disease as well as those who are undergoing or have undergone treatment or therapy for an undesirable or aberrant immune response, immune disorder or immune disease, including subjects where the undesirable or aberrant immune response, immune disorder or immune disease is in remission. Specific non-limiting examples include subjects having or at risk of having an immunodeficiency, such as that caused by chemotherapy or radiotherapy (ionizing or chemical) or immune-suppressive therapy following a transplant (e.g., organ or tissue such as heart, liver, lung, bone marrow, etc.). Additional non-limiting examples include subjects having or at risk of having a graft vs. host disease, e.g., a subject that is a candidate for a transplant or a subject undergoing or having received a transplant. Further non-limiting examples include subjects having or at risk of having an acute symptom (inflammatory response or inflammation) associated with an undesirable or aberrant immune response, immune disorder or immune disease, e.g., a subject at risk of an acute symptom associated with an autoimmune disorder (e.g., SLE, rheumatoid arthritis, multiple sclerosis, inflammatory bowel disease, ulcerative colitis, or Crohn's disease).

Subjects appropriate for treatment include those having or at risk of having a tumor cell, those undergoing as well as those who are undergoing or have undergone anti-tumor therapy, including subjects where the tumor is in remission. The invention is therefore applicable to treating a subject who is at risk of a tumor or a complication associated with a tumor, for example, due to tumor reappearance or regrowth following a period of remission.

"At risk" subjects typically have risk factors associated with undesirable or aberrant immune response, immune disorder or immune disease, development of hyperplasia (e.g., a tumor), or exposure to or contact with a pathogen. Risk factors include gender, lifestyle (diet, smoking), occupation (medical and clinical personnel, agricultural and livestock workers), environmental factors (carcinogen exposure), family history (autoimmune disorders, diabetes, etc.), genetic predisposition, etc. For example, subjects at risk for developing melanoma include excess sun exposure (ultraviolet radiation), fair skin, high numbers of naevi (dysplastic nevus), patient phenotype, family history, or a history of a previous melanoma. Subjects at risk for developing cancer can therefore be identified by lifestyle, occupation, environmental factors, family history, and genetic screens for tumor associated genes, gene deletions or gene mutations. Subjects at risk for developing breast cancer lack Brcal, for example. Subjects at risk for developing colon cancer have early age or high frequency polyp formation, or deleted or mutated tumor suppressor genes, such as adenomatous polyposis coli (APC), for example. Subjects at risk for immunodeficiency with hyper-IgM (HIM) have a defect in the gene TNFSF5, found on chromosome X at q26, for example. Susceptibility to autoimmune disease is frequently associated with MHC genotype. For example, in diabetes there is an association with HLA-DR3 and HLA-DR4.

Compositions and methods of the invention may b contacted or provided in vitro, ex vivo or in vivo. Compositions can be administered to provide the intended effect as a single or multiple dosages, for example, in an effective or sufficient amount. Exemplary doses range from about 25-250, 250-500, 500-1000, 1000-2500 or 2500-5000, 5000-25,000, 5000-50,000 pg/kg; from about 50-500, 500-5000, 5000-25,000 or 25,000-50,000 ng/kg; and from about 25-250, 250-500, 500-1000, 1000-2500 or 2500-5000, 5000-25,000, 5000-50,000 mg/kg, on consecutive days, or alternating days or intermittently. Single or multiple doses can be administered on consecutive days, alternating days or intermittently.

Compositions can be administered and methods may be practiced via systemic, regional or local administration, by any route. For example, a polypeptide having an amino acid sequence that includes a binding site for BTLA (e.g., a polypeptide such as an HVEM, UL144, CD27, 41BB or OX40 amino acid sequence, or an antibody), or a ligand (e.g., an amino acid sequence or an antibody) that binds to a binding site for BTLA, may be administered systemically, regionally or locally, intravenously, orally (e.g., ingestion or inhalation), intramuscularly, intraperitoneally, intradermally, subcutaneously, intracavity, intracranially, transdermally (topical), parenterally, e.g. transmucosally or rectally. Compositions and methods of the invention including pharmaceutical formulations can be administered via a (micro)encapsulated delivery system or packaged into an implant for administration.

Invention compositions and methods include pharmaceutical compositions, which refer to "pharmaceutically acceptable" and "physiologically acceptable" carriers, diluents or excipients. As used herein, the term "pharmaceutically acceptable" and "physiologically acceptable," when referring to carriers, diluents or excipients includes solvents (aqueous or non-aqueous), detergents, solutions, emulsions, dispersion media, coatings, isotonic and absorption promoting or delaying agents, compatible with pharmaceutical administration and with the other components of the formulation. Such formulations can be contained in a tablet (coated or uncoated), capsule (hard or soft), microbead, emulsion, powder, granule, crystal, suspension, syrup or elixir.

Pharmaceutical compositions can be formulated to be compatible with a particular route of administration. Compositions for parenteral, intradermal, or subcutaneous administration can include a sterile diluent, such as water, saline solution, fixed oils, polyethylene glycols, glycerine, propylene glycol or other synthetic solvents. The preparation may contain one or more preservatives to prevent microorganism growth (e.g., antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose).

Pharmaceutical compositions for injection include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (e.g., glycerol, propylene glycol, and polyethylene glycol), and suitable mixtures thereof. Fluidity can be maintained, for example, by the use of a coating such as lecithin, or by the use of surfactants. Antibacterial and antifungal agents include, for example, parabens, chlorobutanol, phenol, ascorbic acid and thimerosal. Including an agent that delays absorption, for example, aluminum monostearate and gelatin can prolonged absorption of injectable compositions.

For transmucosal or transdermal administration, penetrants appropriate to the barrier to be permeated are used in the formulation. Such penetrants are known in the art, and include, for example, for transmucosal administration, detergents, bile salts, and fusidic acid derivatives; for transdermal administration, ointments, salves, gels, or creams.

Additional pharmaceutical formulations and delivery systems are known in the art and are applicable in the methods of the invention (see, e.g., *Remington's Pharmaceutical Sciences* (1990) 18th ed., Mack Publishing Co., Easton, Pa.; *The Merck Index* (1996) 12th ed., Merck Publishing Group, Whitehouse, N.J.; *Pharmaceutical Principles of Solid Dosage Forms*, Technonic Publishing Co., Inc., Lancaster, Pa., (1993); and Poznansky, et al., *Drug Delivery Systems*, R. L. Juliano, ed., Oxford, N.Y. (1980), pp. 253-315).

In accordance with the invention, there are provided, methods of identifying (screening) an agent that binds to a herpesvirus entry mediator (HVEM) or a human cytomegalovirus (HCMV) UL144 binding site for immunoregulatory molecule B-T lymphocyte attenuator (BTLA). In one embodiment, a method includes contacting a binding site for immunoregulatory molecule B-T lymphocyte attenuator (BTLA), comprising a portion of full length HVEM polypeptide or human cytomegalovirus (HCMV) UL144 protein, with a test agent; and measuring binding of the test agent to the binding site for immunoregulatory molecule B-T lymphocyte attenuator (BTLA). Binding of the test agent to the binding site identifies the test agent as an agent that binds to a herpesvirus entry mediator (HVEM) or human cytomegalovirus (HCMV) UL144 binding site for immunoregulatory molecule B-T lymphocyte attenuator (BTLA).

In accordance with the invention, there are provide methods of identifying (screening) an agent that inhibits or prevents lymphocyte or hematopoetic cell proliferation or inflammation. In one embodiment, a method includes contacting a binding site for immunoregulatory molecule B-T lymphocyte attenuator (BTLA), comprising a portion of full length HVEM polypeptide or human cytomegalovirus (HCMV) UL144 protein, with a test agent; measuring binding of the test agent to the binding site for immunoregulatory molecule B-T lymphocyte attenuator (BTLA). Binding of the test agent to the binding site identifies the test agent as an agent that binds to a herpesvirus entry mediator (HVEM) binding site for immunoregulatory molecule B-T lymphocyte attenuator (BTLA); and determining whether the test agent inhibits or prevents lymphocyte or hematopoetic cell proliferation or inflammation. Inhibiting or preventing lymphocyte or hematopoetic cell proliferation or inflammation, identifies the test agent as an agent that inhibits or prevents lymphocyte or hematopoetic cell proliferation or inflammation.

Agents suitable for identifying (screening) in the methods of the invention include small molecules (e.g., organic molecules) and polypeptides (e.g., antibodies). BTLA binding sites suitable for identifying (screening) in the methods of the invention include any of the various polypeptide sequences, subsequences and variants for HVEM, UL144, CD27, 41BB and OX40, such as, but not limited to the sequences set forth herein.

In accordance with the invention, there are provide methods of screening a sample for the presence of an HVEM polypeptide sequence that binds to BTLA. In one embodiment, a method includes analyzing the sample for the presence of an HVEM polypeptide sequence that binds to BTLA. In various aspects, the analysis is done by nucleic acid sequencing or nucleic acid hybridization. In additional aspects, the analysis is done by contacting the sample with BTLA, or contacting an HVEM sequence (e.g., a portion or a subsequence or variant of HVEM) with BTLA in order to ascertain (measure) binding between the HVEM sequence and BTLA. Exemplary HVEM sequences include, for example, an HVEM sequence which has an arginine at position 62, a lysine at position 64, or glutamate at position 65. Further aspects include analyzing HVEM for binding to glycoprotein D of herpes simplex virus (gD), binding to LIGHT or for binding to LTα.

In accordance with the invention, there are provide methods of screening a sample for the presence of an HVEM sequence that does not bind to BTLA. In one embodiment, a method includes analyzing the sample for the presence of an HVEM sequence that does not bind to BTLA. In various aspects, the analysis is done by nucleic acid sequencing or nucleic acid hybridization. In additional aspects, the analysis is done by contacting the sample with BTLA, or contacting an HVEM sequence (e.g., a portion or a subsequence or variant of HVEM) with BTLA in order to ascertain (measure) binding between the HVEM sequence and BTLA. Exemplary HVEM sequences include, for example, a mutation or deletion of lysine at position 64, such as an alanine residue at position 64. Further aspects include analyzing HVEM for binding to glycoprotein D of herpes simplex virus (gD), binding to LIGHT or for binding to LTα.

The invention provides kits including compositions of the invention (e.g., peptides such as binding sites for BTLA, antibodies that bind to binding sites for BTLA, nucleic acids encoding binding sites and corresponding binding antibodies, etc.), combination compositions and pharmaceutical formulations thereof, packaged into suitable packaging material. A kit typically includes a label or packaging insert including a description of the components or instructions for use in vitro, in vivo, or ex vivo, of the components therein. A kit can contain a collection of such components, e.g., two or more binding sites for BTLA, antibodies that bind to binding sites for BTLA, alone, or in combination with another therapeutically useful composition (e.g., an immune modulatory or anti-tumor drug).

The term "packaging material" refers to a physical structure housing the components of the kit. The packaging material can maintain the components sterilely, and can be made of material commonly used for such purposes (e.g., paper, corrugated fiber, glass, plastic, foil, ampules, vials, tubes, etc.).

Kits of the invention can include labels or inserts. Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a disk (e.g., floppy diskette, hard disk, ZIP disk), optical disk such as CD- or DVD-ROM/RAM, DVD, MP3, magnetic tape, or an electrical storage media such as RAM and ROM or hybrids of these such as magnetic/optical storage media, FLASH media or memory type cards.

Labels or inserts can include identifying information of one or more components therein, dose amounts, clinical pharmacology of the active ingredient(s) including mechanism of action, pharmacokinetics and pharmacodynamics. Labels or inserts can include information identifying manufacturer information, lot numbers, manufacturer location and date.

Labels or inserts can include information on a condition, disorder, disease or symptom for which a kit component may be used. Labels or inserts can include instructions for the clinician or for a subject for using one or more of the kit components in a method, treatment protocol or therapeutic regimen. Instructions can include dosage amounts, frequency or duration, and instructions for practicing any of the methods, treatment protocols or therapeutic regimes set forth herein. Exemplary instructions include, instructions for treating an undesirable or aberrant immune response, immune disorder, immune disease, pathogen infection or hyperproliferative disorder. Kits of the invention therefore can additionally include labels or instructions for practicing any of the methods of the invention described herein including treatment, detection, monitoring or diagnostic methods.

Labels or inserts can include information on any benefit that a component may provide, such as a prophylactic or therapeutic benefit. Labels or inserts can include information on potential adverse side effects, such as warnings to the subject or clinician regarding situations where it would not be appropriate to use a particular composition. Adverse side effects could also occur when the subject has, will be or is currently taking one or more other medications that may be incompatible with the composition, or the subject has, will be or is currently undergoing another treatment protocol or therapeutic regimen which would be incompatible with the composition and, therefore, instructions could include information regarding such incompatibilities.

Invention kits can additionally include other components. Each component of the kit can be enclosed within an individual container and all of the various containers can be within a single package. Invention kits can be designed for cold storage. Invention kits can further be designed to contain host cells expressing peptides or antibodies of the invention, or that contain encoding nucleic acids. The cells in the kit can be maintained under appropriate storage conditions until the cells are ready to be used. For example, a kit including one or more cells can contain appropriate cell storage medium so that the cells can be thawed and grown.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All applications, publications, patents and other references, GenBank citations and ATCC citations cited herein are incorporated by reference in their entirety. In case of conflict, the specification, including definitions, will control.

Several abbreviations used in the application include, for example, BTLA: B and T lymphocyte attenuator; CMV: cytomegalovirus; CRD: cysteine-rich domain(s); gD: glycoprotein D; HSV-1: Herpes Simplex virus-1; HVEM: herpesvirus entry mediator; LIGHT (p30, TNFSF14): homologous to lymphotoxins, inducible expression, and competes with HSV-gD for HVEM, a receptor expressed by T lymphocytes; LTα: lymphotoxin-α; TNFSF: tumor necrosis factor superfamily; TNFRSF: TNF receptor superfamily.

As used herein, the singular forms "a", "and," and "the" include plural referents unless the context clearly indicates otherwise. Thus, for example, reference to "a binding site for BTLA" or an "antibody" includes a plurality of such binding sites or antibodies and reference to "a BTLA or HVEM activity or function" can include reference to one or more BTLA or HVEM activities or functions, and so forth.

As used herein, all numerical values or numerical ranges include integers within such ranges and fractions of the values or the integers within ranges unless the context clearly indicates otherwise. Thus, for example, reference to a range of 90-100%, includes 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and so forth.

The invention is generally disclosed herein using affirmative language to describe the numerous embodiments. The invention also specifically includes embodiments in which particular subject matter is excluded, in full or in part, such as substances or materials, method steps and conditions, protocols, procedures, assays or analysis. Thus, even though the invention is generally not expressed herein in terms of what the invention does not include, aspects that are not expressly included in the invention are nevertheless disclosed herein.

A number of embodiments of the invention have been described. Nevertheless, it will be understood that various modifications may be made without departing from the spirit and scope of the invention. Accordingly, the following examples are intended to illustrate but not limit the scope of invention described in the claims.

EXAMPLES

Example 1

This example describes various materials and methods. Fc fusion proteins, HVEM mutants and UL144 variants: Fc fusion proteins were constructed between the ecto domain of the individual TNFR and the Fc region of human IgG 1 as described in detail (Benedict et al., *J Immunol* 162:6967 (1999), Rooney et al., *Meth Enzymol* 322:345 (2000)). The extracellular domain of human BTLA was synthesized by PCR using pfu DNA polymerase (Stratagene, San Diego, USA) and hBTLA cDNA as a template. A Hind III restriction site was introduced into the forward primer (5'~CCTGGC AAGCTTGCCACCATGAAGACATTGCCTGCCAT~3') (SEQ. ID NO: 13), and a Sal I site was introduced into the reverse primer (5'~CGCTCGGTCGACGCTTGCCACT-TCGTCCTTGGA~3') (SEQ. ID NO:14) to facilitate vector-insert ligation. The pCR3 vector (Invitrogen, Carlsbad, USA) containing the Fc region of human IgG1 was ligated with the BTLA insert.

Human and mouse HVEM-Fc, and LTβR-Fc were expressed in insect cells using baculovirus system; human BTLA-Fc and UL144-Fc were expressed in 293T cells. These Fc proteins were purified using protein G affinity chromatography. Human HVEM-Fc was biotinylated using the NHS-$PEO_4$-Biotin reagent according to the manufacture's protocol (Pierce, Rockford, USA). The biotinylation reaction yielded a product of 2 biotin molecules per HVEM-Fc as determined by mass spectrometry (SELDI; Ciphergen Biosystems, ICN, Fremont, USA). HSV-1 gD-Fc (rabbit IgG1) was produced in Hela cells and clarified supernatants used in binding assays. Purified recombinant soluble gD (gD-1Δ290-299)(Nicola et al., *J Virol* 70:3815 (1996)) was used. Mouse BTLA tetramer (BTLA-T) was made as described (Sedy et al., *Nat Immunol* 6:90 (2005)). Recombinant soluble human LIGHT truncated at G66 (LIGHTt66) was produced in 293T cells and purified as described (Rooney et al., *J Biol Chem* 275:14307 (2000)). Purified Human IgG (Gammagard, clinical grade, Baxter) was used as a control for Fc fusion proteins.

HVEM point mutants were made using QuikChange Site-Directed mutagenesis kit (Stratagene). Incorporation of the correct amino acid substitution was confirmed by DNA sequencing of the entire coding region.

CMV genomic DNA was extracted from cells infected with CMV clinical strains representing each of the UL144 sequence groups 1A, 1B, 1C, 2, and 3. The UL144 ORF was amplified by PCR from genomic templates representing each group using the same set of primers. The forward primer contained a BamHI restriction site: 5'ACGTGGATCCTCG-TATTACAAACCGCGGAGAGGAT-3' (SEQ. ID NO: 15), and the reverse primer contained an XhoI restriction site: 5'-ACGTCTCGAGACTCAGACAC GGTTCCGTAA-3' (SEQ. ID NO: 16). The amplified UL144 products were cloned into the pND expression vector (Yue et al., *J Gen Virol* 84:3371 (2003)) and each cloned UL144 product was sequenced to verify the previously determined UL144 group sequence.

Flow cytometry-based binding assays: Flow cytometry-based binding assays were carried out as previously described (Rooney et al., Meth Enzymol 322:345 (2000), Shaikh et al., *J Immunol* 167:6330 (2001)) and yield values for these ligands that match with other immobilized ligand binding assays (ELISA and plasmon resonance). Expression plasmids for BTLA, HVEM, HVEM mutants and UL144 variants were transfected into 293T cells and full length human LIGHT was expressed in EL4 cells by retroviral vector transduction (pMIG). BTLA-expressing human dermal fibroblasts (Clonetics Inc., San Diego) were generated by transduction with human or mouse BTLA-expressing retroviral vectors (Sedy et al., *Nat Immunol* 6:90 (2005)) that were generated by transient transfection of 293T cells (Soneoka et al., *Nucleic Acids Res* 23:628 (1995), Benedict et al., *Immunity* 15:617 (2001)). For saturation binding and competition inhibition assays, graded concentrations of recombinant proteins (hHVEM-Fc, mHVEM-Fc, hBTLA-Fc, hLIGHT-t66, gD-Fc, soluble gD, and mouse anti-hLIGHT recombinant "Omniclone" antibody (Granger et al., *J Immunol* 167:5122 (2001)) were diluted in binding buffer (2% FBS in PBS, pH7.4 with 0.02% $NaN_3$) and incubated for 60 minutes at 4° C. Goat anti-human Fc fragment (IgG) specific antibody conjugated with R-Phycoerythrin or goat anti-rabbit Ig antibody was used for detecting the Fc fusion proteins; anti-FLAG M2 monoclonal antibody (Sigma, St. Louis, USA) was used to detect hLIGHT-t66 and Phycoerythrin-conjugated streptavidin was used to detect biotinylated hHVEM-Fc. Specific mean fluorescence intensity (MFI) was obtained by subtracting the background fluorescence staining of the non-transfected cells or isotype matched control antibody (negative control) from the study group. The KD values were calculated by nonlinear regression analysis using Prism GraphPad (v4; San Diego, USA) and the molecular mass of the purified protein determined by mass spectrometry.

T cell proliferation assays: Human blood was obtained from healthy donors with ethical approval and mononuclear cells were isolated by density gradient centrifugation. Flat-bottomed plates were incubated with varying concentrations of anti-CD3 (clone UCHT1, BD Pharmingen, San Diego, USA) and 5 µg/ml anti-human IgG1 Fc antibody (Caltag Laboratories, Burlingame, USA) overnight at 4° C. Human IgG or various TNFR-Fc proteins were pre-incubated at 37° C. for 2 hours with different concentrations. Purified $CD4^+$ T cells obtained by negative immunomagnetic selection (Miltenyi Biotec, Auburn, USA) were added at a concentration of $2\times10^6$ cells/ml, in DMEM with 5% heat inactivated human AB serum, antibiotics and 1 µg/ml soluble anti-CD28 (R&D Systems, Minneapolis, USA) and cultured for 72 hours with 1 µCi of [$^3$H]-thymidine during the last 12 hours.

Mice: C57BL/6, $Rag^{-/-}$ (C57BL/6 background), and C57BL/6-SJL CD45.1 congenic mice were purchased from the Jackson Laboratories and maintained in our facility. $Btla^{-/-}$ mice (Watanabe et al., *Nature immunology* 4:670 (2003)), $Light^{-/-}$ mice (Scheu et al., *J Exp Med* 195:1613 (2002)), and $Hvem^{-/-}$ mice (Wang et al., *J Clin Invest* 115:711 (2005)) have been described previously. All gene deficient mice were backcrossed for at least six generations onto the C57BL/6 background. $Hvem^{-/-}$ or $Btla^{-/-}$ mice were crossed to $Rag^{-/-}$ mice to generate $Hvem^{-/-}Rag^{-/-}$ and $Btla^{-/-}Rag^{-/-}$ recipient animals, respectively. Mice were maintained at the La Jolla Institute for Allergy and Immunology under specific pathogen-free conditions and sentinels mice from the mice colony were tested to be negative for PCR-detection of *Helicobacter* spp. and *Citrobacter rodentium*. Mice were used at 7-12 weeks of age. Animal care and experimentation were consistent with the NIH guidelines and were approved by the Institutional Animal Care and Use Committee at the La Jolla Institute for Allergy and Immunology.

Antibodies and reagents: The following mouse antigens were purchased from BD-Biosciences (San Diego, Calif.), as conjugated to FITC, PE, PE-Cy5, PerCP-Cy5.5 or allophycocyanin: CD4 (L3T4), CD45RB (16A), CD45.2 (104), TCR β chain (H57-597) and rat anti-hamster IgG (cocktail). A PE-conjugated and purified anti-mouse BTLA mAb (6F7) were purchased from e-Biosciences (San Diego, Calif.) and Bio Express, Inc (West Lebanon, N.H.), respectively. Anti-mouse HVEM antibody (Wang et al., *J Clin Invest* 115:711 (2005)), was generously provided by Dr. Yang Xin Fu (University of Chicago, Chicago, Ill.). Anti-mouse CD16/32 used for Fc receptor blocking was purified in our laboratory. Purified mouse IgG1 was purchased from Chemicon, Inc (Temecula, Calif.).

$CD4^+$ $CD45RB^{high}$ T cell isolation and transfers: Spleens were removed from the donor mice (C57BL/6, $Light^{-/-}$, $Hvem^{-/-}$ or B6-SJL CD45 congenic) and teased into cell-single suspensions in HBSS media (Invitrogen, Carlsbad, Calif.). Cell suspensions were filtered through a 70 µm cell strainer (Fisher Scientific, Hampton, N.H.) and subsequently, $CD4^+$ cells were enriched by positive selection using anti-CD4 (L3T4) microbeads according to the manufacturer's protocol (Miltenyi Biotec, Auburn, Calif.). The $CD4^+$-enriched cells were washed twice and stained with PE-Cy5-conjugated anti-CD4 and PE-conjugated anti-CD45RB antibodies. After staining, the cells were washed and the $CD4^+$ $CD45RB^{high}$ T cell population was sorted by flow cytometry using a FACS-DIVA cell sorter (BD, San Diego, Calif.). Purified $CD4^+CD45RB^{high}$ naïve T cells were washed twice, resuspended in PBS and $5\times10^5$ cells in 200 µl of PBS were injected i.v into the different recipient mice. Transferred mice were monitored regularly for signs of disease including weight loss, hunched over appearance, piloerection of the coat, and diarrhea. For co-transfer experiments, $CD4^+$ $CD45RB^{high}$ T cells were isolated from congenic $CD45.1^+$ and $CD45.2^+Btla^{-/-}$ mice, mixed in equal numbers and injected i.v. into $Rag^{-/-}$ recipients.

Preparation of IEL and LPL: Mucosal lymphocytes were isolated and prepared as previously described (Aranda et al., *J Immunol* 158:3464 (1997)). Briefly, the large intestine was removed and placed in chilled HBSS media containing 5% FCS. The intestine were carefully cleaned from its mesentery and flushed of fecal content. Intestines were opened longitudinally and then cut into 1 cm pieces. The intestinal tissue was transferred to a 250 ml Erlenmeyer flasks containing 25 ml of preheated HBSS supplemented with 2% FBS and 1 mM DTT (Sigma Chemical Co., St. Louis, Mo.) and shaken at 200 rpm for 40 min at 37° C. The tissue suspensions were passed through a stainless steal sieve into 50 ml conical tubes and the cells were pelleted by centrifugation at 1200 rpm for 10 min at 4° C. The cell pellets were resuspended in complete HBSS, layered over a discontinuous 40/70% Percoll (GE Healthcare, Piscataway, N.J.) gradient, and centrifugated at 2000 rpm for 30 min. Cells from the 40/70% interface were collected, washed and resuspended in complete RPMI media (Invitrogen, Carlsbad, Calif.). These purified cells constituted the IEL population. To isolate LPL, the remaining intestinal tissue in the stainless steal sieve was minced and transferred to conical tubes. The minced pieces were resuspended in 20 ml of complete RPMI containing 1 mg,/ml of type IV collagenase (Sigma-Aldrich, St, Louis, Mo.) and shaken at 200 rpm for 40 min at 37° C. The tissue suspension was collected, passed through a 70 µm cell strainer, and then the cells were pelleted by centrifugation at 1200 rpm. The cells were then resuspended and layered onto a 40/70% Percoll gradient, centrifugated and processed as described above for the IEL preparation.

Histology: At various time points following cell transfer, animals were sacrificed for histological analysis. Tissue samples of 3-5 mm obtained from distal and proximal portions of the large intestine were fixed in 4% formalin. Fixed tissues were later embedded in paraffin and 3 µm sections were prepared and stained with hematoxylin-eosin (H&E). To evaluate the severity of the inflammation samples were coded and scored by a pathologist in a blinded fashion using a previously described scoring system (Aranda et al., *J Immunol* 158:3464 (1997)). Scores from the two parts of the intestine were averaged to represent the severity of disease. Higher scores (maximum 14) indicate greater pathology. Categories scored are the following: degree of inflammatory cell infiltrate in the lamina propria; goblet cell depletion; epithelial cell reactive atypia/hyperplasia; number of IEL in epithelial crypts; number of inflammatory foci.

Flow cytometry analysis: Spleen and MLN were removed and then mashed through a 70 μm cell strainer and red blood cells in the cell suspension were removed using a lysing buffer (Sigma-Aldrich, St, Louis, Mo.). IEL and LPL were isolate as describe above. Prior to staining, cells were washed and resuspended in staining buffer containing 1× PBS, 2% BSA, 10 mM EDTA and 0.01 $NaN_3$. To block non-specific staining, anti-CD 16/32 antibody was added. Antibodies for cell surface markers were added and cells were incubated for 20 min on ice. Following the staining the cells were washed twice with staining buffer and analyzed the same day or fixed in PBS containing 1% paraformaldehyde and $0.01 NaN_3$ and analyzed later in a FACSCalibur (BD Biosciences, San Diego, Calif.).

Detection of cytokines by ELISA: Two weeks after the transfer of $CD4^+CD45RB^{high}$ T cells, LPL were isolated from the recipients and $1×10^6$ cells were cultured in RPMI complete medium in the presence of PMA and ionomycin for 48 h. The amounts of IFNλ, IL-4, TNF and IL-2 in the culture supernatants were quantified by ELISA. Antibodies and recombinant cytokine standards were purchased from BD Biosciences (San Diego, Calif.).

RNA isolation and real-time PCR: Two weeks after the transfer of $CD4^+CD45RB^{high}$ T cells, 1.5 cm from the large intestines of the recipients was removed and resuspended in TRI-Zol (Invitrogen, Carlsbad, Calif.). The samples were then frozen −80° C. For RNA isolation, the whole tissue was homogenized, DNA and proteins were removed by precipitation with chloroform, and RNA was extracted with isopropanol. cDNA was synthesized from the total RNA using the Superscript II system (Invitrogen, Carlsbad, Calif.) following the instructions provided by the manufacturer. Subsequently, the cDNA was subject to real-time PCR using SYBR green (Bio-Rad Laboratories, Hercules, Calif.) and the following mouse primers (SEQ ID NOs:17-34): TNF forward, 5'-CATCTTCTCAAAATTCGAGTGACAA-3'; TNF reverse, 5'-TGGGAGTAGACAAGGTACAACCC-3'; IFNλ forward, 5'-TCAAGTGGCATAGATGTGGAAGAA-3'; IFNλ reverse, 5-TGGCTCTGCAGGATTTICATG-3'; IL-4 forward, 5'-ACAGGAGAAGGGACGCCAT-3'; IL-4 reverse, 5'-GAAGCCCTACAGACGAGCTCA-3'; IL-17 forward, 5'-GGTCAACCTCAAAGTCTTTAACTC-3'; IL-17 reverse, 5'-TTAAAAATGCAAGTAAGTTTGCTG-3'; IL-12p35 forward, 5'-TGAAGACGGCCAGAGAAAAAC-3'; IL-12p35 reverse, 5'AAGGAACCCTTAGAGTGCT-TACT-3'; IL-23p19 forward, 5'-AGCgggacatatgaatctactaa-gaga-3'; IL-23p19 reverse, 5'-GTCCTAGTAGGGAGGTGTGAAGTTG-3'; IL-10 forward, 5'-GGTTGCCAAGCCTTATCGGA-3'; IL-10 reverse, 5'-ACCTGCTCCACTGCCTTGCT-3'; TGF β forward, 5'-TGACGTCACTGGAGTTGTACGG-3'; TGF βreverse, 5'-GGTTCATGTCATGGATGGTGC-3'; L32 forward, 5'-GAAACTGGCGGAAACCCA-3' and L32 reverse, 5'-GGATCTGGCCCTTGAACCTT-3'. Gene expression was normalized to L32. Data were collected and analyzed on an iCycler Bio-Rad (Hercules, Calif.).

Generation of bone marrow chimeras: $Rag^{-/-}$ or $Hvem^{-/-}Rag^{-/-}$ hosts were lethally irradiated with 11 Gy that were applied in two irradiations of 5.5 Gy separated by a 3 h interval. Following irradiation, $Hvem^{-/-}Rag^{-/-}$ hosts were transplanted with $5×10^6$ total bone marrow (BM) cells isolated from $Rag^{-/-}$ mice to generate $Rag^{-/-} \Rightarrow Hvem^{-/-}Rag^{-/-}$ chimeric animals. Reciprocal $Hvem^{-/-}Rag^{-/-} \Rightarrow Rag^{-/-}$ chimeras were generated by transplanting $Hvem^{-/-}Rag^{-/-}$ BM cells into irradiated $Rag^{-/-}$ hosts. After transplant, mice were maintained under antibiotic treatment for four weeks and six additional weeks without antibiotic before transfer of the $CD4^+CD45RB^{high}$ T cells.

Statistics: Differences between groups were evaluated for statistical significance by the two-tailed unpaired Student's t-test, except for histological scoring that was evaluated using Wilcoxon's two group test. Results are expressed as mean±s.d. P values<0.05 were considered significant.

Example 2

This example describes data indicating that HVEM is a binding receptor for BTLA on T cells.

The proliferation of T cells in response to a suboptimal costimulatory stimulus was examined in T cells isolated from the spleens of mice genetically deficient in HVEM or LIGHT. Single cell suspensions from spleens of C57Bl/6 wildtype control mice or HVEM−/− or LIGHT−/− mice were prepared on ice. Red blood cells were lysed using red blood cell lysis buffer (eBioscience) for 5 minutes. Splenocytes were washed with cold PBS and suspended at $2×10^6$ cells/ml in complete medium (10% FBS RPMI-1640). Cells were plated at 33 $10^5$ cells/well in a U-bottom 96-well plate and were stimulated by adding graded concentrations of anti-mouse CD3 (145-2C11, BD Pharmingen) in the presence of 2 μg/ml anti-mouse CD28 (37.51, BD Pharmingen). After 48 hours, 1 μCi/well of [$^3$H] thymidine (MP Biomedicals, cat #2405901) was added and incubation continued for an additional 16 hours. Cells were harvested using a cell harvester onto glass fiber filters (Wallac, cat #1205-401) and the amount of [3H] thymidine incorporated into DNA was measured using a beta plate reader.

Figure 1:
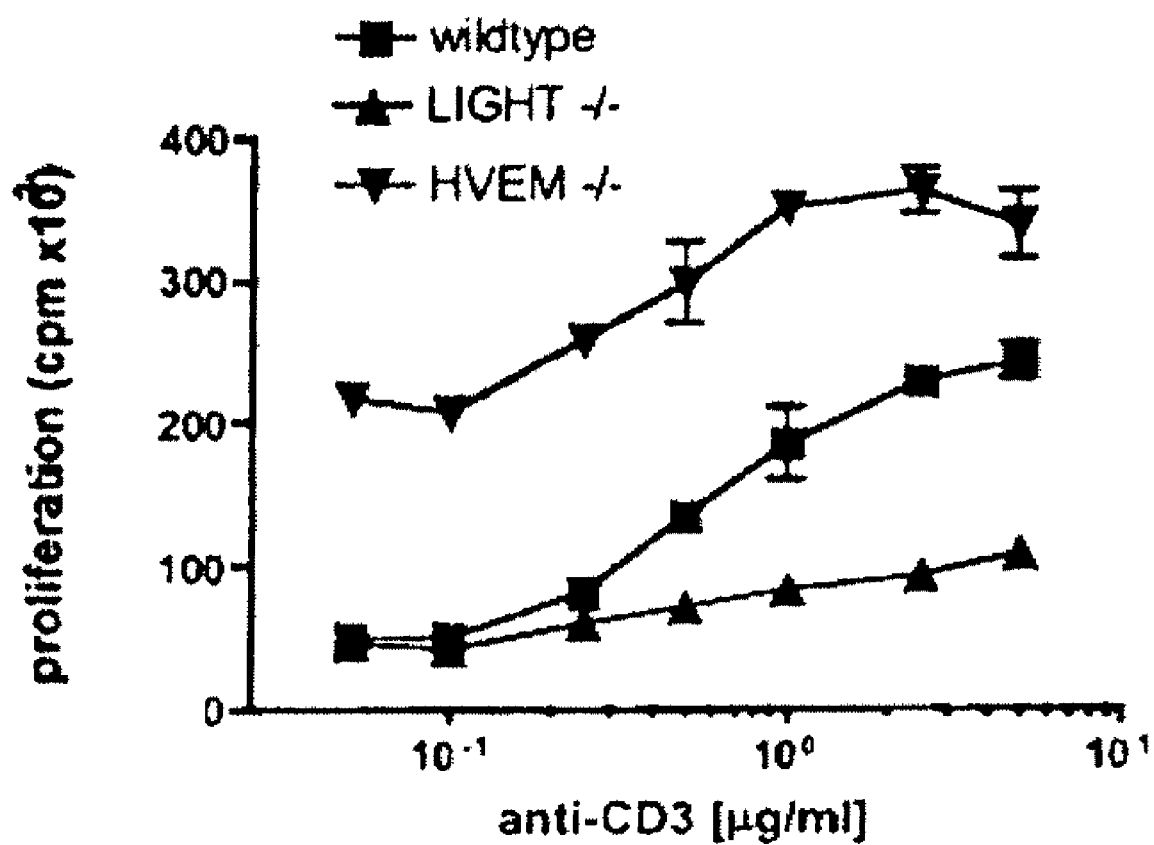
FIG. 1: Altered T cell proliferation in HVEM and LIGHT deficient mice. The data represents the mean±SEM of triplicate wells. The results are a representative of 4 studies with HVEM-/- and three with LIGHT-/- mice.

In FIG. 1, splenocytes were cultured with varying doses of anti-CD3 to activate T lymphocytes. Splenocytes from HVEM−/− T cells showed an enhanced response compared to wild type mice. By contrast, mice lacking the gene for LIGHT showed a poor proliferative response to anti-CD3 relative to wild type or HVEM−/− mice. This discordance in phenotype between HVEM and LIGHT deficient T cells suggests that an alternate mechanism suppresses HVEM dependent costimulatory activity effecting cellular proliferation.

The B-T lymphocyte attenuator (BTLA) is an Ig superfamily member reported to function as an inhibitory protein for T cell activation (Gavrieli et al., *Biochem Biophys Res Commun* 312:1236 (2003); Watanabe et al., *Nat Immunol* 4:670 (2003)) and thus a candidate for negatively regulating HVEM.

293 T cells were transiently transfected with 5 μg mouse BTLA-GFP or 5 μg human BTLA-ires-GFP. Transfection was confirmed by the expression of GFP. Mock, mBTLA, or hBTLA expressing cells (50,000/condition) were added to U-bottom 96 well plates and incubated with varying concentrations of mHVEM:Fc or hHVEM:Fc for 1 hour on ice. Cells were washed twice in cold binding buffer (DPBS, 2% FBS, 0.02% sodium azide). Binding of Fc fusion proteins was detected using 1:200 R-Phycoerythrin-conjugated donkey anti-human IgG (Jackson Immunoresearch, cat #709-116-149) followed by washing twice in binding buffer and analyzing for cell-associated fluorescence by flow cytometry.

Figure 2A:
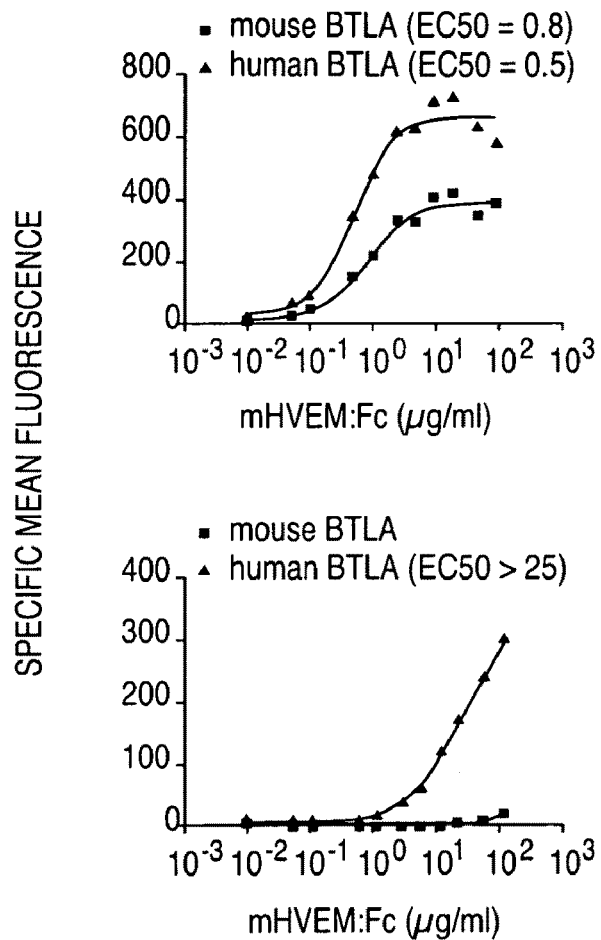
FIGS. 2A-B: BTLA binds HVEM. (A) 293T cells transiently transfected with mouse BTLA-GFP or human BTLA-ires-GFP. Fluorescence staining of the fusion proteins on mock transfected cells was subtracted from mean fluorescence values on mBTLA or hBTLA expressing cells to obtain specific mean fluorescence values. EC50 values were determined using Prism software from the dose response curves. (B) Representative histogram plot of CD4, CD8, and B220 positive cells assessed for binding of the mBTLA tetramer. mBTLA tetramer staining is depicted as a solid dark line and background fluorescence depicted as a dashed line.
Figure 2B:
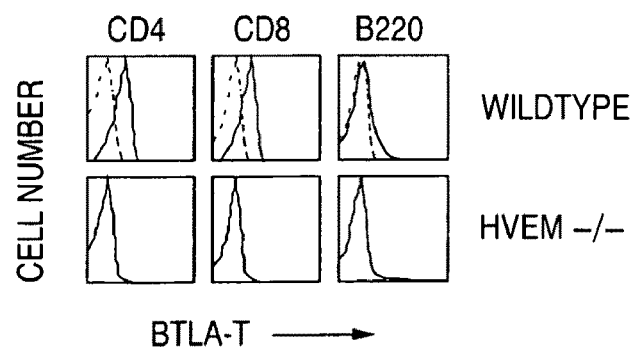

Human 293T cells expressing either mouse or human BTLA bind mouse HVEM-Fc with relatively high affinity as denoted by the concentration of HVEM-Fc required to saturate 50% of the specific binding sites (EC50)(FIG. 2A, upper panel). Human HVEM-Fc binds efficiently to human BTLA relative to mouse BTLA (FIG. 2A, lower panel).

Single cell suspensions from spleens of C57BL/6 wildtype control mice or HVEM−/− mice were directly stained for CD4, CD8, or B220 antibodies (BD Pharmingen) and costained with a mBTLA tetramer reagent. Cells were washed twice with FACS buffer and staining was assessed by flow cytometry. Lymphocyte subsets including CD4, CD8 and B220 positive cells from normal B6 mice bound mouse BTLA tetramer but cells from HVEM−/− mice did not (FIG.

2B). This result indicates that HVEM is the only binding receptor for BTLA on these cell populations.

Example 3

This example describes data indicating that BTLA and LIGHT binding sites on HVEM are spatially distinct.

Figure 3A:
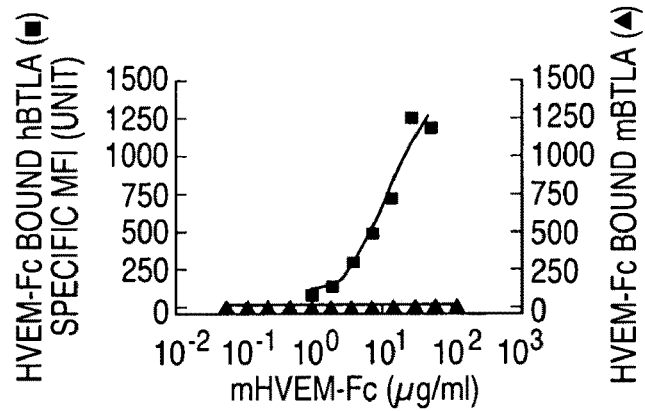
FIGS. 3A-I: Topography of BTLA, LIGHT and gD binding to HVEM. Dermal fibroblasts stably expressing hBTLA or mBTLA were incubated with graded amounts of (A) human or (B) mouse HVEM-Fc. (C) HEK293 cells transfected with hHVEM or hBTLA expression plasmids incubated with either graded concentrations of either hBTLA-Fc or hHVEM-Fc as described in Example 3. (D) HEK293 cells transfected with hHVEM incubated with graded concentrations of hLIGHT-t66 (FLAG epitope) and bound ligand. (E) Competition binding assay with graded concentrations of LIGHT-t66 incubated with hHVEM expressing HEK293 cells in BTLA-Fc. (F) HEK293 cells stably transfected with mHVEM or hLIGHT-EL4 cells incubated with graded concentrations of hLIGHTt66 in the presence of mBTLA tetramer or mHVEM-Fc. (G) Graded concentrations of soluble gD (gDtΔ90-99) was used to compete for mBTLA-T binding to mHVEM-HEK293 cells or mHVEM-Fc to hLIGHT-EL4 cells as in (F). (H) Graded concentrations of hBTLA-Fc or mouse anti-LIGHT Omniclone incubated with hLIGHT expressing EL4 cells in biotinylated hHVEM-Fc. (I) Competition of anti-mHVEM 14C1.1 (solid icons) or anti-mHVEM 4CG4 (open icon) was used as competing ligand.
Figure 3B:
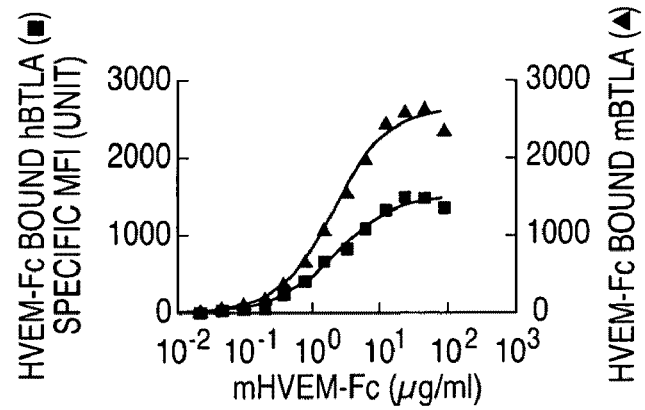
Figure 3C:
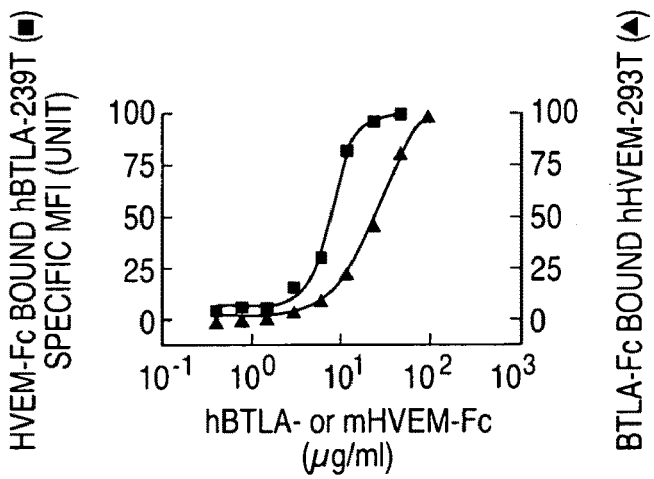

To determine the specificity and molecular topography of the HVEM-BTLA interaction, -Fc fusion proteins were constructed with the ecto domain of HVEM or BTLA as surrogates of their cell bound receptors (Rooney et al., Meth Enzymol 322:345 (2000)). Dermal fibroblasts ($2 \times 10^4$) stably expressing hBTLA or mBTLA were incubated with graded amounts of human or mouse HVEM-Fc in 50 μl of binding buffer for 60 minutes, washed and stained with PE conjugated goat anti-human IgG and fluorescence detected by flow cytometry. Human HVEM-Fc bound with a saturable profile (KD=112 nM) to human BTLA expressed in 293T cells as detected by flow cytometry (FIG. 3A), but failed to bind mouse BTLA over this concentration range. By contrast, mouse HVEM-Fc bound both human (KD=27 nM) and mouse BTLA (KD=24 nM) with similar affinities (FIG. 3B) in agreement with species restriction previously observed (Sedy et al., Nat Immunol 6:90 (2005)). Reciprocally, human BTLA-Fc bound HVEM expressed in 293T cells (KD=636 nM), but less efficiently than when BTLA was positioned in the membrane (FIG. 3C).

Figure 3D:
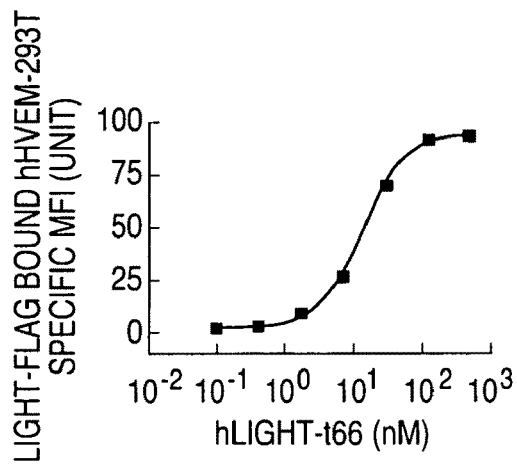
Figure 3E:
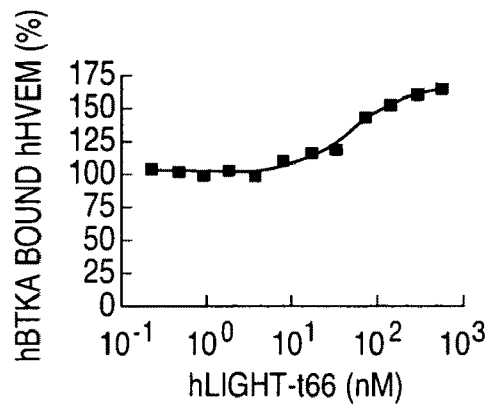

In a similar FACS assay, graded concentrations of LIGHT-t66 (FLAG epitope) were incubated with hHVEM expressing HEK293 cells in the presence of 25 μg/ml of BTLA-Fc and bound ligand detected with goat anti-FLAG-PE. Human HVEM-Fc bound human LIGHT expressed in EL4 thyoma cells with a KD=11 nM. A soluble form of recombinant human LIGHT (LIGHT-t66) also bound with high affinity to cell-expressed human HVEM (KD=13 nM) (FIG. 3D) yet failed to inhibit binding of BTLA-Fc to HVEM, and as the concentration approached saturation (>60 nM) LIGHT enhanced BTLA-Fc binding to HVEM (FIG. 3E), suggesting the formation of a ternary complex.

Competitive binding analysis was performed to determine the topographical relationships of the binding interactions of these ligands with HVEM. HEK293 cells stably transfected with mouse HVEM (293-mHVEM) or EL4 cells transduced with human LIGHT (EL4-hLIGHT) were collected and suspended at $1 \times 10^6$ cells/ml in binding buffer. For competition studies analyzing BTLA bound to HVEM, increasing concentrations of flag epitope tagged-LIGHT (LIGHTt66; described in (Rooney et al., J Biol Chem 275:14307 (2000)) was preincubated with $2.5 \times 10^4$ 293-HVEM cells in a U-bottom 96-well plate for 30 minutes on ice. Mouse BTLA tetramer reagent (1.4 μg/ml) was added to the cells for an additional 30 minute incubation on ice. Staining of the mBTLA tetramer was detected by flow cytometry and data are presented as the percentage of BTLA bound to HVEM expressing cells in the absence LIGHT. For competition studies analyzing HVEM bound to LIGHT, graded concentrations of Flag-LIGHT were preincubated with 2 μg/ml mHVEM:Fc (2 μg/ml, detected with goat and human IgG-PE) for 30 minutes on ice. The mixture was then added to EL4-LIGHT cells for an additional 30 minutes incubation on ice in a U-bottom 96-well plate.

Binding of mHVEM:Fc to LIGHT expressing cells was detected as described in Example 2 and data are presented as the percentage of HVEM bound to LIGHT expressing cells in the absence of soluble LIGHT. Control for nonspecific staining with mBTLA-T was based on 293T cells.

Figure 3F:
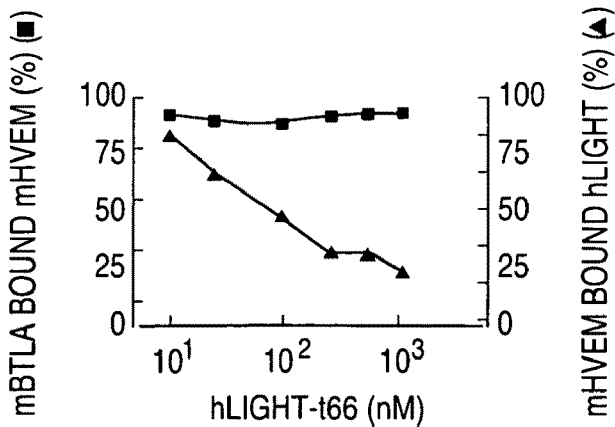

In the mouse system, LIGHT-t66 similarly did not block the binding of mouse HVEM to mouse BTLA-tetramer (BTLA-T)(FIG. 3F), although mouse HVEM-Fc binding to membrane-expressed LIGHT was effectively competed. These results indicate that LIGHT and BTLA have substantially different binding affinities and occupy spatially distinct sites on HVEM.

Figure 3G:
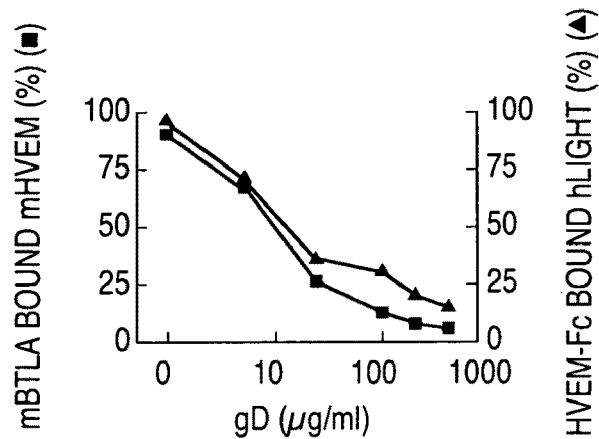

A fourth reactant with HVEM, envelope gD from HSV-1 can bind both human and mouse HVEM (Montgomery et al., Cell 87:427 (1996), Yoon et al., J Virol 77:9221 (2003)). Graded concentrations of soluble gD (gDtΔ90-99) was used to compete for mBTLA-T (1.4 μg/ml) binding to mHVEM-HEK293 cells or mHVEM:Fc (2 μg/ml) to hLIGHT-EL4 cells. With the BTLA site also located in the first CRD, gD may serve as a useful tool to further probe the specific structural requirements for HVEM-BTLA interaction. A soluble deletion mutant of HSV-1 gD (gD) inhibited the binding of BTLA-T to cell-expressed mouse HVEM, yet also blocked binding of HVEM-Fc to membrane LIGHT with similar dose response (KD=~250 nM) (FIG. 3G) (see also Mauri et al., Immunity 8:21 (1998)). However, previous studies reported that gD did not block the binding of soluble LIGHT or LTα to HVEM-Fc in a plate binding format (Sarrias et al., Mol Immunol 37:665 (2000)). This difference in competitive action of gD with soluble versus transmembrane-anchored LIGHT indicates that the membrane position sterically restricts HVEM binding to LIGHT when gD is present.

Figure 3H:
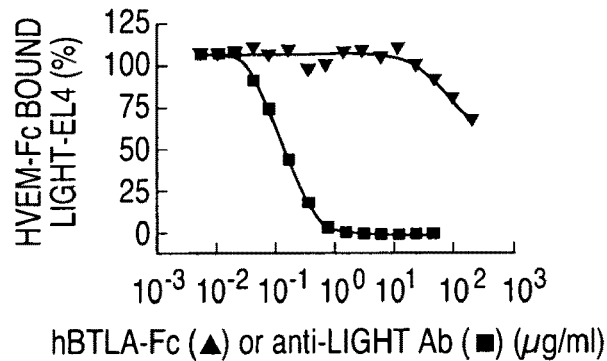

Graded concentrations of hBTLA-Fc or mouse anti-LIGHT Omniclone were incubated with hLIGHT expressing EL4 cells in the presence of 6 μg/ml of biotinylated hHVEM-Fc. The parental EL4 cells were used as negative control. Similarly, BTLA-Fc inhibited the binding of HVEM-Fc to membrane LIGHT in a dose dependent manner (FIG. 3H) suggesting that gD is a viral mimic of BTLA. Together, these results indicate that LIGHT and BTLA occupy distinct sites on HVEM, and identifies the BTLA binding site as topographically close to the site occupied by gD in the CRD1.

Figure 3I:
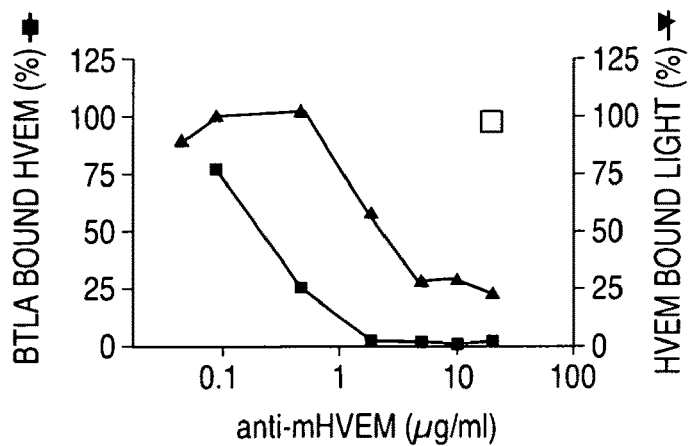

By contrast, recombinant gD was capable of competitively blocking the binding of both BTLA to HVEM-expressing cells and HVEM-Fc binding to LIGHT expressing cells. The effective concentration of gD was similar for both. A monoclonal antibody to mouse HVEM (14C1.1) blocked the binding of BTLA-tetramer to mHVEM expressing cells (FIG. 3I), whereas another mHVEM binding monoclonal antibody 4CG4 was unable to block binding. The blockade of BTLA binding by 14C1.1 was highly efficient (EC50=0.2 μg/ml) when compared to its ability to block mHVEM-Fc binding to LIGHT expressing cells (EC50=5 μg/ml). This result, together with the ability of gD to block BTLA binding, indicated the BTLA binding site is topographically near the gD binding site on HVEM.

Example 4

This example describes data studies identifying amino acid residues of BTLA binding site that affect or have little affect on binding to BTLA.

Human HVEM point mutants were made using the QuikChange Site-Directed Mutagenesis kit (Stratagene) and were chosen based on their role in gD binding (Connolly et al., J Virol 76:10894 (2002)). hHVEM (in pCDNA) or various point mutants were transiently transfected into 293T cells. Transfected 293T cells were collected and $2 \times 10^5$ cells aliquoted per condition of a 96-well V-bottom plate. Cells were stained with 50 μg/ml polyclonal goat anti-hHVEM or with hBTLA-Fc supernatant for 1 hour on ice. Detection of the Fc fusion protein was as described in Example 2. Detection of HVEM staining was by incubation with 1:100 R-phycoerythrin-conjugated donkey anti-goat IgG (Jackson Immunoresearch, cat #705-116-147) followed by washing twice in FACS buffer and analyzing for cell-associated fluorescence by flow cytometry.

Figure 4A:
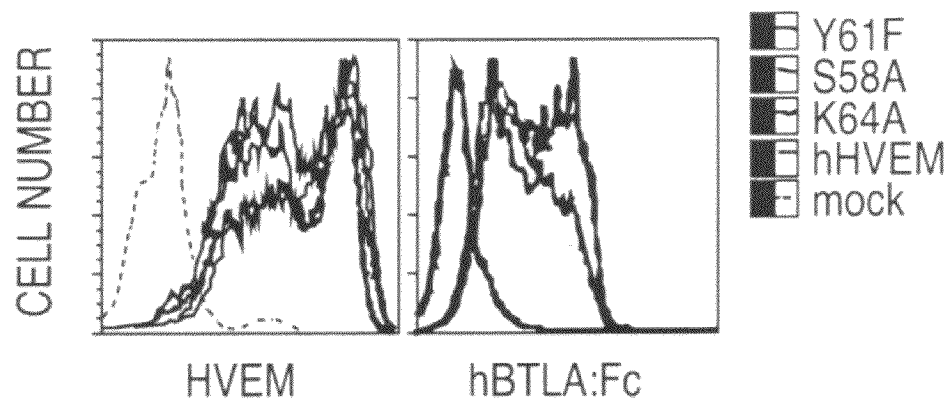
FIGS. 4A-B: Site specific mutations reveal a unique BTLA binding site. (A) Human HVEM point mutants (in pCDNA) or various point mutants were transiently transfected into 293T cells and stained with polyclonal goat anti-hHVEM or with hBTLA-Fc supernatant. The data are depicted as raw histograms from a representative study and show staining for HVEM (left panel) and binding of hBTLA:Fc (right panel). (B) western blots of cell extracts transfected with the mutant HVEM or wild type HVEM.

Point mutations in human HVEM that inhibit the binding of gD and affect infection by HSV-1 were constructed to determine if the BTLA, LIGHT and gD binding sites were similar or distinct. The mutations selected in human HVEM included at tyrosine-61 mutated to phenylalanine (Y61F); serine-58 to alanine (S58A) and lysine-64 to alanine (K64A) all of which lose gD binding and reduce virus infection. The introduction of K64A mutation completely inhibited binding of BTLA, whereas the S58A and Y61F mutants did not affect binding of BTLA (FIG. 4A).

Figure 4B:

To confirm equivalent expression of the mutant HVEM proteins, lysates of the transfected 293T cells were obtained following lysis of 2×10⁶ cells with 100 μl 1% NP-40 lysis buffer containing protease inhibitors. Total protein of the lysates was determined and normalized using the BCA protein assay reagent kit (Pierce) and analyzed on SDS-PAGE. Western analysis was performed using 1:500 anti-hHVEM CW3 followed by 1:3000 HRP anti-mouse antibody. Following washing, membrane filters were reacted with ECL reagent and revealed by brief exposure using autoradiography film. All mutants, including K64A were efficiently expressed in cells as detected by western blots of cell extracts transfected with the mutant HVEM or wild type HVEM (FIG. 4B). None of these mutants affected LIGHT binding, yet all mutants substantially reduced infection by HSV-1 as measured by gD expression and late viral protein expression of VP21-GFP. These results, particularly the K64A mutant distinguishes the BTLA binding site on HVEM from that of gD and LIGHT.

Example 5

This example describes data indicating that BTLA and gD bind to a distinct, but overlapping site on HVEM.

HVEM in complex with gD (1JMA) (Carfi et al., *Molecular Cell* 8:169 (2001)) was viewed using molecular graphics software (Swiss-PDV viewer). FIG. 5, left panel, is the ecto domain of HVEM; FIG. 5, right panel, is a detailed view of the BTLA binding region.

Figure 5A:
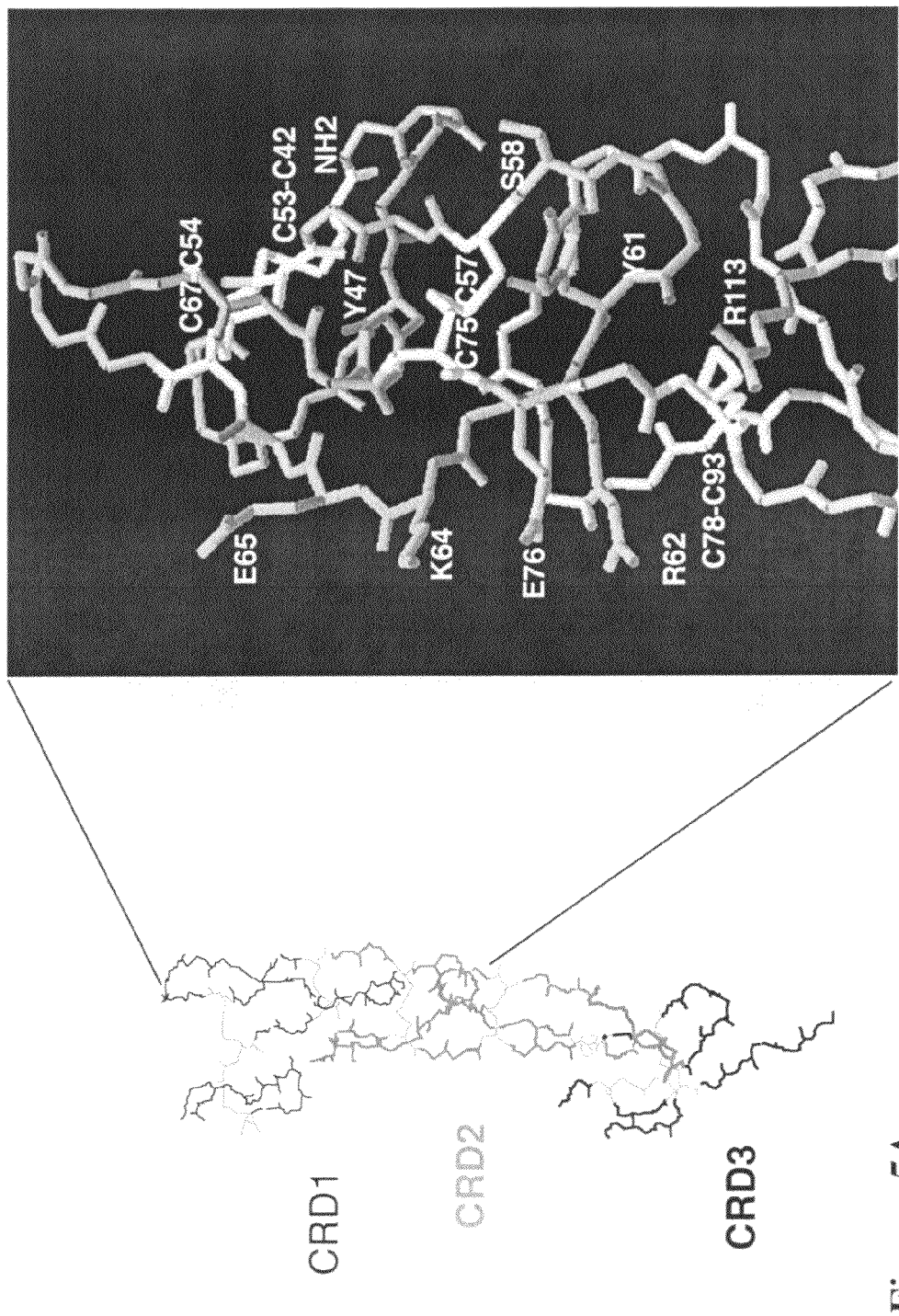
FIGS. 5A-B: Binding analyses of BTLA-Fc, soluble LIGHT and gD to HVEM mutants. (A) Location of site-directed mutations in the structure of hHVEM (1JMA.pdb, Swiss-PDV viewer). The α-carbon backbone of hHVEM with side chains of mutated amino acids. Color scheme Left panel, the cysteine-rich domains (CRD) CRD1 (gray); CRD2 (purple) and CRD3 (blue); cysteine residues (yellow); mutated amino acid residues; arginine-62 (R62), lysine-64 (K64) and glutamic acid-65 (E65) (red); Y47, S58, Y61, E76 and R113 (green); residues colored turquoise are within the complex BTLA loop; some side chains not shown for clarity. (B) 293T cells transfected with the expression plasmids of wild type hHVEM or individual substitution mutants were stained with anti-HVEM antibody, hBTLA-Fc (100 µg/ml), soluble hLIGHT (400 nM), and gD-Fc (0.4 µg/ml). Binding analyses were performed by flow cytometry. Binding profiles of HVEM ligands to HVEM-293T cells (dark line) and mock transfected 293T parental cells (thin line).
Figure 5B:
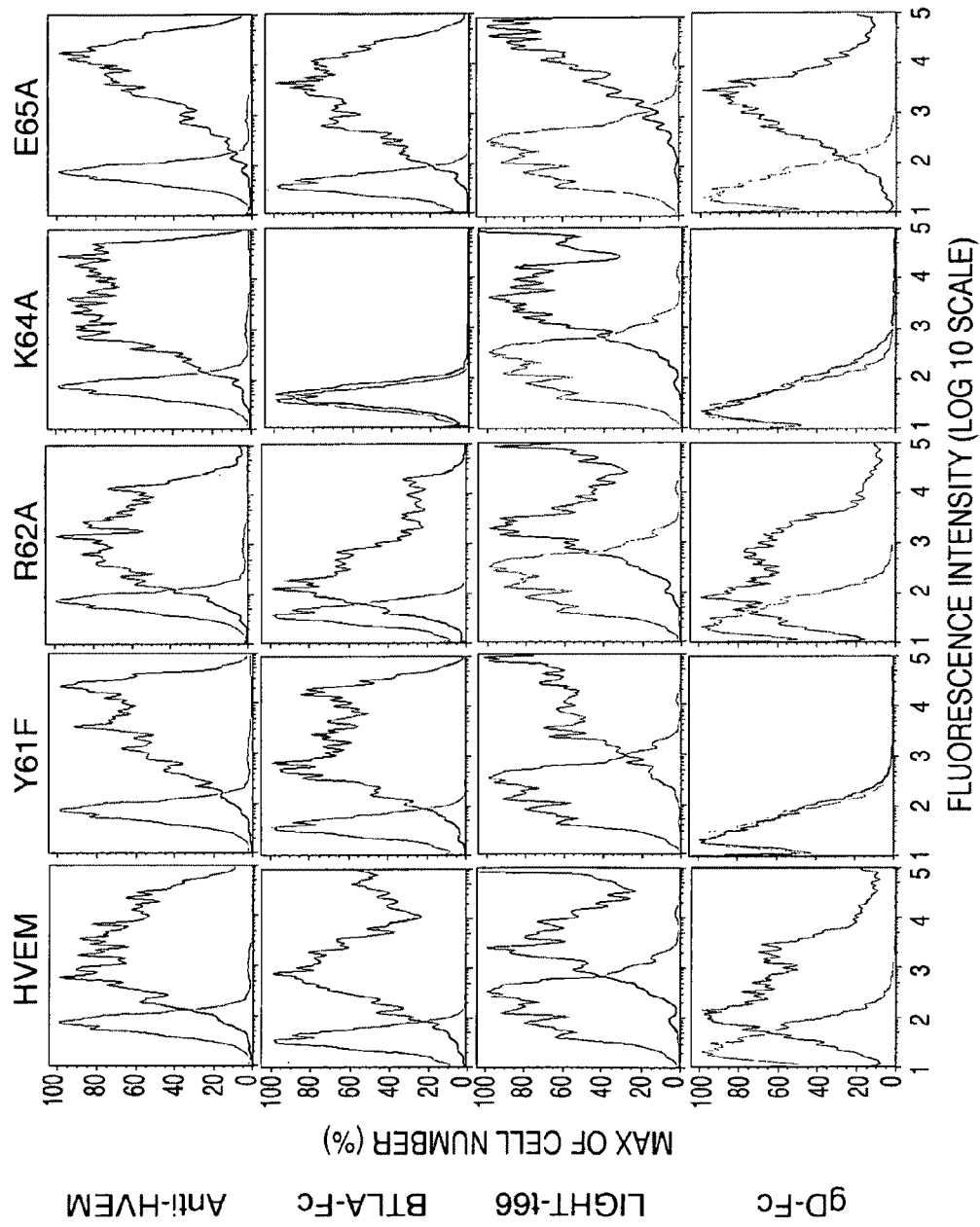

To address whether BTLA occupies the gD binding site on HVEM, alanine/phenylalanine substitution mutations were introduced into human HVEM in residues within CRD1 and 2 (FIG. 5A). None of the mutants affected expression of HVEM on the cell surface (FIG. 5B) or total protein as detected with a polyclonal anti-HVEM in western blots. Mutations Y61F and K64A in CRD1 were particularly informative. The K64A, but not Y61F mutation, abolished binding to BTLA, yet both resulted in a complete loss of gD-Fc binding and virus infectivity as measured by gD expression and viral protein expression (FIG. 3B; Connolly et al., *J Virol* 77:8127 (2003)). These mutants indicate that the BTLA binding site on HVEM is distinct from that of gD.

Saturation binding analysis of the HVEM mutants revealed decreased binding affinity of BTLA-Fc to HVEM mutants R62A and E65A (2-3 fold increase in KD) and K64A, but not to several other mutants in CRD1 or 2 (Table 1). None of the HVEM mutants affected the affinity of LIGHT-t66 binding, further indicating that the mutations were unlikely to have altered the global conformation of HVEM. These results lead to a model in which the gD and BTLA binding sites are located primarily within the CDR1, yet are topographically close, but distinct.

Example 6

This example describes data indicating that the BTLA binding site is conserved in the cytomegalovirus UL144.

Alignments were performed on sequence of the mature ecto domain. Signal peptide cleavage site to deduce the mature protein was predicted by SignalP. Alignments were made using ClustalW (PAM series) MacVector software. Paired cysteines forming disulfide bonds are shown by connecting lines. The amino acid sequence homology of human and mouse HVEM are highly conserved in the region surrounding lysine 64 (FIG. 6).

Mutational analysis indicated K64 is a major determinant in the ability of HVEM to engage BTLA with additional contributions from R62 and E65. These three residues form a charged ridge on the solvent exposed surface of HVEM that is part of the loop formed by disulfide bonds C57-C75 and C67-054 in CRD1 (FIG. 5A). The sequence of CRD 1, including the positioning of the cysteines and the equivalent K64 residue, is highly conserved between human and mouse HVEM (62% overall identity in CRD1) (FIG. 7). UL144 ORF in human cytomegalovirus showed significant homology to HVEM in CRD1 (FIG. 7). It has been previously reported that UL144 is a member of the TNFR family that contained only two CRD, exhibiting the closest sequence homology to HVEM and TRAILR2, however UL144 failed to bind any of the known members of the TNF ligand family including LIGHT, thus had no known function (Benedict et al., *J Immunol* 162:6967 (1999)). However, the conservation of UL144 with HVEM in this region suggested in this invention that UL144 functions as a BTLA binding protein.

Sequence hypervariation exists in the ecto domain of UL144 from human CMV isolated from different clinical sources that can be categorized into 5 major groups, 1A, 1B, 1C, 2 and 3 (Lurain et al., *J Virol* 73:10040 (1999 December) (FIG. 7). Expression plasmids encoding representatives of each UL144 group were transfected into 293T cells and the binding of human BTLA-Fc was examined by flow cytom-

TABLE 1

Binding Analysis of BTLA, LIGHT, gD to HVEM

| Binding Partners[2] | HVEM mutants[1] | | | | | | | |
|---|---|---|---|---|---|---|---|---|
| | HVEM | Y47F[3] | S58A | Y61F | R62A | K64A | E65A | E76A | R113A |
| BTLA-Fc (KD[4]; nM) | 636 | 520 | 551 | 753 | 1453 | NB[5] | 1686 | 381 | 626 |
| LIGHTt66 (KD[4]; nM) | 13 | 14 | 19 | 17 | 17 | 14 | 18 | 22 | 18 |
| gD-Fc[6] | + | + | + | − | + | − | + | + | + |

Figures 1, 8A:
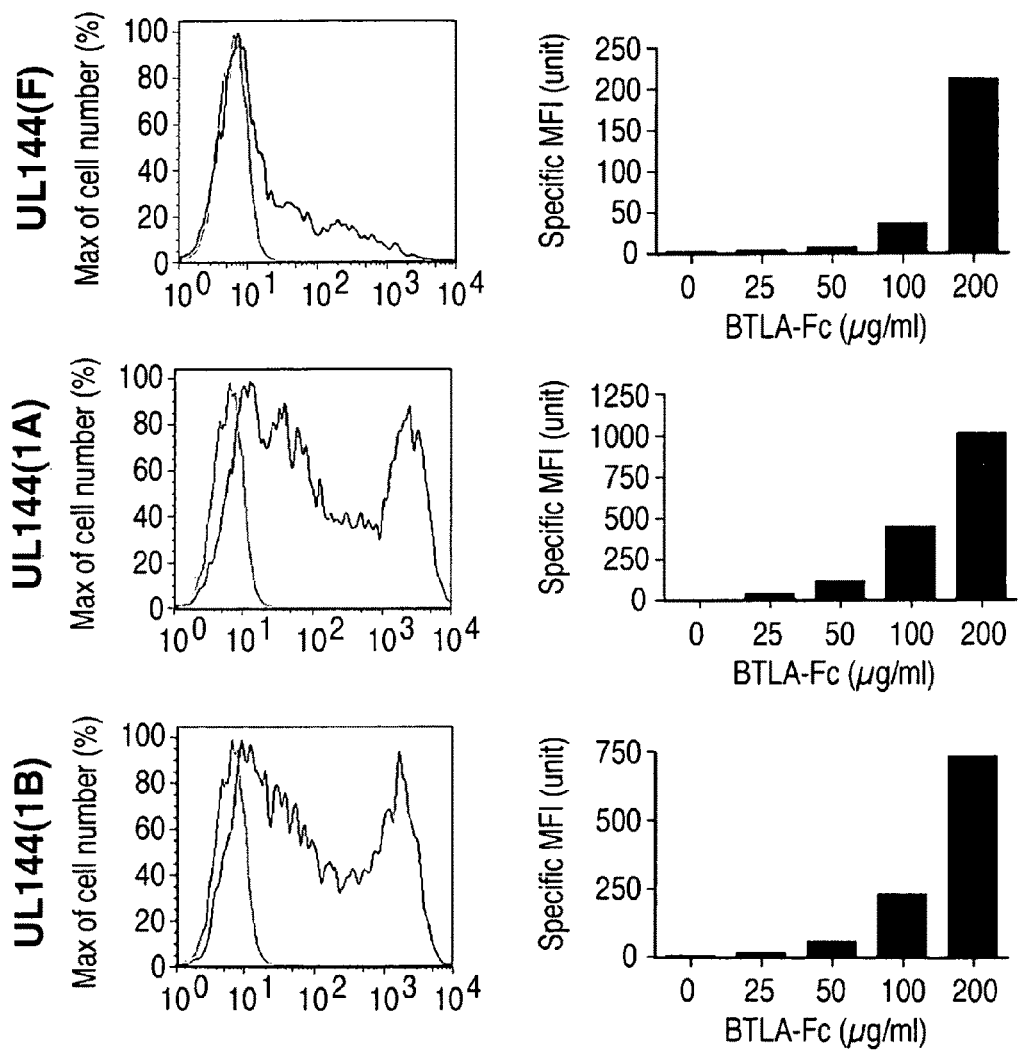
FIGS. 8A-B: Specific binding between UL144 and BTLA. (A) Graded concentrations of human BTLA-Fc incubated with UL144 transfected 293T cells (1A, 1B, 1C, 2, 3 and Fiala (type 3). Histograms show transfected cells stained with hBTLA-Fc (dark line) or mock-transfected control 293T cells (thin line). Specific fluorescence of cells stained with graded concentrations (25, 50, 100, and 200 µg/ml) of hBTLA-Fc. (B) Competition binding assay for hBTLA-Fc binding to UL144(1C).
Figures 2, 8A:
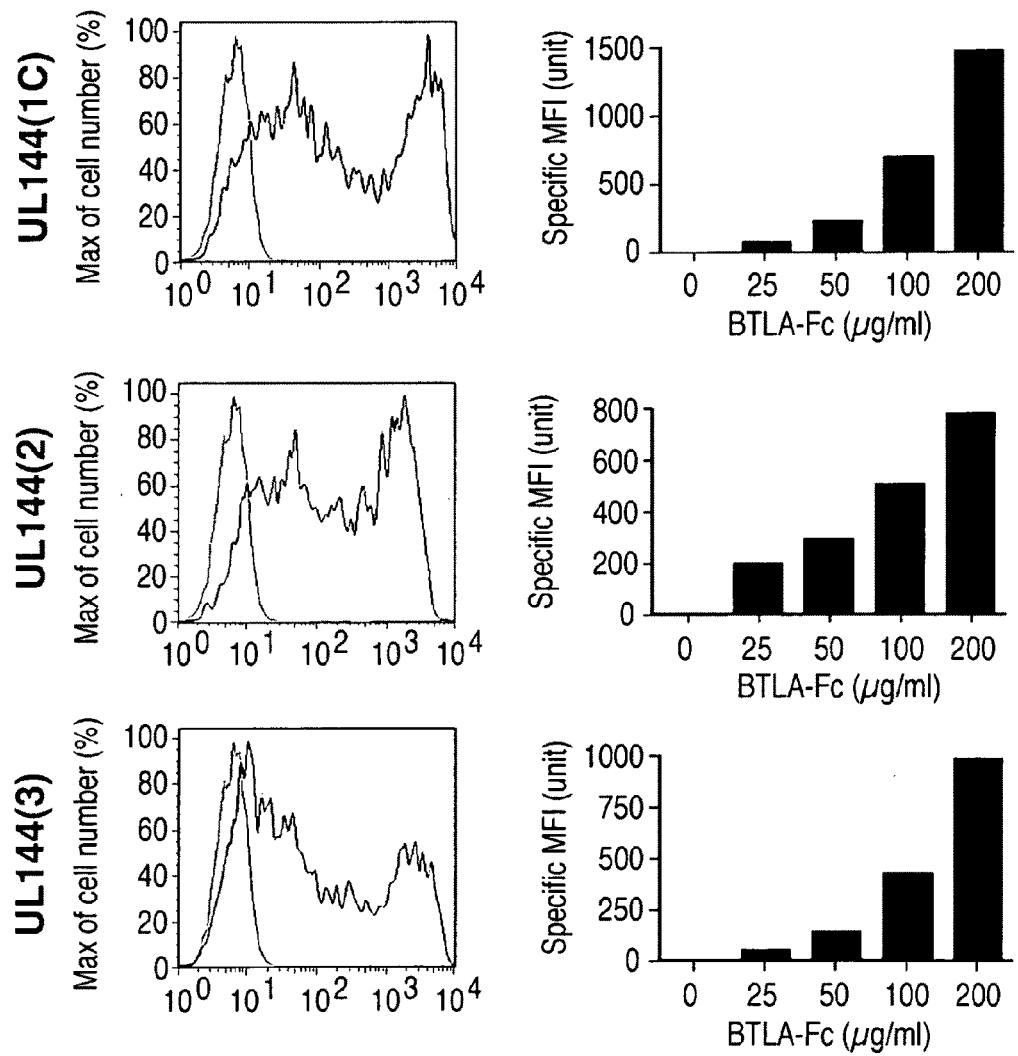
Figure 8B:
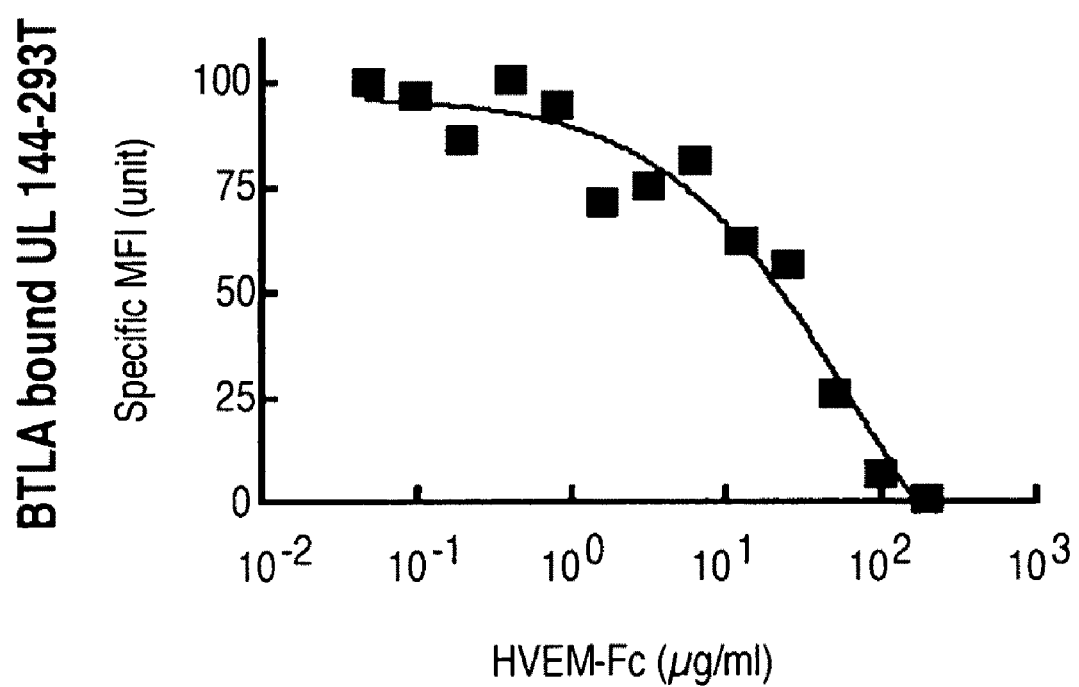

[1]293T cells were transfected with wild type or mutant HVEM expression plasmids. Binding analyses were performed on day 3 after transfection.
[2]BTLA-Fc, extracellular domain of human BTLA was fused to Fc of human IgG; FLAG epitope tagged soluble LIGHT (LIGHT-t66).
[3]The numbering of amino acid residues in HVEM is based on translation of the mature mRNA transcript.
[4]Saturation binding analysis measured by flow cytometry-based assay was used to estimate the equilibrium binding constant (KD) as described in Materials and Methods (representative of two studies).
[5]NB, Not bound.
[6]Glycoprotein D of herpes simplex virus was fused to Fc of rabbit Ig and used in the binding assays at 0.4 μg/ml.

etry. Transfected cells were stained with hBTLA-Fc at 200 µg/ml or mock transfected control 293T cells. Binding profiles revealed specific interactions between human BTLA-Fc with cells transfected with each of the UL144 variants from human CMV (FIG. 8A). Reciprocally, UL144-Fc generated from the Fiala (F) strain of human CMV (a group 3 sequence) (Benedict et al., *J Immunol* 162:6967 (1999)) specifically bound human, but not mouse BTLA. Graded concentrations of hHVEM-Fc were added to UL144(1C) transfected 293T cells in the presence of hBTLA-Fc (50 µg/ml). However, human BTLA-Fc bound to cell-expressed UL144 from each group with similar affinity (KD=2-4 µM) despite the sequence variation in CRD1, although binding was weaker than that seen for HVEM (~5 fold). Human HVEM-Fc effectively competed with cell-expressed UL144(1C) for binding BTLA-Fc (FIG. 8B) indicating they engage a spatially related interaction site on BTLA.

Figure 9A:
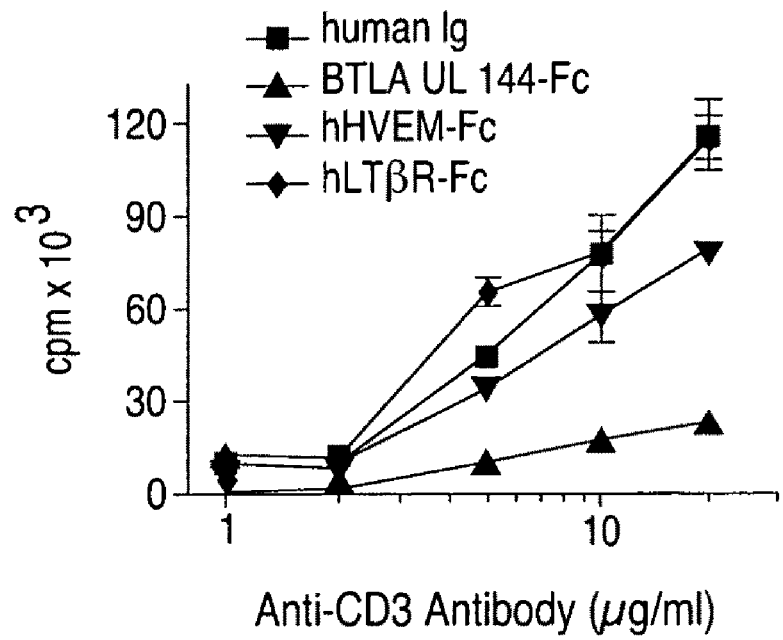
FIGS. 9A-B: Inhibition of T cell proliferation by HVEM-Fc and UL144-Fc. (A) Purified CD4+ T cells from human peripheral blood cultured in 96-well plates at $4 \times 10^5$ cells/well and stimulated with graded concentrations of plate-bound anti-CD3 and 1 µg/ml soluble anti-CD28 in the presence of human IgG, hLTβR-Fc, UL144:Fc (Fiala, group 3) or hHVEM:Fc immobilized with anti-human IgG1Fc antibody. (B) Graded amounts of hIgG, UL144-Fc (Fiala), or HVEM- Fc incubated with anti-human IgG1Fc antibody. Results represent mean values±SEM of triplicate wells and are representative of three studies.
Figure 9B:
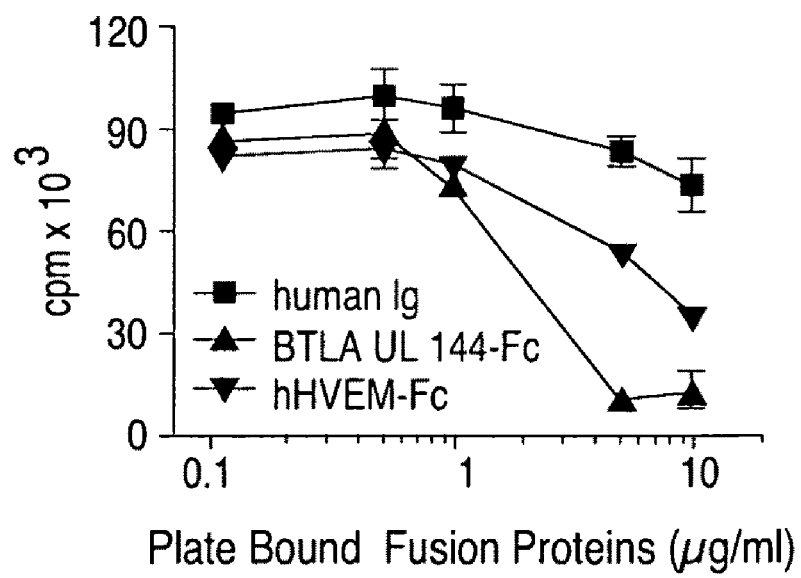

Purified CD4+ T cells from human peripheral blood were cultured in 96-well plates at $4 \times 10^5$ cells/well and stimulated with graded concentrations of plate-bound anti-CD3 and 1 µg/ml soluble anti-CD28 in the presence of (10 µg/ml) human IgG, hLTβR-Fc, UL144:Fc (Fiala, group 3) or hHVEM:Fc immobilized with anti-human IgG1Fc antibody adsorbed to plastic. Graded amounts of hIgG, UL144-Fc (Fiala), or HVEM-Fc were incubated with anti-human IgG1Fc antibody adsorbed to plastic. Wells were coated with 10 µg/ml anti-CD3 and anti-CD28 were used to stimulate purified CD4+ T cells. Cells were cultured for 72 hours, and pulsed with 3H-thymidine in the final 16 hours. The functional similarity of UL144 and HVEM was observed in the ability of UL144-Fc to inhibit the proliferation of human CD4+ T cells when activated with limiting amounts of anti-CD3 and anti-CD28 in the presence of immobilized fusion proteins. HVEM-Fc and UL144-Fc, but not LTβR-Fc, were effective at inhibiting proliferation (FIG. 9A), however UL144-Fc was significantly more potent than HVEM-Fc in this assay (FIG. 9B). Both HVEM-Fc and UL144-Fc were most potent in blocking T cell proliferation when immobilized indicating that crosslinking is probably needed for these proteins to be effective. In contrast, to human and mouse HVEM, UL144(F) did not function as an entry factor for HSV-1 and did not bind LIGHT (Benedict et al., *J Immunol* 162:6967 (1999)).

Example 7

This example describes data indicating that a UL144 protein from humans and from primates have a binding site for BTLA.

Figure 10:
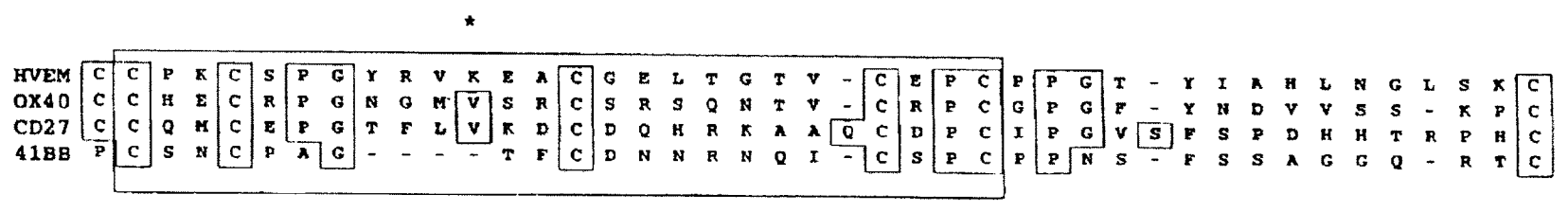

Alignments were performed on sequences of the mature ecto domains. Signal peptide cleavage site to deduce the mature protein was predicted by SignalP. Alignments were made using ClustalW (PAM series) MacVector software. The BTLA specific binding site formed by the conserved disulfide bonds and charged residues are found in several other TNFR superfamily members including CD27, 41BB, and OX40 FIG. 10. This is likely true for other receptors that map to Chr 12p13 and Chr1p36 in humans including AITR, CD30, DR3 since these show close genetic origins and costimulatory activities for T cells. The similarity in this region of the ecto domain predicts that BTLA or related molecules may bind to these receptors and attenuate T cell responses. Since the sequence diverges somewhat between these different receptors implies that other "BTLA like" molecules (structural and functional homologues) may engage these receptors.

The human cytomegalovirus (HCMV) protein UL144 is a structural homologue of HVEM in the first CRD (Benedict et al., *J. Immunol* 126:6967 (1999)). Human UL144 proteins contain significant homology with the region encompassing the BTLA binding site in HVEM, particularly the conservation of lysine equivalent to HVEM-K64. In UL144 the equivalent is lysine 46 (K46). However, HCMV-Fiala lacks the equivalent K64 (as do all other group 3 HCMV UL144 variants) replaced by a glycine glutamine (conserved substitution with another basic residue) (Lurain et al., *J Virol* 73:10040 (1999 December)). A UL144 isolate from Rhesus macaque CMV (RhCMV) however, contains the K64 conserved lysine residue (K64). Thus, UL144-Fiala and RhUL144 were tested for their ability to bind mouse and human BTLA.

Figures 11A, 11B, 11C:
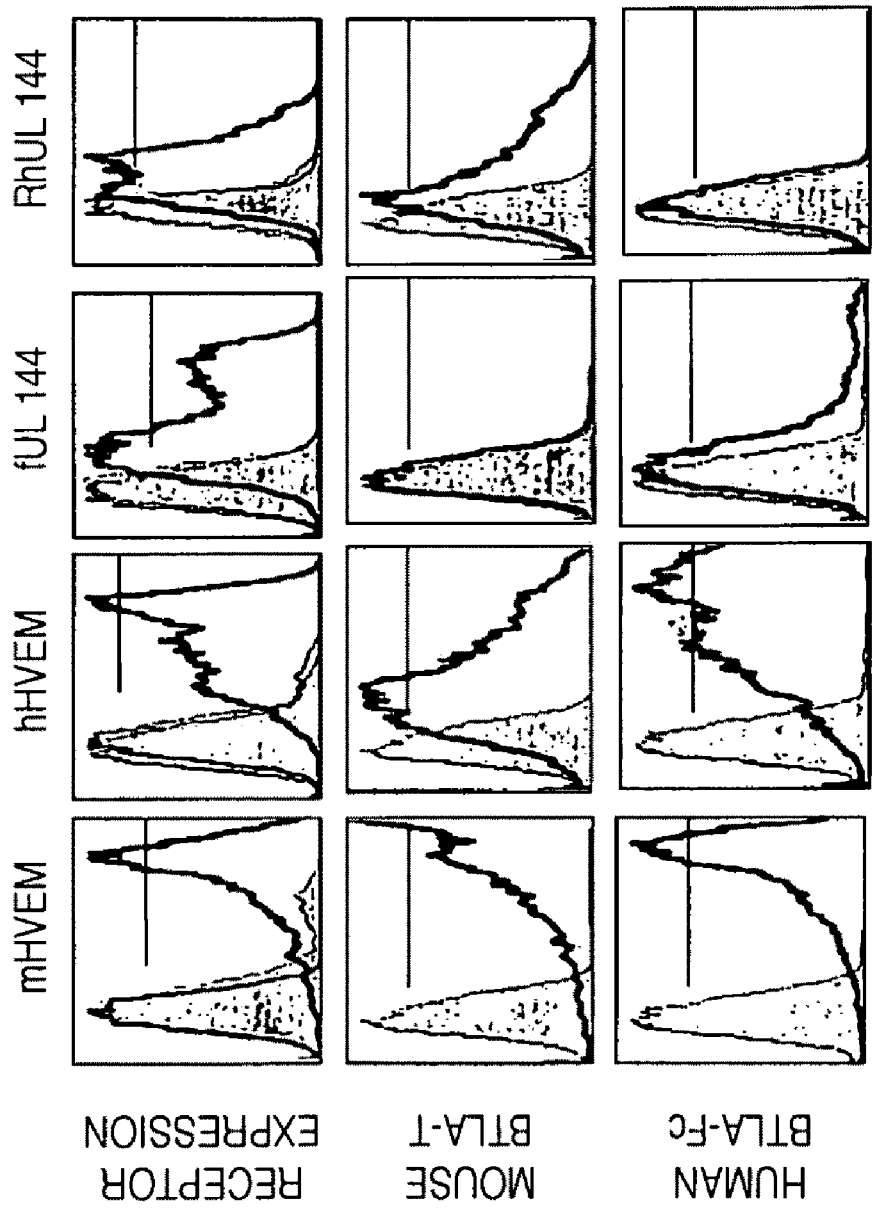
FIGS. 11A-B: Binding of virus encoded UL144 to BTLA. The relevant receptor expression is shown for each transfected cDNA as a marker of transfection efficiency (A) and the corresponding BTLA-T binding (B, C). Mock transduced cells stained with antibody or BTLA reagent (filled histogram); staining with isotype control antibody shown as light black line; antibody or BTLA reagent staining of transduced cells in dark line.

Human 293T cells were transiently transfected with cDNA (1 µg) encoding mHVEM, hHVEM, UL144-Fiala, or RhUL144. Mock and transfected cells were cultured and harvested as described in Example 4. Cells were incubated with the relevant anti-receptor antibody (rat anti-mHVEM IgM, 14C1.1), polyclonal goat anti-hHVEM, rat anti-UL144 (2F11) IgG, or polyclonal rat anti-RhUL144 with the relevant isotype controls. Transfected cells were stained with a mouse BTLA tetramer reagent or human BTLA-Fc. Cells ($10^4$) were analyzed by flow cytometry. Mouse BTLA binds to cells that express the UL144 RhCMV protein, but does not bind UL144 from HCMV-Fiala, although human BTLA binds UL144-Fiala, but not RhUL144 (FIG. 11). This analysis indicates that the UL144 protein from human and primate CMV can serve as a binding protein for BTLA and thus may alter the functional ability of BTLA.

Together these results reveal a novel domain in HVEM and various UL144 that isolates that bind to BTLA. The equivalent region in other tumor necrosis factor receptors (TNFR) may serve a similar function to bind BTLA like molecules and thus be subject to regulation by specific inhibitors.

Example 8

This example describes data indicating that a 4-18B-deficiency versus a 4-1BBL-deficiency suggests the existence of an alternative binding partner for 4-1BB that acts in a negative, regulatory manner.

The interaction between 4-1BB and 4-1BBL has been reported to positively affect T cell responses and enhance T cell proliferation and survival. This has been shown in several ways including the use of naturally occurring antigen presenting cells (APCs) expressing 4-1BBL, and 4-1BBL-transfected APCs, that augment T cell responses (DeBenedette et al., *J Exp Med* 181:985 (1995); Gramaglia et al., *Eur J Immunol* 30:392 (2000); Melero et al., *Nat Med* 3:682 (1997)) and this was indirectly confirmed with agonist antibodies to 4-1BB that can enhance T cell division or survival (Shuford et al., *J Exp Med* 186:47 (1997); Takahashi et al., *J Immunol* 162:5037 (1999)). Additionally, mice deficient in 4-1BBL show reduced T cell responses to LCMV and influenza virus (Bertram et al., *J Immunol* 168:3777 (2002); DeBenedette et al., *J Immunol* 163:4833 (1999); Tan et al., *J Immunol* 162: 5037 (1999)) and to skin allografts (DeBenedette et al., *J Immunol* 163:4833 (1999)). Also, in studies where wild-type TCR transgenic T cells are adoptively transferred into 4-1BBL-deficient mice, impaired T cell priming is observed (Dawicki et al., *Eur J Immunol* 34:743 (2004)).

Figure 12:
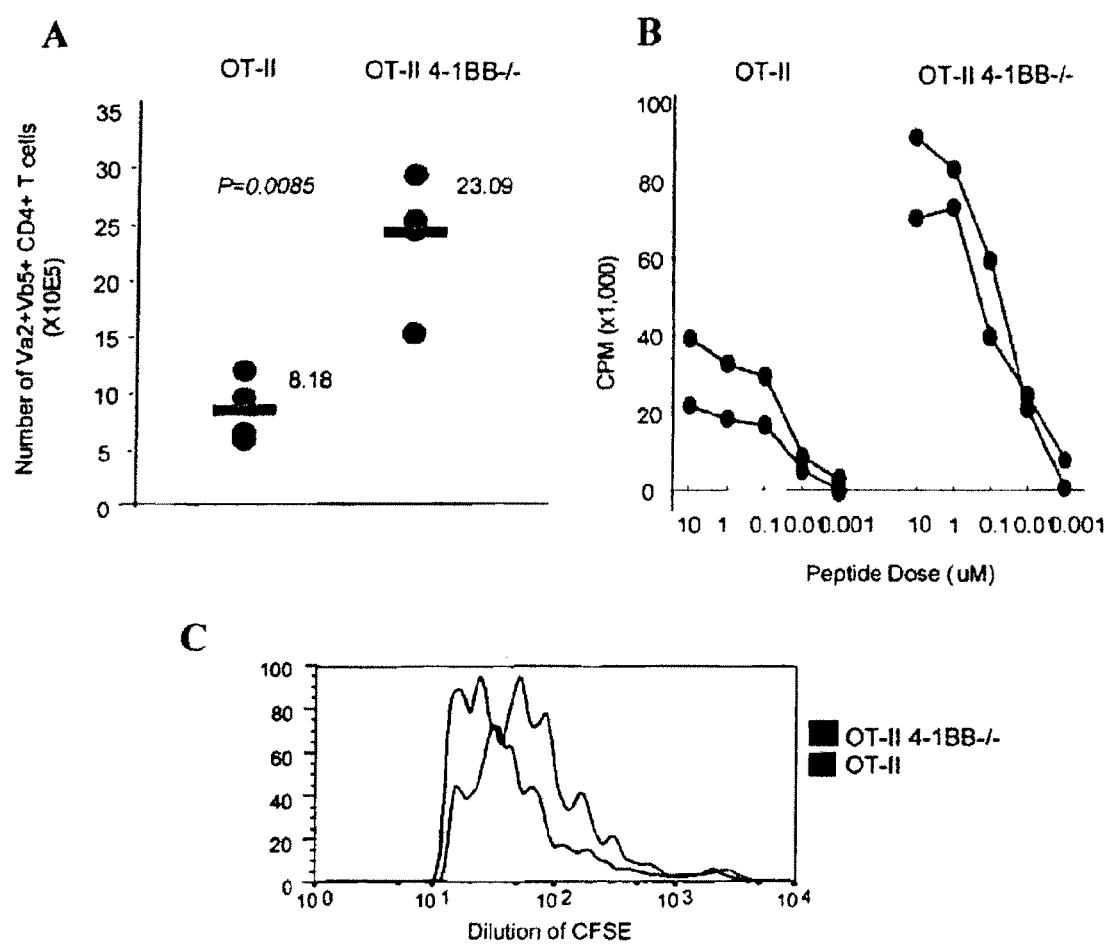
FIGS. 12A-C: T cells lacking 4-1BB display enhanced responsiveness. (A) Accumulation of OT-II T cells on day 5 after immunization, based on enumerating the number of $V\alpha2/V\beta5$ CD4 T cells. Each point represents one mouse. (B) Recall in vitro proliferation on day 5, after culturing lymph node cells with varying doses of OVA. Data are cpm after incorporation of tritiated thymidine overnight. Data from two individual mice are shown. (C) Cell division of OT-II T cells on day 3 after immunization. Data shows dilution of the dye CFSE, with lower intensity staining indicating greater levels of division.

CD4 T cells from wild-type or 4-1BB-deficient OT-II TCR transgenic mice were isolated, labeled with CFSE, and one million adoptively transferred into wild-type B6 mice. These mice were immunized with OVA in Alum at day 0. T cells from 4-1BB-deficient mice show enhanced and not reduced responsiveness. 4-1BB-deficient mice were crossed with OT-II TCR transgenic mice and T cells from these mice adoptively transferred into wild-type (4-1BBL positive) mice. In response to antigen, the 4-1BB-deficient T cells expanded in numbers to a greater extent (FIG. 12a) and displayed greater reactivity in recall responses (FIG. 12b), and this was accompanied by a faster division rate in vivo (FIG. 12c). This suggests that a lack of 4-1BB relieves a negative signal and allows T cells to respond better. This data is supported by a published study where splenocytes from 4-1BB-deficient mice reported enhanced proliferation to anti-CD3 (Kwon et al., *J Immunol* 168:5483 (2002)).

Figure 13:
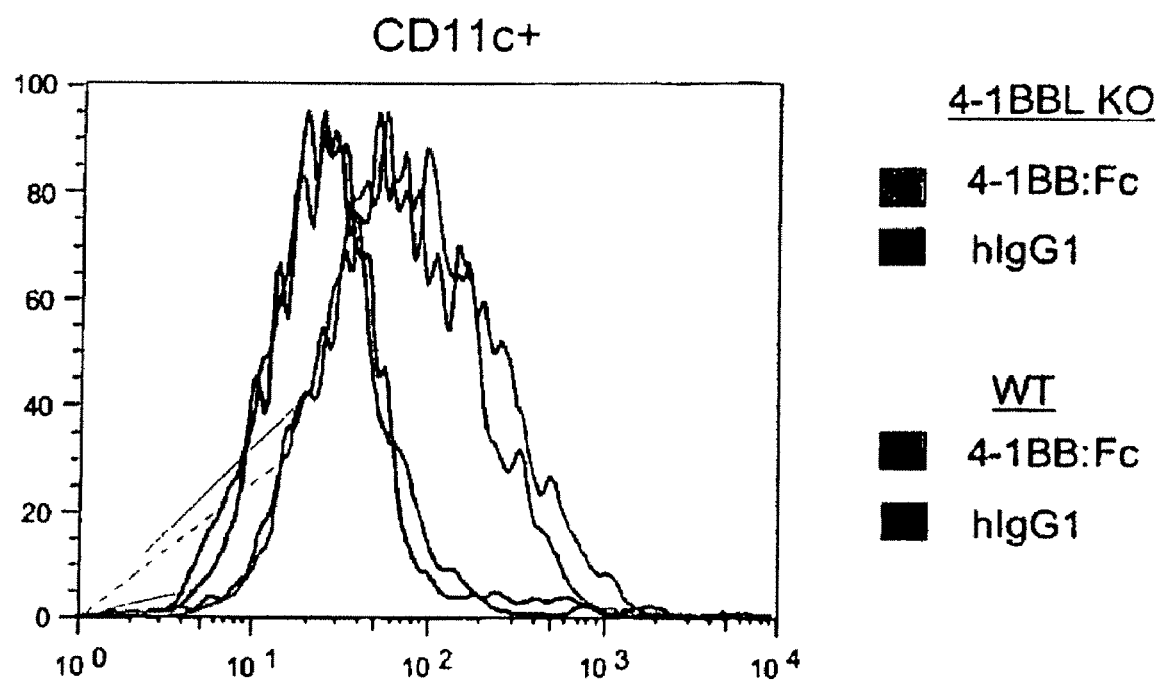
FIG. 13: 4-1BB-Fc binds to the surface of 4-1BBL-deficient CD11c+ Cells.

Together, the contrasting data with a 4-1BB-deficiency versus a 4-1BBL-deficiency suggest the existence of an alternative binding partner for 4-1BB that acts in a negative, regulatory manner. In support of this, FACS analysis was performed using splenocytes from wild-type and 4-1BBL-deficient mice. Cells were initially stimulated in vitro for 24 hours with LPS and CpG, and then stained with CD11c to delineate dendritic populations and counter-stained with a chimeric Fc fusion protein of human IgG and mouse 4-1BB or as a control human IgG. The data indicate that 4-1BB.Fc equally stains CD11c dendritic cell populations from wild-type and 4-1BBL-deficient mice (FIG. 13).

Example 9

This example describes data indicating that HVEM-BTLA interaction can result in reduced dendritic cell numbers.

Dendritic cells (DC) are bone marrow-derived cells that present antigen to T cells and play a crucial role bridging innate and adaptive immune responses to activate T cell immune responses. LTβR has been reported to control the number of dendritic cells in lymphoid organs and transgenic expression of LTβ was reported to increase DC numbers in spleens of mice (Kabashima et al., *Immunity* 22:439 (2005)).

Figure 15A:
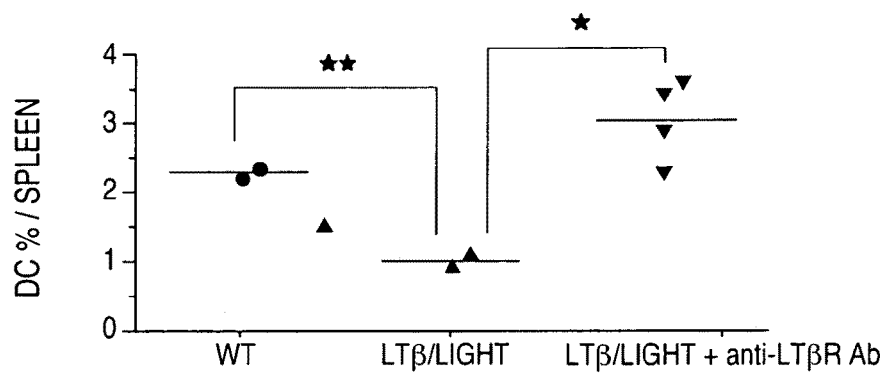
FIGS. 15A-C: Restoration of spleen CD4+ and CD8− CD4− double negative (DN) DC subsets in LTβ/LIGHT deficient mice treated with anti-LTβR agonistic antibody. (A) The frequencies of DCs in WT (filled circle) and anti-LTβR Ab untreated and treated LTβ/LIGHT-deficient mice (filled triangle and reverse filled triangle, respectively). The frequencies (B) and number (C) of CD4+, CD8a+ and DN DC subsets within gated DCs were calculated in WT and anti-LTβR Ab untreated and treated LTβ/LIGHT-deficient mice. Each dot represents the value obtained from an individual animal (A). Bars show the mean±SD from at least two mice per group and the data are representative of one independent experiment (B, C). A test was performed between the indicated groups and one and two asterisks mean $p<0.05$ and $p<0.01$, respectively.
Figure 15B:
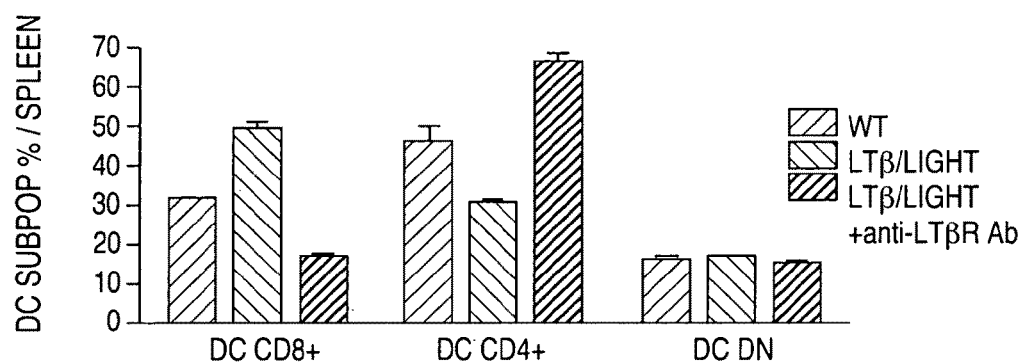
Figure 15C:
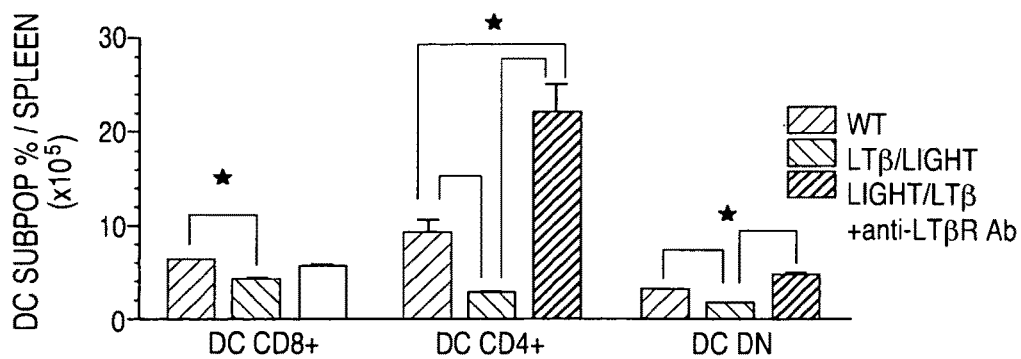
Figure 16A:
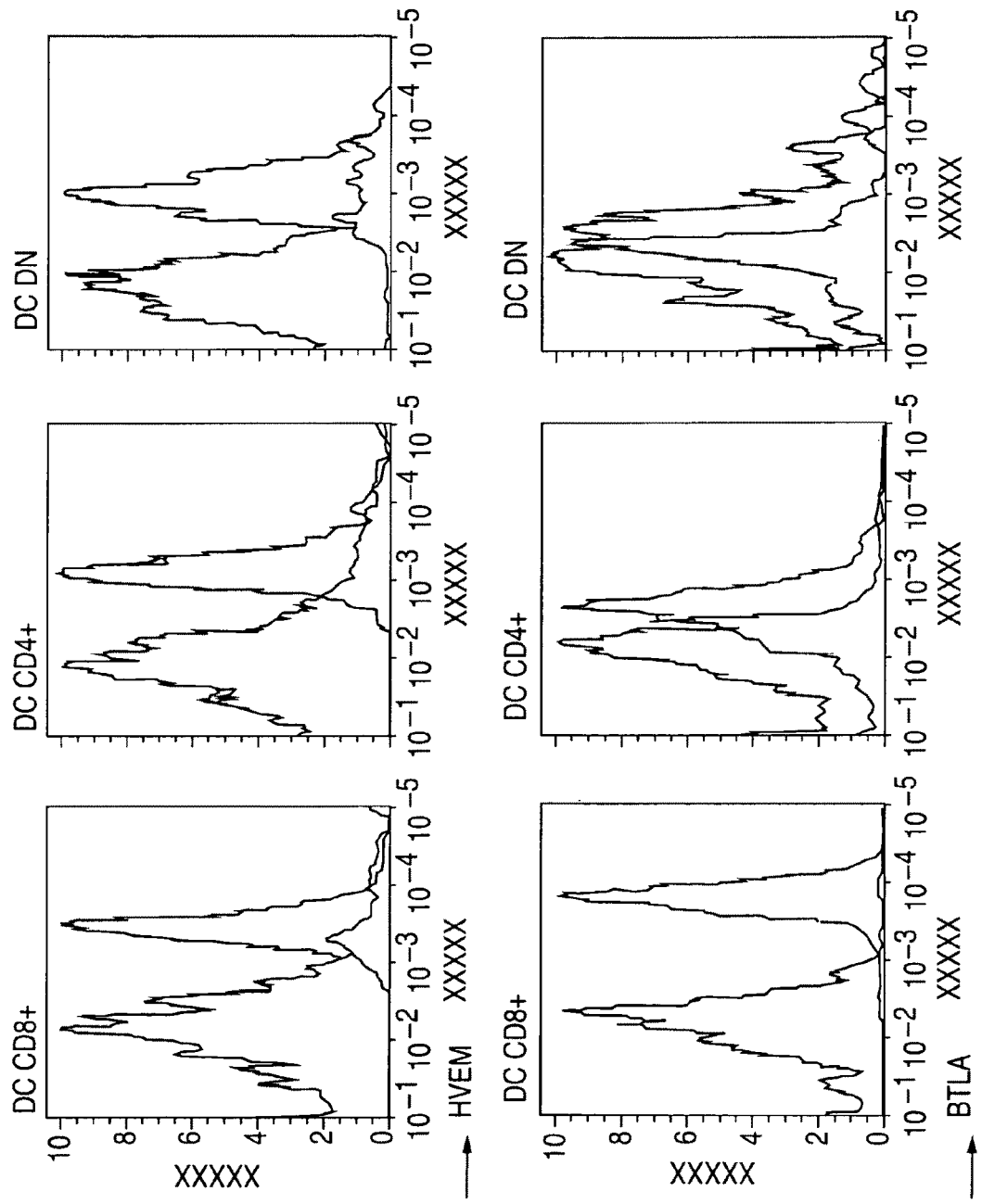
FIGS. 16A-B: (A) Flow cytometric analysis of HVEM and BTLA expression in CD4+, CDαα+ and CD4/8 double negative (DN) DC subsets from C57Bl/6 mice. The expression of HVEM and BTLA (red) was detected using rat anti-HVEM (14C1.1) and hamster anti-C57BL/6 BTLA (6A6) mAb followed by anti-rat Igm-phycoerythrin (PE) and anti-armenian hamster-PE (Pharmingen), respectively. As negative controls (blue line) splenocytes from HVEM−/− mice or control hamster IgG for BTLA staining was used. Cells were gated according to size and scatter to eliminate dead cells and debris from analysis. DC subsets were identified based on their high level of CD11c expression and CD4 and CD8. (B) Increased CD in HVEM and BTLA-deficient mice. The frequencies of DC in spleen of WT, HVEM and BTLA-deficient mice were assessed by flow cytometry. Each data point represents the value obtained from and individual animal. The differences between wt and either HVEM or BTLA is significant $p<0.001$.
Figure 16B:
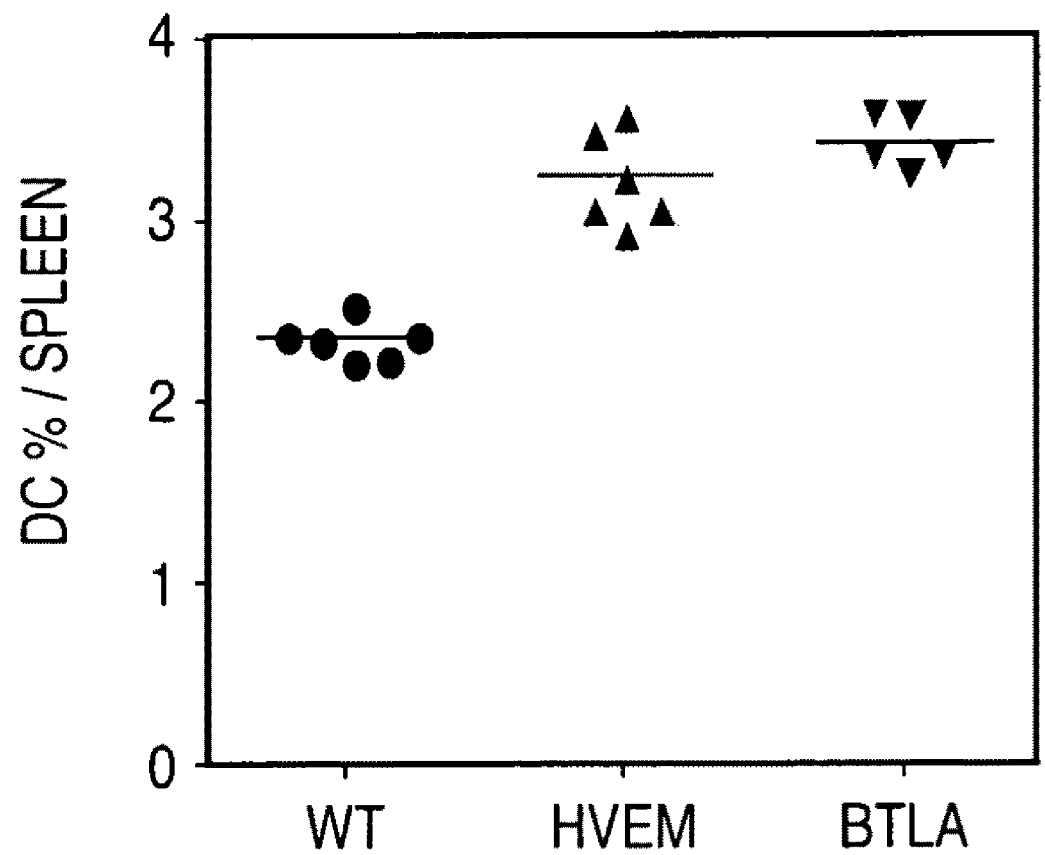
Figure 17C:
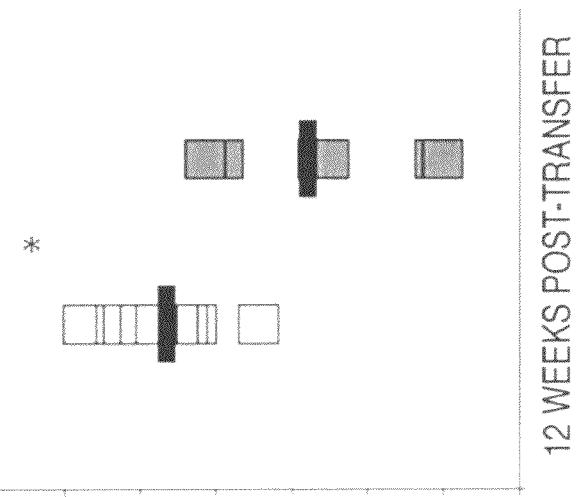
FIG. 17A-C: CD4+CD45RB$^{high}$ T cells do not require HVEM to induce colitis. (A) Weight loss curves of Rag$^{-/-}$ recipients transferred with $5\times10^5$ CD4+CD45RB$^{high}$ T cells isolated from either WT C57BL/6 mice (open squares) or Hvem$^{-/-}$ mice (filled squares). The graph shows the average weight loss as a percentage of the initial weight of 4 mice in each group and they are representative of four independent experiments. (B) H&E staining of proximal and distal colon of Rag$^{-/-}$ mice transferred with WT or Hvem$^{-/-}$ T cells. Magnifications are indicated and the histological scores of the representative sections shown are indicated (lower right of each panel). GC=goblet cells. (C) Average scores of the proximal and distal colon sections were evaluated 12 weeks after the transfer of T cells. Sections of the large intestine isolated from different recipients were microscopically analyzed as described in Materials and Methods. Each square represents a single mouse (eight per group). *, $p<0.05$.
Figure 17A:
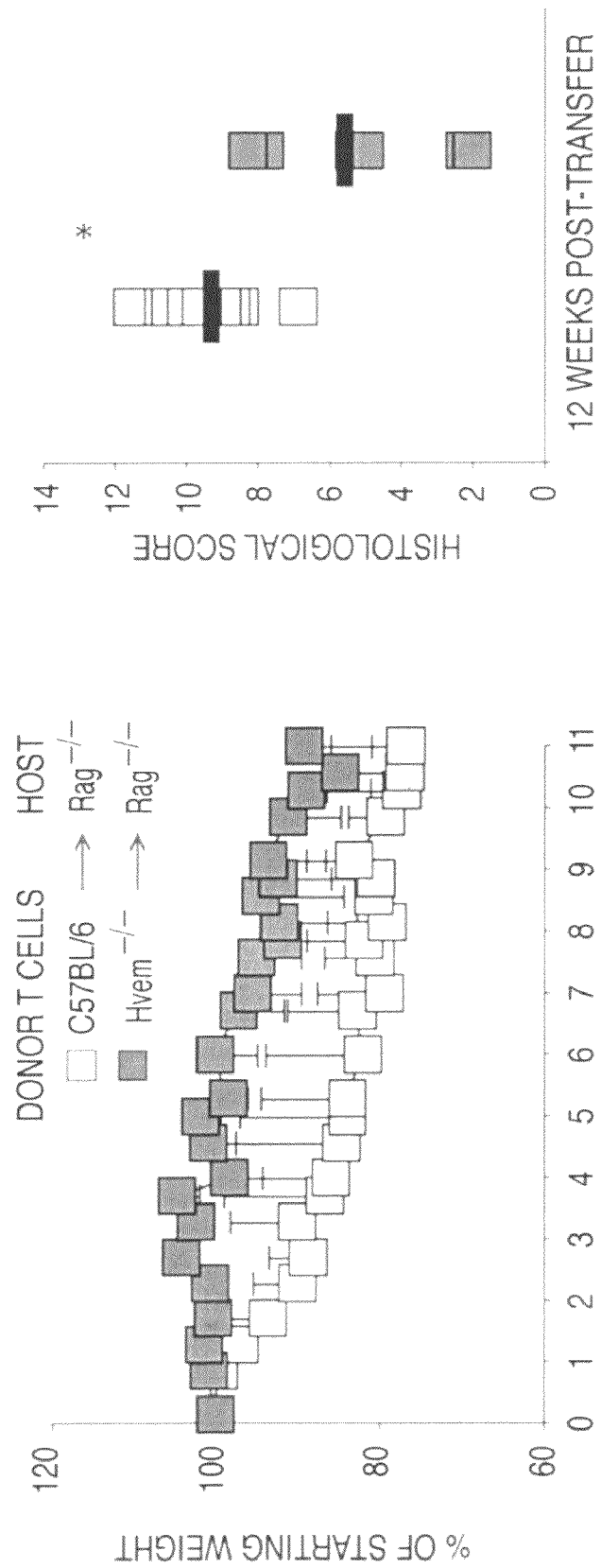
Figure 17B:
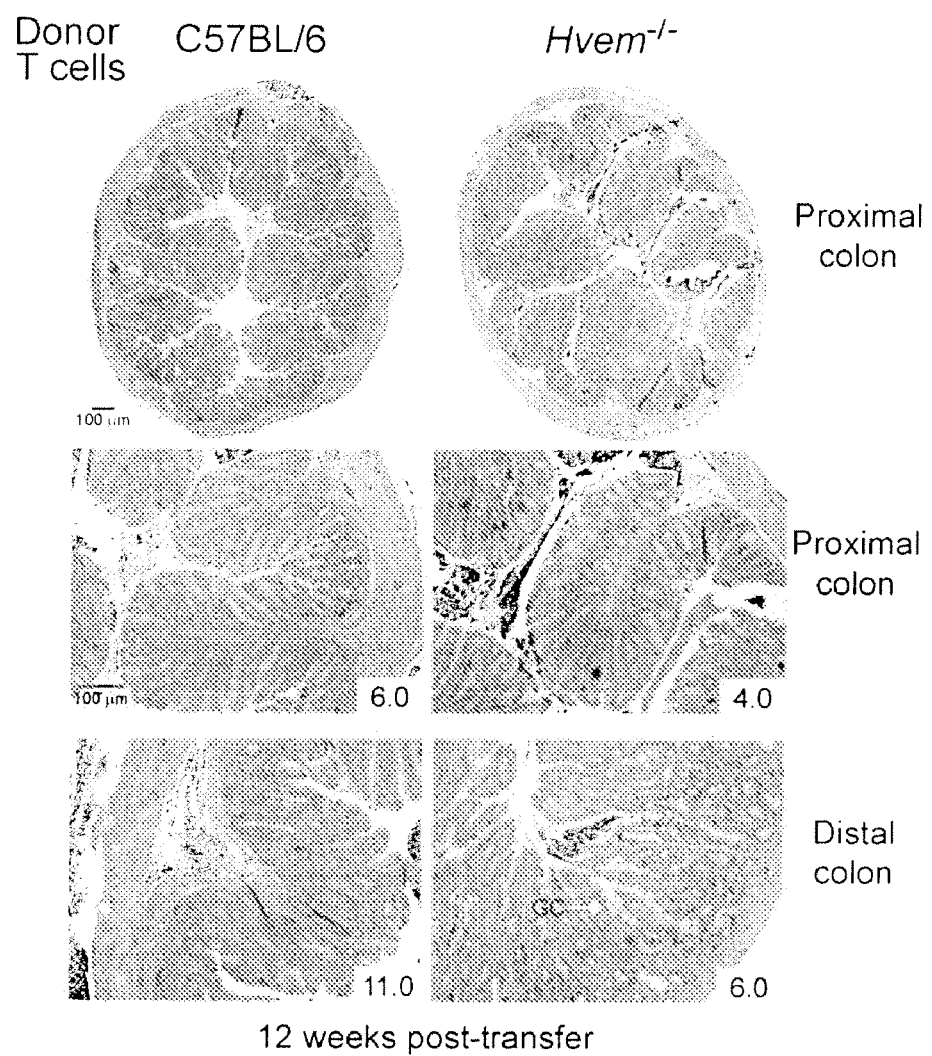

The blockade of LTαβ and LIGHT with a decoy receptor of the LTβR (LTβR-Fc) decreased DC numbers in the spleen (FIG. 14). Moreover, treatment with an agonist antibody to LTβR restored DC numbers in spleens of mice genetically deficient in the ligands for LTβR (FIG. 15). Dendritic cells express both HVEM and BTLA on their cell surface (FIG. 16, upper panel) and therefore can be subject to their signals. The data indicates that mice deficient in either HVEM or BTLA have increased numbers of DC compared to wild type mice (FIG. 16, lower panel), which is the opposite phenotype to LTβR deficient mice. This result indicates that HVEM-BTLA provides signals that counteract those provided by LTβR in controlling DC numbers. Consequently, blocking the HVEM-BTLA pathway together with activating LTβR with an agonist, dendritic cell numbers should be increased. Thus, an increase in DC numbers should assist in activating T cells to provide protective immunity to infectious agents and malignant cells. Similarly, blocking activation of LTβR or activating BTLA should inhibit DC numbers, which in turn may decrease T cell reactions, such as those that cause autoimmune diseases. Using HVEM-Fc that lacks LIGHT binding activity, or an agonist antibody to BTLA, or an antibody to HVEM that blocks its BTLA-activating activity should diminish T cell reactions.

Example 10

This example includes a discussion and analysis of some of the data described herein.

The N-terminal extracellular region of HVEM is composed of four pseudo-repeats of a cysteine-rich domain (CRD), characteristic of the TNFR superfamily, each repeat contains three disulfide bonds that fold into complex loops depending in part on the spacing of the cysteines (Bodmer et al., *Trends Biochem Sci* 27:19 (2002)). Mutagenesis studies (Rooney et al., *J Biol Chem* 275:14307 (2000)) and conservation of LIGHT with LTα in the LTα-TNFR1 complex (Banner et al., *Cell* 73:431 (1993)) imply the $2^{nd}$ and $3^{rd}$ CRD of HVEM contains the LIGHT-binding site. Crystallographic analyses (Carfi et al., *Molecular Cell* 8:169 (2001)) and mutagenesis studies (Whitbeck et al., *J Virol* 75:171 (2001)) of HVEM-gD complex revealed the viral protein bound primarily to CRD 1 on the side opposite of the LIGHT binding site. Glycoprotein D contains an Ig-like fold with an extended N-terminal hairpin loop that binds HVEM (Carfi et al., *Molecular Cell* 8:169 (2001)). Thus, HVEM has at least two spatially distinct ligand binding regions, yet gD can competitively block the binding of membrane bound LIGHT to HVEM (Mauri et al., *Immunity* 8:21 (1998)).

The potential of HVEM to serve as a molecular switch for positive or inhibitory signaling during T cell activation will depend upon which of its four ligands are engaged. The hierarchy of occupancy of HVEM by BTLA and LIGHT, which engage distinct sites on HVEM, has been defined. Viral ligand for HVEM, Herpes Simplex virus gD, acted as a dual antagonist by competitive displacement of BTLA, and non-competitive blockade of LIGHT (p30). Moreover, the molecular definition of the BTLA binding site on HVEM provided the key clue revealing a function for the orphaned TNFR encoded by the UL144 ORF in human CMV. These two viral proteins provide insight into mechanisms regulating the HVEM molecular switch.

Domain-swapping studies revealed the CRD1 of HVEM was sufficient to mediate BTLA binding. Although not wishing to be bound by theory, the data indicate that the BTLA binding site on HVEM is centered on K64 and adjacent residues R62 and E65 embedded within the loop formed by disulfide bonds at C57-C75 and C67-054 in CRD1. This would position the BTLA binding site on the face opposite the LIGHT binding site on HVEM, similar to HSV-1 gD. This region is referred to as DARC (gD and BTLA binding site on the TNF Receptor HVEM in the Cysteine-rich domain-1).

Based on structural models of TNF-TNFR complexes (Banner et al., *Cell* 73:431 (1993)), orientation of LIGHT and HVEM must be on juxtaposed membranes for binding to occur, with the N-terminus of HVEM proximal to the membrane in which LIGHT resides. The ability of HVEM to activate BTLA signaling when presented in trans from another cell suggests the juxtaposition of HVEM and BTLA in distinct membranes is sufficient for proper orientation (Sedy et al., *Nat Immunol* 6:90 (2005)), but does not exclude the possibility of an interaction in cis. Because of the non-competitive interaction of BTLA-Fc and LIGHTt66, both molecules appear to be capable of simultaneously occupying HVEM. Moreover, the binding of soluble LIGHTt66 to HVEM at levels approaching saturation enhanced binding of BTLA-Fc, as indicated by the data described herein, and reported in a paper (Gonzalez et al., *Proc Natl Acad Sci USA* 102:1116 (2005)) the binding of HVEM-Fc was also enhanced when cells co-expressed LIGHT and BTLA. These results are consistent with an ability of the soluble reactants to form a trimolecular complex, and at least theoretically, simultaneously initiate both positive and inhibitory signaling.

The evidence for a trimolecular LIGHT-HVEM-BTLA complex was generated with one or more reactants in soluble form, and whether such a complex forms in their normal membrane anchored positions remains to be determined. Three findings suggest that LIGHT will displace BTLA-HVEM interaction, indicating a trimolecular complex is unlikely to form in the normal membrane anchored positions.

First, the affinity of the LIGHT-HVEM interaction (binding) is an order of magnitude greater than for the observed HVEM-BTLA complex (KD=11 nM, HVEM-Fc binding membrane LIGHT; KD=112 nM, HVEM-Fc binding membrane BTLA). This indicates that the LIGHT-HVEM interaction (binding) will predominate when HVEM is the limiting reactant, which may occur when HVEM is down modulated after T cell activation, concurrent with the induction of LIGHT (Sedy et al., *Nat Immunol* 6:90 (2005), Mauri et al., *Immunity* 8:21 (1998), Morel et al., *J Immunol* 165:4397 (2000)). Second, the viral inhibitor protein gD may influence ligand binding without directly occupying the binding site (non-competitive inhibition). In this regard, glycoprotein D inhibited the interactions of HVEM with BTLA in a competitive fashion supported by the fact their binding sites overlap. However, gD inhibited HVEM binding only when LIGHT was in its membrane anchored position (FIG. 1G); soluble LIGHT was not blocked by gD (Sarrias et al., *Mol Immunol* 37:665 (2000), Sarrias et al., *J Virol* 73:5681 (1999)). The noncompetitive blockade of HVEM-LIGHT by gD parallels the behavior of BTLA in that BTLA blocks HVEM-Fc binding to membrane anchored LIGHT. These results suggest the possibility that the proximity of the membrane sterically excludes HVEM from binding LIGHT when gD occupies its binding site in the DARC region (noncompetitive behavior). Promoted by high affinity binding, the LIGHT-HVEM complex, may in turn, sterically exclude membrane BTLA from binding HVEM, thus acting in a noncompetitive fashion to disrupt inhibitory signaling by BTLA, which in turn results in inhibiting T cell proliferation and other activities.

A third line of evidence supporting the notion that LIGHT may act as a noncompetitive inhibitor of the HVEM-BTLA complex is provided by UL144. UL144-Fc was far more efficient than HVEM-Fc in blocking T cell proliferation, even though its binding affinity for BTLA was measurably less (5 fold). The enhanced anti-proliferative activity of UL144 relative to HVEM could be due to an inability to bind LIGHT, resulting in continued engagement with BTLA even when LIGHT is expressed. Thus, compounds that do not bind to LIGHT, but that bind to BTLA, are likely to provide a means of suppressing immune responses, such as one or more of the various immune responses set forth herein, and those associated with BTLA signal transduction pathway.

BTLA may serve as a constitutive "off" pathway for T cells since both HVEM and BTLA are expressed on resting lymphocytes albeit at low levels on naïve CD4$^+$ T cells (Hurchla et al., *J Immunol* 174:3377 (2005)). The induction of LIGHT during T cell activation (Mauri et al., *Immunity* 8:21 (1998)) and occupancy of HVEM may displace BTLA and diminish inhibitory action on antigen receptor signals as one potential mechanism regulating the ability of HVEM to act as a molecular switch. Temporal expression of LIGHT may also influence inhibitory signaling. In addition, signals induced through these pathways may lead to differential regulation of the cellular ligands for HVEM. LIGHT may inhibit BTLA activity indirectly by promoting maturation and/or activation of dendritic cells via its alternate receptor LTβR (Kabashima et al., *Immunity* 22:439 (2005)). Furthermore, exogenous factors such as decoy receptor-3 or proteolysis of LIGHT may also act as mechanisms regulating HVEM-BTLA pathway.

Herpesviruses cause persistent infection without overt pathogenicity, yet immune control is essential to maintain this coexistence. What selective advantage does altering the LIGHT-HVEM-BTLA pathway have for herpesviruses?

The results indicate that gD can inhibit HVEM signaling by blocking engagement of HVEM with both ligands, LIGHT and BTLA, thus potentially nullifying this circuit. It is tempting to speculate that gD may represent an evolutionary descendent BTLA, reflected by their common Ig domain structure and shared functional properties, including overlapping binding sites and uncompetitive blockade of LIGHT. Blocking LIGHT-HVEM signaling could diminish proinflammatory signals in T cells, appearing as an advantage for the virus. However, when unchecked by LIGHT, the HVEM-BTLA pathway may maintain too much inhibitory signaling. In this case, the adaptation of gD to include blockade of HVEM-BTLA pathway would counter balance the loss of LIGHT. By contrast, human CMV mimics only one function of the HVEM switch, the engagement of BTLA, and initiates inhibitory signaling without potential countering influence from LIGHT. The relatively high sequence variation in the ectodomain of UL144 displayed by different clinical isolates of CMV (Lurain et al., *J Virol* 73:10040 (1999 December)), yet retention of BTLA binding activity by all isolates suggests significant immune pressure is sculpting the evolution of this molecule, which is supported by the finding that specific antibody responses to UL144 are detected in humans (Benedict et al., *J Immunol* 162:6967 (1999)).

Each mechanism must be viewed in the context of other immune altering functions that have shaped unique niches by each herpesvirus. That evolutionary divergent α and β herpesviruses target the LIGHT-HVEM-BTLA pathway, although by distinct mechanisms, implicates the importance of this cytokine circuit in immune regulation. These immune evasion mechanisms of herpesviruses may provide information on how to modulate immunity without overt pathogenicity.

Example 11

This example describes data indicating that $CD4^+$ $CD45RB^{high}$ T cells do not require HVEM to induce colitis.

To investigate the participation of HVEM in colitis pathogenesis, we used an experimental mouse model initiated by the adoptive transfer of $CD4^+CD45RB^{high}$ naïve T cells, depleted of $CD25^+$ regulatory T cells, into syngeneic $Rag^{-/-}$ mice. This leads to a progressive disease, with weight loss and colitis appearing five to ten weeks after the transfer (Powrie, *Immunity* 3:171 (1995)).

To evaluate if the expression of HVEM in T cells is required for colitis induction, we transferred $CD4CD45RB^{high}$ T cells isolated from $Hvem^{-/-}$ or wild type (WT) mice into $Rag^{-/-}$ recipients. As expected, WT donor $CD4^+CD45RB^{high}$ T cells induced a gradual weight loss in $Rag^{-/-}$ recipients that correlated with disease progression, as did the transfer of $Hvem^{-/-}$ $CD4^+CD45RB^{high}$ T cells (FIG. 17A). Although at early time points after the transfer weight loss in the $Rag^{-/-}$ recipient mice of $Hvem^{-/-}$ T cells was slightly less pronounced, the recipients unquestionably became ill, eventually all the transferred Rag recipients showed an equivalent weight loss (FIG. 17A), and the overall difference between $Hvem^{-/-}$ and WT donor T cells did not reach statistical significance. Microscopic analysis of hematoxylin and eosin (H&E) stained tissue sections obtained from the large intestine of transferred mice revealed severe inflammation in all of the recipients. However, mice transferred with $Hvem^{-/-}$ T cells had lower mononuclear cell infiltrates in the proximal and distal colon. In addition, these recipients had a higher number of goblet cells in the distal colon, indicating that inflammation in these animals was milder (FIG. 17B). Scoring of sections obtained from the recipients transferred with $Hvem^{-/-}$ T cells showed a lower average histological score than in the animals that received WT T cells (FIG. 17C).

Overall, these results suggest that HVEM expression on donor T cells contributed to a limited extent to increasing intestinal inflammation, however, HVEM expression in T cells was not absolutely required for colitis development.

Example 12

This example describes data indicating that colitis is accelerated in Hvem$^{-/-}$Rag$^{-/-}$ recipients.

Figure 18A:
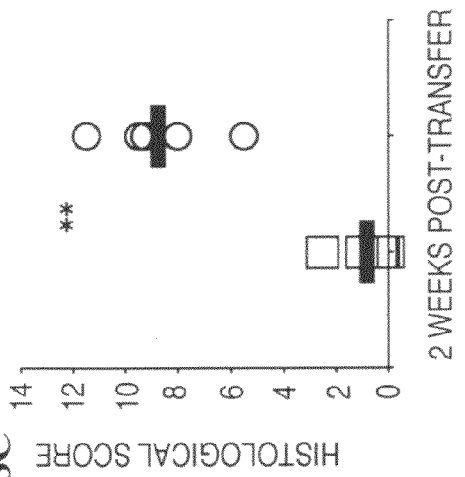
FIG. 18A-E: Colitis acceleration in Hvem$^{-/-}$Rag$^{-/-}$ mice. Transfer of CD4+CD45RB$^{high}$ T cells into Hvem$^{-/-}$ Rag$^{-/-}$ mice dramatically accelerated colitis. (A) Weight loss curves of Rag$^{-/-}$ (squares) and Hvem$^{-/-}$Rag$^{-/-}$ (circles) recipients of $5\times10^5$ WT T cells showed an extremely rapid disease progression in Hvem$^{-/-}$Rag$^{-/-}$ animals. Data correspond to the average of 5 mice per group and are representative of five independent experiments. (B) H&E staining of proximal and distal colon sections are shown. Magnifications are indicated (C) Average scores of the proximal and distal colon sections from individual mice were evaluated 2 weeks after the transfer of T cells. Each symbol represents an individual mouse (n=5), representative data from four experiments are shown. **, $p<0.005$. (D) Weight loss comparison following transfer of WT (open circles) or Hvem$^{-/-}$ (filled circles) CD4+ CD45RB$^{high}$ T cells into Hvem$^{-/-}$Rag$^{-/-}$ recipients (n=6-7). (E) Combined proximal and distal histological analysis of colon sections performed 2 weeks after the transfers described in part (D). Each symbol represents an individual mouse (n=7).
Figure 18C:
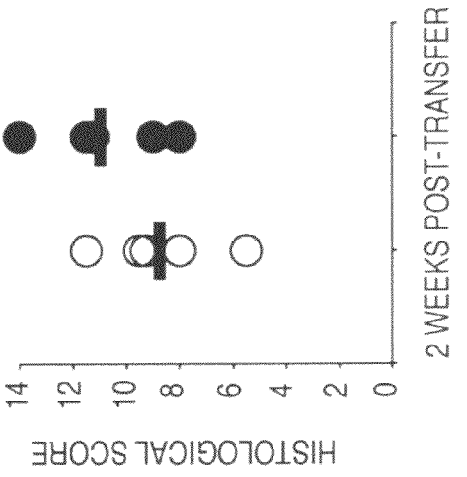
Figure 18D:
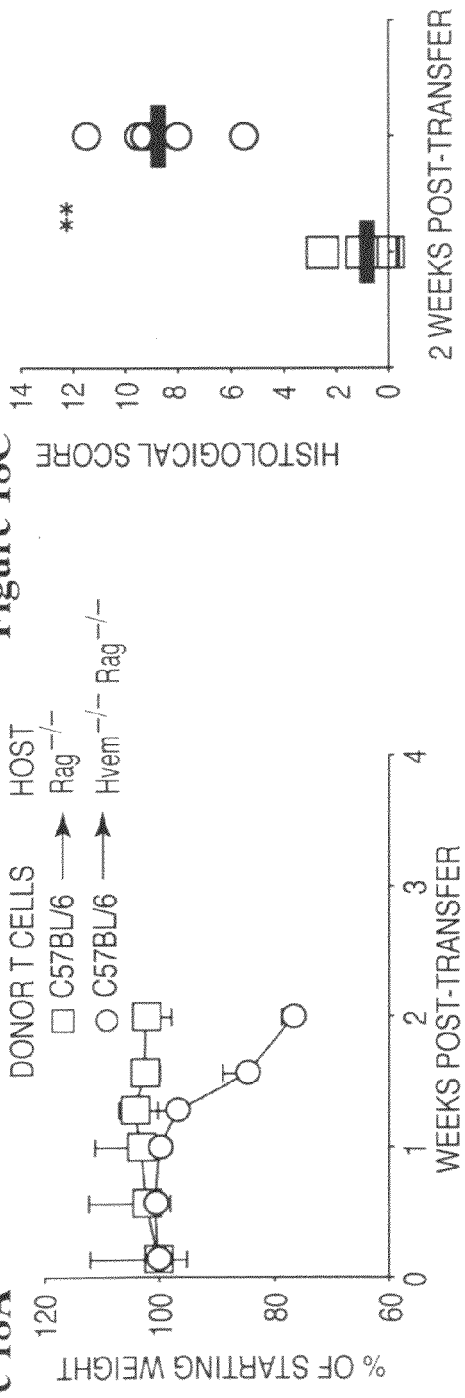
Figure 18E:
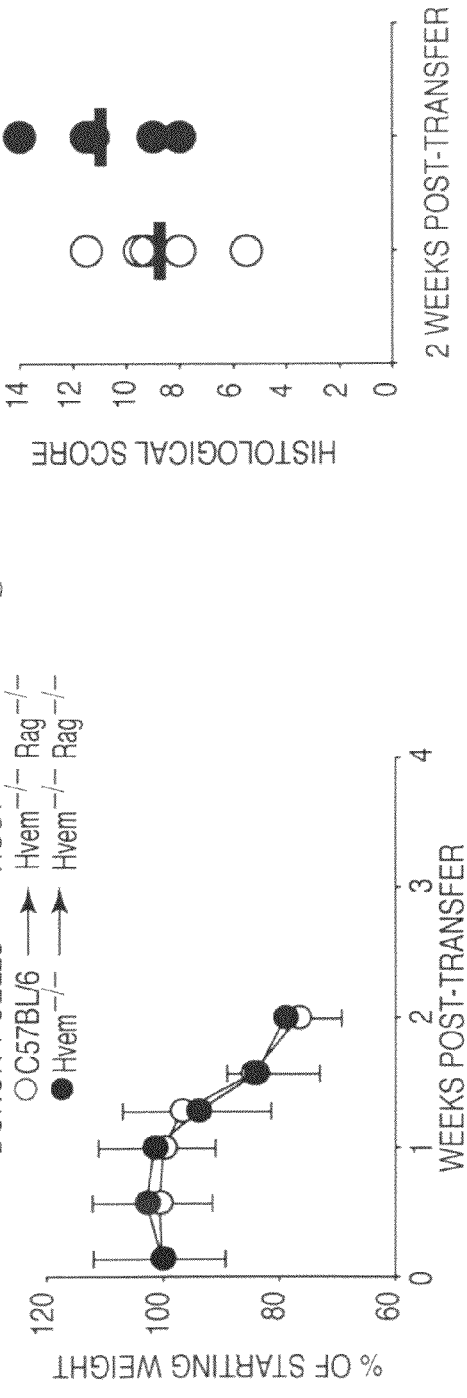
Figure 18B:
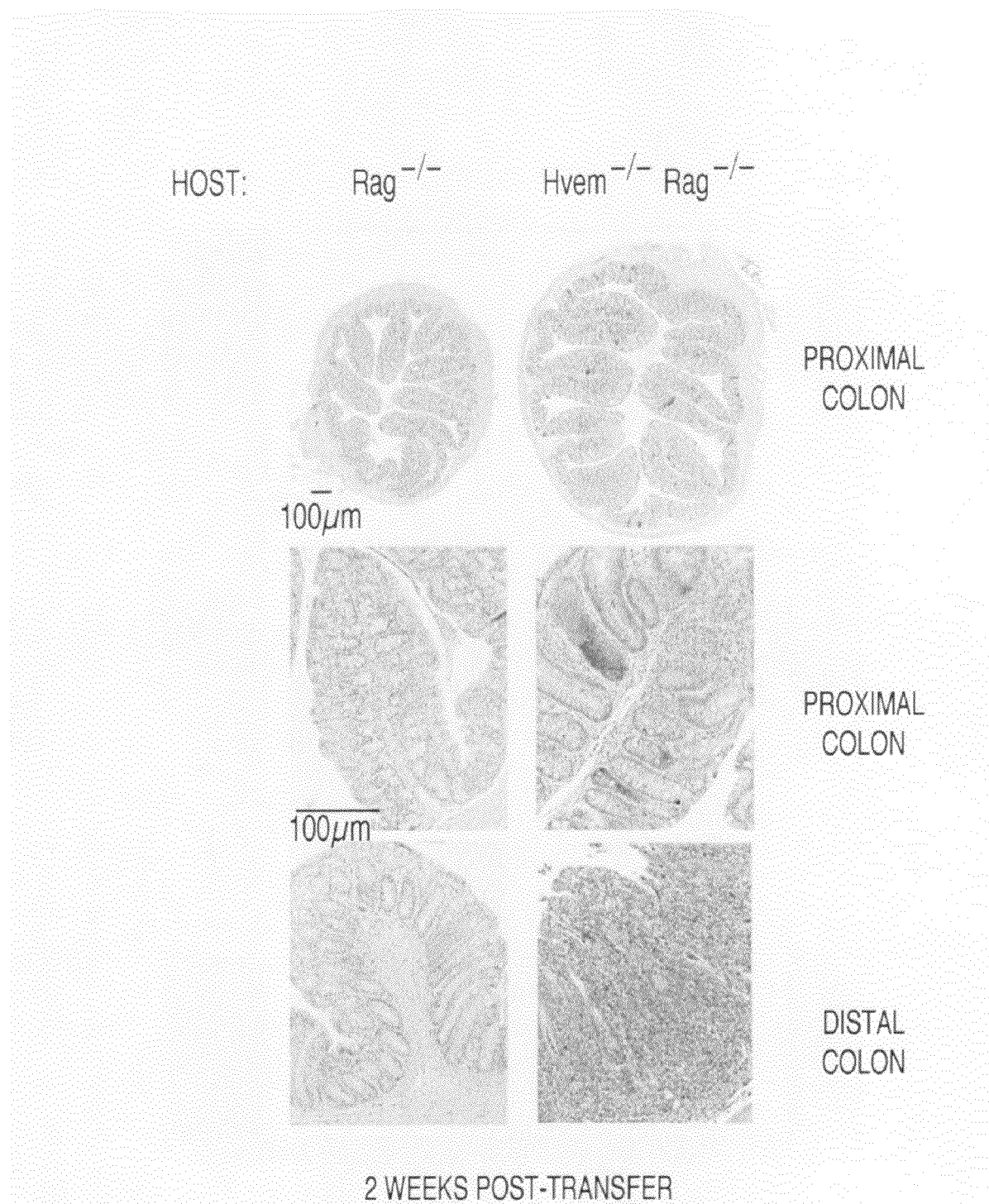

HVEM expression is not restricted to T cells, and therefore in order to evaluate if HVEM expressed by non-T cells participates in colitis pathogenesis, HVEM-deficient Rag$^{-/-}$ (Hvem$^{-/-}$Rag$^{-/-}$) animals were used as recipients. Hvem$^{-/-}$Rag$^{-/-}$ recipients that were transferred with WT CD4$^+$ CD45RB$^{high}$ T cells exhibited a surprising acceleration of weight loss and colitis, as determined by the presence of diarrhea and other clinical signs, such as reduced mobility and piloerection of the fur. Notably, recipient Hvem$^{-/-}$Rag$^{-/-}$ mice showed a reduction of approximately 20% of their initial starting weight only two weeks after transfer (FIG. 18A). The intestinal inflammation in these recipients was progressive and lethal, and in most cases the recipients did not survive beyond 3-4 weeks post transfer. This accelerated inflammation was confined, however, predominantly to the large intestine (data not shown). Conversely, in the same brief period, Rag$^{-/-}$ recipients did not show any weight loss (FIG. 18A). In addition to the faster weight loss, transferred Hvem$^{-/-}$Rag$^{-/-}$ mice presented early evidence of severe intestinal inflammation. Examination of H&E stained sections obtained from Hvem$^{-/-}$Rag$^{-/-}$ recipients revealed prominent epithelial cell hyperplasia, absence of goblet cells and a massive infiltration of mononuclear cells in the colons of these animals (FIG. 18B). Histological analysis performed on samples isolated from large intestine of these recipients two weeks after transfer had an average pathology score of 8.8±2.2 out of a possible of 14 (FIG. 18C). Samples from Rag$^{-/-}$ recipients at the same early time after transfer showed almost intact epithelial crypts with absence of epithelial cell hyperplasia and only few mononuclear cell infiltrates (FIG. 18B). The average score for samples obtained from the transferred Rag mice at this time was only 0.8±1.0 (FIG. 18C).

Hvem$^{-/-}$ donor T cells were transferred into Hvem$^{-/-}$Rag$^{-/-}$ mice in order to analyze the situation in which HVEM is entirely missing. Induced colitis and wasting disease in the completely HVEM deficient situation were still accelerated compared to transfers to Rag$^{-/-}$ animals. Weight loss in Hvem$^{-/-}$Rag$^{-/-}$ mice transferred with HVEM-deficient T cells was equally accelerated compared with the same recipients transferred with WT T cells (FIG. 18D). Histological scores in these recipients completely lacking HVEM were also equivalent to those observed in Hvem$^{-/-}$ Rag$^{-/-}$ animals transferred with WT T cells (FIG. 18E)

Overall, these results demonstrate that the absence of HVEM expression in Rag$^{-/-}$ host cells led to a dramatic acceleration of colitis, and they show that this dramatic effect was dominant over any deceleration of disease caused by the absence of HVEM expression by donor T cells.

Example 13

This example describes data indicating that T cells rapidly accumulate in the large intestine of Hvem$^{-/-}$Rag$^{-/-}$ recipients.

In order to characterize the colitis acceleration observed in Hvem$^{-/-}$Rag$^{-/-}$ mice, the fate of the transferred T cells were studied. The number of CD4$^+$ T lymphocytes in the spleen and mesenteric lymph nodes (MLN) of transferred mice was determined; two sites where T cells expand dramatically after transfer to immune deficient hosts (Aranda et al., *J Immunol* 158:3464 (1997)). One week after transfer, the number of CD4$^+$ T cells in the MLN of Hvem$^{-/-}$Rag$^{-/-}$ animals was approximately three-fold higher than in Rag$^{-/-}$ mice (FIG. 19A); this difference was highly significant (p=0.005). The number of T cells in the spleen of Hvem$^{-/-}$Rag$^{-/-}$ mice was also slightly higher than in Rag$^{-/-}$ recipients, although not statistically significant (FIG. 19A). Elevated numbers of T cells in the MLN of Hvem$^{-/-}$Rag$^{-/-}$ animals were only observed at early time points after the transfer, and by two weeks following transfer, the number of CD4$^+$ TCRβ$^+$ lymphocytes in the MLN was essentially equivalent in both recipients (FIG. 19B).

To study if the early accumulation of transferred T cells in inductive sites such as MLN in the Hvem$^{-/-}$Rag$^{-/-}$ mice also affected the target organ, we assessed the accumulation of CD4$^+$ TCRβ$^+$ T cells in the large intestine of the recipients was determined. As early as seven days following transfer, T lymphocytes were detectable in the large intestine. At this time, the average number of CD4$^+$ TCRβ$^+$ cells infiltrating the epithelium of the Hvem$^{-/-}$Rag$^{-/-}$ mice was 2.3 fold higher than in Rag mice (FIG. 19A). However, by two weeks post transfer, intraepithelial CD4+ TCRβ$^+$ cell numbers in Hvem$^{-/-}$Rag$^{-/-}$ mice were ten-fold higher (p<0.005) (FIG. 19B). Accordingly, the number of CD4$^+$ TCRβ$^+$ lamina propria lymphocytes (LPL) was also significantly higher in Hvem$^{-/-}$Rag$^{-/-}$ recipients at two weeks (FIG. 19B).

Altogether, these results demonstrate that the absence of HVEM in the Rag$^{-/-}$ mice led to a more rapid accumulation of transferred T cells in the MLN and large intestine.

Exhibit 14

This example describes data indicating that T cell cytokine production is increased in Hvem$^{-/-}$Rag$^{-/-}$ recipients.

In order to further characterize the colitis acceleration observed in Hvem$^{-/-}$Rag$^{-/-}$ mice, the profile of cytokines produced in the large intestine of the recipient animals was analyzed. Two weeks after transfer, total mRNA was purified from the colon and subjected to real-time reverse transcription PCR (RT-PCR) analysis for several cytokines.

RT-PCR revealed the presence of TNF and IFNγ mRNAs, and lower levels of IL-17 mRNA (FIG. 19C). Notably, the amount of mRNA for these cytokines, and in particular for TNF, was considerably higher in samples isolated from Hvem$^{-/-}$Rag$^{-/-}$ mice (FIG. 19C). The higher level of pro-inflammatory cytokines in the intestine of Hvem$^{-/-}$Rag$^{-/-}$ animals correlated with the rapid and severe intestinal inflammation observed. It should be noted that increased mRNA for TGF-β and IL-10 in the Hvem$^{-/-}$Rag$^{-/-}$ mice were also observed when compared to Rag$^{-/-}$ recipients. The increased presence of these anti-inflammatory cytokine mRNAs in the Hvem$^{-/-}$Rag$^{-/-}$ recipients could reflect a compensatory regulatory mechanism in the face of inflammation, although the amount of IL-10 mRNA was very low in all the samples (FIG. 19D). The amount of mRNA for IL-12 family cytokines in the colon was not very great, but in accord with the higher levels of IFNγ mRNA observed in Hvem$^{-/-}$Rag$^{-/-}$ mice, we also detected an increase in IL-12 mRNA in the colon of these animals (FIG. 19E). The level of mRNA for IL-23, however, was equivalent in both Rag$^{-/-}$ and Hvem$^{-/-}$Rag$^{-/-}$ mice (FIG. 19E).

To determine if the transferred T cells had the capacity to produce pro-inflammatory cytokines in the colon of the Hvem$^{-/-}$Rag$^{-/-}$ recipient mice, cytokine production by donor derived LPL re-stimulated in vitro were evaluated. LPL were purified from the large intestine of Rag$^{-/-}$ or Hvem$^{-/-}$Rag$^{-/-}$ recipient mice, stimulated with PMA and ionomycin, and 48 h later cytokines were determined by ELISA. The amounts of IFNλ TNF and IL-2 in the culture supernatants of cells obtained from Hvem$^{-/-}$Rag$^{-/-}$ mice were considerably higher than those secreted by cells isolated from Rag$^{-/-}$ recipients (FIG. 19F). Rather than an increased capacity to produce cytokines, the higher amounts of cytokines in the cultures of cells isolated from Hvem$^{-/-}$Rag$^{-/-}$ mice could have been due to the increased number of T cells in the LPL preparations. Indeed, the percentage of CD4$^+$ TCRβ$^+$ within the LPL suspension isolated from Hvem$^{-/-}$Rag$^{-/-}$ mice was about two-fold higher than that observed in Rag$^{-/-}$ animals (data not shown). The increment in cytokines in the isolated LPL from Hvem$^{-/-}$Rag$^{-/-}$ mice was increased more than two-fold, however, suggesting that increased pro-inflammatory cytokines in the LPL of these recipients could be due to a combination of increased cell number and increased effectors.

Altogether, these findings indicate that the presence of increased CD4$^+$ T cells secreting high amounts of pro-inflammatory cytokines in the intestine of Hvem$^{-/-}$Rag$^{-/-}$ recipients contributed to the more rapid development of colitis.

Example 15

This example describes data indicating that DCs were not greatly affected in Hvem$^{-/-}$ mice.

Figure 20A:
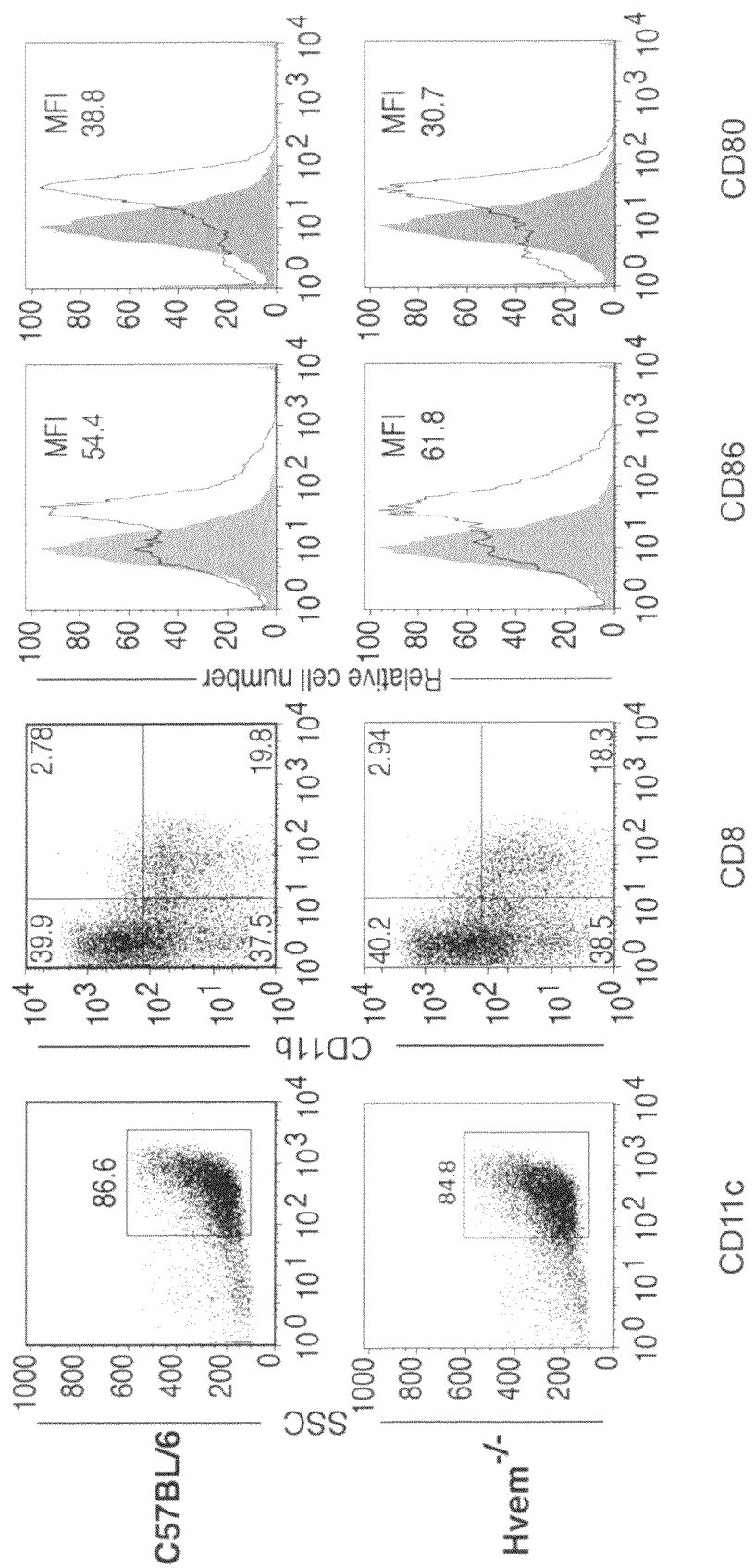
FIG. 20A-C: HVEM deficiency does not greatly affect DC maturation and function. (A; left) CD11c+ cells freshly isolated from the MLNs of WT or Hvem$^{-/-}$ mice showed equivalent percentages of the "lymphoid" (CD8+CD11b−) and "myeloid" (CD11b+CD8−) DC subsets (dot plots). (Right) Histograms show the expression of CD86 and CD80 on total CD11c+ cells. Mean fluorescence intensity (MFI) for each molecule is indicated. Filled histograms represent isotype controls. (B; left) CD11c+ cells isolated from the MLNs of WT or Hvem$^{-/-}$ mice were cultured ex vivo for 24 h in the presence of 5 µg/ml LPS, and the expression of CD86 and CD40 (open histograms) was monitored by flow cytometry. The MFI for each molecule is indicated. Filled histograms represent isotype controls. (Right) After LPS stimulation, equivalent percentages of WT and Hvem$^{-/-}$ MLN CD11c+ cells were positive for intracellular IL-12 staining (dot plot). Data shown are representative of three independent experiments. (C) Comparison of CD4+ T cell proliferation after polyclonal stimulation in co-cultures with WT or Hvem$^{-/-}$ DCs. CFSE-labeled WT CD4+CD45RB$^{high}$ T cells were cultured with either splenic or MLN CD11c+ cells isolated from WT (filled histograms), Hvem$^{-/-}$ (top, open histograms), or Btla$^{-/-}$ mice (bottom, open histograms) DCs. T cells cultured with splenic or MLN DCs were stimulated for 72 h with 0.01 or 0.1 µg/ml anti-CD3ε mAb, respectively. Histograms depict CFSE dilution profiles of activated T cells gated on CD4+ and Thy1.2+. Data are representative of two independent experiments.

Previous reports have suggested a role for HVEM in DC maturation and cytokine production (Morel et al., *J Immunol* 167:2479 (2001); Scheu et al., *J Exp Med* 195:1613 (2002)), and therefore the absence of HVEM expression on DC in the Rag$^{-/-}$ recipients might cause an abnormal development and/or function of these cells. In WT or Hvem$^{-/-}$ mice, however, the percentage of DC in the spleen and MLN was essentially equivalent, and the two major subsets of DC, those expressing high levels of CD11c and CD8α, and those expressing CD11b, were similarly represented in the MLN of WT and Hvem$^{-/-}$ animals (FIG. 20A). CD11c$^+$ cells freshly isolated from the MLN of the two types of mice expressed equivalent levels of the co-stimulatory molecules CD86 and CD80, indicating that the DC maturation state was not greatly affected by the absence of HVEM (FIG. 20A).

Figure 20B:
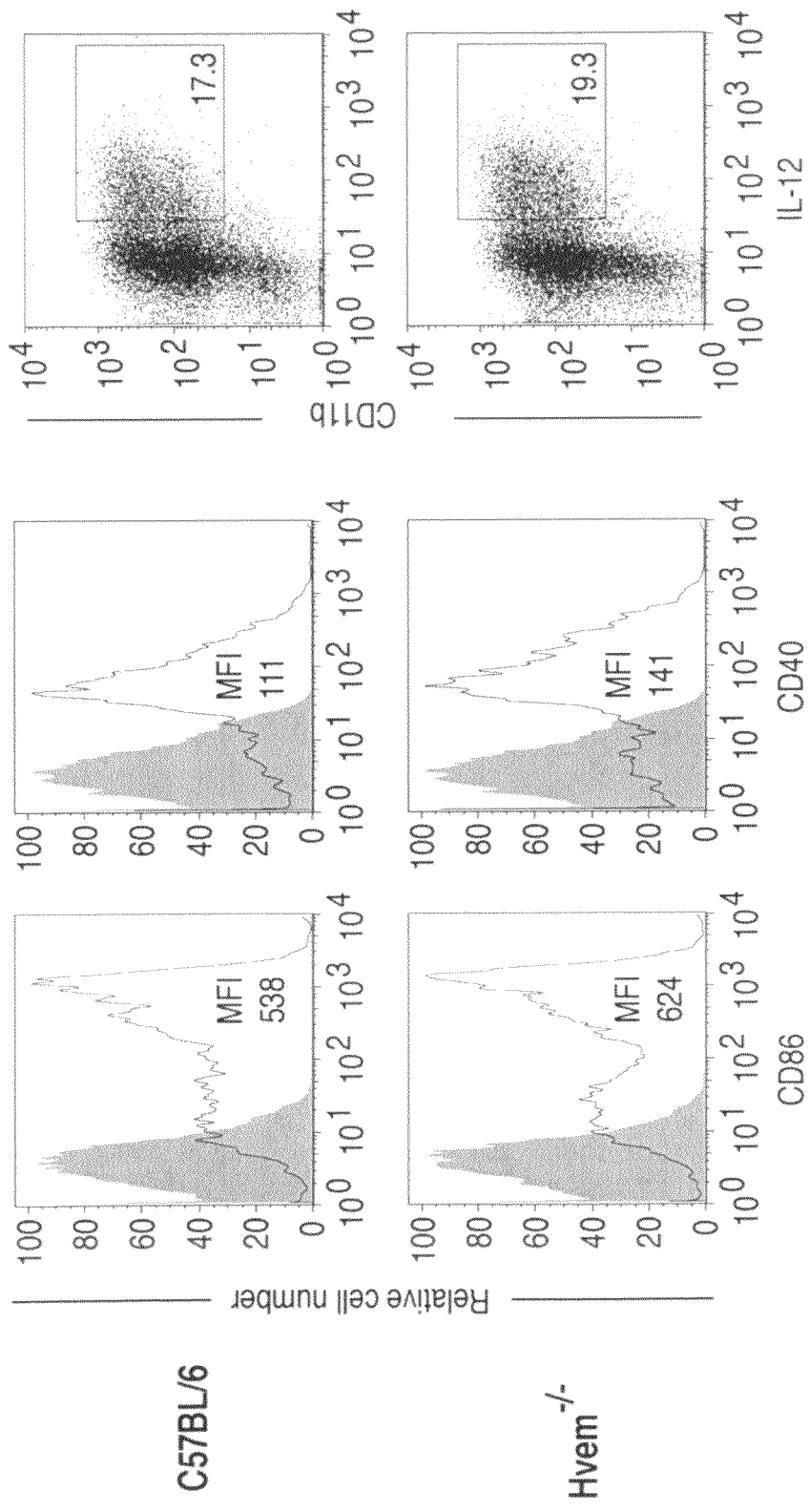

To determine if the threshold for stimulation for DC is altered in the absence of HVEM, CD11c$^+$ cells from MLN were stimulated with LPS. Upon stimulation, both WT and Hvem$^{-/-}$ DC expressed similar levels of CD40 and CD86 (FIG. 20B). Moreover, after LPS stimulation, the percentage of WT and Hvem$^{-/-}$ MLN DC expressing IL-12 was essentially equivalent (FIG. 20B).

Figure 20C:
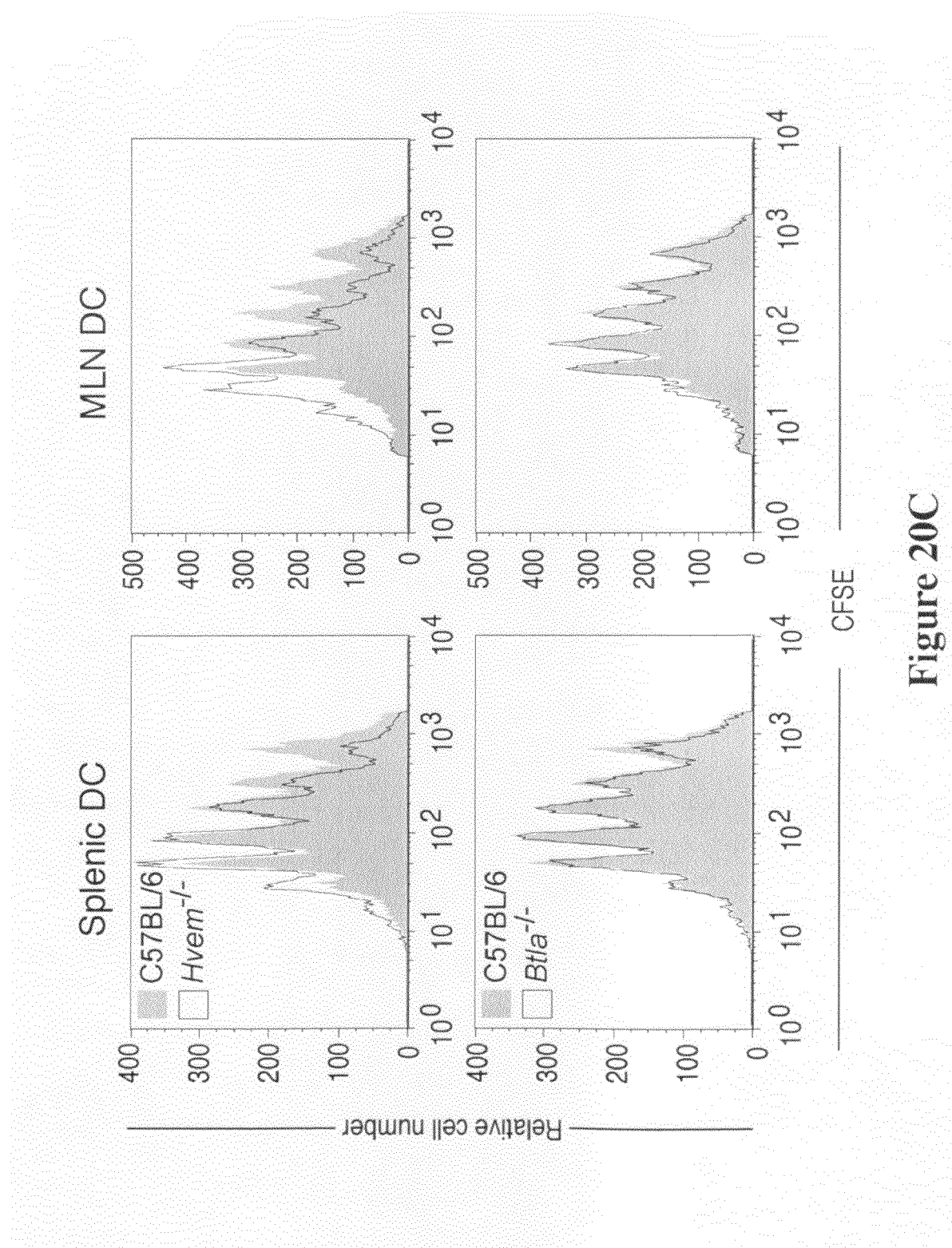

Altogether, these results demonstrate that the absence of HVEM in DC did not significantly affect their percentage, maturation state or their capacity to secrete cytokines. For priming naïve CD4$^+$ T cells, freshly isolated DC from the MLN of Hvem$^{-/-}$ mice were slightly more effective than their wild type counterparts (proliferation indices of 2.6 and 2.1, respectively), although splenic DC from these mice were not different from WT mice (FIG. 20C). Likewise MLN DC from mice deficient for the HVEM ligand BTLA did not prime more effectively (FIG. 20C).

In summary, HVEM deficiency did not grossly alter DC, and the small increase in proliferation of naïve T cells stimulated with Hvem$^{-/-}$ DC from MLN is unlikely to account by itself for the accelerated T cell expansion and colitis pathogenesis in Hvem$^{-/-}$ recipients.

Example 16

This example describes data indicating that HVEM expression in radio-resistant cells is required to prevent colitis acceleration.

Because there was not an obvious APC defect in the Hvem$^{-/-}$ mice, to begin to identify the critical cell type(s) that must express HVEM, chimeric Rag$^{-/-}$ recipient mice that expressed HVEM only in irradiation resistant cells, or only in cells derived from bone marrow progenitors, were analyzed. To construct the chimeras, after lethal irradiation, Hvem$^{-/-}$ Rag$^{-/-}$ mice were reconstituted with Rag$^{-/-}$ bone marrow (BM) cells (Rag$^{-/-}$ ⇒ Hvem$^{-/-}$Rag$^{-/-}$), and reciprocal chimeras were constructed in Rag$^{-/-}$ mice given Hvem$^{-/-}$Rag$^{-/-}$ BM cells (Hvem$^{-/-}$Rag$^{-/-}$ ⇒ Rag$^{-/-}$) (FIG. 21A). To verify that the chimeric mice were properly reconstituted, eight weeks after BM transplantation HVEM expression in peripheral blood cells from these animals was monitored. As expected, blood cells isolated from Hvem$^{-/-}$Rag$^{-/-}$ ⇒ Rag$^{-/-}$ mice expressing the hematopoietic lineage marker CD45 did not have detectable surface HVEM, indicating reconstitution by the Hvem$^{-/-}$ donor BM cells (FIG. 21B). In Rag$^{-/-}$ ⇒ Hvem$^{-/-}$Rag$^{-/-}$ chimeric mice by contrast, the vast majority of the hematopoietic cells expressed intermediate or high levels of HVEM, indicating that they derived from the Hvem$^{+/+}$ donors (FIG. 21B). A similar degree of reconstitution was observed when organs containing immune cells from the chimeras were analyzed (data not shown).

Figure 21C:
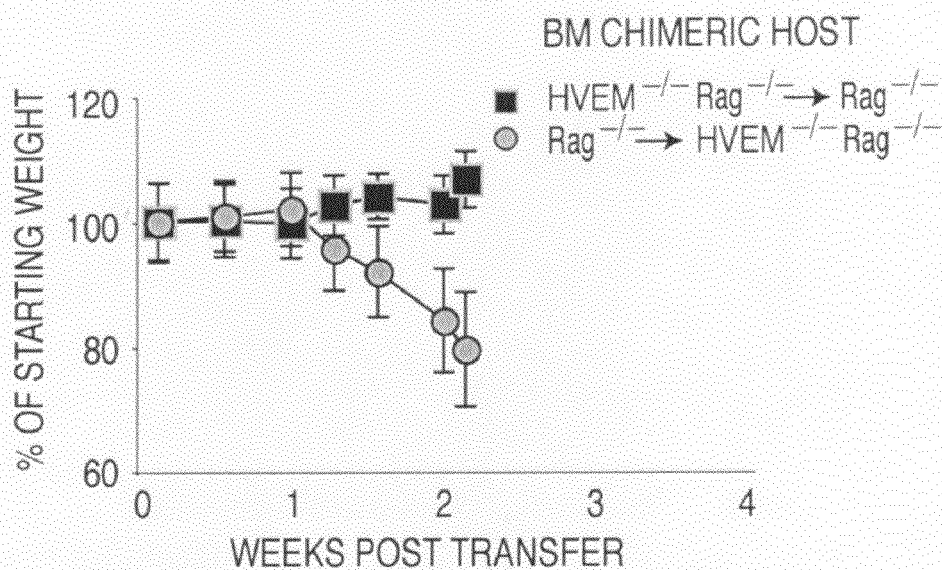
Figure 21D:
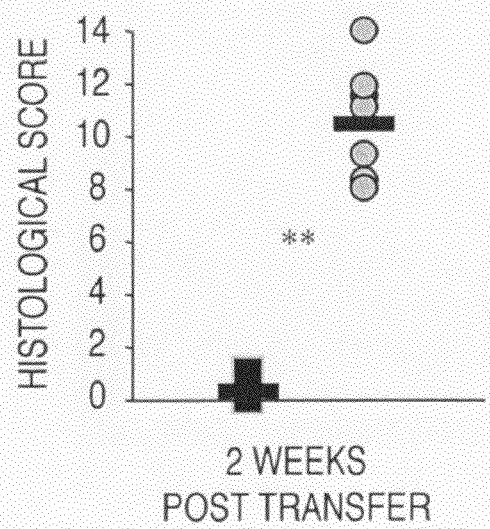

Surprisingly, the transfer of CD4$^+$CD45RB$^{high}$ T cells into Rag$^{-/-}$ ⇒ Hvem$^{-/-}$Rag$^{-/-}$ chimeric recipients induced a rapidly developing disease (FIG. 21C). Similar to the intact Hvem$^{-/-}$Rag$^{-/-}$ mice, Rag$^{-/-}$ ⇒ Hvem$^{-/-}$Rag$^{-/-}$ recipients lost more than 20% of their initial weight by two weeks after T cell transfer. Conversely, Hvem$^{-/-}$Rag$^{-/-}$ ⇒ Rag$^{-/-}$ chimeric recipients that received CD4$^+$CD45RB$^{high}$ T lymphocytes did not lose body weight in the same period of time (FIG. 21C). Consistent with the difference in weight loss, histological scoring performed in large intestine samples collected from the transferred chimeric recipients revealed a more severe inflammation and tissue damage in Rag$^{-/-}$ ⇒ Hvem$^{-/-}$Rag$^{-/-}$ mice than in the Hvem$^{-/-}$Rag$^{-/-}$ ⇒ Rag$^{-/-}$ recipients (average score=10.4±2.0 in Rag$^{-/-}$ ⇒ Hvem$^{-/-}$Rag$^{-/-}$ animals as opposed to 0.3±0.5 in Hvem$^{-/-}$Rag$^{-/-}$ ⇒ Rag$^{-/-}$ mice) (FIG. 21D). These results indicate that HVEM prevents colitis acceleration principally when expressed by radio-resistant cells in the Rag$^{-/-}$ hosts.

Figure 22A:
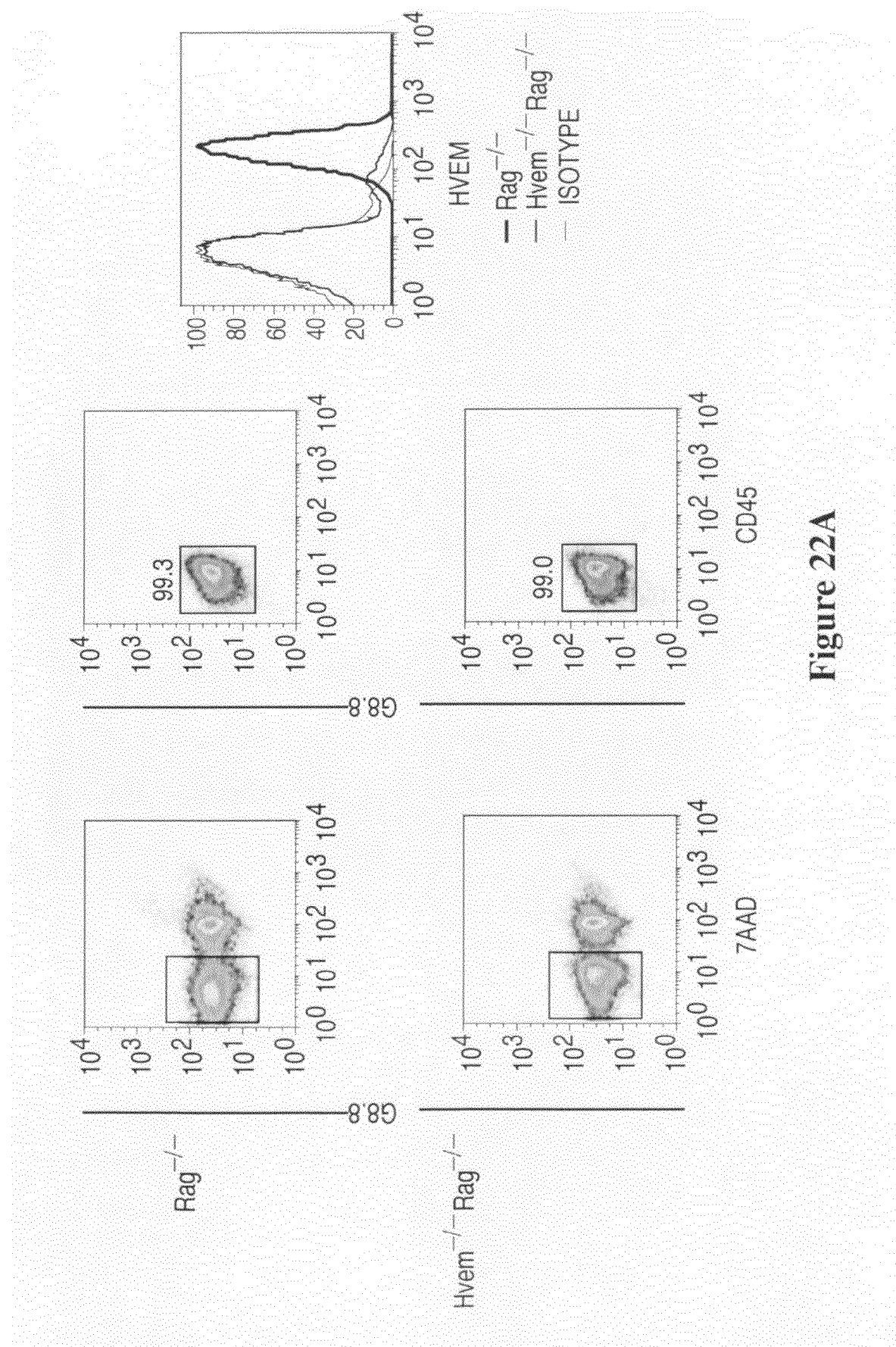
FIG. 22A-B: HVEM expression by IECs (A) Primary colonic IECs were isolated from Rag$^{-/-}$ or Hvem$^{-/-}$Rag$^{-/-}$ mice using a previously described procedure (Baumgart et al. *Cell. Immunol.* 187:52 (1998)). The purity of the IEC preparations was evaluated by EpCAM (G8.8) mAb staining and by determining the level of contamination by CD45+ hematopoietic cells using flow cytometry. Analysis of HVEM expression by freshly isolated colonic IECs was monitored by flow cytometry. Histogram represents HVEM expression by 7AAD$^-$ cells. (B) Assessment of intestinal permeability. Colons were removed from 8-wk-old C57BL/6 or Hvem$^{-/-}$ mice, opened longitudinally, and cleaned from fecal matter. Sections of distal and proximal colon as well as cecum were removed and carefully stripped of underlying muscle layers by blunt dissection. Each section exposing the epithelial layer and the underlying lamina propria was mounted in an Ussing chamber. The tissues were bathed bilaterally with 5 ml of Ringer's solution and equilibrated for 20 min. 1 µCi of D-[1-$^{14}$C]-mannitol (GE Healthcare) was added to the mucosal side and allowed to equilibrate for 1 min before baseline mucosal (100 µl) and serosal (500 µl) samples were taken. Afterward, 500 µl of serosal side sample fluid was taken every 20 min for 2 h and replaced with the same volume of nonradioactive buffer. A final mucosal sample was taken at the end of the 2-h experiment. Radioactivity was measured using a liquid scintillation analyzer, and fluxes were calculated from the disintegrations per minute (dpm) using a previously described apparent permeability coefficient (P.app) equation (Anderberg et al., *J Pharm Sci* 82:392 (1993); Lindmark et al., *J Drug Target* 5:215 (1998)). Data shown represent the average P.app of samples isolated from five to six mice in each group. For the positive control obtained from an inflamed intestine (triangles), WT mice (n=3) were treated for 6 d with 4% DSS dissolved in drinking water followed for an additional 2 d with regular water. Permeability was measured as indicated above.
Figure 22B:
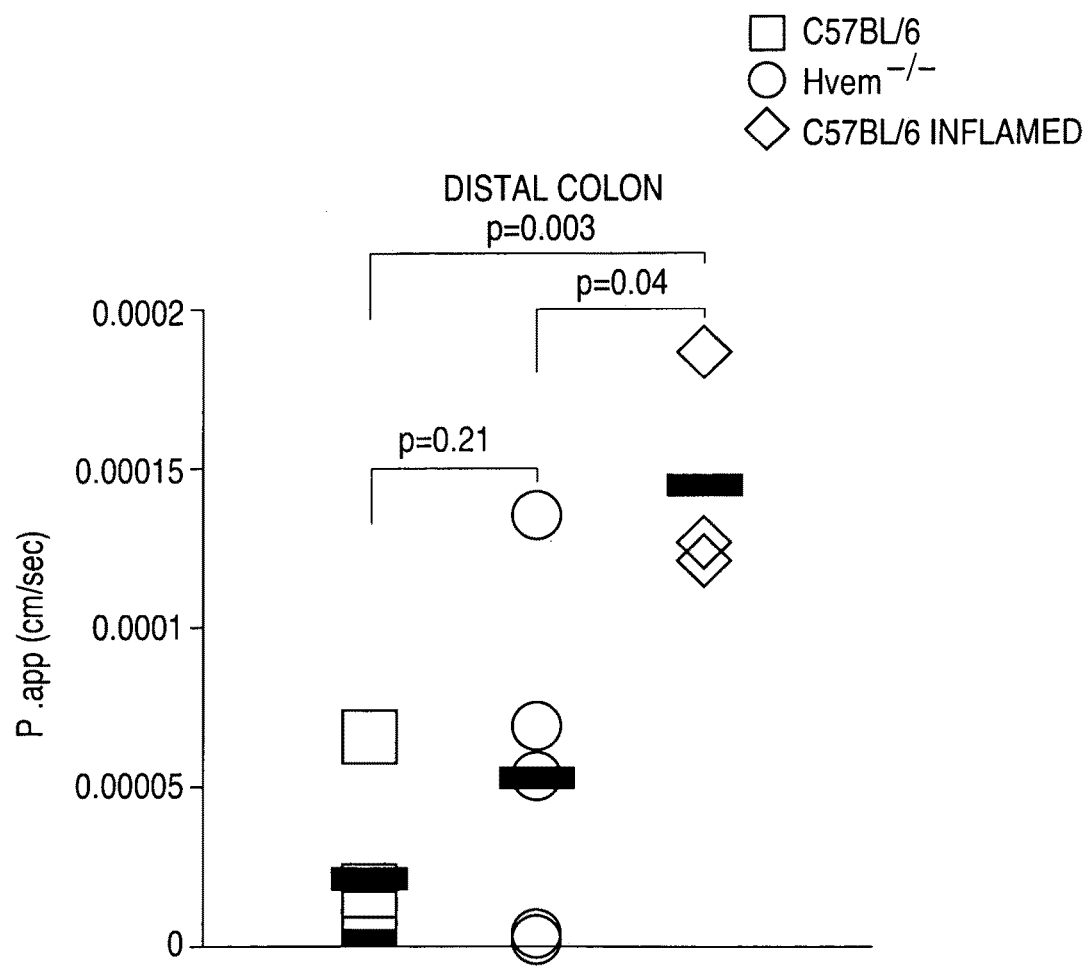
Figure 23B:
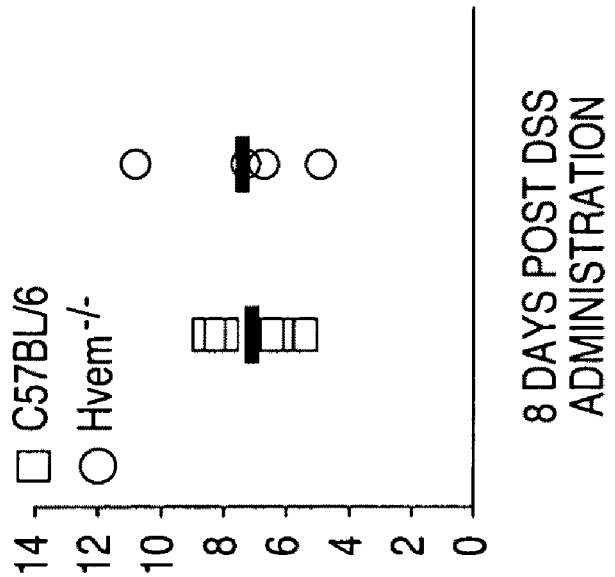
FIG. 23A-B: DSS-induced colitis is comparable in Hvem$^{-/-}$ and WT mice. WT (squares) or Hvem$^{-/-}$ (circles) mice were treated for 6 d with 2.5% DSS dissolved in drinking water and afterward regular drinking water to interrupt the treatment. (A) The graph represents weight loss of WT and Hvem$^{-/-}$ mice beginning at the time of DSS administration. Data shown are the average of four mice in each group and are representative of the results from three independent experiments. (B) Histological scores analyzed 8 d after DSS administration. Each symbol represents an individual mouse of a total of four mice in each group.
Figure 23A:
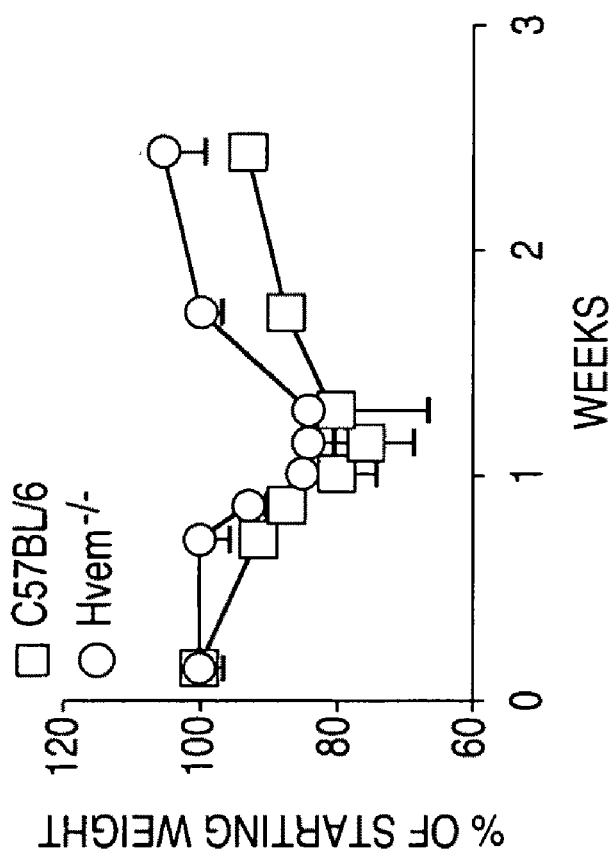

A radiation resistant cell that might prevent accelerated inflammation through HVEM expression is the intestinal epithelial cell. In fact, human epithelial carcinoma cell lines (data not shown) and freshly isolated mouse colonic epithelial cells express HVEM (FIG. 22A). A feature of IBD, in particular, Crohn's Disease, is increased intestinal permeability arising from a defect in the intestinal epithelium. Permeability to D-[1-$^{14}$C]-mannitol therefore was measured across tissues from proximal and distal large intestine, as well as the cecum, which were stripped of underlying smooth muscle and mounted in Ussing chambers. Although the trend was towards increased permeability in the distal colon of Hvem$^{-/-}$ mice, the difference was not significant when compared with WT tissues. However, permeability in the distal colon of both WT and Hvem$^{-/-}$ mice was significantly lower than that observed in inflamed tissues isolated from WT mice with colitis that had been induced by dextran sodium sulfate (DSS) (FIG. 22B). Similar to the results from the distal large intestine, permeability in the proximal colon and cecum of WT and Hvem$^{-/-}$ animals was essentially equivalent. Therefore, epithelial permeability is not compromised under non-inflammatory conditions in the absence of HVEM expression. Colitis induced by DSS represents a well-established epithelial injury model of intestinal inflammation. Hvem$^{-/-}$ mice also displayed no increase in susceptibility to DSS-induced colitis when compared with WT mice (FIG. 23A-B).

Example 17

This example describes studies identifying the effects of HVEM ligand expression by T cells.

An appealing explanation for the accelerated colitis in Hvem$^{-/-}$Rag$^{-/-}$ recipients is that enhanced disease is caused by absence of an interaction between HVEM expressed by a cell type in the Rag$^{-/-}$ recipients with an HVEM binding partner expressed by the donor T cells. Recent publications have repeatedly suggested that expression of LIGHT by T cells is able to regulate innate immune responses by interacting with the HVEM receptor (Morel et al., *J Immunol* 167: 2479 (2001); Duhen et al., *Eur J Immunol* 34:3534 (2004); Fan et al., *Blood* 107:1342 (2006); Heo et al., *J Leukoc Biol* 79:330 (2006); Haselmayer et al., *Immunology* 119:404 (2006)). Therefore the absence of interactions between T cell-derived LIGHT and HVEM on host cells might lead to a dysregulated innate immune response in Rag$^{-/-}$ animals and accelerated development of disease.

Figure 24:
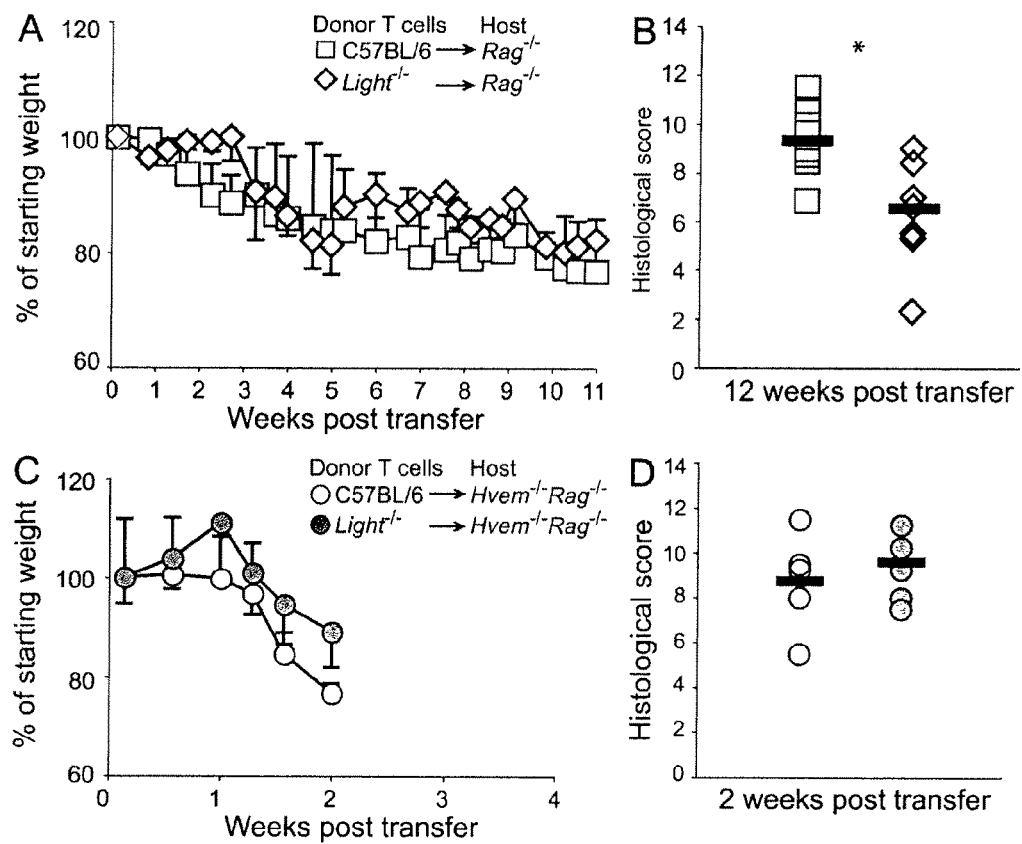
FIG. 24A-D: Light$^{-/-}$ T cells do not cause accelerated colitis. (A) Weight loss curves of Rag$^{-/-}$ recipients transferred with either WT (open squares) or Light$^{-/-}$ CD4+CD45RB$^{high}$ T cells (open diamonds). The graph shows the average of 4 mice per group and is representative of one of three independent experiments. (B) Average histological scores evaluated 12 weeks after T cell transfer. Each square represents a single mouse of a total of 6-7 mice in each group. *, p<0.05. (C) Results from the transfer of either WT (open circles) or Light$^{-/-}$ (filled circles) T cells into Hvem$^{-/-}$Rag$^{-/-}$ mice. Data shown correspond to the average weight loss of 6 mice per group. (D) Average histological scores analyzed 2 weeks after WT or Light$^{-/-}$ CD4CD45RB$^{high}$ T cell transfer to Hvem$^{-/-}$Rag$^{-/-}$ animals. Each circle represents a single mouse in a total of 6 mice per group.

Transfer experiments using Light$^{-/-}$ donor T cells were performed. The results showed similar weight loss in Rag$^{-/-}$ mice transferred with either Light$^{-/-}$ or WT CD4$^+$ CD45RB$^{high}$ T cells (FIG. 24A). However, histological analysis performed in samples obtained from the large intestine of Rag$^{-/-}$ recipients twelve weeks after the transfer revealed lower levels of inflammation in animals transferred with Light$^{-/-}$ T cells (FIG. 24B). This is consistent with other data indicating that LIGHT is a co-stimulatory molecule for T lymphocytes. Because the outcome following transfer of Light$^{-/-}$ T cells was opposite to the results following transfer to Hvem$^{-/-}$Rag$^{-/-}$ recipients, we conclude that the accelerating effects of host HVEM deficiency were not due to the absence of interactions with LIGHT expressed by the donor T cells.

Importantly, transfer of Light$^{-/-}$ CD4$^+$CD45RB$^{high}$ T cells into Hvem$^{-/-}$Rag$^{-/-}$ recipients induced a dramatic acceleration of weight loss (FIG. 24C) and colitis progression assessed by the presence of diarrhea and other clinical signs. The disease acceleration was similar to that observed in Hvem$^{-/-}$Rag$^{-/-}$ mice transferred with WT T cells. Furthermore, histological scores obtained with samples isolated from these Hvem$^{-/-}$Rag$^{-/-}$ animals two weeks after the transfer showed equivalent levels of intestinal inflammation, regardless of the presence of LIGHT expression by the donor T cells (FIG. 24D). Therefore rapid colitis induction in the absence of HVEM expression is dominant over the decreased inflammation observed when Light$^{-/-}$ T cells were transferred.

Figure 25A:
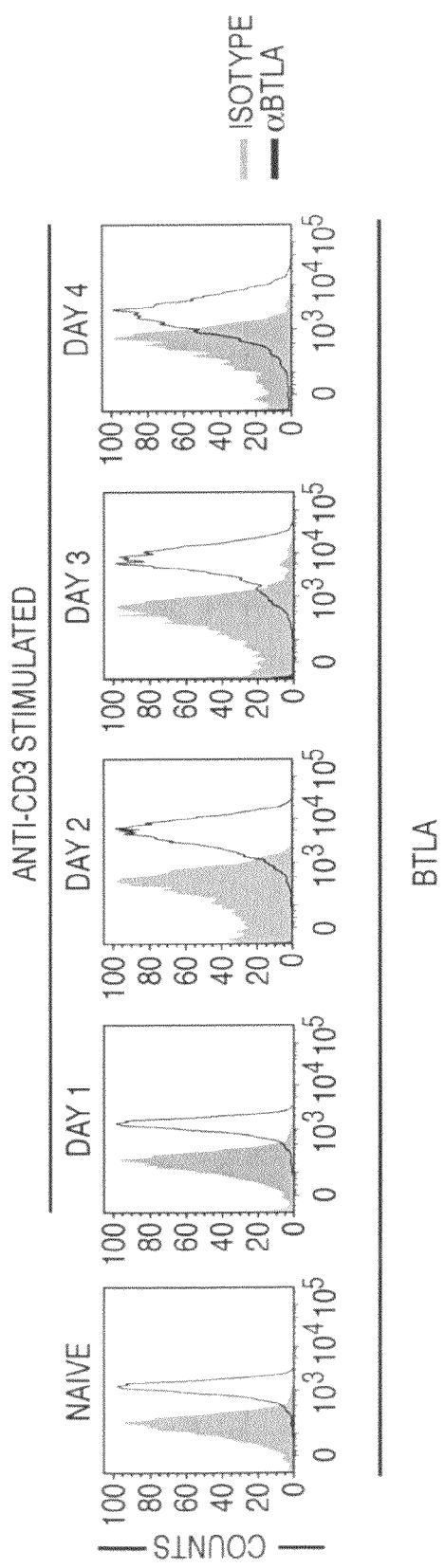
Figure 25B:
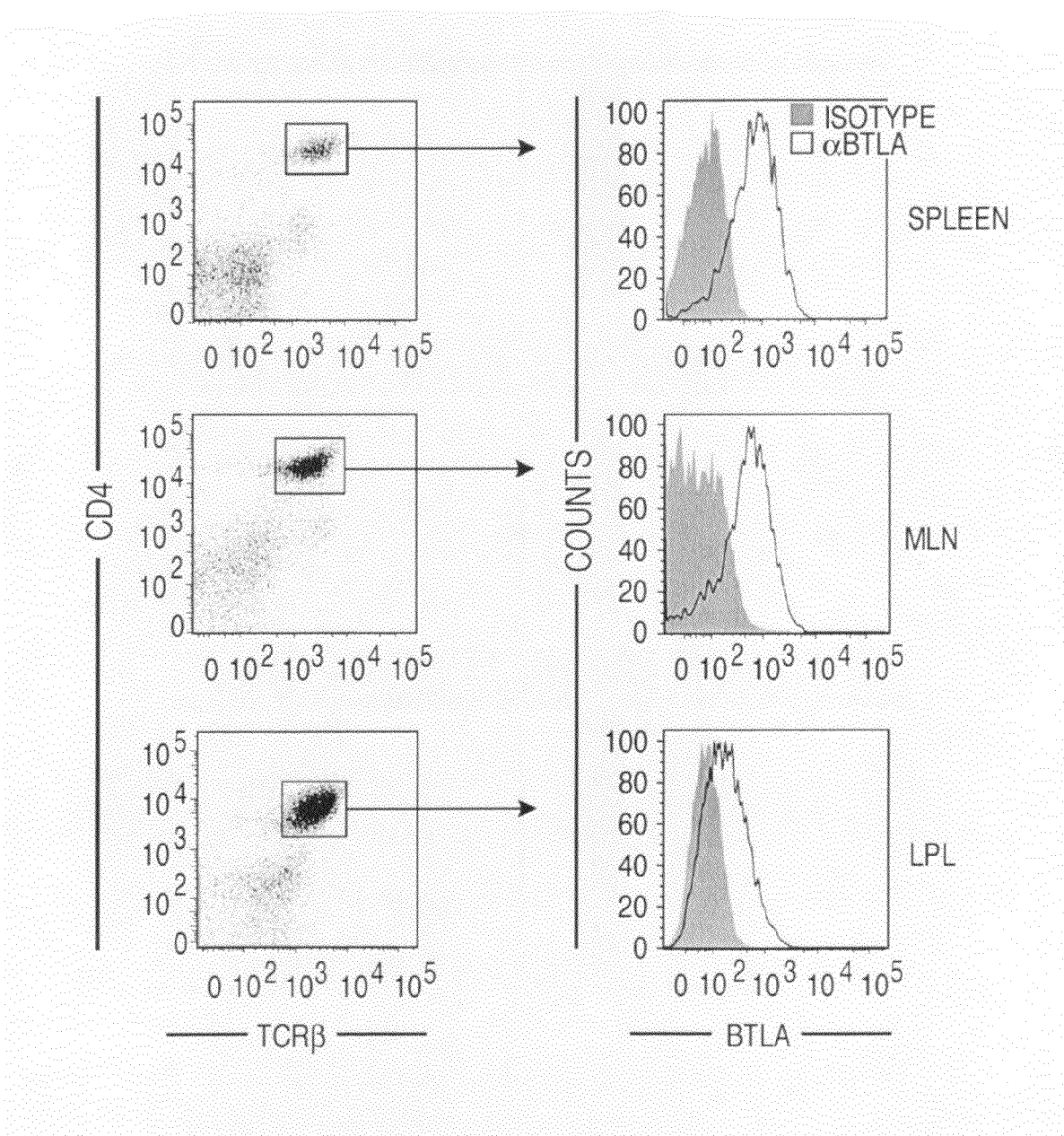

The inhibitory HVEM ligand BTLA is expressed by activated T cells, and therefore interactions between Rag$^{-/-}$ host HVEM and T cell BTLA could alter the acceleration of colitis. BTLA expression by naïve CD4$^+$ T cells and by CD4$^+$ T cells following transfer was therefore calculated. Consistent with previous reports (Hurchla et al., *J Immunol* 174:3377 (2005)), BTLA expression on naïve and activated CD4$^+$ T lymphocytes was detected. In vitro TCR-stimulation enhanced BTLA expression on CD4$^+$ T cells, with the highest level of BTLA observed 2-3 days following stimulation (FIG. 25A). Likewise, BTLA was expressed on CD4$^+$ T cells isolated from spleen, MLN and lamina propria of transferred Rag$^{-/-}$ recipients (FIG. 25B). Although BTLA expression on LPL was slightly lower than that observed on T cells from the spleen or MLN, this was likely a consequence of the reduced surface protein expression caused by the collagenase digestion during LPL isolation. Consistent with this, the amount of CD4 was also reduced, MFI=7456 for LPL vs. MFI=26183 for MLN. Surprisingly, although BTLA is an inhibitory receptor, Btla$^{-/-}$ T cells transferred into Rag$^{-/-}$ animals induced colitis similar to WT donors when weight loss was measured (FIG. 25C). Histological analysis performed two weeks post-transfer revealed higher average scores for recipients transferred with Btla$^{-/-}$ T cells, but there was no difference at five weeks (FIG. 25D).

Example 18

This example describes data indicating that there is a reduced number of BTLA-deficient T cells in Rag$^{-/-}$ recipients.

Figure 26A:
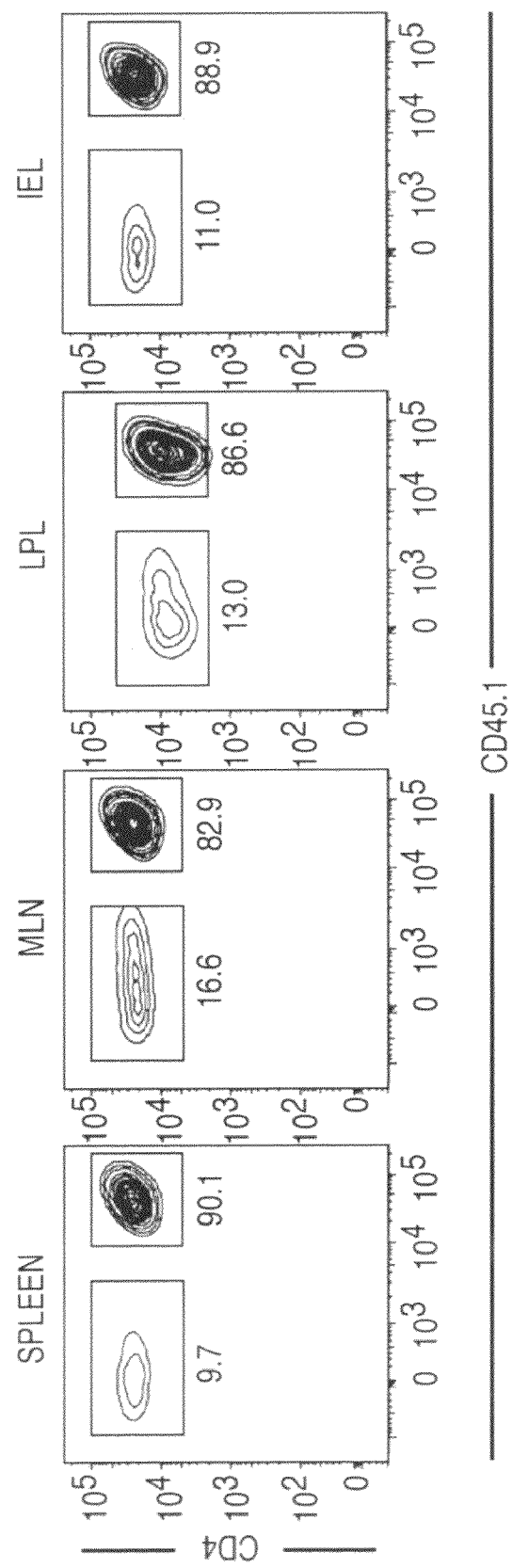
FIG. 26A-C: Reduced accumulation of Btla$^{-/-}$ T cells in Rag$^{-/-}$ recipients. Co-transfer of congenic CD45.1+ and CD45.2+ Btla$^{-/-}$ CD4+CD45RB$^{high}$ T cells into R$^{-/-}$ recipients. (A) Representative percentages of CD45.1+ (Btla$^{+/+}$) and CD45.1$^-$ (Btla$^{-/-}$) CD4+TCRΘ+ cells in the spleen, MLN, LPL and IEL of Rag$^{-/-}$ mice analyzed two weeks after T cell transfer. (B) Same as (A) but showing absolute numbers of CD45.1+ (squares) and CD45.1$^-$ (circles) CD4+ TCRβ+ T cells. Each symbol represents an individual mouse (n=4). *, p<0.05. (C) Intracellular IFNλ staining of CD4+ TCRβ+
Figure 26B:
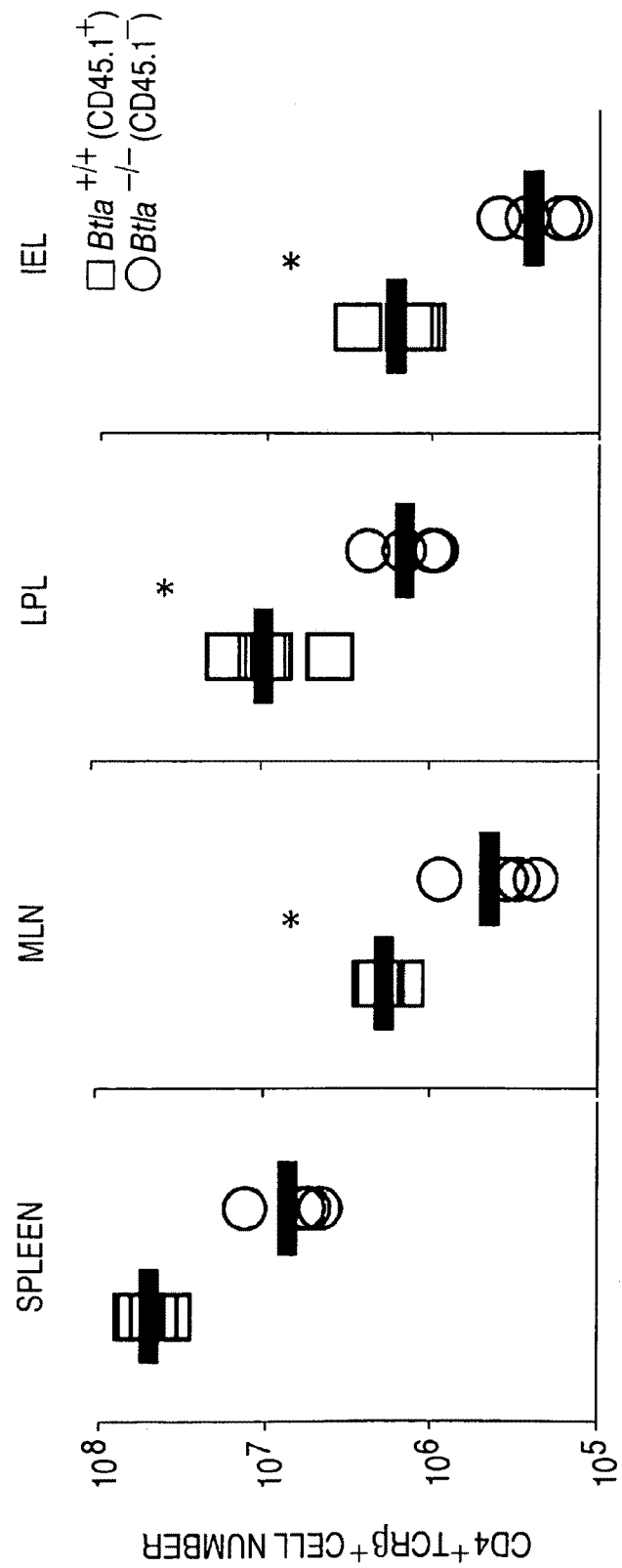
Figure 26C:
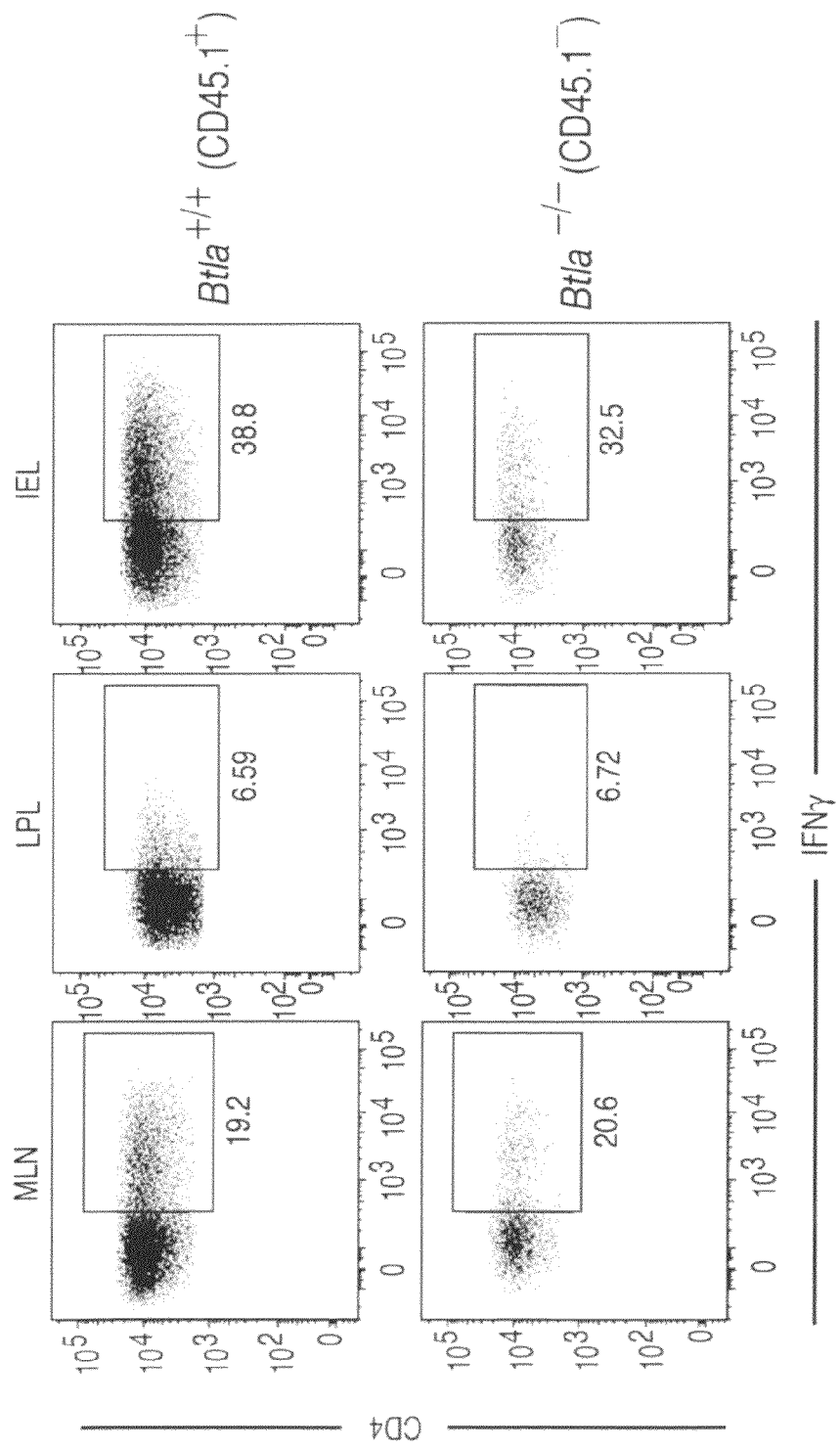

It has been reported that BTLA plays a role in the survival of T cells activated in a mouse GVHD model (Hurchla et al., *J Immunol* 178:6073 (2007)). In light of the finding that Rag$^{-/-}$ recipients of BTLA-deficient T cells did not develop accelerated colitis, BTLA-deficient T cells transferred into Rag$^{-/-}$ recipients might have a survival defect, leading to a reduced number of effector T cells that ultimately might affect the onset of colitis. To address this possibility, co-transfers of equal numbers of WT CD45.1$^+$ congenic and Btla$^{-/-}$ CD45.2$^+$ CD4$^+$CD45RB$^{high}$ T cells into Rag$^{-/-}$ recipients were performed. Btla$^{-/-}$ T cells did not accumulate as much as WT cells. The percentages (FIG. 26A) and absolute numbers (FIG. 26B) of CD45.1$^+$CD4$^+$TCRβ$^+$ cells in the spleen, MLN, LPL and IEL were considerably higher than those for Btla$^{-/-}$ (CD45.1$^-$) T cells, two weeks after transfer. Although the Btla$^{-/-}$ T cells did not accumulate as much as WT donors, the BTLA-deficient T cells in Rag$^{-/-}$ mice were capable of secreting pro-inflammatory cytokines to a similar extent (FIG. 26C). Based on these findings, although not wishing to be bound by any theory, it could be that transfer of Btla$^{-/-}$ T cells did not recapitulate the results in Hvem$^{-/-}$Rag$^{-/-}$ recipients in part because the lower numbers of effector T cells prevented disease acceleration.

Example 19

This example describes data indicating that signaling through BTLA prevented colitis acceleration and that BTLA antibody inhibited T cell responses.

Figure 27A:
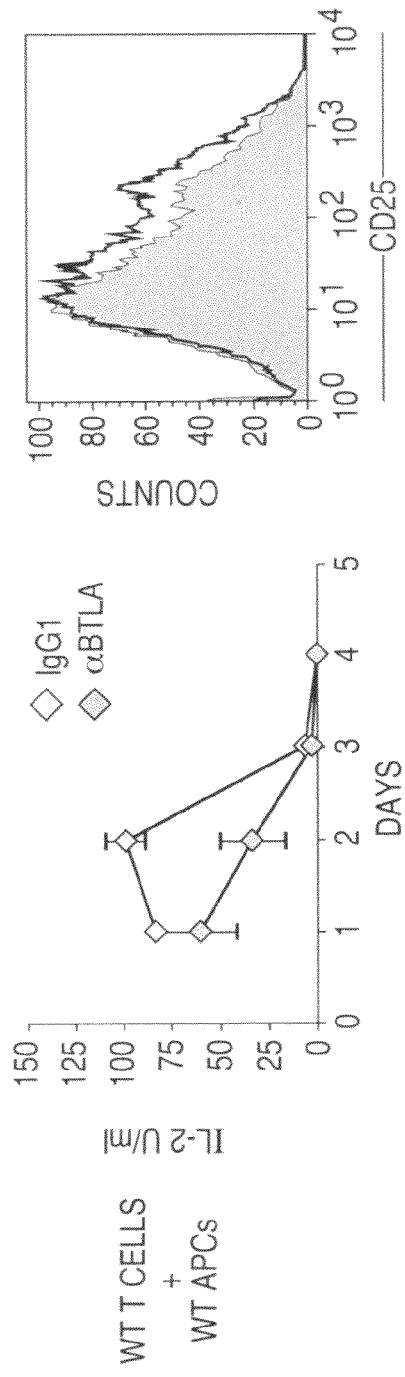
Figure 27B:
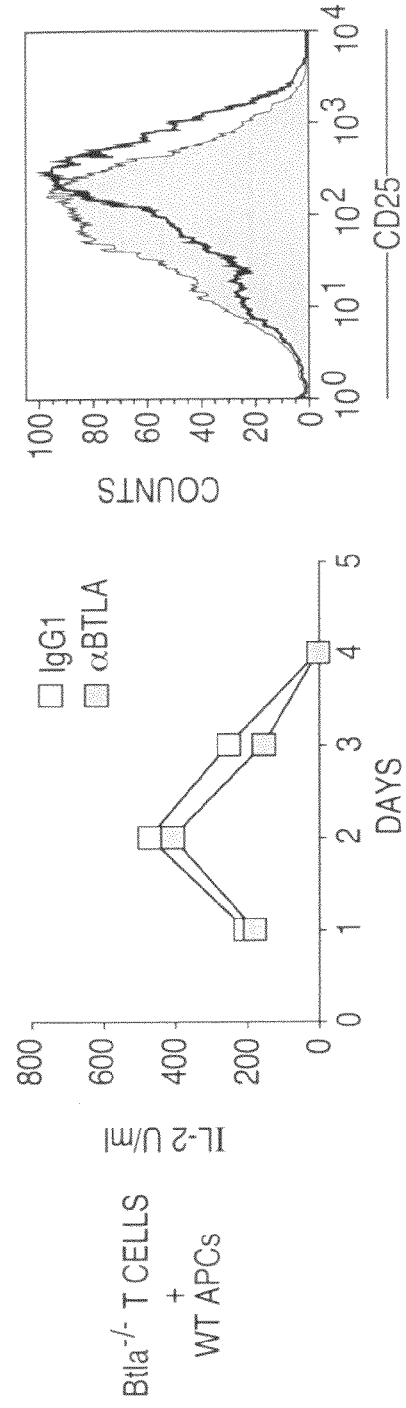
Figure 27C:
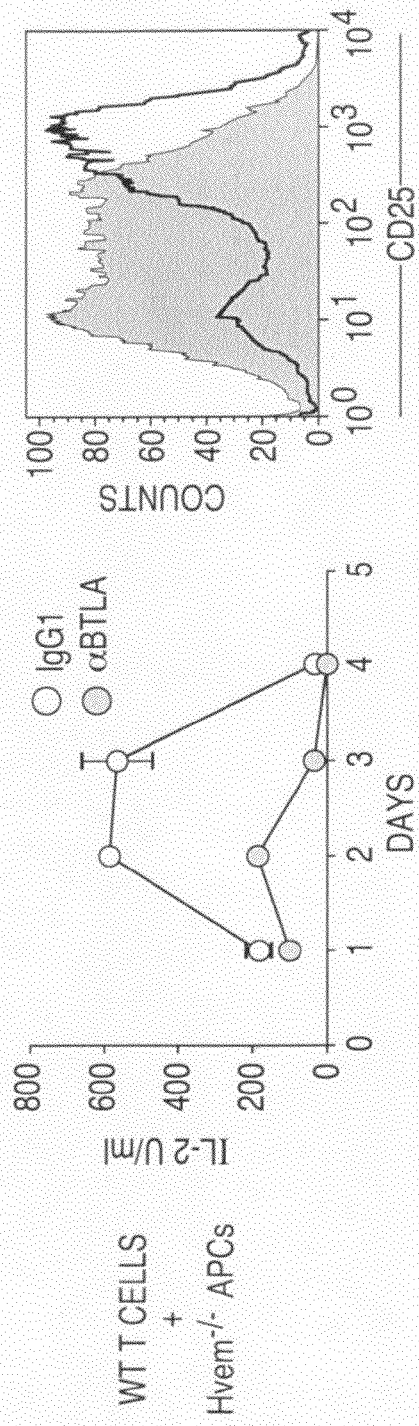
Figure 27D:
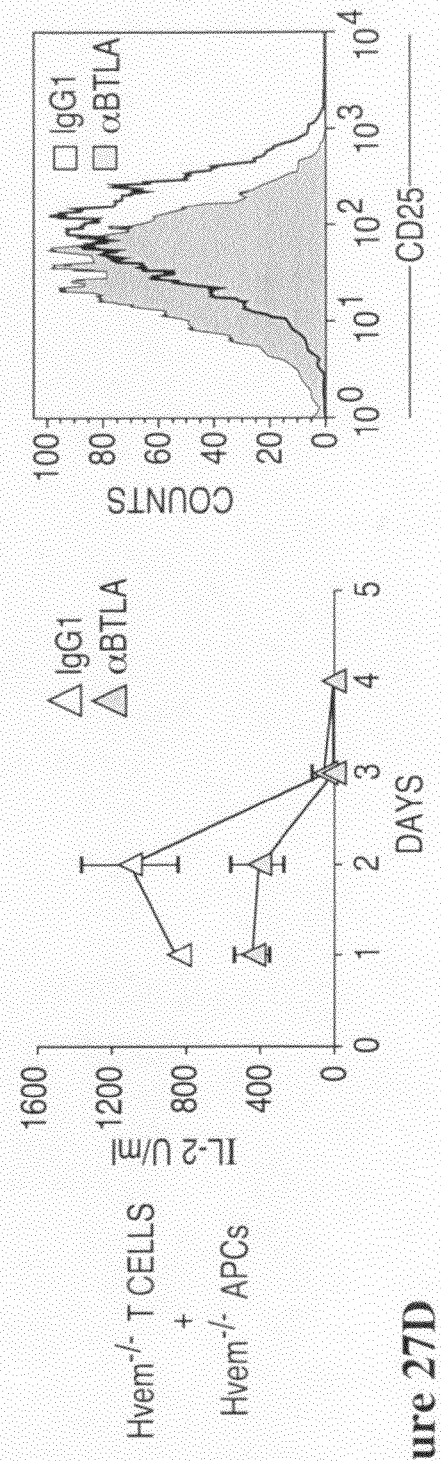

To further explore the role of the BTLA inhibitory receptor, colitis development in recipient Hvem$^{-/-}$Rag$^{-/-}$ mice treated with an anti-BTLA mAb (clone 6F7) was evaluated. When added to T cell-APC co-cultures stimulated with an anti-CD3ε antibody, 6F7 antibody attenuated T cell responses. Expression of CD25 and the production of IL-2 by anti-BTLA-treated T cells were reduced compared to the IgG-treated control (FIG. 27). Importantly, the inhibitory effect on immune responses mediated by 6F7 antibody was specific to BTLA expressing T cells, as the activation and proliferation of Btla$^{-/-}$ T cells was essentially equivalent in cultures treated with the 6F7 mAb or an irrelevant IgG control (FIG. 27B). The anti-BTLA mAb reduced IL-2 and CD25 induction even when Hvem$^{-/-}$ T cells and APC were co-cultured (FIG. 27D), indicating that the mAb acts directly by engaging BTLA, as opposed to blocking interactions with HVEM. These results indicate that the anti-BTLA mAb 6F7 has agonistic activity that stimulates BTLA-mediated inhibitory signals leading to decreased T cell immune responses in vitro.

Figure 28:
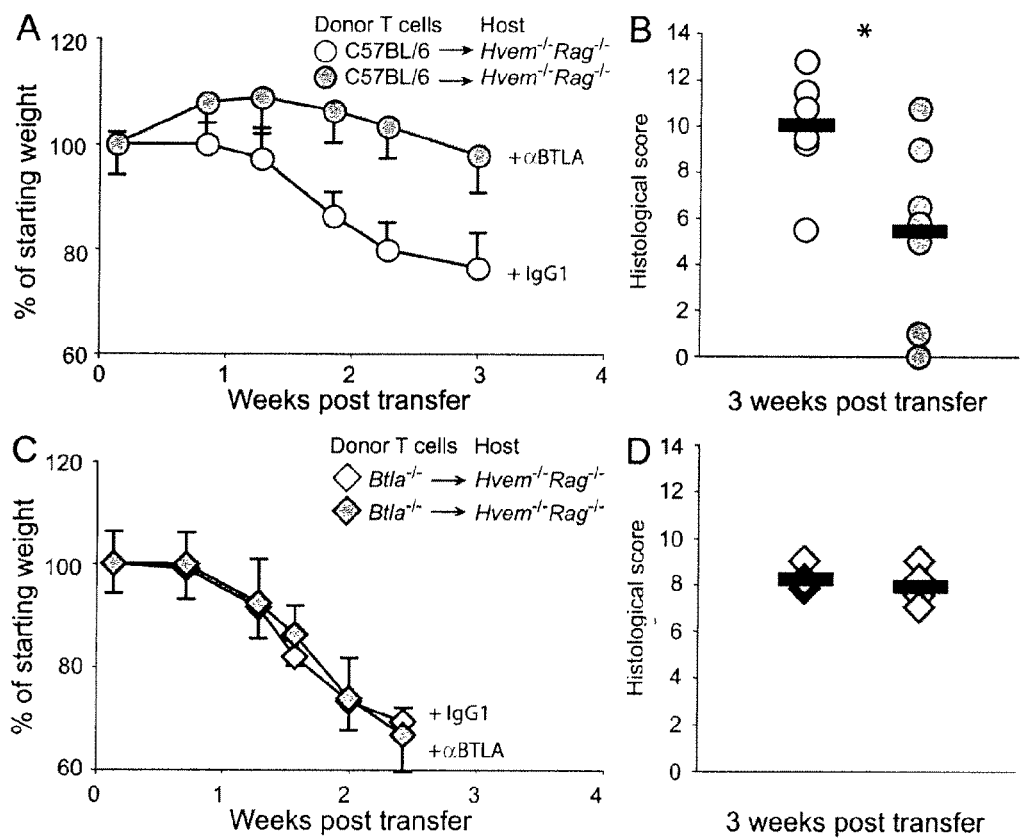

The anti-BTLA mAb also has agonistic activity in vivo. Injection of anti-BTLA mAb every three days beginning at the time of T cell transfer greatly delayed weight loss and disease progression (FIG. 28A). Furthermore, Hvem$^{-/-}$Rag$^{-/-}$ recipients treated with the anti-BTLA mAb had lower average histological scores (FIG. 28B).

Altogether, these results demonstrate that BTLA engagement prevented colitis acceleration, indicating that rapid development of colitis in Hvem$^{-/-}$Rag$^{-/-}$ mice is likely to be caused by the absence of BTLA signaling.

To evaluate if the anti-BTLA mAb prevents colitis by acting on donor T cells, Btla$^{-/-}$ CD4$^+$CD45RB$^{high}$ T cells were transferred into Hvem$^{-/-}$Rag$^{-/-}$ recipients which were then treated with the anti-BTLA mAb. Hvem$^{-/-}$Rag$^{-/-}$ mice transferred with Btla$^{-/-}$ T cells showed faster weight loss regardless of treatment with the anti-BTLA mAb (FIG. 28C). In addition, all the transferred animals presented severe intestinal inflammation and similar histological average scores (FIG. 28D).

These results demonstrate that the anti-BTLA mAb prevents colitis acceleration when the donor T cells express BTLA. Therefore, BTLA signaling on T cells mediated by HVEM expressed by an irradiation resistant cell is crucial in preventing colitis acceleration.

Example 20

This example describes data indicating that colitis in Btla$^{-/-}$Rag$^{-/-}$ recipients is accelerated.

Although the effect of the agonistic anti-BTLA mAb required BTLA expression by T cells, the studies described above prove only that T cell expression of BTLA is necessary, but not sufficient. It therefore remained possible that BTLA expression by host cells in the Rag$^{-/-}$ mice may also be required for preventing colitis acceleration.

Figure 29:
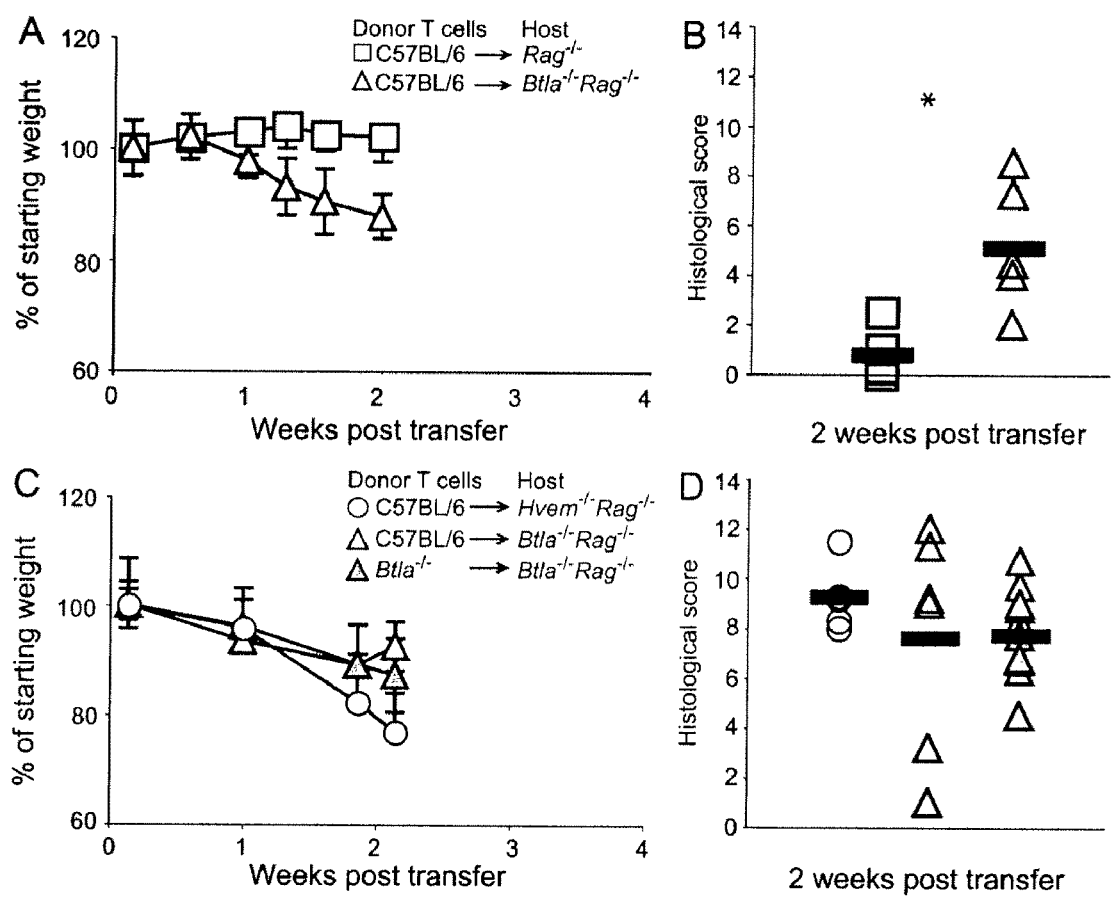

To investigate this possibility, Btla$^{-/-}$Rag$^{-/-}$ animals were used as recipients of WT CD4$^+$CD45RB$^{high}$ T cells. The transfer of T cells into Btla$^{-/-}$Rag$^{-/-}$ recipients led to faster weight loss (FIG. 29A). Furthermore, histological analysis performed two weeks after the transfer on samples isolated from the large intestine revealed a more severe intestinal inflammation in Btla$^{-/-}$Rag$^{-/-}$ mice (FIG. 29B).

To determine if disease acceleration in Btla$^{-/-}$Rag$^{-/-}$ mice was comparable to that observed in HVEM-deficient host, WT CD4$^+$CD45RB$^{high}$ were simultaneously transferred into Btla$^{-/-}$Rag$^{-/-}$ or Hvem$^{-/-}$Rag$^{-/-}$ mice. In the two groups of recipients, colitis development was essentially equivalent. Although the trend was towards slightly less weight loss and less severe histological scores in Btla$^{-/-}$Rag$^{-/-}$ mice than in Hvem$^{-/-}$Rag$^{-/-}$ mice, the difference did not reach statistical significance (FIG. 29C-D). Similar results were obtained when Btla$^{-/-}$Rag$^{-/-}$ recipients were transferred with Btla$^{-/-}$ CD4$^+$CD45RB$^{high}$, a situation where BTLA was absent in both donor and host cells (FIG. 29C-D).

Altogether, these results demonstrate that BTLA expression by Rag$^{-/-}$ host cells also prevents accelerated colitis in the T cell transfer model.

Example 21

This example describes studies indicating that in collagen induced arthritis (CIA), an animal model of rheumatoid arthritis and other autoimmune diseases, that mice responded to anti-BTLA antibody treatment.

The collagen-induced arthritis (CIA) is a well accepted arthritis model in rodents and primates that closely recapitulates the histopathological features of rheumatoid arthritis (RA) in humans. CIA is genetically linked to the specific MHC II haplotype I-Aq associated with high disease susceptibility in mice. The DBA/1 mouse strain with the H-2q haplotype is commonly used for induction of CIA (disease incidence of 90-100%) as a model to assess the molecular and cellular mechanisms leading to the development of autoimmune arthritis. This model was used to study the role of the Ig superfamily member, B and T lymphocyte attenuator (BTLA), in the development of RA in mice.

DBA/1 mice were immunized with 100 ul of a 1:1 (v/v) emulsion of IFA containing 1 mg/ml of M. tuberculosis (CFA) with 1 mg/ml of chicken type II collagen. 21 days after immunization female and male DBA/1 mice were boosted with 1 mg/ml of chicken type II collagen emulsified with CFA or IFA, respectively. From primary immunization, DBA/1 mice were treated weekly with 200 ug of the anti-BTLA antibody or PBS as control. Arthritis score in each animal was quantified according to a graded scale of 0 to 28. For each individual, the total score correspond to the sum of the number of digits, paws and ankles presenting signs of inflammation. Arthritis scores were measured twice a week starting at boost and until day 70. The results are illustrated in FIG. 30 and discussed below in detail.

To evaluate inflammation in each joint of the treated animals, the thickness of every paw of each DBA/1 mouse was measured twice a week starting at boost until the end of the experiment. Measurements were taken using a digital caliper. Values shown represent the average of the thickness of all four extremities in each animal and the average of three DBA/1 mice per group. Paw thickness index are shown with index=1 corresponding to the thickness of the paws at boost. The results are illustrated in FIG. 31 and discussed below in detail.

Incidence of disease was assessed by determine the number of animals in each treatment group presenting an arthritis score $\geq 1$. The results are illustrated in FIG. 32 and discussed below in detail.

Figure 33:
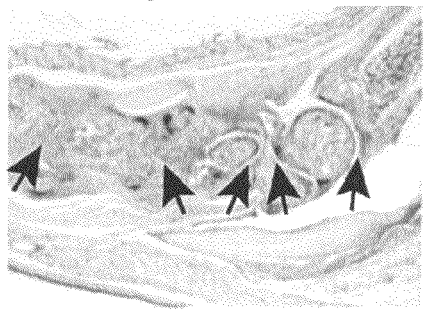
Figure 33:
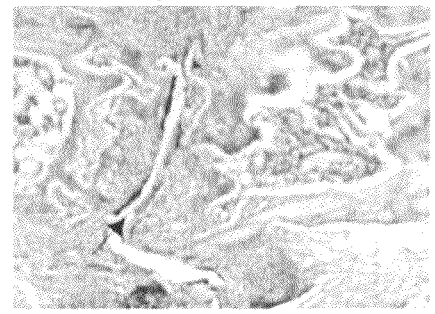
Figure 33:
Figure 33:
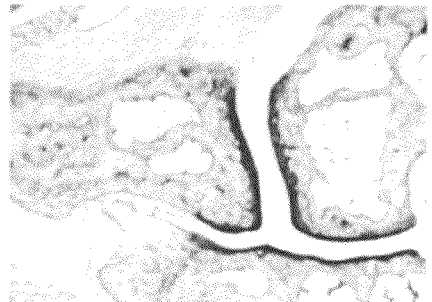

Histological analysis was performed by pathologists at HistoTox Labs, Inc. Briefly, treated mice were sacrificed at day 70 after boost and ankles from were removed and fix in 1:10 (v/v) formalin. Tissues were decalcified, trimmed, processed for paraffin embedding, sectioned at 8 µm and stained with toluidine blue (T-blue). The results are illustrated in FIG. 33 and discussed below in detail.

Agonistic engagement of BTLA with an anti-BTLA antibody (clone 6F7) greatly delayed inflammation and the onset of RA in DBA/1 mice. DBA/1 mice treated weekly with 200 ug of the anti-BTLA antibody presented lower inflammatory scores than animals treated with PBS (FIG. 30). In agreement with this observation, animals treated with the anti-BTLA antibody also presented reduced joint inflammation than animals treated with PBS, when inflammation was assessed by measuring the thickness of the paws of treated mice (FIG. 31). Furthermore, agonistic engagement of BTLA led to a significantly lower disease incidence, compared with DBA mice treated with PBS (FIG. 32). The differences in joint inflammation observed between PBS and anti-BTLA antibody treated animals was confirmed by histological analysis of the affected joints. The results demonstrated more severe inflammation in PBS treated mice, with prominent leulocyte infiltrates, cartilage destruction and bone resorption (FIG. 33, upper panel). Contrarely, joints from animals treated with the anti-BTLA antibody presented none or mild inflammation, intact cartilage and bone structures and absence of leukocyte infiltrates (FIG. 33, lower panel).

Although female DBA/1 mice showed heightened sensitivity to the anti-BTLA antibody treatment, male DBA/1 mice treated with the antibody also showed reduced arthritis, indicating that the anti-inflammatory effect of the anti-BTLA antibody is gender independent.

T cell proliferation was assessed in vitro by measuring $H^3$-Thymidine ($H^3$-Thy) incorporation following re-stimulation of $5 \times 10^5$ lymph node (LN) cells with 50 ug/ml of type II collagen or an anti-CD3ε antibody (1 ug/ml). Cells were culture in 96 well plates for 96 hours, the last 16 hours in the presence of 1 uCi/well of H³-Thy. H³-Thy incorporation was then measured in a liquid beta counter. The results are illustrated in FIG. 34 and discussed below in detail.

The phenotype of the B lymphocytes in DBA/1 mice treated with PBS or anti-BTLA mAb was assessed by flow cytometry. Splenic cells were stained for surface markers using anti-B220, anti-CD21 and anti-CD23 specific antibodies. Dot-plots represent CD23 and CD21 staining of B220+ B cells from spleens of male DBA/1 mice. The results are illustrated in FIG. 35 and discussed below in detail.

Ex vivo studies provided evidence that engagement of BTLA by the anti-BTLA antibody is important to attenuate proliferation of pathogenic T cells required for RA development. Indeed, T cell proliferative responses assessed by H³-Thymidine incorporation following restimulation of lymph node (LN) cells with collagen or an anti-CD3ε antibody were significantly reduced in those cells isolated from anti-BTLA treated mice (FIG. 34). Although T cell numbers were slightly reduced in the anti-BTLA antibody treated mice, a much bigger reduction was observed for B lymphocytes, in particular B cells isolated from draining LN of DBA/1 animals (Table 2). Interestingly, a subset of follicular B cells expressing high levels of surface BTLA and the surface markers B220, CD23hi and CD21 int, was preferentially targeted by the anti-BTLA antibody (FIG. 35).

These data demonstrate that the anti-BTLA antibody has a "dual-function" effect, resulting in both B-cell depletion and decreased antigen-specific T-cell function.

In summary, the data indicate that agonistic engagement of BTLA with an anti-BTLA antibody greatly attenuated CIA in mice. Additionally, treatment with anti-BTLA antibody also reduced numbers of potentially pathogenic T and B lymphocyte populations. These findings indicate that engagement of the inhibitory receptor BTLA by agonists is a candidate treatments for inflammatory diseases, such us RA.

Table 2 shows the average of the absolute number of total cells, T and B cells isolated from lymph nodes (LN) or spleen of male DBA/I mice treated with PBS (n=3) or anti-BTLA mAb (n=3).

TABLE 2

| LN cell numbers | | Spleen cell numbers | |
|---|---|---|---|
| T cells | | T cells | |
| PBS | 2.86E+06 | PBS | 1.21E+07 |
| anti-BTLA | 2.13E+06 | anti-BTLA | 6.63E+06 |
| B cells | | B cells | |
| PBS | 2.15E+06 | PBS | 4.85E+07 |
| anti-BTLA | 5.02E+05 | anti-BTLA | 1.26E+07 |
| Total cells | | Total cells | |
| PBS | 5.34E+06 | PBS | 7.50E+07 |
| anti-BTLA | 2.91E+06 | anti-BTLA | 3.04E+07 |

What is claimed:

1. A method of selectively modulating a response mediated or associated with immunoregulatory molecule B-T lymphocyte attenuator (BTLA) activity or expression for treatment of a subject having or at risk of having inflammatory bowel disease (IBD), comprising administering an anti-BTLA agonist antibody that modulates a response mediated or associated with immunoregulatory molecule B-T lymphocyte attenuator (BTLA) activity or expression to the subject.

2. The method of claim 1, wherein the antibody comprises an agonist of BTLA activity.

3. The method of claim 1, wherein the antibody increases a response mediated or associated with immunoregulatory molecule B-T lymphocyte attenuator (BTLA) activity or expression.

4. The method of claim 3, wherein the response comprises inhibiting or reducing inflammation.

5. The method of claim 3, wherein the response comprises inhibiting or reducing proliferation, survival, differentiation, death, or activity of T cells, antigen presenting cells or B cells.

6. The method of claim 3, wherein the response comprises inhibiting or reducing cytotoxic or helper activity of activated T cells; or B cell production of antibody.

7. The method of claim 1, wherein the subject is a human.

8. The method of claim 1, wherein the inflammatory bowel disease comprises ulcerative colitis, or Crohn's disease.

9. The method of claim 1, wherein the inflammatory bowel disease is associated with or caused by undesirable or aberrant proliferation, survival, differentiation, death, or activity of a T cell, antigen presenting cell or B cell.

10. The method of claim 1, wherein the method reduces the occurrence, frequency, severity, progression, or duration of a symptom caused by or associated with IBD.

11. The method of claim 1, wherein the method reduces gut or bowel infiltration or tissue destruction.

12. The method of claim 1, wherein the anti-BTLA agonist antibody is monoclonal.

13. The method of claim 1, wherein the anti-BTLA agonist antibody is mammalian.

14. The method of claim 1, wherein the anti-BTLA agonist antibody is human.

15. The method of claim 1, wherein the anti-BTLA agonist antibody is humanized.

16. The method of claim 1, wherein the anti-BTLA agonist antibody comprises an IgG, IgA, IgM, IgE or IgD.

17. The method of claim 1, wherein the anti-BTLA agonist antibody comprises a subsequence or a fragment that binds to BTLA.

* * * * *